United States Patent
Lillard, Jr.

(10) Patent No.: US 8,563,476 B2
(45) Date of Patent: Oct. 22, 2013

(54) ANTI-CXCL9, ANTI-CXCL10, ANTI-CXCL11, ANTI-CXCL13, ANTI-CXCR3 AND ANTI-CXCR5 AGENTS FOR INFLAMMATORY DISORDERS

(75) Inventor: James W. Lillard, Jr., Smyrna, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 13/535,215

(22) Filed: Jun. 27, 2012

(65) Prior Publication Data

US 2012/0264645 A1 Oct. 18, 2012

Related U.S. Application Data

(63) Continuation-in-part of application No. 13/105,335, filed on May 11, 2011, which is a continuation of application No. 10/712,393, filed on Nov. 14, 2003, now Pat. No. 7,964,194.

(60) Provisional application No. 60/426,350, filed on Nov. 15, 2002.

(51) Int. Cl.
| | |
|---|---|
| *A61K 39/00* | (2006.01) |
| *A61K 39/395* | (2006.01) |
| *C40B 30/04* | (2006.01) |
| *C40B 40/10* | (2006.01) |
| *G01N 33/53* | (2006.01) |
| *C12Q 1/68* | (2006.01) |
| *G01N 33/566* | (2006.01) |

(52) U.S. Cl.
USPC .............. 506/9; 506/18; 435/7.1; 435/6.12; 435/7.92; 424/145.1; 424/141.1; 436/501

(58) Field of Classification Search
None
See application file for complete search history.

(56) References Cited

U.S. PATENT DOCUMENTS

| | | | | |
|---|---|---|---|---|
| 6,140,064 | A | * 10/2000 | Loetscher et al. | ............. 435/7.2 |
| 6,329,510 | B1 | 12/2001 | Qin et al. | |
| 2003/0166589 | A1 | 9/2003 | Karin | |

(Continued)

FOREIGN PATENT DOCUMENTS

| | | |
|---|---|---|
| WO | 02/15932 A1 | 2/2002 |
| WO | 2012/024236 A1 | 2/2012 |

OTHER PUBLICATIONS

Wang et al., (J Proteom Res. 2002;1(4):337-343. Epub Jun. 21, 2002).*

(Continued)

*Primary Examiner* — Cherie M Stanfield
(74) *Attorney, Agent, or Firm* — Ping Wang; Andrews Kurth LLP

(57) ABSTRACT

A method for detecting an inflammatory disease in a subject is disclosed. The method comprises the steps of (a) detecting a level of expression of one or more inflammatory disease markers in a biological sample obtained from the subject; and (b) comparing the level of expression of said one or more inflammatory disease markers in the biological sample to a normal level of expression of the one or more inflammatory disease markers, wherein the one or more inflammatory disease markers comprise one or more markers selected from the group consisting of CXCL9, CXCL10, CXCL11, CXCL13, CXCR3 and CXCR5. Also disclosed are a method for monitoring the course of treatment for an inflammatory disease in a subject and a kit for detecting an inflammatory disease in a subject.

23 Claims, 34 Drawing Sheets

(56) References Cited

U.S. PATENT DOCUMENTS

| | | |
|---|---|---|
| 2005/0064469 A1 | 3/2005 | Schulz et al. |
| 2006/0275782 A1 | 12/2006 | Gunderson et al. |
| 2010/0233718 A1 | 9/2010 | Aubert et al. |
| 2011/0280872 A1 | 11/2011 | Lillard et al. |
| 2012/0144504 A1 | 6/2012 | Wallach et al. |

OTHER PUBLICATIONS

Dreses-Werringloer, U., et al., "Persistence of *Chlamydia trachomatis* Is Induced by Ciprofloxacin and Ofloxacin in Vitro", Antimicrob. Agents Chemother., vol. 44, No. 12, pp. 3288-3297 (2000).

International Search Report (Application No. PCT/US2003/036556, filed Nov. 14, 2003).

Angostini, et al., "CXCR3 and Its Ligand CXCL10 are Expressed by Inflammatory Cells Infiltrating Lung Allografts and Mediate Chemotaxis of T Cells at Sites of Rejection", American Society for Investigative Pathology, Vil. 158, pp. 1703-1711 (2001).

Constantini, S. et al., "Serum cytokine levels as putative prognostic markers in the progression of chronic HCV hepatitis to cirrhosis", European Cytokine Network, vol. 21, No. 4, Dec. 2010, pp. 251-256.

Moura, A. S. et al., "Soluble inflammatory markers as predictors of hepatocellular damage and therapeutic response in chronic hepatitis C", Brazilian Journal of Infectious Diseases, vol. 13, No. 5, Oct. 2009, pp. 375-382.

The International Search Report and the Written Opinion of the International Searching Authority of International Application No. PCT/US2012/044475 mailed Apr. 30, 2013.

\* cited by examiner

CONTROL

HEAT-KILLED MAP

LIVE MAP

CONTROL

HEAT-KILLED MAP

LIVE MAP

```
SEQUENCE LISTING

<160> NUMBER OF SEQ ID NOS: 141

<210> SEQ ID NO 1
<211> LENGTH: 125
<212> TYPE: PRT
<213> ORGANISM: Homo sapiens
<220> FEATURE:
<221> NAME/KEY: CXCL9
<222> LOCATION: (1)..(125)

<400> SEQUENCE: 1

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
                20                  25                  30

Cys Ile Ser Thr Asn Gln Gly Thr Ile His Leu Gln Ser Leu Lys Asp
            35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
                100                 105                 110

Val Arg Lys Ser Gln Arg Ser Arg Gln Lys Lys Thr Thr
            115                 120                 125

<210> SEQ ID NO 2
<211> LENGTH: 98
<212> TYPE: PRT
<213> ORGANISM: Homo sapiens
<220> FEATURE:
<221> NAME/KEY: CXCL10
<222> LOCATION: (1)..(98)

<400> SEQUENCE: 2

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
                20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80
```

```
Ala Ile Lys Asn Leu Leu Lys Ala Val Ser Lys Glu Arg Ser Lys Arg
                85                  90                  95

Ser Pro

<210> SEQ ID NO 3
<211> LENGTH: 93
<212> TYPE: PRT
<213> ORGANISM: Homo sapiens
<220> FEATURE:
<221> NAME/KEY: CXCL11
<222> LOCATION: (1)..(93)
<220> FEATURE:
<221> NAME/KEY: CXCL11b
<222> LOCATION: (1)..(93)

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 4
<211> LENGTH: 93
<212> TYPE: PRT
<213> ORGANISM: Homo sapiens
<220> FEATURE:
<221> NAME/KEY: CXCL12
<222> LOCATION: (1)..(93)

<400> SEQUENCE: 4

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 5
<211> LENGTH: 109
<212> TYPE: PRT
<213> ORGANISM: Homo sapiens
<220> FEATURE:
<221> NAME/KEY: CXCL13
<222> LOCATION: (1)..(109)
```

```
<400> SEQUENCE: 5

Met Lys Phe Ile Ser Thr Ser Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
                35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
                100                 105

<210> SEQ ID NO 6
<211> LENGTH: 368
<212> TYPE: PRT
<213> ORGANISM: Homo sapiens
<220> FEATURE:
<221> NAME/KEY: CXCR3-1
<222> LOCATION: (1)..(368)

<400> SEQUENCE: 6

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
```

```
                   245                 250                 255
Val Val Val Val Val Ala Phe Ala Leu Cys Trp Thr Pro Tyr His
                260                 265                 270

Leu Val Val Leu Val Asp Ile Leu Met Asp Leu Gly Ala Leu Ala Arg
                275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
                355                 360                 365

<210> SEQ ID NO 7
<211> LENGTH: 415
<212> TYPE: PRT
<213> ORGANISM: Homo sapiens
<220> FEATURE:
<221> NAME/KEY: CXCR3-2
<222> LOCATION: (1)..(415)

<400> SEQUENCE: 7

Met Glu Leu Arg Lys Tyr Gly Pro Gly Arg Leu Ala Gly Thr Val Ile
1               5                   10                  15

Gly Gly Ala Ala Gln Ser Lys Ser Gln Thr Lys Ser Asp Ser Ile Thr
                20                  25                  30

Lys Glu Phe Leu Pro Gly Leu Tyr Thr Ala Pro Ser Ser Pro Phe Pro
                35                  40                  45

Pro Ser Gln Val Ser Asp His Gln Val Leu Asn Asp Ala Glu Val Ala
        50                  55                  60

Ala Leu Leu Glu Asn Phe Ser Ser Ser Tyr Asp Tyr Gly Glu Asn Glu
65                  70                  75                  80

Ser Asp Ser Cys Cys Thr Ser Pro Pro Cys Pro Gln Asp Phe Ser Leu
                85                  90                  95

Asn Phe Asp Arg Ala Phe Leu Pro Ala Leu Tyr Ser Leu Leu Phe Leu
            100                 105                 110

Leu Gly Leu Leu Gly Asn Gly Ala Val Ala Ala Val Leu Leu Ser Arg
        115                 120                 125

Arg Thr Ala Leu Ser Ser Thr Asp Thr Phe Leu Leu His Leu Ala Val
130                 135                 140

Ala Asp Thr Leu Leu Val Leu Thr Leu Pro Leu Trp Ala Val Asp Ala
145                 150                 155                 160

Ala Val Gln Trp Val Phe Gly Ser Gly Leu Cys Lys Val Ala Gly Ala
                165                 170                 175

Leu Phe Asn Ile Asn Phe Tyr Ala Gly Ala Leu Leu Leu Ala Cys Ile
            180                 185                 190

Ser Phe Asp Arg Tyr Leu Asn Ile Val His Ala Thr Gln Leu Tyr Arg
        195                 200                 205

Arg Gly Pro Pro Ala Arg Val Thr Leu Thr Cys Leu Ala Val Trp Gly
    210                 215                 220

Leu Cys Leu Leu Phe Ala Leu Pro Asp Phe Ile Phe Leu Ser Ala His
225                 230                 235                 240

His Asp Glu Arg Leu Asn Ala Thr His Cys Gln Tyr Asn Phe Pro Gln
```

```
                        245                 250                 255
Val Gly Arg Thr Ala Leu Arg Val Leu Gln Leu Val Ala Gly Phe Leu
                    260                 265                 270

Leu Pro Leu Leu Val Met Ala Tyr Cys Tyr Ala His Ile Leu Ala Val
                275                 280                 285

Leu Leu Val Ser Arg Gly Gln Arg Leu Arg Ala Met Arg Leu Val
            290                 295                 300

Val Val Val Val Val Ala Phe Ala Leu Cys Trp Thr Pro Tyr His Leu
305                 310                 315                 320

Val Val Leu Val Asp Ile Leu Met Asp Leu Gly Ala Leu Ala Arg Asn
                325                 330                 335

Cys Gly Arg Glu Ser Arg Val Asp Val Ala Lys Ser Val Thr Ser Gly
                340                 345                 350

Leu Gly Tyr Met His Cys Cys Leu Asn Pro Leu Leu Tyr Ala Phe Val
                355                 360                 365

Gly Val Lys Phe Arg Glu Arg Met Trp Met Leu Leu Arg Leu Gly
            370                 375                 380

Cys Pro Asn Gln Arg Gly Leu Gln Arg Gln Pro Ser Ser Ser Arg Arg
385                 390                 395                 400

Asp Ser Ser Trp Ser Glu Thr Ser Glu Ala Ser Tyr Ser Gly Leu
                405                 410                 415

<210> SEQ ID NO 8
<211> LENGTH: 372
<212> TYPE: PRT
<213> ORGANISM: Homo sapiens
<220> FEATURE:
<221> NAME/KEY: CXCR5-1
<222> LOCATION: (1)..(372)

<400> SEQUENCE: 8

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
                20                  25                  30

Val Glu Asn His Leu Cys Pro Ala Thr Glu Gly Pro Leu Met Ala Ser
                35                  40                  45

Phe Lys Ala Val Phe Val Pro Val Ala Tyr Ser Leu Ile Phe Leu Leu
            50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
                100                 105                 110

Val Gly Trp Val Leu Gly Thr Phe Leu Cys Lys Thr Val Ile Ala Leu
            115                 120                 125

His Lys Val Asn Phe Tyr Cys Ser Ser Leu Leu Leu Ala Cys Ile Ala
            130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
                180                 185                 190

Gly His His Asn Asn Ser Leu Pro Arg Cys Thr Phe Ser Gln Glu Asn
```

```
                195                 200                 205
Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Pro Gln Arg Gln Lys
    245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 9
<211> LENGTH: 327
<212> TYPE: PRT
<213> ORGANISM: Homo sapiens
<220> FEATURE:
<221> NAME/KEY: CXCR5-2
<222> LOCATION: (1)..(327)

<400> SEQUENCE: 9

Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
            20                  25                  30

Arg His Arg Gln Thr Arg Ser Ser Thr Glu Thr Phe Leu Phe His Leu
        35                  40                  45

Ala Val Ala Asp Leu Leu Leu Val Phe Ile Leu Pro Phe Ala Val Ala
    50                  55                  60

Glu Gly Ser Val Gly Trp Val Leu Gly Thr Phe Leu Cys Lys Thr Val
65                  70                  75                  80

Ile Ala Leu His Lys Val Asn Phe Tyr Cys Ser Ser Leu Leu Leu Ala
                85                  90                  95

Cys Ile Ala Val Asp Arg Tyr Leu Ala Ile Val His Ala Val His Ala
            100                 105                 110

Tyr Arg His Arg Arg Leu Leu Ser Ile His Ile Thr Cys Gly Thr Ile
        115                 120                 125

Trp Leu Val Gly Phe Leu Leu Ala Leu Pro Glu Ile Leu Phe Ala Lys
    130                 135                 140

Val Ser Gln Gly His His Asn Asn Ser Leu Pro Arg Cys Thr Phe Ser
145                 150                 155                 160

Gln Glu Asn Gln Ala Glu Thr His Ala Trp Phe Thr Ser Arg Phe Leu
                165                 170                 175

Tyr His Val Ala Gly Phe Leu Leu Pro Met Leu Val Met Gly Trp Cys
```

```
                    180                 185                 190
Tyr Val Gly Val Val His Arg Leu Arg Gln Ala Gln Arg Pro Gln
                195                 200                 205
Arg Gln Lys Ala Val Arg Val Ala Ile Leu Val Thr Ser Ile Phe Phe
            210                 215                 220
Leu Cys Trp Ser Pro Tyr His Ile Val Ile Phe Leu Asp Thr Leu Ala
225                 230                 235                 240
Arg Leu Lys Ala Val Asp Asn Thr Cys Lys Leu Asn Gly Ser Leu Pro
                245                 250                 255
Val Ala Ile Thr Met Cys Glu Phe Leu Gly Leu Ala His Cys Cys Leu
                260                 265                 270
Asn Pro Met Leu Tyr Thr Phe Ala Gly Val Lys Phe Arg Ser Asp Leu
                275                 280                 285
Ser Arg Leu Leu Thr Lys Leu Gly Cys Thr Gly Pro Ala Ser Leu Cys
                290                 295                 300
Gln Leu Phe Pro Ser Trp Arg Arg Ser Ser Leu Ser Glu Ser Glu Asn
305                 310                 315                 320
Ala Thr Ser Leu Thr Thr Phe
                325

<210> SEQ ID NO 10
<211> LENGTH: 107
<212> TYPE: PRT
<213> ORGANISM: Homo sapiens
<220> FEATURE:
<221> NAME/KEY: CXCL1
<222> LOCATION: (1)..(107)

<400> SEQUENCE: 10

Met Ala Arg Ala Ala Leu Ser Ala Ala Pro Ser Asn Pro Arg Leu Leu
1               5                   10                  15
Arg Val Ala Leu Leu Leu Leu Leu Val Ala Ala Gly Arg Arg Ala
            20                  25                  30
Ala Gly Ala Ser Val Ala Thr Glu Leu Arg Cys Gln Cys Leu Gln Thr
            35                  40                  45
Leu Gln Gly Ile His Pro Lys Asn Ile Gln Ser Val Asn Val Lys Ser
    50                  55                  60
Pro Gly Pro His Cys Ala Gln Thr Glu Val Ile Ala Thr Leu Lys Asn
65                  70                  75                  80
Gly Arg Lys Ala Cys Leu Asn Pro Ala Ser Pro Ile Val Lys Lys Ile
                85                  90                  95
Ile Glu Lys Met Leu Asn Ser Asp Lys Ser Asn
                100                 105

<210> SEQ ID NO 11
<211> LENGTH: 107
<212> TYPE: PRT
<213> ORGANISM: Homo sapiens
<220> FEATURE:
<221> NAME/KEY: CXCL2
<222> LOCATION: (1)..(107)

<400> SEQUENCE: 11

Met Ala Arg Ala Thr Leu Ser Ala Ala Pro Ser Asn Pro Arg Leu Leu
1               5                   10                  15
Arg Val Ala Leu Leu Leu Leu Leu Val Ala Ala Ser Arg Arg Ala
            20                  25                  30
Ala Gly Ala Pro Leu Ala Thr Glu Leu Arg Cys Gln Cys Leu Gln Thr
            35                  40                  45
```

```
Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105
```

<210> SEQ ID NO 12
<211> LENGTH: 107
<212> TYPE: PRT
<213> ORGANISM: Homo sapiens
<220> FEATURE:
<221> NAME/KEY: CXCL3
<222> LOCATION: (1)..(107)

<400> SEQUENCE: 12

```
Met Ala His Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala Ala
                20                  25                  30

Gly Ala Ser Val Val Thr Glu Leu Arg Cys Gln Cys Leu Gln Thr Leu
            35                  40                  45

Gln Gly Ile His Leu Lys Asn Ile Gln Ser Val Asn Val Arg Ser Pro
    50                  55                  60

Gly Pro His Cys Ala Gln Thr Glu Val Ile Ala Thr Leu Lys Asn Gly
65                  70                  75                  80

Lys Lys Ala Cys Leu Asn Pro Ala Ser Pro Met Val Gln Lys Ile Ile
                85                  90                  95

Glu Lys Ile Leu Asn Lys Gly Ser Thr Asn
            100                 105
```

<210> SEQ ID NO 13
<211> LENGTH: 101
<212> TYPE: PRT
<213> ORGANISM: Homo sapiens
<220> FEATURE:
<221> NAME/KEY: CXCL4
<222> LOCATION: (1)..(101)

<400> SEQUENCE: 13

```
Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
                20                  25                  30

Ala Glu Glu Asp Gly Asp Leu Gln Cys Leu Cys Val Lys Thr Thr Ser
            35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100
```

<210> SEQ ID NO 14
<211> LENGTH: 114

```
<212> TYPE: PRT
<213> ORGANISM: Homo sapiens
<220> FEATURE:
<221> NAME/KEY: CXCL5
<222> LOCATION: (1)..(114)

<400> SEQUENCE: 14

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly
            20                  25                  30

Pro Ile Ala Ser Ala Gly Pro Ala Ala Val Leu Arg Glu Leu Arg
            35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn

<210> SEQ ID NO 15
<211> LENGTH: 114
<212> TYPE: PRT
<213> ORGANISM: Homo sapiens
<220> FEATURE:
<221> NAME/KEY: CXCL6
<222> LOCATION: (1)..(114)

<400> SEQUENCE: 15

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Thr Pro Pro Gly
            20                  25                  30

Pro Leu Ala Ser Ala Gly Pro Val Ser Ala Val Leu Thr Glu Leu Arg
            35                  40                  45

Cys Thr Cys Leu Arg Val Thr Leu Arg Val Asn Pro Lys Thr Ile Gly
    50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn

<210> SEQ ID NO 16
<211> LENGTH: 128
<212> TYPE: PRT
<213> ORGANISM: Homo sapiens
<220> FEATURE:
<221> NAME/KEY: CXCL7
<222> LOCATION: (1)..(128)

<400> SEQUENCE: 16

Met Ser Leu Arg Leu Asp Thr Thr Pro Ser Cys Asn Ser Ala Arg Pro
1               5                   10                  15

Leu His Ala Leu Gln Val Leu Leu Leu Leu Ser Leu Leu Leu Thr Ala
```

```
                    20                  25                  30
Leu Ala Ser Ser Thr Lys Gly Gln Thr Lys Arg Asn Leu Ala Lys Gly
                35                  40                  45

Lys Glu Glu Ser Leu Asp Ser Asp Leu Tyr Ala Glu Leu Arg Cys Met
 50                  55                  60

Cys Ile Lys Thr Thr Ser Gly Ile His Pro Lys Asn Ile Gln Ser Leu
 65                  70                  75                  80

Glu Val Ile Gly Lys Gly Thr His Cys Asn Gln Val Glu Val Ile Ala
                 85                  90                  95

Thr Leu Lys Asp Gly Arg Lys Ile Cys Leu Asp Pro Asp Ala Pro Arg
                100                 105                 110

Ile Lys Lys Ile Val Gln Lys Lys Leu Ala Gly Asp Glu Ser Ala Asp
                115                 120                 125

<210> SEQ ID NO 17
<211> LENGTH: 99
<212> TYPE: PRT
<213> ORGANISM: Homo sapiens
<220> FEATURE:
<221> NAME/KEY: CXCL8/IL-8
<222> LOCATION: (1)..(99)

<400> SEQUENCE: 17

Met Thr Ser Lys Leu Ala Val Ala Leu Leu Ala Phe Leu Ile Ser
 1               5                  10                  15

Ala Ala Leu Cys Glu Gly Ala Val Leu Pro Arg Ser Ala Lys Glu Leu
                 20                  25                  30

Arg Cys Gln Cys Ile Lys Thr Tyr Ser Lys Pro Phe His Pro Lys Phe
                 35                  40                  45

Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
                 85                  90                  95

Glu Asn Ser

<210> SEQ ID NO 18
<211> LENGTH: 273
<212> TYPE: PRT
<213> ORGANISM: Homo sapiens
<220> FEATURE:
<221> NAME/KEY: CXCL16
<222> LOCATION: (1)..(273)

<400> SEQUENCE: 18

Met Ser Gly Ser Gln Ser Glu Val Ala Pro Ser Pro Gln Ser Pro Arg
 1               5                  10                  15

Ser Pro Glu Met Gly Arg Asp Leu Arg Pro Gly Ser Arg Val Leu Leu
                 20                  25                  30

Leu Leu Leu Leu Leu Leu Val Tyr Leu Thr Gln Pro Gly Asn Gly
                35                  40                  45

Asn Glu Gly Ser Val Thr Gly Ser Cys Tyr Cys Gly Lys Arg Ile Ser
 50                  55                  60

Ser Asp Ser Pro Pro Ser Val Gln Phe Met Asn Arg Leu Arg Lys His
 65                  70                  75                  80

Leu Arg Ala Tyr His Arg Cys Leu Tyr Tyr Thr Arg Phe Gln Leu Leu
                 85                  90                  95
```

-continued

Ser Trp Ser Val Cys Gly Gly Asn Lys Asp Pro Trp Val Gln Glu Leu
            100                 105                 110

Met Ser Cys Leu Asp Leu Lys Glu Cys Gly His Ala Tyr Ser Gly Ile
        115                 120                 125

Val Ala His Gln Lys His Leu Leu Pro Thr Ser Pro Pro Ile Ser Gln
    130                 135                 140

Ala Ser Glu Gly Ala Ser Ser Asp Ile His Thr Pro Ala Gln Met Leu
145                 150                 155                 160

Leu Ser Thr Leu Gln Ser Thr Gln Arg Pro Thr Leu Pro Val Gly Ser
                165                 170                 175

Leu Ser Ser Asp Lys Glu Leu Thr Arg Pro Asn Glu Thr Thr Ile His
            180                 185                 190

Thr Ala Gly His Ser Leu Ala Ala Gly Pro Glu Ala Gly Glu Asn Gln
        195                 200                 205

Lys Gln Pro Glu Lys Asn Ala Gly Pro Thr Ala Arg Thr Ser Ala Thr
    210                 215                 220

Val Pro Val Leu Cys Leu Leu Ala Ile Ile Phe Ile Leu Thr Ala Ala
225                 230                 235                 240

Leu Ser Tyr Val Leu Cys Lys Arg Arg Gly Gln Ser Pro Gln Ser
                245                 250                 255

Ser Pro Asp Leu Pro Val His Tyr Ile Pro Val Ala Pro Asp Ser Asn
            260                 265                 270

Thr

<210> SEQ ID NO 19
<211> LENGTH: 350
<212> TYPE: PRT
<213> ORGANISM: Homo sapiens
<220> FEATURE:
<221> NAME/KEY: CXCR1
<222> LOCATION: (1)..(350)

<400> SEQUENCE: 19

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly

-continued

```
                180                 185                 190
Asn Asp Thr Ala Lys Trp Arg Met Val Leu Arg Ile Leu Pro His Thr
            195                 200                 205
Phe Gly Phe Ile Val Pro Leu Phe Val Met Leu Phe Cys Tyr Gly Phe
            210                 215                 220
Thr Leu Arg Thr Leu Phe Lys Ala His Met Gly Gln Lys His Arg Ala
225                 230                 235                 240
Met Arg Val Ile Phe Ala Val Val Leu Ile Phe Leu Leu Cys Trp Leu
                245                 250                 255
Pro Tyr Asn Leu Val Leu Leu Ala Asp Thr Leu Met Arg Thr Gln Val
                260                 265                 270
Ile Gln Glu Ser Cys Glu Arg Arg Asn Asn Ile Gly Arg Ala Leu Asp
                275                 280                 285
Ala Thr Glu Ile Leu Gly Phe Leu His Ser Cys Leu Asn Pro Ile Ile
            290                 295                 300
Tyr Ala Phe Ile Gly Gln Asn Phe Arg His Gly Phe Leu Lys Ile Leu
305                 310                 315                 320
Ala Met His Gly Leu Val Ser Lys Glu Phe Leu Ala Arg His Arg Val
                325                 330                 335
Thr Ser Tyr Thr Ser Ser Ser Val Asn Val Ser Ser Asn Leu
                340                 345                 350

<210> SEQ ID NO 20
<211> LENGTH: 360
<212> TYPE: PRT
<213> ORGANISM: Homo sapiens
<220> FEATURE:
<221> NAME/KEY: CXCR2
<222> LOCATION: (1)..(360)

<400> SEQUENCE: 20

Met Glu Asp Phe Asn Met Glu Ser Asp Ser Phe Glu Asp Phe Trp Lys
1               5                   10                  15
Gly Glu Asp Leu Ser Asn Tyr Ser Tyr Ser Ser Thr Leu Pro Pro Phe
            20                  25                  30
Leu Leu Asp Ala Ala Pro Cys Glu Pro Glu Ser Leu Glu Ile Asn Lys
        35                  40                  45
Tyr Phe Val Val Ile Ile Tyr Ala Leu Val Phe Leu Leu Ser Leu Leu
    50                  55                  60
Gly Asn Ser Leu Val Met Leu Val Ile Leu Tyr Ser Arg Val Gly Arg
65                  70                  75                  80
Ser Val Thr Asp Val Tyr Leu Leu Asn Leu Ala Leu Ala Asp Leu Leu
                85                  90                  95
Phe Ala Leu Thr Leu Pro Ile Trp Ala Ala Ser Lys Val Asn Gly Trp
            100                 105                 110
Ile Phe Gly Thr Phe Leu Cys Lys Val Val Ser Leu Leu Lys Glu Val
        115                 120                 125
Asn Phe Tyr Ser Gly Ile Leu Leu Leu Ala Cys Ile Ser Val Asp Arg
    130                 135                 140
Tyr Leu Ala Ile Val His Ala Thr Arg Thr Leu Thr Gln Lys Arg Tyr
145                 150                 155                 160
Leu Val Lys Phe Ile Cys Leu Ser Ile Trp Gly Leu Ser Leu Leu Leu
                165                 170                 175
Ala Leu Pro Val Leu Leu Phe Arg Arg Thr Val Tyr Ser Ser Asn Val
            180                 185                 190
Ser Pro Ala Cys Tyr Glu Asp Met Gly Asn Asn Thr Ala Asn Trp Arg
```

```
                195                 200                 205
Met Leu Leu Arg Ile Leu Pro Gln Ser Phe Gly Phe Ile Val Pro Leu
210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 21
<211> LENGTH: 356
<212> TYPE: PRT
<213> ORGANISM: Homo sapiens
<220> FEATURE:
<221> NAME/KEY: CXCR4a
<222> LOCATION: (1)..(356)

<400> SEQUENCE: 21

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile
        50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
```

```
                195                 200                 205
Met Val Gly Leu Ile Leu Pro Gly Ile Val Ile Leu Ser Cys Tyr Cys
210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355

<210> SEQ ID NO 22
<211> LENGTH: 352
<212> TYPE: PRT
<213> ORGANISM: Homo sapiens
<220> FEATURE:
<221> NAME/KEY: CXCR4b
<222> LOCATION: (1)..(352)

<400> SEQUENCE: 22

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
```

```
                195                 200                 205
Ile Leu Pro Gly Ile Val Ile Leu Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 23
<211> LENGTH: 342
<212> TYPE: PRT
<213> ORGANISM: Homo sapiens
<220> FEATURE:
<221> NAME/KEY: CXCR6
<222> LOCATION: (1)..(342)

<400> SEQUENCE: 23

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
                20                  25                  30

Phe Leu Pro Cys Met Tyr Leu Val Val Phe Val Cys Gly Leu Val Gly
            35                  40                  45

Asn Ser Leu Val Leu Val Ile Ser Ile Phe Tyr His Lys Leu Gln Ser
50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
            115                 120                 125

Ile Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
            195                 200                 205

Val Cys Tyr Ser Val Ile Ile Lys Thr Leu Leu His Ala Gly Gly Phe
```

```
                    210                 215                 220
Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
                260                 265                 270

Thr Glu Ala Ile Ala Tyr Leu Arg Ala Cys Leu Asn Pro Val Leu Tyr
                275                 280                 285

Ala Phe Val Ser Leu Lys Phe Arg Lys Asn Phe Trp Lys Leu Val Lys
                290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                    325                 330                 335

Thr Ser Met Phe Gln Leu
                340
```

<210> SEQ ID NO 24
<211> LENGTH: 96
<212> TYPE: PRT
<213> ORGANISM: Homo sapiens
<220> FEATURE:
<221> NAME/KEY: CCL1
<222> LOCATION: (1)..(96)

<400> SEQUENCE: 24

```
Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
                20                  25                  30

Cys Cys Phe Ser Phe Ala Glu Gln Glu Ile Pro Leu Arg Ala Ile Leu
            35                  40                  45

Cys Tyr Arg Asn Thr Ser Ser Ile Cys Ser Asn Glu Gly Leu Ile Phe
        50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95
```

<210> SEQ ID NO 25
<211> LENGTH: 99
<212> TYPE: PRT
<213> ORGANISM: Homo sapiens
<220> FEATURE:
<221> NAME/KEY: CCL2
<222> LOCATION: (1)..(99)

<400> SEQUENCE: 25

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80
```

Lys Trp Val Gln Asp Ser Met Asp His Leu Asp Lys Gln Thr Gln Thr
                    85                  90                  95

Pro Lys Thr

<210> SEQ ID NO 26
<211> LENGTH: 92
<212> TYPE: PRT
<213> ORGANISM: Homo sapiens
<220> FEATURE:
<221> NAME/KEY: CCL3
<222> LOCATION: (1)..(92)

<400> SEQUENCE: 26

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 27
<211> LENGTH: 92
<212> TYPE: PRT
<213> ORGANISM: Homo sapiens
<220> FEATURE:
<221> NAME/KEY: CCL4-1
<222> LOCATION: (1)..(92)

<400> SEQUENCE: 27

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 28
<211> LENGTH: 92
<212> TYPE: PRT
<213> ORGANISM: Homo sapiens
<220> FEATURE:
<221> NAME/KEY: CCL4L1
<222> LOCATION: (1)..(92)

<400> SEQUENCE: 28

Met Lys Leu Cys Val Thr Val Leu Ser Leu Leu Val Leu Val Ala Ala
1               5                   10                  15

Phe Cys Ser Leu Ala Leu Ser Ala Pro Met Gly Ser Asp Pro Pro Thr
            20                  25                  30

-continued

Ala Cys Cys Phe Ser Tyr Thr Ala Arg Lys Leu Pro Arg Asn Phe Val
              35                  40                  45

Val Asp Tyr Tyr Glu Thr Ser Ser Leu Cys Ser Gln Pro Ala Val Val
 50                  55                  60

Phe Gln Thr Lys Arg Gly Lys Gln Val Cys Ala Asp Pro Ser Glu Ser
 65                  70                  75                  80

Trp Val Gln Glu Tyr Val Tyr Asp Leu Glu Leu Asn
              85                  90

<210> SEQ ID NO 29
<211> LENGTH: 91
<212> TYPE: PRT
<213> ORGANISM: Homo sapiens
<220> FEATURE:
<221> NAME/KEY: CCL5
<222> LOCATION: (1)..(91)

<400> SEQUENCE: 29

Met Lys Val Ser Ala Ala Ala Leu Ala Val Ile Leu Ile Ala Thr Ala
 1               5                  10                  15

Leu Cys Ala Pro Ala Ser Ala Ser Pro Tyr Ser Ser Asp Thr Thr Pro
              20                  25                  30

Cys Cys Phe Ala Tyr Ile Ala Arg Pro Leu Pro Arg Ala His Ile Lys
              35                  40                  45

Glu Tyr Phe Tyr Thr Ser Gly Lys Cys Ser Asn Pro Ala Val Val Phe
 50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
              85                  90

<210> SEQ ID NO 30
<211> LENGTH: 99
<212> TYPE: PRT
<213> ORGANISM: Homo sapiens
<220> FEATURE:
<221> NAME/KEY: CCL7
<222> LOCATION: (1)..(99)

<400> SEQUENCE: 30

Met Lys Ala Ser Ala Ala Leu Leu Cys Leu Leu Leu Thr Ala Ala Ala
 1               5                  10                  15

Phe Ser Pro Gln Gly Leu Ala Gln Pro Val Gly Ile Asn Thr Ser Thr
              20                  25                  30

Thr Cys Cys Tyr Arg Phe Ile Asn Lys Lys Ile Pro Lys Gln Arg Leu
              35                  40                  45

Glu Ser Tyr Arg Arg Thr Thr Ser Ser His Cys Pro Arg Glu Ala Val
 50                  55                  60

Ile Phe Lys Thr Lys Leu Asp Lys Glu Ile Cys Ala Asp Pro Thr Gln
 65                  70                  75                  80

Lys Trp Val Gln Asp Phe Met Lys His Leu Asp Lys Lys Thr Gln Thr
              85                  90                  95

Pro Lys Leu

<210> SEQ ID NO 31
<211> LENGTH: 99
<212> TYPE: PRT
<213> ORGANISM: Homo sapiens
<220> FEATURE:
<221> NAME/KEY: CCL8

<222> LOCATION: (1)..(99)

<400> SEQUENCE: 31

Met Lys Val Ser Ala Ala Leu Leu Cys Leu Leu Met Ala Ala Thr
1               5                   10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
            35                  40                  45

Glu Ser Tyr Thr Arg Ile Thr Asn Ile Gln Cys Pro Lys Glu Ala Val
    50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 32
<211> LENGTH: 97
<212> TYPE: PRT
<213> ORGANISM: Homo sapiens
<220> FEATURE:
<221> NAME/KEY: CCL11
<222> LOCATION: (1)..(97)

<400> SEQUENCE: 32

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro

<210> SEQ ID NO 33
<211> LENGTH: 98
<212> TYPE: PRT
<213> ORGANISM: Homo sapiens
<220> FEATURE:
<221> NAME/KEY: CCL13
<222> LOCATION: (1)..(98)

<400> SEQUENCE: 33

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
            20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
    50                  55                  60

Phe Arg Thr Lys Leu Gly Lys Glu Ile Cys Ala Asp Pro Lys Glu Lys
65                  70                  75                  80

```
Trp Val Gln Asn Tyr Met Lys His Leu Gly Arg Lys Ala His Thr Leu
                85                  90                  95

Lys Thr

<210> SEQ ID NO 34
<211> LENGTH: 93
<212> TYPE: PRT
<213> ORGANISM: Homo sapiens
<220> FEATURE:
<221> NAME/KEY: CCL14-1
<222> LOCATION: (1)..(93)

<400> SEQUENCE: 34

Met Lys Ile Ser Val Ala Ala Ile Pro Phe Phe Leu Leu Ile Thr Ile
1               5                   10                  15

Ala Leu Gly Thr Lys Thr Glu Ser Ser Arg Gly Pro Tyr His Pro
            20                  25                  30

Ser Glu Cys Cys Phe Thr Tyr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 35
<211> LENGTH: 109
<212> TYPE: PRT
<213> ORGANISM: Homo sapiens
<220> FEATURE:
<221> NAME/KEY: CCL14-2
<222> LOCATION: (1)..(109)

<400> SEQUENCE: 35

Met Lys Ile Ser Val Ala Ala Ile Pro Phe Phe Leu Leu Ile Thr Ile
1               5                   10                  15

Ala Leu Gly Thr Lys Thr Glu Ser Ser Ser Gln Thr Gly Gly Lys Pro
            20                  25                  30

Lys Val Val Lys Ile Gln Leu Lys Leu Val Gly Gly Pro Tyr His Pro
        35                  40                  45

Ser Glu Cys Cys Phe Thr Tyr Thr Tyr Lys Ile Pro Arg Gln Arg
    50                  55                  60

Ile Met Asp Tyr Tyr Glu Thr Asn Ser Gln Cys Ser Lys Pro Gly Ile
65                  70                  75                  80

Val Phe Ile Thr Lys Arg Gly His Ser Val Cys Thr Asn Pro Ser Asp
                85                  90                  95

Lys Trp Val Gln Asp Tyr Ile Lys Asp Met Lys Glu Asn
            100                 105

<210> SEQ ID NO 36
<211> LENGTH: 113
<212> TYPE: PRT
<213> ORGANISM: Homo sapiens
<220> FEATURE:
<221> NAME/KEY: CCL15
<222> LOCATION: (1)..(113)

<400> SEQUENCE: 36

Met Lys Val Ser Val Ala Ala Leu Ser Cys Leu Met Leu Val Ala Val
1               5                   10                  15
```

```
Leu Gly Ser Gln Ala Gln Phe Ile Asn Asp Ala Glu Thr Glu Leu Met
            20                  25                  30

Met Ser Lys Leu Pro Leu Glu Asn Pro Val Val Leu Asn Ser Phe His
        35                  40                  45

Phe Ala Ala Asp Cys Cys Thr Ser Tyr Ile Ser Gln Ser Ile Pro Cys
    50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Leu Lys Pro Tyr Ser
                100                 105                 110

Ile

<210> SEQ ID NO 37
<211> LENGTH: 120
<212> TYPE: PRT
<213> ORGANISM: Homo sapiens
<220> FEATURE:
<221> NAME/KEY: CCL16
<222> LOCATION: (1)..(120)

<400> SEQUENCE: 37

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
                100                 105                 110

Gln Pro Gln Leu Leu Asn Ser Gln
            115                 120

<210> SEQ ID NO 38
<211> LENGTH: 94
<212> TYPE: PRT
<213> ORGANISM: Homo sapiens
<220> FEATURE:
<221> NAME/KEY: CCL17
<222> LOCATION: (1)..(94)

<400> SEQUENCE: 38

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
```

```
                            65                  70                  75                  80
Val Lys Asn Ala Val Lys Tyr Leu Gln Ser Leu Glu Arg Ser
                85                  90

<210> SEQ ID NO 39
<211> LENGTH: 89
<212> TYPE: PRT
<213> ORGANISM: Homo sapiens
<220> FEATURE:
<221> NAME/KEY: CCL18
<222> LOCATION: (1)..(89)

<400> SEQUENCE: 39

Met Lys Gly Leu Ala Ala Ala Leu Leu Val Leu Val Cys Thr Met Ala
 1               5                  10                  15

Leu Cys Ser Cys Ala Gln Val Gly Thr Asn Lys Glu Leu Cys Cys Leu
                20                  25                  30

Val Tyr Thr Ser Trp Gln Ile Pro Gln Lys Phe Ile Val Asp Tyr Ser
            35                  40                  45

Glu Thr Ser Pro Gln Cys Pro Lys Pro Gly Val Ile Leu Leu Thr Lys
        50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 40
<211> LENGTH: 98
<212> TYPE: PRT
<213> ORGANISM: Homo sapiens
<220> FEATURE:
<221> NAME/KEY: CCL19
<222> LOCATION: (1)..(98)

<400> SEQUENCE: 40

Met Ala Leu Leu Leu Ala Leu Ser Leu Leu Val Leu Trp Thr Ser Pro
 1               5                  10                  15

Ala Pro Thr Leu Ser Gly Thr Asn Asp Ala Glu Asp Cys Cys Leu Ser
                20                  25                  30

Val Thr Gln Lys Pro Ile Pro Gly Tyr Ile Val Arg Asn Phe His Tyr
            35                  40                  45

Leu Leu Ile Lys Asp Gly Cys Arg Val Pro Ala Val Val Phe Thr Thr
        50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 41
<211> LENGTH: 96
<212> TYPE: PRT
<213> ORGANISM: Homo sapiens
<220> FEATURE:
<221> NAME/KEY: CCL20-1
<222> LOCATION: (1)..(96)

<400> SEQUENCE: 41

Met Cys Cys Thr Lys Ser Leu Leu Leu Ala Ala Leu Met Ser Val Leu
 1               5                  10                  15

Leu Leu His Leu Cys Gly Glu Ser Glu Ala Ala Ser Asn Phe Asp Cys
```

```
                 20                  25                  30

Cys Leu Gly Tyr Thr Asp Arg Ile Leu His Pro Lys Phe Ile Val Gly
             35                  40                  45

Phe Thr Arg Gln Leu Ala Asn Glu Gly Cys Asp Ile Asn Ala Ile Ile
 50                  55                  60

Phe His Thr Lys Lys Lys Leu Ser Val Cys Ala Asn Pro Lys Gln Thr
 65                  70                  75                  80

Trp Val Lys Tyr Ile Val Arg Leu Leu Ser Lys Lys Val Lys Asn Met
                 85                  90                  95

<210> SEQ ID NO 42
<211> LENGTH: 95
<212> TYPE: PRT
<213> ORGANISM: Homo sapiens
<220> FEATURE:
<221> NAME/KEY: CCL20-2
<222> LOCATION: (1)..(95)

<400> SEQUENCE: 42

Met Cys Cys Thr Lys Ser Leu Leu Leu Ala Ala Leu Met Ser Val Leu
 1               5                  10                  15

Leu Leu His Leu Cys Gly Glu Ser Glu Ala Ser Asn Phe Asp Cys Cys
                 20                  25                  30

Leu Gly Tyr Thr Asp Arg Ile Leu His Pro Lys Phe Ile Val Gly Phe
             35                  40                  45

Thr Arg Gln Leu Ala Asn Glu Gly Cys Asp Ile Asn Ala Ile Ile Phe
 50                  55                  60

His Thr Lys Lys Lys Leu Ser Val Cys Ala Asn Pro Lys Gln Thr Trp
 65                  70                  75                  80

Val Lys Tyr Ile Val Arg Leu Leu Ser Lys Lys Val Lys Asn Met
                 85                  90                  95

<210> SEQ ID NO 43
<211> LENGTH: 93
<212> TYPE: PRT
<213> ORGANISM: Homo sapiens
<220> FEATURE:
<221> NAME/KEY: CCL22
<222> LOCATION: (1)..(93)

<400> SEQUENCE: 43

Met Asp Arg Leu Gln Thr Ala Leu Leu Val Val Leu Val Leu Leu Ala
 1               5                  10                  15

Val Ala Leu Gln Ala Thr Glu Ala Gly Pro Tyr Gly Ala Asn Met Glu
                 20                  25                  30

Asp Ser Val Cys Cys Arg Asp Tyr Val Arg Tyr Arg Leu Pro Leu Arg
             35                  40                  45

Val Val Lys His Phe Tyr Trp Thr Ser Asp Ser Cys Pro Arg Pro Gly
 50                  55                  60

Val Val Leu Leu Thr Phe Arg Asp Lys Glu Ile Cys Ala Asp Pro Arg
 65                  70                  75                  80

Val Pro Trp Val Lys Met Ile Leu Asn Lys Leu Ser Gln
                 85                  90

<210> SEQ ID NO 44
<211> LENGTH: 120
<212> TYPE: PRT
<213> ORGANISM: Homo sapiens
<220> FEATURE:
<221> NAME/KEY: CCL23-CKbeta8
<222> LOCATION: (1)..(120)
```

```
<400> SEQUENCE: 44

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
            115                 120

<210> SEQ ID NO 45
<211> LENGTH: 137
<212> TYPE: PRT
<213> ORGANISM: Homo sapiens
<220> FEATURE:
<221> NAME/KEY: CCL23-CKbeta8-1
<222> LOCATION: (1)..(137)

<400> SEQUENCE: 45

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Met Leu Trp
        35                  40                  45

Arg Arg Lys Ile Gly Pro Gln Met Thr Leu Ser His Ala Ala Gly Phe
    50                  55                  60

His Ala Thr Ser Ala Asp Cys Cys Ile Ser Tyr Thr Pro Arg Ser Ile
65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Val Arg Met Leu Lys Leu
        115                 120                 125

Asp Thr Arg Ile Lys Thr Arg Lys Asn
    130                 135

<210> SEQ ID NO 46
<211> LENGTH: 119
<212> TYPE: PRT
<213> ORGANISM: Homo sapiens
<220> FEATURE:
<221> NAME/KEY: CCL24
<222> LOCATION: (1)..(119)

<400> SEQUENCE: 46

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
```

```
                    20                  25                  30
Cys Cys Met Phe Phe Val Ser Lys Arg Ile Pro Glu Asn Arg Val Val
                35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
            115

<210> SEQ ID NO 47
<211> LENGTH: 150
<212> TYPE: PRT
<213> ORGANISM: Homo sapiens
<220> FEATURE:
<221> NAME/KEY: CCL25-1
<222> LOCATION: (1)..(150)

<400> SEQUENCE: 47

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
                20                  25                  30

Ala Tyr His Tyr Pro Ile Gly Trp Ala Val Leu Arg Arg Ala Trp Thr
            35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
            115                 120                 125

Phe Ser Asn Pro Ile Ser Ser Ser Lys Arg Asn Val Ser Leu Leu Ile
        130                 135                 140

Ser Ala Asn Ser Gly Leu
145                 150

<210> SEQ ID NO 48
<211> LENGTH: 149
<212> TYPE: PRT
<213> ORGANISM: Homo sapiens
<220> FEATURE:
<221> NAME/KEY: CCL25-2
<222> LOCATION: (1)..(149)

<400> SEQUENCE: 48

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
                20                  25                  30

Ala Tyr His Tyr Pro Ile Gly Trp Ala Val Leu Arg Arg Ala Trp Thr
            35                  40                  45
```

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
 65              70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Gly Pro His Ala
               100                 105                 110

Val Lys Lys Leu Ser Ser Gly Asn Ser Lys Leu Ser Ser Ser Lys Phe
            115                 120                 125

Ser Asn Pro Ile Ser Ser Ser Lys Arg Asn Val Ser Leu Leu Ile Ser
130                 135                 140

Ala Asn Ser Gly Leu
145

<210> SEQ ID NO 49
<211> LENGTH: 84
<212> TYPE: PRT
<213> ORGANISM: Homo sapiens
<220> FEATURE:
<221> NAME/KEY: CCL25-CRA_a
<222> LOCATION: (1)..(84)

<400> SEQUENCE: 49

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
                20                  25                  30

Ala Tyr His Tyr Pro Ile Gly Trp Ala Val Leu Arg Arg Ala Trp Thr
            35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
 65              70                  75                  80

Ile Ile Gln Val

<210> SEQ ID NO 50
<211> LENGTH: 94
<212> TYPE: PRT
<213> ORGANISM: Homo sapiens
<220> FEATURE:
<221> NAME/KEY: CCL26
<222> LOCATION: (1)..(94)

<400> SEQUENCE: 50

Met Met Gly Leu Ser Leu Ala Ser Ala Val Leu Leu Ala Ser Leu Leu
 1               5                  10                  15

Ser Leu His Leu Gly Thr Ala Thr Arg Gly Ser Asp Ile Ser Lys Thr
                20                  25                  30

Cys Cys Phe Gln Tyr Ser His Lys Pro Leu Pro Trp Thr Trp Val Arg
            35                  40                  45

Ser Tyr Glu Phe Thr Ser Asn Ser Cys Ser Gln Arg Ala Val Ile Phe
    50                  55                  60

Thr Thr Lys Arg Gly Lys Lys Val Cys Thr His Pro Arg Lys Lys Trp
 65              70                  75                  80

Val Gln Lys Tyr Ile Ser Leu Leu Lys Thr Pro Lys Gln Leu
                85                  90

```
<210> SEQ ID NO 51
<211> LENGTH: 112
<212> TYPE: PRT
<213> ORGANISM: Homo sapiens
<220> FEATURE:
<221> NAME/KEY: CCL27
<222> LOCATION: (1)..(112)

<400> SEQUENCE: 51

Met Lys Gly Pro Pro Thr Phe Cys Ser Leu Leu Leu Leu Ser Leu Leu
1               5                   10                  15

Leu Ser Pro Asp Pro Thr Ala Ala Phe Leu Leu Pro Pro Ser Thr Ala
                20                  25                  30

Cys Cys Thr Gln Leu Tyr Arg Lys Pro Leu Ser Asp Lys Leu Leu Arg
            35                  40                  45

Lys Val Ile Gln Val Glu Leu Gln Glu Ala Asp Gly Asp Cys His Leu
50                  55                  60

Gln Ala Phe Val Leu His Leu Ala Gln Arg Ser Ile Cys Ile His Pro
65                  70                  75                  80

Gln Asn Pro Ser Leu Ser Gln Trp Phe Glu His Gln Glu Arg Lys Leu
                85                  90                  95

His Gly Thr Leu Pro Lys Leu Asn Phe Gly Met Leu Arg Lys Met Gly
            100                 105                 110

<210> SEQ ID NO 52
<211> LENGTH: 374
<212> TYPE: PRT
<213> ORGANISM: Homo sapiens
<220> FEATURE:
<221> NAME/KEY: CCR2-A
<222> LOCATION: (1)..(374)

<400> SEQUENCE: 52

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
            195                 200                 205
```

```
Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                    245                 250                 255

Thr Pro Tyr Asn Ile Val Ile Leu Leu Asn Thr Phe Gln Glu Phe Phe
                260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
        290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                    325                 330                 335

Val Arg Pro Gly Lys Asn Val Lys Val Thr Thr Gln Gly Leu Leu Asp
                340                 345                 350

Gly Arg Gly Lys Gly Lys Ser Ile Gly Arg Ala Pro Glu Ala Ser Leu
            355                 360                 365

Gln Asp Lys Glu Gly Ala
        370

<210> SEQ ID NO 53
<211> LENGTH: 360
<212> TYPE: PRT
<213> ORGANISM: Homo sapiens
<220> FEATURE:
<221> NAME/KEY: CCR2-B
<222> LOCATION: (1)..(360)

<400> SEQUENCE: 53

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190
```

```
Tyr Phe Pro Arg Gly Trp Asn Asn Phe His Thr Ile Met Arg Asn Ile
            195                 200                 205

Leu Gly Leu Val Leu Pro Leu Leu Ile Met Val Ile Cys Tyr Ser Gly
        210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
        290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360

<210> SEQ ID NO 54
<211> LENGTH: 355
<212> TYPE: PRT
<213> ORGANISM: Homo sapiens
<220> FEATURE:
<221> NAME/KEY: CCR3-1
<222> LOCATION: (1)..(355)

<400> SEQUENCE: 54

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190
```

```
Tyr Ser Trp Arg His Phe His Thr Leu Arg Met Thr Ile Phe Cys Leu
        195                 200                 205
Val Leu Pro Leu Leu Val Met Ala Ile Cys Tyr Thr Gly Ile Ile Lys
        210                 215                 220
Thr Leu Leu Arg Cys Pro Ser Lys Lys Lys Tyr Lys Ala Ile Arg Leu
225                 230                 235                 240
Ile Phe Val Ile Met Ala Val Phe Phe Ile Phe Trp Thr Pro Tyr Asn
                245                 250                 255
Val Ala Ile Leu Leu Ser Ser Tyr Gln Ser Ile Leu Phe Gly Asn Asp
                260                 265                 270
Cys Glu Arg Ser Lys His Leu Asp Leu Val Met Leu Val Thr Glu Val
        275                 280                 285
Ile Ala Tyr Ser His Cys Cys Met Asn Pro Val Ile Tyr Ala Phe Val
        290                 295                 300
Gly Glu Arg Phe Arg Lys Tyr Leu Arg His Phe Phe His Arg His Leu
305                 310                 315                 320
Leu Met His Leu Gly Arg Tyr Ile Pro Phe Leu Pro Ser Glu Lys Leu
                325                 330                 335
Glu Arg Thr Ser Ser Val Ser Pro Ser Thr Ala Glu Pro Glu Leu Ser
                340                 345                 350
Ile Val Phe
        355

<210> SEQ ID NO 55
<211> LENGTH: 376
<212> TYPE: PRT
<213> ORGANISM: Homo sapiens
<220> FEATURE:
<221> NAME/KEY: CCR3-2
<222> LOCATION: (1)..(376)

<400> SEQUENCE: 55

Met Pro Phe Gly Ile Arg Met Leu Leu Arg Ala His Lys Pro Gly Ser
1               5                   10                  15
Ser Arg Arg Ser Glu Met Thr Thr Ser Leu Asp Thr Val Glu Thr Phe
                20                  25                  30
Gly Thr Thr Ser Tyr Tyr Asp Asp Val Gly Leu Leu Cys Glu Lys Ala
            35                  40                  45
Asp Thr Arg Ala Leu Met Ala Gln Phe Val Pro Pro Leu Tyr Ser Leu
        50                  55                  60
Val Phe Thr Val Gly Leu Leu Gly Asn Val Val Val Val Met Ile Leu
65                  70                  75                  80
Ile Lys Tyr Arg Arg Leu Arg Ile Met Thr Asn Ile Tyr Leu Leu Asn
                85                  90                  95
Leu Ala Ile Ser Asp Leu Leu Phe Leu Val Thr Leu Pro Phe Trp Ile
                100                 105                 110
His Tyr Val Arg Gly His Asn Trp Val Phe Gly His Gly Met Cys Lys
        115                 120                 125
Leu Leu Ser Gly Phe Tyr His Thr Gly Leu Tyr Ser Glu Ile Phe Phe
    130                 135                 140
Ile Ile Leu Leu Thr Ile Asp Arg Tyr Leu Ala Ile Val His Ala Val
145                 150                 155                 160
Phe Ala Leu Arg Ala Arg Thr Val Thr Phe Gly Val Ile Thr Ser Ile
                165                 170                 175
Val Thr Trp Gly Leu Ala Val Leu Ala Ala Leu Pro Glu Phe Ile Phe
                180                 185                 190
```

-continued

Tyr Glu Thr Glu Glu Leu Phe Glu Thr Leu Cys Ser Ala Leu Tyr
         195                 200                 205

Pro Glu Asp Thr Val Tyr Ser Trp Arg His Phe His Thr Leu Arg Met
210                 215                 220

Thr Ile Phe Cys Leu Val Leu Pro Leu Leu Val Met Ala Ile Cys Tyr
225                 230                 235                 240

Thr Gly Ile Ile Lys Thr Leu Leu Arg Cys Pro Ser Lys Lys Lys Tyr
                245                 250                 255

Lys Ala Ile Arg Leu Ile Phe Val Ile Met Ala Val Phe Phe Ile Phe
                260                 265                 270

Trp Thr Pro Tyr Asn Val Ala Ile Leu Leu Ser Ser Tyr Gln Ser Ile
        275                 280                 285

Leu Phe Gly Asn Asp Cys Glu Arg Ser Lys His Leu Asp Leu Val Met
    290                 295                 300

Leu Val Thr Glu Val Ile Ala Tyr Ser His Cys Cys Met Asn Pro Val
305                 310                 315                 320

Ile Tyr Ala Phe Val Gly Glu Arg Phe Arg Lys Tyr Leu Arg His Phe
                325                 330                 335

Phe His Arg His Leu Leu Met His Leu Gly Arg Tyr Ile Pro Phe Leu
                340                 345                 350

Pro Ser Glu Lys Leu Glu Arg Thr Ser Ser Val Ser Pro Ser Thr Ala
        355                 360                 365

Glu Pro Glu Leu Ser Ile Val Phe
    370                 375

<210> SEQ ID NO 56
<211> LENGTH: 373
<212> TYPE: PRT
<213> ORGANISM: Homo sapiens
<220> FEATURE:
<221> NAME/KEY: CCR3-3
<222> LOCATION: (1)..(373)

<400> SEQUENCE: 56

Met Pro Phe Gly Ile Arg Met Leu Leu Arg Ala His Lys Pro Gly Arg
1               5                   10                  15

Ser Glu Met Thr Thr Ser Leu Asp Thr Val Glu Thr Phe Gly Thr Thr
                20                  25                  30

Ser Tyr Tyr Asp Asp Val Gly Leu Leu Cys Glu Lys Ala Asp Thr Arg
            35                  40                  45

Ala Leu Met Ala Gln Phe Val Pro Pro Leu Tyr Ser Leu Val Phe Thr
50                  55                  60

Val Gly Leu Leu Gly Asn Val Val Val Met Ile Leu Ile Lys Tyr
65                  70                  75                  80

Arg Arg Leu Arg Ile Met Thr Asn Ile Tyr Leu Leu Asn Leu Ala Ile
                85                  90                  95

Ser Asp Leu Leu Phe Leu Val Thr Leu Pro Phe Trp Ile His Tyr Val
            100                 105                 110

Arg Gly His Asn Trp Val Phe Gly His Gly Met Cys Lys Leu Leu Ser
        115                 120                 125

Gly Phe Tyr His Thr Gly Leu Tyr Ser Glu Ile Phe Phe Ile Ile Leu
    130                 135                 140

Leu Thr Ile Asp Arg Tyr Leu Ala Ile Val His Ala Val Phe Ala Leu
145                 150                 155                 160

Arg Ala Arg Thr Val Thr Phe Gly Val Ile Thr Ser Ile Val Thr Trp
                165                 170                 175

-continued

```
Gly Leu Ala Val Leu Ala Ala Leu Pro Glu Phe Ile Phe Tyr Glu Thr
                180                 185                 190

Glu Glu Leu Phe Glu Glu Thr Leu Cys Ser Ala Leu Tyr Pro Glu Asp
            195                 200                 205

Thr Val Tyr Ser Trp Arg His Phe His Thr Leu Arg Met Thr Ile Phe
210                 215                 220

Cys Leu Val Leu Pro Leu Leu Val Met Ala Ile Cys Tyr Thr Gly Ile
225                 230                 235                 240

Ile Lys Thr Leu Leu Arg Cys Pro Ser Lys Lys Lys Tyr Lys Ala Ile
                245                 250                 255

Arg Leu Ile Phe Val Ile Met Ala Val Phe Phe Ile Phe Trp Thr Pro
            260                 265                 270

Tyr Asn Val Ala Ile Leu Leu Ser Ser Tyr Gln Ser Ile Leu Phe Gly
        275                 280                 285

Asn Asp Cys Glu Arg Ser Lys His Leu Asp Leu Val Met Leu Val Thr
290                 295                 300

Glu Val Ile Ala Tyr Ser His Cys Cys Met Asn Pro Val Ile Tyr Ala
305                 310                 315                 320

Phe Val Gly Glu Arg Phe Arg Lys Tyr Leu Arg His Phe Phe His Arg
                325                 330                 335

His Leu Leu Met His Leu Gly Arg Tyr Ile Pro Phe Leu Pro Ser Glu
            340                 345                 350

Lys Leu Glu Arg Thr Ser Ser Val Ser Pro Ser Thr Ala Glu Pro Glu
        355                 360                 365

Leu Ser Ile Val Phe
    370

<210> SEQ ID NO 57
<211> LENGTH: 360
<212> TYPE: PRT
<213> ORGANISM: Homo sapiens
<220> FEATURE:
<221> NAME/KEY: CCR4
<222> LOCATION: (1)..(360)

<400> SEQUENCE: 57

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
        50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
130                 135                 140

Ser Leu Arg Ala Arg Thr Leu Thr Tyr Gly Val Ile Thr Ser Leu Ala
145                 150                 155                 160
```

```
Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360

<210> SEQ ID NO 58
<211> LENGTH: 352
<212> TYPE: PRT
<213> ORGANISM: Homo sapiens
<220> FEATURE:
<221> NAME/KEY: CCR5
<222> LOCATION: (1)..(352)

<400> SEQUENCE: 58

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160
```

```
Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
            245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
            290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 59
<211> LENGTH: 374
<212> TYPE: PRT
<213> ORGANISM: Homo sapiens
<220> FEATURE:
<221> NAME/KEY: CCR6
<222> LOCATION: (1)..(374)

<400> SEQUENCE: 59

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175
```

Ile Ile Ser Ser Ser Thr Phe Val Phe Asn Gln Lys Tyr Asn Thr Gln
                180                 185                 190

Gly Ser Asp Val Cys Glu Pro Lys Tyr Gln Thr Val Ser Glu Pro Ile
            195                 200                 205

Arg Trp Lys Leu Leu Met Leu Gly Leu Glu Leu Phe Gly Phe
210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
                260                 265                 270

Val Leu Leu Val Thr Ala Ala Asn Leu Gly Lys Met Asn Arg Ser Cys
            275                 280                 285

Gln Ser Glu Lys Leu Ile Gly Tyr Thr Lys Thr Val Thr Glu Val Leu
        290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
            355                 360                 365

Ala Ser Ser Phe Thr Met
            370

<210> SEQ ID NO 60
<211> LENGTH: 355
<212> TYPE: PRT
<213> ORGANISM: Homo sapiens
<220> FEATURE:
<221> NAME/KEY: CCR8
<222> LOCATION: (1)..(355)

<400> SEQUENCE: 60

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys Leu Leu Leu Ala Val Phe Tyr Cys Leu Leu Phe Val Phe
            35                  40                  45

Ser Leu Leu Gly Asn Ser Leu Val Ile Leu Val Leu Val Val Cys Lys
        50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
        115                 120                 125

Val Asp Arg Tyr Leu Ala Val Val His Ala Val Tyr Ala Leu Lys Val
    130                 135                 140

Arg Thr Ile Arg Met Gly Thr Thr Leu Cys Leu Ala Val Trp Leu Thr
145                 150                 155                 160

```
Ala Ile Met Ala Thr Ile Pro Leu Leu Val Phe Tyr Gln Val Ala Ser
                165                 170                 175
Glu Asp Gly Val Leu Gln Cys Tyr Ser Phe Tyr Asn Gln Gln Thr Leu
            180                 185                 190
Lys Trp Lys Ile Phe Thr Asn Phe Lys Met Asn Ile Leu Gly Leu Leu
        195                 200                 205
Ile Pro Phe Thr Ile Phe Met Phe Cys Tyr Ile Lys Ile Leu His Gln
210                 215                 220
Leu Lys Arg Cys Gln Asn His Asn Lys Thr Lys Ala Ile Arg Leu Val
225                 230                 235                 240
Leu Ile Val Val Ile Ala Ser Leu Leu Phe Trp Val Pro Phe Asn Val
                245                 250                 255
Val Leu Phe Leu Thr Ser Leu His Ser Met His Ile Leu Asp Gly Cys
            260                 265                 270
Ser Ile Ser Gln Gln Leu Thr Tyr Ala Thr His Val Thr Glu Ile Ile
        275                 280                 285
Ser Phe Thr His Cys Cys Val Asn Pro Val Ile Tyr Ala Phe Val Gly
290                 295                 300
Glu Lys Phe Lys Lys His Leu Ser Glu Ile Phe Gln Lys Ser Cys Ser
305                 310                 315                 320
Gln Ile Phe Asn Tyr Leu Gly Arg Gln Met Pro Arg Glu Ser Cys Glu
                325                 330                 335
Lys Ser Ser Ser Cys Gln Gln His Ser Ser Arg Ser Ser Ser Val Asp
            340                 345                 350
Tyr Ile Leu
        355

<210> SEQ ID NO 61
<211> LENGTH: 369
<212> TYPE: PRT
<213> ORGANISM: Homo sapiens
<220> FEATURE:
<221> NAME/KEY: CCR9A
<222> LOCATION: (1)..(369)

<400> SEQUENCE: 61

Met Thr Pro Thr Asp Phe Thr Ser Pro Ile Pro Asn Met Ala Asp Asp
1               5                   10                  15
Tyr Gly Ser Glu Ser Thr Ser Ser Met Glu Asp Tyr Val Asn Phe Asn
            20                  25                  30
Phe Thr Asp Phe Tyr Cys Glu Lys Asn Asn Val Arg Gln Phe Ala Ser
        35                  40                  45
His Phe Leu Pro Pro Leu Tyr Trp Leu Val Phe Ile Val Gly Ala Leu
    50                  55                  60
Gly Asn Ser Leu Val Ile Leu Val Tyr Trp Tyr Cys Thr Arg Val Lys
65                  70                  75                  80
Thr Met Thr Asp Met Phe Leu Leu Asn Leu Ala Ile Ala Asp Leu Leu
                85                  90                  95
Phe Leu Val Thr Leu Pro Phe Trp Ala Ile Ala Ala Asp Gln Trp
            100                 105                 110
Lys Phe Gln Thr Phe Met Cys Lys Val Val Asn Ser Met Tyr Lys Met
        115                 120                 125
Asn Phe Tyr Ser Cys Val Leu Leu Ile Met Cys Ile Ser Val Asp Arg
    130                 135                 140
Tyr Ile Ala Ile Ala Gln Ala Met Arg Ala His Thr Trp Arg Glu Lys
145                 150                 155                 160
```

```
Arg Leu Leu Tyr Ser Lys Met Val Cys Phe Thr Ile Trp Val Leu Ala
                165                 170                 175

Ala Ala Leu Cys Ile Pro Glu Ile Leu Tyr Ser Gln Ile Lys Glu Glu
                180                 185                 190

Ser Gly Ile Ala Ile Cys Thr Met Val Tyr Pro Ser Asp Glu Ser Thr
                195                 200                 205

Lys Leu Lys Ser Ala Val Leu Thr Leu Lys Val Ile Leu Gly Phe Phe
                210                 215                 220

Leu Pro Phe Val Val Met Ala Cys Cys Tyr Thr Ile Ile His Thr
225                 230                 235                 240

Leu Ile Gln Ala Lys Lys Ser Lys His Lys Ala Leu Lys Val Thr
                245                 250                 255

Ile Thr Val Leu Thr Val Phe Val Leu Ser Gln Phe Pro Tyr Asn Cys
                260                 265                 270

Ile Leu Leu Val Gln Thr Ile Asp Ala Tyr Ala Met Phe Ile Ser Asn
                275                 280                 285

Cys Ala Val Ser Thr Asn Ile Asp Ile Cys Phe Gln Val Thr Gln Thr
                290                 295                 300

Ile Ala Phe Phe His Ser Cys Leu Asn Pro Val Leu Tyr Val Phe Val
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
                340                 345                 350

Leu Lys Leu Ser Ser Met Leu Leu Glu Thr Thr Ser Gly Ala Leu Ser
                355                 360                 365

Leu

<210> SEQ ID NO 62
<211> LENGTH: 357
<212> TYPE: PRT
<213> ORGANISM: Homo sapiens
<220> FEATURE:
<221> NAME/KEY: CCR9B
<222> LOCATION: (1)..(357)

<400> SEQUENCE: 62

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
                20                  25                  30

Gln Phe Ala Ser His Phe Leu Pro Pro Leu Tyr Trp Leu Val Phe Ile
                35                  40                  45

Val Gly Ala Leu Gly Asn Ser Leu Val Ile Leu Val Tyr Trp Tyr Cys
            50                  55                  60

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
                85                  90                  95

Ala Asp Gln Trp Lys Phe Gln Thr Phe Met Cys Lys Val Val Asn Ser
                100                 105                 110

Met Tyr Lys Met Asn Phe Tyr Ser Cys Val Leu Leu Ile Met Cys Ile
                115                 120                 125

Ser Val Asp Arg Tyr Ile Ala Ile Ala Gln Ala Met Arg Ala His Thr
                130                 135                 140
```

```
Trp Arg Glu Lys Arg Leu Leu Tyr Ser Lys Met Val Cys Phe Thr Ile
145                 150                 155                 160

Trp Val Leu Ala Ala Ala Leu Cys Ile Pro Glu Ile Leu Tyr Ser Gln
                165                 170                 175

Ile Lys Glu Glu Ser Gly Ile Ala Ile Cys Thr Met Val Tyr Pro Ser
            180                 185                 190

Asp Glu Ser Thr Lys Leu Lys Ser Ala Val Leu Thr Leu Lys Val Ile
        195                 200                 205

Leu Gly Phe Phe Leu Pro Phe Val Met Ala Cys Cys Tyr Thr Ile
210                 215                 220

Ile Ile His Thr Leu Ile Gln Ala Lys Lys Ser Ser Lys His Lys Ala
225                 230                 235                 240

Leu Lys Val Thr Ile Thr Val Leu Thr Val Phe Val Leu Ser Gln Phe
                245                 250                 255

Pro Tyr Asn Cys Ile Leu Leu Val Gln Thr Ile Asp Ala Tyr Ala Met
            260                 265                 270

Phe Ile Ser Asn Cys Ala Val Ser Thr Asn Ile Asp Ile Cys Phe Gln
        275                 280                 285

Val Thr Gln Thr Ile Ala Phe Phe His Ser Cys Leu Asn Pro Val Leu
290                 295                 300

Tyr Val Phe Val Gly Glu Arg Phe Arg Arg Asp Leu Val Lys Thr Leu
305                 310                 315                 320

Lys Asn Leu Gly Cys Ile Ser Gln Ala Gln Trp Val Ser Phe Thr Arg
            325                 330                 335

Arg Glu Gly Ser Leu Lys Leu Ser Ser Met Leu Leu Glu Thr Thr Ser
        340                 345                 350

Gly Ala Leu Ser Leu
        355

<210> SEQ ID NO 63
<211> LENGTH: 362
<212> TYPE: PRT
<213> ORGANISM: Homo sapiens
<220> FEATURE:
<221> NAME/KEY: CCR10
<222> LOCATION: (1)..(362)

<400> SEQUENCE: 63

Met Gly Thr Glu Ala Thr Glu Gln Val Ser Trp Gly His Tyr Ser Gly
1               5                   10                  15

Asp Glu Glu Asp Ala Tyr Ser Ala Glu Pro Leu Pro Glu Leu Cys Tyr
            20                  25                  30

Lys Ala Asp Val Gln Ala Phe Ser Arg Ala Phe Gln Pro Ser Val Ser
        35                  40                  45

Leu Thr Val Ala Ala Leu Gly Leu Ala Gly Asn Gly Leu Val Leu Ala
50                  55                  60

Thr His Leu Ala Ala Arg Arg Ala Ala Arg Ser Pro Thr Ser Ala His
65                  70                  75                  80

Leu Leu Gln Leu Ala Leu Ala Asp Leu Leu Leu Ala Leu Thr Leu Pro
                85                  90                  95

Phe Ala Ala Ala Gly Ala Leu Gln Gly Trp Ser Leu Gly Ser Ala Thr
            100                 105                 110

Cys Arg Thr Ile Ser Gly Leu Tyr Ser Ala Ser Phe His Ala Gly Phe
        115                 120                 125

Leu Phe Leu Ala Cys Ile Ser Ala Asp Arg Tyr Val Ala Ile Ala Arg
130                 135                 140
```

```
Ala Leu Pro Ala Gly Pro Arg Pro Ser Thr Pro Gly Arg Ala His Leu
145                 150                 155                 160

Val Ser Val Ile Val Trp Leu Leu Ser Leu Leu Ala Leu Pro Ala
                165                 170                 175

Leu Leu Phe Ser Gln Asp Gly Gln Arg Glu Gly Gln Arg Cys Arg
        180                 185                 190

Leu Ile Phe Pro Glu Gly Leu Thr Gln Thr Val Lys Gly Ala Ser Ala
        195                 200                 205

Val Ala Gln Val Ala Leu Gly Phe Ala Leu Pro Leu Gly Val Met Val
        210                 215                 220

Ala Cys Tyr Ala Leu Leu Gly Arg Thr Leu Leu Ala Arg Gly Pro
225                 230                 235                 240

Glu Arg Arg Arg Ala Leu Arg Val Val Ala Leu Val Ala Ala Phe
                245                 250                 255

Val Val Leu Gln Leu Pro Tyr Ser Leu Ala Leu Leu Leu Asp Thr Ala
        260                 265                 270

Asp Leu Leu Ala Ala Arg Glu Arg Ser Cys Pro Ala Ser Lys Arg Lys
        275                 280                 285

Asp Val Ala Leu Leu Val Thr Ser Gly Leu Ala Leu Ala Arg Cys Gly
        290                 295                 300

Leu Asn Pro Val Leu Tyr Ala Phe Leu Gly Leu Arg Phe Arg Gln Asp
305                 310                 315                 320

Leu Arg Arg Leu Leu Arg Gly Gly Ser Cys Pro Ser Gly Pro Gln Pro
                325                 330                 335

Arg Arg Gly Cys Pro Arg Arg Pro Arg Leu Ser Ser Cys Ser Ala Pro
                340                 345                 350

Thr Glu Thr His Ser Leu Ser Trp Asp Asn
                355                 360

<210> SEQ ID NO 64
<211> LENGTH: 350
<212> TYPE: PRT
<213> ORGANISM: Homo sapiens
<220> FEATURE:
<221> NAME/KEY: CCR11
<222> LOCATION: (1)..(350)

<400> SEQUENCE: 64

Met Ala Leu Glu Gln Asn Gln Ser Thr Asp Tyr Tyr Tyr Glu Glu Asn
1               5                   10                  15

Glu Met Asn Gly Thr Tyr Asp Tyr Ser Gln Tyr Glu Leu Ile Cys Ile
                20                  25                  30

Lys Glu Asp Val Arg Glu Phe Ala Lys Val Phe Leu Pro Val Phe Leu
            35                  40                  45

Thr Ile Val Phe Val Ile Gly Leu Ala Gly Asn Ser Met Val Val Ala
    50                  55                  60

Ile Tyr Ala Tyr Tyr Lys Lys Gln Arg Thr Lys Thr Asp Val Tyr Ile
65                  70                  75                  80

Leu Asn Leu Ala Val Ala Asp Leu Leu Leu Phe Thr Leu Pro Phe
                85                  90                  95

Trp Ala Val Asn Ala Val His Gly Trp Val Leu Gly Lys Ile Met Cys
                100                 105                 110

Lys Ile Thr Ser Ala Leu Tyr Thr Leu Asn Phe Val Ser Gly Met Gln
            115                 120                 125

Phe Leu Ala Cys Ile Ser Ile Asp Arg Tyr Val Ala Val Thr Lys Val
    130                 135                 140
```

-continued

```
Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
        195                 200                 205

Phe Val Val Pro Phe Leu Ile Met Gly Val Cys Tyr Phe Ile Thr Ala
    210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270

Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
    290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Phe Pro Phe
                325                 330                 335

Asp Ser Glu Gly Pro Thr Glu Pro Thr Ser Thr Phe Ser Ile
            340                 345                 350

<210> SEQ ID NO 65
<211> LENGTH: 344
<212> TYPE: PRT
<213> ORGANISM: Homo sapiens
<220> FEATURE:
<221> NAME/KEY: CCRL2-1
<222> LOCATION: (1)..(344)

<400> SEQUENCE: 65

Met Ala Asn Tyr Thr Leu Ala Pro Glu Asp Glu Tyr Asp Val Leu Ile
1               5                   10                  15

Glu Gly Glu Leu Glu Ser Asp Glu Ala Glu Gln Cys Asp Lys Tyr Asp
                20                  25                  30

Ala Gln Ala Leu Ser Ala Gln Leu Val Pro Ser Leu Cys Ser Ala Val
            35                  40                  45

Phe Val Ile Gly Val Leu Asp Asn Leu Leu Val Val Leu Ile Leu Val
        50                  55                  60

Lys Tyr Lys Gly Leu Lys Arg Val Glu Asn Ile Tyr Leu Leu Asn Leu
65                  70                  75                  80

Ala Val Ser Asn Leu Cys Phe Leu Leu Thr Leu Pro Phe Trp Ala His
                85                  90                  95

Ala Gly Gly Asp Pro Met Cys Lys Ile Leu Ile Gly Leu Tyr Phe Val
            100                 105                 110

Gly Leu Tyr Ser Glu Thr Phe Phe Asn Cys Leu Leu Thr Val Gln Arg
        115                 120                 125

Tyr Leu Val Phe Leu His Lys Gly Asn Phe Phe Ser Ala Arg Arg Arg
    130                 135                 140

Val Pro Cys Gly Ile Ile Thr Ser Val Leu Ala Trp Val Thr Ala Ile
145                 150                 155                 160
```

-continued

```
Leu Ala Thr Leu Pro Glu Phe Val Tyr Lys Pro Gln Met Glu Asp
            165                 170                 175

Gln Lys Tyr Lys Cys Ala Phe Ser Arg Thr Pro Phe Leu Pro Ala Asp
            180                 185                 190

Glu Thr Phe Trp Lys His Phe Leu Thr Leu Lys Met Asn Ile Ser Val
            195                 200                 205

Leu Val Leu Pro Leu Phe Ile Phe Thr Phe Leu Tyr Val Gln Met Arg
            210                 215                 220

Lys Thr Leu Arg Phe Arg Glu Gln Arg Tyr Ser Leu Phe Lys Leu Val
225                 230                 235                 240

Phe Ala Ile Met Val Val Phe Leu Leu Met Trp Ala Pro Tyr Asn Ile
            245                 250                 255

Ala Phe Phe Leu Ser Thr Phe Lys Glu His Phe Ser Leu Ser Asp Cys
            260                 265                 270

Lys Ser Ser Tyr Asn Leu Asp Lys Ser Val His Ile Thr Lys Leu Ile
            275                 280                 285

Ala Thr Thr His Cys Cys Ile Asn Pro Leu Leu Tyr Ala Phe Leu Asp
            290                 295                 300

Gly Thr Phe Ser Lys Tyr Leu Cys Arg Cys Phe His Leu Arg Ser Asn
305                 310                 315                 320

Thr Pro Leu Gln Pro Arg Gly Gln Ser Ala Gln Gly Thr Ser Arg Glu
            325                 330                 335

Glu Pro Asp His Ser Thr Glu Val
            340

<210> SEQ ID NO 66
<211> LENGTH: 356
<212> TYPE: PRT
<213> ORGANISM: Homo sapiens
<220> FEATURE:
<221> NAME/KEY: CCRL2-2
<222> LOCATION: (1)..(356)

<400> SEQUENCE: 66

Met Ile Tyr Thr Arg Phe Leu Lys Gly Ser Leu Lys Met Ala Asn Tyr
1               5                   10                  15

Thr Leu Ala Pro Glu Asp Glu Tyr Asp Val Leu Ile Glu Gly Glu Leu
            20                  25                  30

Glu Ser Asp Glu Ala Glu Gln Cys Asp Lys Tyr Asp Ala Gln Ala Leu
            35                  40                  45

Ser Ala Gln Leu Val Pro Ser Leu Cys Ser Ala Val Phe Val Ile Gly
            50                  55                  60

Val Leu Asp Asn Leu Leu Val Val Leu Ile Leu Val Lys Tyr Lys Gly
65                  70                  75                  80

Leu Lys Arg Val Glu Asn Ile Tyr Leu Leu Asn Leu Ala Val Ser Asn
            85                  90                  95

Leu Cys Phe Leu Leu Thr Leu Pro Phe Trp Ala His Ala Gly Gly Asp
            100                 105                 110

Pro Met Cys Lys Ile Leu Ile Gly Leu Tyr Phe Val Gly Leu Tyr Ser
            115                 120                 125

Glu Thr Phe Phe Asn Cys Leu Leu Thr Val Gln Arg Tyr Leu Val Phe
            130                 135                 140

Leu His Lys Gly Asn Phe Phe Ser Ala Arg Arg Arg Val Pro Cys Gly
145                 150                 155                 160

Ile Ile Thr Ser Val Leu Ala Trp Val Thr Ala Ile Leu Ala Thr Leu
            165                 170                 175
```

```
Pro Glu Phe Val Val Tyr Lys Pro Gln Met Glu Asp Gln Lys Tyr Lys
            180                 185                 190

Cys Ala Phe Ser Arg Thr Pro Phe Leu Pro Ala Asp Glu Thr Phe Trp
            195                 200                 205

Lys His Phe Leu Thr Leu Lys Met Asn Ile Ser Val Leu Val Leu Pro
210                 215                 220

Leu Phe Ile Phe Thr Phe Leu Tyr Val Gln Met Arg Lys Thr Leu Arg
225                 230                 235                 240

Phe Arg Glu Gln Arg Tyr Ser Leu Phe Lys Leu Val Phe Ala Ile Met
                245                 250                 255

Val Val Phe Leu Leu Met Trp Ala Pro Tyr Asn Ile Ala Phe Phe Leu
            260                 265                 270

Ser Thr Phe Lys Glu His Phe Ser Leu Ser Asp Cys Lys Ser Ser Tyr
            275                 280                 285

Asn Leu Asp Lys Ser Val His Ile Thr Lys Leu Ile Ala Thr Thr His
290                 295                 300

Cys Cys Ile Asn Pro Leu Leu Tyr Ala Phe Leu Asp Gly Thr Phe Ser
305                 310                 315                 320

Lys Tyr Leu Cys Arg Cys Phe His Leu Arg Ser Asn Thr Pro Leu Gln
                325                 330                 335

Pro Arg Gly Gln Ser Ala Gln Gly Thr Ser Arg Glu Glu Pro Asp His
            340                 345                 350

Ser Thr Glu Val
            355

<210> SEQ ID NO 67
<211> LENGTH: 114
<212> TYPE: PRT
<213> ORGANISM: Homo sapiens
<220> FEATURE:
<221> NAME/KEY: XCL1
<222> LOCATION: (1)..(114)

<400> SEQUENCE: 67

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 68
<211> LENGTH: 333
<212> TYPE: PRT
<213> ORGANISM: Homo sapiens
<220> FEATURE:
<221> NAME/KEY: XCR1
<222> LOCATION: (1)..(333)

<400> SEQUENCE: 68
```

Met Glu Ser Ser Gly Asn Pro Glu Ser Thr Thr Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
            35                  40                  45

Asn Ser Leu Val Leu Trp Val Leu Val Lys Tyr Glu Ser Leu Glu Ser
        50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
                100                 105                 110

Leu Tyr Ser Ser Ile Phe Phe Leu Thr Ile Met Thr Ile His Arg Tyr
            115                 120                 125

Leu Ser Val Val Ser Pro Leu Ser Thr Leu Arg Val Pro Thr Leu Arg
        130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
                180                 185                 190

Phe Phe Leu Leu Ser Leu Gly Ile Ile Leu Phe Cys Tyr Val Glu Ile
            195                 200                 205

Leu Arg Thr Leu Phe Arg Ser Arg Ser Lys Arg His Arg Thr Val
        210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
                260                 265                 270

Arg Asn Leu Ala Phe Ser His Cys Cys Phe Asn Pro Val Leu Tyr Val
            275                 280                 285

Phe Val Gly Val Lys Phe Arg Thr His Leu Lys His Val Leu Arg Gln
        290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330

<210> SEQ ID NO 69
<211> LENGTH: 387
<212> TYPE: PRT
<213> ORGANISM: Homo sapiens
<220> FEATURE:
<221> NAME/KEY: CX3CR1a
<222> LOCATION: (1)..(387)

<400> SEQUENCE: 69

Met Arg Glu Pro Leu Glu Ala Phe Lys Leu Ala Asp Leu Asp Phe Arg
1               5                   10                  15

Lys Ser Ser Leu Ala Ser Gly Trp Arg Met Ala Ser Gly Ala Phe Thr
            20                  25                  30

```
Met Asp Gln Phe Pro Glu Ser Val Thr Glu Asn Phe Glu Tyr Asp Asp
            35                  40                  45

Leu Ala Glu Ala Cys Tyr Ile Gly Asp Ile Val Val Phe Gly Thr Val
 50                  55                  60

Phe Leu Ser Ile Phe Tyr Ser Val Ile Phe Ala Ile Gly Leu Val Gly
 65                  70                  75                  80

Asn Leu Leu Val Val Phe Ala Leu Thr Asn Ser Lys Lys Pro Lys Ser
                 85                  90                  95

Val Thr Asp Ile Tyr Leu Leu Asn Leu Ala Leu Ser Asp Leu Leu Phe
                100                 105                 110

Val Ala Thr Leu Pro Phe Trp Thr His Tyr Leu Ile Asn Glu Lys Gly
            115                 120                 125

Leu His Asn Ala Met Cys Lys Phe Thr Thr Ala Phe Phe Phe Ile Gly
            130                 135                 140

Phe Phe Gly Ser Ile Phe Phe Ile Thr Val Ile Ser Ile Asp Arg Tyr
145                 150                 155                 160

Leu Ala Ile Val Leu Ala Ala Asn Ser Met Asn Asn Arg Thr Val Gln
                165                 170                 175

His Gly Val Thr Ile Ser Leu Gly Val Trp Ala Ala Ile Leu Val
                180                 185                 190

Ala Ala Pro Gln Phe Met Phe Thr Lys Gln Lys Glu Asn Glu Cys Leu
            195                 200                 205

Gly Asp Tyr Pro Glu Val Leu Gln Glu Ile Trp Pro Val Leu Arg Asn
            210                 215                 220

Val Glu Thr Asn Phe Leu Gly Phe Leu Leu Pro Leu Leu Ile Met Ser
225                 230                 235                 240

Tyr Cys Tyr Phe Arg Ile Ile Gln Thr Leu Phe Ser Cys Lys Asn His
                245                 250                 255

Lys Lys Ala Lys Ala Ile Lys Leu Ile Leu Leu Val Val Ile Val Phe
            260                 265                 270

Phe Leu Phe Trp Thr Pro Tyr Asn Val Met Ile Phe Leu Glu Thr Leu
            275                 280                 285

Lys Leu Tyr Asp Phe Phe Pro Ser Cys Asp Met Arg Lys Asp Leu Arg
            290                 295                 300

Leu Ala Leu Ser Val Thr Glu Thr Val Ala Phe Ser His Cys Cys Leu
305                 310                 315                 320

Asn Pro Leu Ile Tyr Ala Phe Ala Gly Glu Lys Phe Arg Arg Tyr Leu
                325                 330                 335

Tyr His Leu Tyr Gly Lys Cys Leu Ala Val Leu Cys Gly Arg Ser Val
                340                 345                 350

His Val Asp Phe Ser Ser Ser Glu Ser Gln Arg Ser Arg His Gly Ser
            355                 360                 365

Val Leu Ser Ser Asn Phe Thr Tyr His Thr Ser Asp Gly Asp Ala Leu
            370                 375                 380

Leu Leu Leu
385

<210> SEQ ID NO 70
<211> LENGTH: 355
<212> TYPE: PRT
<213> ORGANISM: Homo sapiens
<220> FEATURE:
<221> NAME/KEY: CX3CR1b
<222> LOCATION: (1)..(355)

<400> SEQUENCE: 70
```

```
Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Phe Gly Thr Val
            20                  25                  30

Phe Leu Ser Ile Phe Tyr Ser Val Ile Phe Ala Ile Gly Leu Val Gly
            35                  40                  45

Asn Leu Leu Val Val Phe Ala Leu Thr Asn Ser Lys Lys Pro Lys Ser
50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
            115                 120                 125

Leu Ala Ile Val Leu Ala Ala Asn Ser Met Asn Asn Arg Thr Val Gln
130                 135                 140

His Gly Val Thr Ile Ser Leu Gly Val Trp Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
            195                 200                 205

Tyr Cys Tyr Phe Arg Ile Ile Gln Thr Leu Phe Ser Cys Lys Asn His
210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
            275                 280                 285

Asn Pro Leu Ile Tyr Ala Phe Ala Gly Glu Lys Phe Arg Arg Tyr Leu
290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 71
<211> LENGTH: 397
<212> TYPE: PRT
<213> ORGANISM: Homo sapiens

<400> SEQUENCE: 71

Met Ala Pro Ile Ser Leu Ser Trp Leu Leu Arg Leu Ala Thr Phe Cys
1               5                   10                  15
```

His Leu Thr Val Leu Leu Ala Gly Gln His Gly Val Thr Lys Cys
        20                  25                  30
Asn Ile Thr Cys Ser Lys Met Thr Ser Lys Ile Pro Val Ala Leu Leu
        35                  40                  45
Ile His Tyr Gln Gln Asn Gln Ala Ser Cys Gly Lys Arg Ala Ile Ile
50                  55                  60
Leu Glu Thr Arg Gln His Arg Leu Phe Cys Ala Asp Pro Lys Glu Gln
65                  70                  75                  80
Trp Val Lys Asp Ala Met Gln His Leu Asp Arg Gln Ala Ala Leu
                85                  90                  95
Thr Arg Asn Gly Gly Thr Phe Glu Lys Gln Ile Gly Glu Val Lys Pro
                100                 105                 110
Arg Thr Thr Pro Ala Ala Gly Gly Met Asp Glu Ser Val Val Leu Glu
                115                 120                 125
Pro Glu Ala Thr Gly Glu Ser Ser Ser Leu Glu Pro Thr Pro Ser Ser
    130                 135                 140
Gln Glu Ala Gln Arg Ala Leu Gly Thr Ser Pro Glu Leu Pro Thr Gly
145                 150                 155                 160
Val Thr Gly Ser Ser Gly Thr Arg Leu Pro Pro Thr Pro Lys Ala Gln
                165                 170                 175
Asp Gly Gly Pro Val Gly Thr Glu Leu Phe Arg Val Pro Pro Val Ser
                180                 185                 190
Thr Ala Ala Thr Trp Gln Ser Ser Ala Pro His Gln Pro Gly Pro Ser
                195                 200                 205
Leu Trp Ala Glu Ala Lys Thr Ser Glu Ala Pro Ser Thr Gln Asp Pro
    210                 215                 220
Ser Thr Gln Ala Ser Thr Ala Ser Ser Pro Ala Pro Glu Glu Asn Ala
225                 230                 235                 240
Pro Ser Glu Gly Gln Arg Val Trp Gly Gln Gly Gln Ser Pro Arg Pro
                245                 250                 255
Glu Asn Ser Leu Glu Arg Glu Glu Met Gly Pro Val Pro Ala His Thr
                260                 265                 270
Asp Ala Phe Gln Asp Trp Gly Pro Gly Ser Met Ala His Val Ser Val
                275                 280                 285
Val Pro Val Ser Ser Glu Gly Thr Pro Ser Arg Glu Pro Val Ala Ser
    290                 295                 300
Gly Ser Trp Thr Pro Lys Ala Glu Glu Pro Ile His Ala Thr Met Asp
305                 310                 315                 320
Pro Gln Arg Leu Gly Val Leu Ile Thr Pro Val Pro Asp Ala Gln Ala
                325                 330                 335
Ala Thr Arg Arg Gln Ala Val Gly Leu Leu Ala Phe Leu Gly Leu Leu
                340                 345                 350
Phe Cys Leu Gly Val Ala Met Phe Thr Tyr Gln Ser Leu Gln Gly Cys
                355                 360                 365
Pro Arg Lys Met Ala Gly Glu Met Ala Glu Gly Leu Arg Tyr Ile Pro
    370                 375                 380
Arg Ser Cys Gly Ser Asn Ser Tyr Val Leu Val Pro Val
385                 390                 395

<210> SEQ ID NO 72
<211> LENGTH: 2545
<212> TYPE: DNA
<213> ORGANISM: Homo sapiens
<220> FEATURE:
<221> NAME/KEY: CXCL9

<222> LOCATION: (1)..(2545)

<400> SEQUENCE: 72

```
atccaataca ggagtgactt ggaactccat tctatcacta tgaagaaaag tggtgttctt    60
ttcctcttgg gcatcatctt gctggttctg attggagtgc aaggaacccc agtagtgaga   120
aagggtcgct gttcctgcat cagcaccaac caagggacta tccacctaca atccttgaaa   180
gaccttaaac aatttgcccc aagcccttcc tgcgagaaaa ttgaaatcat tgctacactg   240
aagaatggag ttcaaacatg tctaaaccca gattcagcag atgtgaagga actgattaaa   300
aagtgggaga acaggtcagc caaaagaaa agcaaaaga tgggaaaaa acatcaaaaa    360
aagaaagttc tgaaagttcg aaaatctcaa cgttctcgtc aaaagaagac tacataagag   420
accacttcac caataagtat tctgtgttaa aaatgttcta tttaattat accgctatca    480
ttccaaagga ggatggcata taatacaaag gcttattaat ttgactagaa aatttaaaac   540
attactctga aattgtaact aaagttagaa agttgatttt aagaatccaa acgttaagaa   600
ttgttaaagg ctatgattgt ctttgttctt ctaccaccca ccagttgaat ttcatcatgc   660
ttaaggccat gattttagca atacccatgt ctacacagat gttcacccaa ccacatccca   720
ctcacaacag ctgcctggaa gagcagccct aggcttccac gtactgcagc tccagagag    780
tatctgaggc acatgtcagc aagtcctaag cctgttagca tgctggtgag ccaagcagtt   840
tgaaattgag ctggacctca ccaagctgct gtggccatca acctctgtat ttgaatcagc   900
ctacaggcct cacacacaat gtgtctgaga gattcatgct gattgttatt gggtatcacc   960
actggagatc accagtgtgt ggctttcaga gcctcctttc tggctttgga agccatgtga  1020
ttccatcttg cccgctcagg ctgaccactt tatttctttt tgttccccctt tgcttcattc  1080
aagtcagctc ttctccatcc taccacaatg cagtgccttt cttctctcca gtgcacctgt  1140
catatgctct gatttatctg agtcaactcc tttctcatct tgtccccaac accccacaga  1200
agtgctttct tctcccaatt catcctcact cagtccagct tagttcaagt cctgcctctt  1260
aaataaacct ttttggacac acaaattatc ttaaaactcc tgtttcactt ggttcagtac  1320
cacatgggtg aacactcaat ggttaactaa ttcttgggtg tttatcctat ctctccaacc  1380
agattgtcag ctccttgagg gcaagagcca cagtatattt ccctgtttct tccacagtgc  1440
ctaataatac tgtggaacta ggttttaata atttttttaat tgatgttgtt atgggcagga  1500
tggcaaccag accattgtct cagagcaggt gctggctctt tcctggctac tccatgttgg  1560
ctagcctctg gtaacctctt acttattatc ttcaggacac tcactacagg gaccagggat  1620
gatgcaacat ccttgtcttt ttatgacagg atgtttgctc agcttctcca acaataagaa  1680
gcacgtggta aaacacttgc ggatattctg gactgttttt aaaaaatata cagtttaccg  1740
aaaatcatat aatcttacaa tgaaaaggac tttatagatc agccagtgac caaccttttc  1800
ccaaccatac aaaaattcct tttcccgaag gaaaagggac ttctcaataa gcctcagctt  1860
tctaagatct aacaagatag ccaccgagat cctttatcgaa actcatttta ggcaaatatg  1920
agttttattg tccgtttact tgtttcagag tttgtattgt gattatcaat taccacacca  1980
tctcccatga agaaagggaa cggtgaagta ctaagcgcta gaggaagcag ccaagtcggt  2040
tagtggaagc atgattggtg cccagttagc ctctgcagga tgtggaaacc tccttccagg  2100
ggaggttcag tgaattgtgt aggagaggtt gtctgtggcc agaatttaaa cctatactca  2160
cttttcccaaa ttgaatcact gctcacactg ctgatgattt agagtgctgt ccggtggaga  2220
tcccacccga acgtcttatc taatcatgaa actccctagt tccttcatgt aacttccctg  2280
```

-continued

| | | | | |
|---|---|---|---|---|
| aaaaatctaa | gtgtttcata | aatttgagag | tctgtgaccc | acttaccttg | catctcacag | 2340 |
| gtagacagta | taactaac | aaccaaagac | tacatattgt | cactgacaca | cacgttataa | 2400 |
| tcatttatca | tatatataca | tacatgcata | cactctcaaa | gcaaataatt | tttcacttca | 2460 |
| aaacagtatt | gacttgtata | ccttgtaatt | tgaaatattt | tctttgttaa | aatagaatgg | 2520 |
| tatcaataaa | tagaccatta | atcag | | | | 2545 |

<210> SEQ ID NO 73
<211> LENGTH: 1227
<212> TYPE: DNA
<213> ORGANISM: Homo sapiens
<220> FEATURE:
<221> NAME/KEY: CXCL10
<222> LOCATION: (1)..(1227)

<400> SEQUENCE: 73

| | | | | | | |
|---|---|---|---|---|---|---|
| ctttgcagat | aaatatggca | cactagcccc | acgttttctg | agacattcct | caattgctta | 60 |
| gacatattct | gagcctacag | cagaggaacc | tccagtctca | gcaccatgaa | tcaaactgcc | 120 |
| attctgattt | gctgccttat | ctttctgact | ctaagtggca | ttcaaggagt | acctctctct | 180 |
| agaactgtac | gctgtacctg | catcagcatt | agtaatcaac | ctgttaatcc | aaggtcttta | 240 |
| gaaaaacttg | aaattattcc | tgcaagccaa | ttttgtccac | gtgttgagat | cattgctaca | 300 |
| atgaaaaaga | agggtgagaa | gagatgtctg | aatccagaat | cgaaggccat | caagaattta | 360 |
| ctgaaagcag | ttagcaagga | aaggtctaaa | agatctcctt | aaaaccagag | gggagcaaaa | 420 |
| tcgatgcagt | gcttccaagg | atggaccaca | cagaggctgc | ctctcccatc | acttccctac | 480 |
| atggagtata | tgtcaagcca | taattgttct | tagtttgcag | ttacactaaa | aggtgaccaa | 540 |
| tgatggtcac | caaatcagct | gctactactc | ctgtaggaag | gttaatgttc | atcatcctaa | 600 |
| gctattcagt | aataactcta | ccctggcact | ataatgtaag | ctctactgag | gtgctatgtt | 660 |
| cttagtggat | gttctgaccc | tgcttcaaat | atttcctca | cctttcccat | cttccaaggg | 720 |
| tactaaggaa | tctttctgct | ttggggttta | tcagaattct | cagaatctca | ataactaaa | 780 |
| aggtatgcaa | tcaaatctgc | ttttaaga | atgctcttta | cttcatggac | ttccactgcc | 840 |
| atcctcccaa | ggggcccaaa | ttctttcagt | ggctacctac | atacaattcc | aaacacatac | 900 |
| aggaaggtag | aaatatctga | aaatgtatgt | gtaagtattc | ttatttaatg | aaagactgta | 960 |
| caaagtagaa | gtcttagatg | tatatatttc | ctatattgtt | ttcagtgtac | atggaataac | 1020 |
| atgtaattaa | gtactatgta | tcaatgagta | acaggaaaat | tttaaaaata | cagatagata | 1080 |
| tatgctctgc | atgttacata | agataaatgt | gctgaatggt | tttcaaaata | aaaatgaggt | 1140 |
| actctcctgg | aaatattaag | aaagactatc | taaatgttga | aagatcaaaa | ggttaataaa | 1200 |
| gtaattataa | ctaagaaaaa | aaaaaaa | | | | 1227 |

<210> SEQ ID NO 74
<211> LENGTH: 1610
<212> TYPE: DNA
<213> ORGANISM: Homo sapiens
<220> FEATURE:
<221> NAME/KEY: CXCL11
<222> LOCATION: (1)..(1610)

<400> SEQUENCE: 74

| | | | | | | |
|---|---|---|---|---|---|---|
| agagaacaaa | acagaaactc | ttggaagcag | gaaaggtgca | tgactcaaag | agggaaattc | 60 |
| ctgtgccata | aaaggattgc | tggtgtataa | aatgctctat | atatgccaat | tatcaatttc | 120 |
| ctttcatgtt | cagcatttct | actccttcca | agaagagcag | caaagctgaa | gtagcagcag | 180 |

| | |
|---|---|
| cagcaccagc agcaacagca aaaaacaaac atgagtgtga agggcatggc tatagccttg | 240 |
| gctgtgatat tgtgtgctac agttgttcaa ggcttcccca tgttcaaaag aggacgctgt | 300 |
| cttttgcatag gccctggggt aaaagcagtg aaagtggcag atattgagaa agcctccata | 360 |
| atgtacccaa gtaacaactg tgacaaaata gaagtgatta ttaccctgaa agaaaataaa | 420 |
| ggacaacgat gcctaaatcc caaatcgaag caagcaaggc ttataatcaa aaagttgaa | 480 |
| agaaagaatt tttaaaaata tcaaaacata tgaagtcctg aaaagagca tctgaaaaac | 540 |
| ctagaacaag tttaactgtg actactgaaa tgacaagaat tctacagtag gaaactgaga | 600 |
| cttttctatg gttttgtgac tttcaacttt tgtacagtta tgtgaaggat gaaaggtggg | 660 |
| tgaaaggacc aaaaacagaa atacagtctt cctgaatgaa tgacaatcag aattccactg | 720 |
| cccaaaggag tccaacaatt aaatggattt ctaggaaaag ctaccttaag aaaggctggt | 780 |
| taccatcgga gtttacaaag tgctttcacg ttcttacttg ttgcattata cattcatgca | 840 |
| tttctaggct agagaacctt ctagatttga tgcttacaac tattctgttg tgactatgag | 900 |
| aacatttctg tctctagaag tcatctgtct gtattgatct ttatgctata ttactatctg | 960 |
| tggttacggt ggagacattg acattattac tggagtcaag cccttataag tcaaaagcat | 1020 |
| ctatgtgtcg taaaacattc ctcaaacatt ttttcatgca aatacacact tctttcccca | 1080 |
| aacatcatgt agcacatcaa tatgtaggga gacattctta tgcatcattt ggtttgtttt | 1140 |
| ataaccaatt cattaaatgt aattcataaa atgtactatg aaaaaaatta tacgctatgg | 1200 |
| gatactggca aaagtgcaca tatttcataa ccaaattagt agcaccagtc ttaatttgat | 1260 |
| gtttttcaac ttttattcat tgagatgttt tgaagcaatt aggatatgtg tgtttactgt | 1320 |
| acttttttgtt ttgatccgtt tgtataaatg atagcaatat cttggacaca tctgaaatac | 1380 |
| aaaatgtttt tgtctaccaa agaaaaatgt tgaaaaataa gcaaatgtat acctagcaat | 1440 |
| cacttttact ttttgtaatt ctgtctctta gaaaaataca taatctaatc aatttctttg | 1500 |
| ttcatgccta tatactgtaa aatttaggta tactcaagac tagtttaaag aatcaaagtc | 1560 |
| attttttttct ctaataaact accacaacct ttcttttta aaaaaaaaa | 1610 |

<210> SEQ ID NO 75
<211> LENGTH: 3545
<212> TYPE: DNA
<213> ORGANISM: Homo sapiens
<220> FEATURE:
<221> NAME/KEY: CXCL12b
<222> LOCATION: (1)..(3545)

<400> SEQUENCE: 75

| | |
|---|---|
| gccgcacttt cactctccgt cagccgcatt gcccgctcgg cgtccggccc ccgaccecgcg | 60 |
| ctcgtccgcc cgcccgcccg cccgcccgcg ccatgaacgc caaggtcgtg gtcgtgctgg | 120 |
| tcctcgtgct gaccgcgctc tgcctcagcg acgggaagcc cgtcagcctg agctacagat | 180 |
| gcccatgccg attcttcgaa agccatgttg ccagagccaa cgtcaagcat ctcaaaattc | 240 |
| tcaacactcc aaactgtgcc cttcagattg tagcccggct gaagaacaac aacagacaag | 300 |
| tgtgcattga cccgaagcta aagtggattc aggagtacct ggagaaagct ttaaacaaga | 360 |
| ggttcaagat gtgagagggt cagacgcctg aggaaccctt acagtaggag cccagctctg | 420 |
| aaaccagtgt tagggaaggg cctgccacag cctcccctgc cagggcaggg ccccaggcat | 480 |
| tgccaagggc tttgttttgc acactttgcc atattttcac catttgatta tgtagcaaaa | 540 |
| tacatgacat ttattttca tttagtttga ttattcagtg tcactggcga cacgtagcag | 600 |
| cttagactaa ggccattatt gtacttgcct tattagagtg tctttccacg gagccactcc | 660 |

```
tctgactcag ggctcctggg ttttgtattc tctgagctgt gcaggtgggg agactgggct    720
gagggagcct ggccccatgg tcagccctag ggtggagagc caccaagagg gacgcctggg    780
ggtgccagga ccagtcaacc tgggcaaagc ctagtgaagg cttctctctg tgggatggga    840
tggtggaggg ccacatggga ggctcacccc cttctccatc cacatgggag ccgggtctgc    900
ctcttctggg agggcagcag ggctaccctg agctgaggca gcagtgtgag gccagggcag    960
agtgagaccc agccctcatc ccgagcacct ccacatcctc cacgttctgc tcatcattct   1020
ctgtctcatc catcatcatg tgtgtccacg actgtctcca tggccccgca aaaggactct   1080
caggaccaaa gctttcatgt aaactgtgca ccaagcagga aatgaaaatg tcttgtgtta   1140
cctgaaaaca ctgtgcacat ctgtgtcttg tttggaatat tgtccattgt ccaatcctat   1200
gtttttgttc aaagccagcg tcctcctctg tgaccaatgt cttgatgcat gcactgttcc   1260
ccctgtgcag ccgctgagcg aggagatgct ccttgggccc tttgagtgca gtcctgatca   1320
gagccgtggt cctttggggt gaactacctt ggttccccca ctgatcacaa aaacatggtg   1380
ggtccatggg cagagcccaa gggaattcgg tgtgcaccag ggttgacccc agaggattgc   1440
tgccccatca gtgctccctc acatgtcagt accttcaaac tagggccaag cccagcactg   1500
cttgaggaaa caagcattc acaacttgtt tttggttttt aaacccagt ccacaaaata   1560 accaatcctg acatgaaga ttcttttccca attcacatct aacctcatct tcttcaccat   1620
ttggcaatgc catcatctcc tgccttcctc ctgggccctc tctgctctgc gtgtcacctg   1680
tgcttcgggc ccttcccaca ggacatttct ctaagagaac aatgtgctat gtgaagagta   1740
agtcaacctg cctgacattt ggagtgttcc ccttccactg agggcagtcg atagagctgt   1800
attaagccac ttaaaatgtt cacttttgac aaaggcaagc acttgtgggt ttttgttttg   1860
tttttcattc agtcttacga atactttgc cctttgatta aagactccag ttaaaaaaaa   1920
ttttaatgaa gaaagtggaa acaaggaag tcaaagcaag gaaactatgt aacatgtagg   1980
aagtaggaag taaattatag tgatgtaatc ttgaattgta actgttcttg aatttaataa   2040
tctgtagggt aattagtaac atgtgttaag tattttcata agtatttcaa attggagctt   2100
catggcagaa ggcaaaccca tcaacaaaaa ttgtcccctta aacaaaaatt aaaatcctca   2160
atccagctat gttatattga aaaaatagag cctgagggat ctttactagt tataaagata   2220
cagaactctt tcaaaacctt ttgaaattaa cctctcacta taccagtata attgagtttt   2280
cagtggggca gtcattatcc aggtaatcca agatatttta aaatctgtca cgtagaactt   2340
ggatgtacct gccccccaatc catgaaccaa gaccattgaa ttcttggttg aggaaacaaa   2400
catgacccta aatcttgact acagtcagga aaggaatcat ttctatttct cctccatggg   2460
agaaaataga taagagtaga aactgcaggg aaaattattt gcataacaat tcctctacta   2520
acaatcagct ccttcctgga gactgcccag ctaaagcaat atgcatttaa atacagtctt   2580
ccatttgcaa gggaaaagtc tcttgtaatc cgaatctctt tttgctttcg aactgctagt   2640
caagtgcgtc cacgagctgt ttactaggga tccctcatct gtccctccgg gacctggtgc   2700
tgcctctacc tgacactccc ttgggctccc tgtaacctct tcagaggccc tcgctgccag   2760
ctctgtatca ggacccagag gaaggggcca gaggctcgtt gactggctgt gtgttgggat   2820
tgagtctgtg ccacgtgttt tgctgtggt gtgtcccct ctgtccaggc actgagatac   2880
cagcgaggag gctccagagg gcactctgct tgttattaga gattacctcc tgagaaaaaa   2940
ggttccgctt ggagcagagg ggctgaatag cagaaggttg cacctccccc aaccttagat   3000
gttctaagtc tttccattgg atctcattgg acccttccat ggtgtgatcg tctgactggt   3060
```

```
gttatcaccg tgggctccct gactgggagt tgatcgcctt tcccaggtgc tacacccttt    3120
tccagctgga tgagaatttg agtgctctga tccctctaca gagcttccct gactcattct    3180
gaaggagccc cattcctggg aaatattccc tagaaacttc caaatcccct aagcagacca    3240
ctgataaaac catgtagaaa atttgttatt ttgcaacctc gctggactct cagtctctga    3300
gcagtgaatg attcagtgtt aaatgtgatg aatactgtat tttgtattgt ttcaattgca    3360
tctcccagat aatgtgaaaa tggtccagga aaggccaat  tcctatacgc agcgtgcttt    3420
aaaaaataaa taagaaacaa ctctttgaga aacaacaatt tctactttga agtcatacca    3480
atgaaaaaat gtatatgcac ttataatttt cctaataaag ttctgtactc aaatgtagcc    3540
accaa                                                                 3545

<210> SEQ ID NO 76
<211> LENGTH: 1219
<212> TYPE: DNA
<213> ORGANISM: Homo sapiens
<220> FEATURE:
<221> NAME/KEY: CXCL13
<222> LOCATION: (1)..(1219)

<400> SEQUENCE: 76
gagaagatgt tgaaaaaac tgactctgct aatgagcctg gactcagagc tcaagtctga      60
actctacctc cagacagaat gaagttcatc tcgacatctc tgcttctcat gctgctggtc    120
agcagcctct ctccagtcca aggtgttctg gaggtctatt acacaagctt gaggtgtaga    180
tgtgtccaag agagctcagt ctttatccct agacgcttca ttgatcgaat tcaaatcttg    240
ccccgtggga atggttgtcc aagaaaagaa atcatagtct ggaagaagaa caagtcaatt    300
gtgtgtgtgg accctcaagc tgaatggata caaagaatga tggaagtatt gagaaaaaga    360
agttcttcaa ctctaccagt tccagtgttt aagagaaaga ttccctgatg ctgatatttc    420
cactaagaac acctgcattc ttcccttatc cctgctctgg attttagttt tgtgcttagt    480
taaatctttt ccaggaaaaa gaacttcccc atacaaataa gcatgagact atgtaaaaat    540
aaccttgcag aagctgatgg ggcaaactca agcttcttca ctcacagcac cctatataca    600
cttggagttt gcattcttat tcatcaggga ggaaagtttc tttgaaaata gttattcagt    660
tataagtaat acaggattat tttgattata tacttgttgt ttaatgttta aaatttctta    720
gaaaacaatg gaatgagaat ttaagcctca aatttgaaca tgtggcttga attaagaaga    780
aaattatggc atatattaaa agcaggcttc tatgaaagac tcaaaagct  gcctgggagg    840 cagatggaac ttgagcctgt caagaggcaa aggaatccat gtagtagata tcctctgctt    900
aaaaactcac tacggaggag aattaagtcc tacttttaaa gaatttcttt ataaaattta    960
ctgtctaaga ttaatagcat tcgaagatcc ccagacttca tagaatactc agggaaagca   1020
tttaaagggt gatgtacaca tgtatccttt cacacatttg ccttgacaaa cttctttcac   1080
tcacatcttt ttcactgact ttttttgtgg ggggcggggc cggggggact ctggtatcta   1140
attctttaat gattcctata aatctaatga cattcaataa agttgagcaa acattttact   1200
taaaaaaaaa aaaaaaaaa                                                 1219

<210> SEQ ID NO 77
<211> LENGTH: 1670
<212> TYPE: DNA
<213> ORGANISM: Homo sapiens
<220> FEATURE:
<221> NAME/KEY: CXCR3-1
<222> LOCATION: (1)..(1670)
```

<400> SEQUENCE: 77

```
ccaaccacaa gcaccaaagc agaggggcag gcagcacacc acccagcagc cagagcacca         60
gcccagccat ggtccttgag gtgagtgacc accaagtgct aaatgacgcc gaggttgccg        120
ccctcctgga gaacttcagc tcttcctatg actatggaga aaacgagagt gactcgtgct        180
gtacctcccc gccctgccca caggacttca gcctgaactt cgaccgggcc ttcctgccag        240
ccctctacag cctcctcttt ctgctggggc tgctgggcaa cggcgcggtg gcagccgtgc        300
tgctgagccg gcggacagcc ctgagcagca ccgacacctt cctgctccac ctagctgtag        360
cagacacgct gctggtgctg acactgccgc tctgggcagt ggacgctgcc gtccagtggg        420
tctttggctc tggcctctgc aaagtggcag gtgccctctt caacatcaac ttctacgcag        480
gagccctcct gctggcctgc atcagctttg accgctacct gaacatagtt catgccaccc        540
agctctaccg ccggggggcc ccggcccgcg tgaccctcac ctgcctggct gtctggggc         600
tctgcctgct tttcgccctc ccagacttca tcttcctgtc ggcccaccac gacgagcgcc        660
tcaacgccac ccactgccaa tacaacttcc cacaggtggg ccgcacggct ctgcgggtgc        720
tgcagctggt ggctggcttt ctgctgcccc tgctggtcat ggcctactgc tatgcccaca        780
tcctggccgt gctgctggtt ccaggggcc agcggcgcct gcgggccatg cggctggtgg        840
tggtggtcgt ggtggccttt gccctctgct ggacccccta tcacctggtg gtgctggtgg        900
acatcctcat ggacctgggc gctttggccc gcaactgtgg ccgagaaagc agggtagacg        960
tggccaagtc ggtcacctca ggcctgggct acatgcactg ctgcctcaac ccgctgctct       1020
atgcctttgt agggggtcaag ttccgggagc ggatgtggat gctgctcttg cgcctgggct       1080
gccccaacca gagagggctc cagaggcagc catcgtcttc ccgccgggat tcatcctggt       1140
ctgagacctc agaggcctcc tactcgggct tgtgaggccg gaatccgggc tccccttcg        1200
cccacagtct gacttccccg cattccaggc tcctccctcc ctctgccggc tctggctctc       1260
cccaatatcc tcgctcccgg gactcactgg cagccccagc accaccaggt ctcccgggaa       1320
gccaccctcc cagctctgag gactgcacca ttgctgctcc ttagctgcca gccccatcc        1380
tgccgcccga ggtggctgcc tggagcccca ctgcccttct catttggaaa ctaaaacttc       1440
atcttcccca agtgcgggga gtacaaggca tggcgtagag ggtgctgccc catgaagcca       1500
cagcccaggc ctccagctca gcagtgactg tggccatggt ccccaagacc tctatatttg       1560
ctcttttatt tttatgtcta aaatcctgct taaaactttt caataaacaa gatcgtcagg       1620
accaaaaaaa aaaaaaaaa aaaaaaaaaa aaaaaaaaaa aaaaaaaaa                    1670
```

<210> SEQ ID NO 78
<211> LENGTH: 1914
<212> TYPE: DNA
<213> ORGANISM: Homo sapiens
<220> FEATURE:
<221> NAME/KEY: CXCR3-2
<222> LOCATION: (1)..(1914)

<400> SEQUENCE: 78

```
ccaaccacaa gcaccaaagc agaggggcag gcagcacacc acccagcagc cagagcacca         60
gcccagccat ggtccttgag gggtccctgg ccgatgggga tcacgcagaa gaatgcgaga        120
gaagcagcct ttgagaaggg aagtcactat cccagagccc aggctgagcg gatggagttg        180
aggaagtacg gccctggaag actggcgggg acagttatag gaggagctgc tcagagtaaa        240
tcacagacta aatcagactc aatcacaaaa gagttcctgc caggccttta cacagcccct        300
```

-continued

| | |
|---|---|
| tcctccccgt tcccgccctc acaggtgagt gaccaccaag tgctaaatga cgccgaggtt | 360 |
| gccgccctcc tggagaactt cagctcttcc tatgactatg gagaaaacga gagtgactcg | 420 |
| tgctgtacct ccccgccctg cccacaggac ttcagcctga acttcgaccg ggccttcctg | 480 |
| ccagccctct acagcctcct ctttctgctg gggctgctgg gcaacggcgc ggtggcagcc | 540 |
| gtgctgctga gccggcggac agccctgagc agcaccgaca ccttcctgct ccacctagct | 600 |
| gtagcagaca cgctgctggt gctgacactg ccgctctggg cagtggacgc tgccgtccag | 660 |
| tgggtctttg gctctggcct ctgcaaagtg gcaggtgccc tcttcaacat caacttctac | 720 |
| gcaggagccc tcctgctggc ctgcatcagc tttgaccgct acctgaacat agttcatgcc | 780 |
| acccagctct accgccgggg gccccccggcc cgcgtgaccc tcacctgcct ggctgtctgg | 840 |
| gggctctgcc tgcttttcgc cctcccagac ttcatcttcc tgtcggccca ccacgacgag | 900 |
| cgcctcaacg ccacccactg ccaatacaac ttcccacagg tgggccgcac ggctctgcgg | 960 |
| gtgctgcagc tggtggctgg cttttctgctg cccctgctgg tcatggccta ctgctatgcc | 1020 |
| cacatcctgg ccgtgctgct ggtttccagg ggccagcggc gcctgcgggc catgcggctg | 1080 |
| gtggtggtgg tcgtggtggc cttttgccctc tgctggaccc cctatcacct ggtggtgctg | 1140 |
| gtggacatcc tcatggacct gggcgctttg gcccgcaact gtggccgaga aagcagggta | 1200 |
| gacgtggcca gtcggtcac ctcaggcctg gctacatgc actgctgcct caacccgctg | 1260 |
| ctctatgcct ttgtaggggt caagttccgg gagcggatgt ggatgctgct cttgcgcctg | 1320 |
| ggctgcccca accagagagg gctccagagg cagccatcgt cttcccgccg ggattcatcc | 1380 |
| tggtctgaga cctcagaggc ctcctactcg ggcttgtgag gccggaatcc gggctcccct | 1440 |
| ttcgcccaca gtctgacttc cccgcattcc aggctcctcc ctccctctgc cggctctggc | 1500 |
| tctccccaat atcctcgctc ccgggactca ctggcagccc cagcaccacc aggtctcccg | 1560 |
| ggaagccacc ctcccagctc tgaggactgc accattgctg ctccttagct gccaagcccc | 1620 |
| atcctgccgc ccgaggtggc tgcctggagc cccactgccc ttctcatttg gaaactaaaa | 1680 |
| cttcatcttc cccaagtgcg gggagtacaa ggcatggcgt agagggtgct gccccatgaa | 1740 |
| gccacagccc aggcctccag ctcagcagtg actgtggcca tggtcccaa gacctctata | 1800 |
| tttgctcttt tattttttatg tctaaaatcc tgcttaaaac ttttcaataa acaagatcgt | 1860 |
| caggaccaaa aaaaaaaaaa aaaaaaaaaa aaaaaaaaaa aaaaaaaaaa aaaa | 1914 |

<210> SEQ ID NO 79
<211> LENGTH: 2919
<212> TYPE: DNA
<213> ORGANISM: Homo sapiens
<220> FEATURE:
<221> NAME/KEY: CXCR5-1
<222> LOCATION: (1)..(2919)

<400> SEQUENCE: 79

| | |
|---|---|
| aaaaaaaaaa agtgatgagt tgtgaggcag gtcgcggccc tactgcctca ggagacgatg | 60 |
| cgcagctcat ttgcttaaat ttgcagctga cggctgccac ctctctagag gcacctggcg | 120 |
| gggagcctct caacataaga cagtgaccag tctggtgact cacagccggc acagccatga | 180 |
| actacccgct aacgctggaa atggaccctc agaacctgga ggacctgttc tgggaactgg | 240 |
| acagattgga caactataac gacacctccc tggtggaaaa tcatctctgc cctgccacag | 300 |
| aggggccct catggcctcc ttcaaggccg tgttcgtgcc cgtggcctac agcctcatct | 360 |
| tcctcctggg cgtgatcggc aacgtcctgg tgctggtgat cctggagcgg caccggcaga | 420 |
| cacgcagttc cacggagacc ttcctgttcc acctggccgt ggccgacctc ctgctggtct | 480 |

```
tcatcttgcc ctttgccgtg gccgagggct ctgtgggctg ggtcctgggg accttcctct    540
gcaaaactgt gattgccctg cacaaagtca acttctactg cagcagcctg ctcctggcct    600
gcatcgccgt ggaccgctac ctggccattg tccacgccgt ccatgcctac cgccaccgcc    660
gcctcctctc catccacatc acctgtggga ccatctggct ggtgggcttc ctccttgcct    720
tgccagagat tctcttcgcc aaagtcagcc aaggccatca caacaactcc ctgccacgtt    780
gcaccttctc ccaagagaac caagcagaaa cgcatgcctg gttcacctcc cgattcctct    840
accatgtggc gggattcctg ctgcccatgc tggtgatggg ctggtgctac gtggggtag    900
tgcacaggtt gcgccaggcc cagcggcgcc ctcagcggca gaaggcagtc agggtggcca    960
tcctggtgac aagcatcttc ttcctctgct ggtcaccta ccacatcgtc atcttcctgg   1020
acaccctggc gaggctgaag gccgtggaca atacctgcaa gctgaatggc tctctccccg   1080
tggccatcac catgtgtgag ttcctgggcc tggcccactg ctgcctcaac cccatgctct   1140
acactttcgc cggcgtgaag ttccgcagtg acctgtcgcg gctcctgacg aagctgggct   1200
gtaccggccc tgcctccctg tgccagctct ccctagctg gcgcaggagc agtctctctg   1260
agtcagagaa tgccacctct ctcaccacgt tctaggtccc agtgtcccct tttattgctg   1320
cttttccttg gggcaggcag tgatgctgga tgctccttcc aacaggagct gggatcctaa   1380
gggctcaccg tggctaagag tgtcctagga gtatcctcat ttggggtagc tagaggaacc   1440
aaccccatt tctagaacat ccctgccagc tcttctgccg gccctggggc taggctggag    1500
cccagggagc ggaaagcagc tcaaaggcac agtgaaggct gtccttaccc atctgcaccc   1560
ccctgggctg agagaacctc acgcacctcc catcctaatc atccaatgct caagaaacaa   1620
cttctacttc tgcccttgcc aacggagagc gcctgcccct cccagaacac actccatcag   1680
cttaggggct gctgacctcc acagcttccc ctctctcctc ctgcccacct gtcaaacaaa   1740
gccgaaagct gagcaccagg ggatgagtgg aggttaaggc tgaggaaagg ccagctggca   1800
gcagagtgtg gccttcggac aactcagtcc ctaaaaacac agacattctg ccaggccccc   1860
aagcctgcag tcatcttgac caagcaggaa gctcagactg gttgagttca ggtagctgcc   1920
cctggctctg accgaaacag cgctgggtcc accccatgtc accggatcct gggtggtctg   1980
caggcagggc tgactctagg tgcccttgga ggccagccag tgacctgagg aagcgtgaag   2040
gccgagaagc aagaaagaaa cccgacagag ggaagaaaag agctttcttc ccgaacccca   2100
aggagggaga tggatcaatc aaacccggcg gtcccctccg ccaggcgaga tgggtgggg    2160
tggagaactc ctagggtggc tgggtccagg ggatgggagg ttgtgggcat tgatggggaa   2220
ggaggctggc ttgtccctc ctcactccct tcccataagc tatagacccg aggaaactca   2280
gagtcggaac ggagaaaggt ggactggaag gggcccgtgg gagtcatctc aaccatcccc   2340
tccgtggcat caccttaggc agggaagtgt aagaaacaca ctgaggcagg gaagtcccca   2400
ggccccagga agccgtgccc tgcccccgtg aggatgtcac tcagatggaa ccgcaggaag   2460
ctgctccgtg cttgtttgct cacctggggt gtgggaggcc cgtccggcag ttctgggtgc   2520
tccctaccac ctccccagcc tttgatcagg tggggagtca gggaccccctg cccttgtccc   2580
actcaagcca agcagccaag ctccttggga ggcccactg gggaaataac agctgtggct    2640
cacgtgagag tgtcttcacg gcaggacaac gaggaagccc taagacgtcc cttttttctc   2700
tgagtatctc ctcgcaagct gggtaatcga tgggggagtc tgaagcagat gcaaagaggc   2760
aagaggctgg attttgaatt ttcttttaa taaaaaggca cctataaaac aggtcaatac   2820
agtacaggca gcacagagac ccccggaaca agcctaaaaa ttgtttcaaa ataaaaacca   2880
```

```
agaagatgtc ttcacatatt gtaaaaaaaa aaaaaaaa                             2919

<210> SEQ ID NO 80
<211> LENGTH: 2896
<212> TYPE: DNA
<213> ORGANISM: Homo sapiens
<220> FEATURE:
<221> NAME/KEY: CXCR5-2
<222> LOCATION: (1)..(2896)

<400> SEQUENCE: 80
ccactctaag gaatgcggtc cctttgacag gcgaaaaact gaagttggaa aagacaaagt       60
gatttgttca aaattgaaat ttgaaacttg acatttggtc agtgggccct atgtaggaaa      120
aaacctccaa gagagctagg gttcctctca gagaggaaag acaggtcctt aggtcctcac      180
cctcccgtct ccttgccctt gcagttctgg gaactggaca gattggacaa ctataacgac      240
acctccctgg tggaaaatca tctctgccct gccacagagg ggcccctcat ggcctccttc      300
aaggccgtgt tcgtgcccgt ggcctacagc ctcatcttcc tcctgggcgt gatcggcaac      360
gtcctggtgc tggtgatcct ggagcggcac cggcagacac gcagttccac ggagaccttc      420
ctgttccacc tggccgtggc cgacctcctg ctggtcttca tcttgccctt tgccgtggcc      480
gagggctctg tgggctgggt cctggggacc ttcctctgca aaactgtgat tgccctgcac      540
aaagtcaact tctactgcag cagcctgctc ctggcctgca tcgccgtgga ccgctacctg      600
gccattgtcc acgccgtcca tgcctaccgc accgccgcc tcctctccat ccacatcacc      660
tgtgggacca tctggctggt gggcttcctc cttgccttgc cagagattct cttcgccaaa      720
gtcagccaag gccatcacaa caactccctg ccacgttgca ccttctccca agagaaccaa      780
gcagaaacgc atgcctggtt cacctcccga ttcctctacc atgtggcggg attcctgctg      840
cccatgctgg tgatgggctg gtgctacgtg ggggtagtgc acaggttgcg ccaggcccag      900
cggcgccctc agcggcagaa ggcagtcagg gtggccatcc tggtgacaag catcttcttc      960
ctctgctggt caccctacca catcgtcatc ttcctggaca ccctggcgag gctgaaggcc     1020
gtggacaata cctgcaagct gaatggctct ctccccgtgg ccatcaccat gtgtgagttc     1080
ctgggcctgg cccactgctg cctcaacccc atgctctaca ctttcgccgg cgtgaagttc     1140
cgcagtgacc tgtcgcggct cctgacgaag ctgggctgta ccggccctgc ctccctgtgc     1200
cagctcttcc ctagctggcg caggagcagt ctctctgagt cagagaatgc cacctctctc     1260
accacgttct aggtcccagt gtccccttt attgctgctt ttccttgggg caggcagtga     1320
tgctggatgc tccttccaac aggagctggg atcctaaggg ctcaccgtgg ctaagagtgt     1380
cctaggagta tcctcatttg gggtagctag aggaaccaac ccccatttct agaacatccc     1440
tgccagctct tctgccggcc ctggggctag gctggagccc agggagcgga aagcagctca     1500
aaggcacagt gaaggctgtc cttacccatc tgcaccccc tgggctgaga gaacctcacg     1560
cacctcccat cctaatcatc caatgctcaa gaaacaactt ctacttctgc ccttgccaac     1620
ggagagcgcc tgcccctccc agaacacact ccatcagctt aggggctgct gacctccaca     1680
gcttcccctc tctcctcctg cccacctgtc aaacaaagcc agaagctgag caccagggga     1740
tgagtggagg ttaaggctga ggaaaggcca gctggcagca gagtgtggcc ttcggacaac     1800
tcagtcccta aaaacacaga cattctgcca ggcccccaag cctgcagtca tcttgaccaa     1860
gcaggaagct cagactggtt gagttcaggt agctgcccct ggctctgacc gaaacagcgc     1920
tgggtccacc ccatgtcacc ggatcctggg tggtctgcag gcagggctga ctctaggtgc     1980
```

| | | | | |
|---|---|---|---|---|
| ccttggaggc | cagccagtga | cctgaggaag | cgtgaaggcc | gagaagcaag | aaagaaaccc | 2040 |
| gacagaggga | agaaaagagc | tttcttcccg | aaccccaagg | agggagatgg | atcaatcaaa | 2100 |
| cccggcggtc | ccctccgcca | ggcgagatgg | ggtggggtgg | agaactccta | gggtggctgg | 2160 |
| gtccagggga | tgggaggttg | tgggcattga | tggggaagga | ggctggcttg | tccctcctc | 2220 |
| actcccttcc | cataagctat | agacccgagg | aaactcagag | tcggaacgga | gaaaggtgga | 2280 |
| ctggaagggg | cccgtgggag | tcatctcaac | catcccctcc | gtggcatcac | cttaggcagg | 2340 |
| gaagtgtaag | aaacacactg | aggcagggaa | gtccccaggc | ccaggaagc | cgtgccctgc | 2400 |
| ccccgtgagg | atgtcactca | gatggaaccg | caggaagctg | ctccgtgctt | gtttgctcac | 2460 |
| ctggggtgtg | ggaggcccgt | ccggcagttc | tgggtgctcc | ctaccacctc | cccagccttt | 2520 |
| gatcaggtgg | ggagtcaggg | acccctgccc | ttgtcccact | caagccaagc | agccaagctc | 2580 |
| cttgggaggc | cccactgggg | aaataacagc | tgtggctcac | gtgagagtgt | cttcacggca | 2640 |
| ggacaacgag | gaagccctaa | gacgtcccct | ttttctctga | gtatctcctc | gcaagctggg | 2700 |
| taatcgatgg | gggagtctga | agcagatgca | aagaggcaag | aggctggatt | ttgaattttc | 2760 |
| tttttaataa | aaaggcacct | ataaaacagg | tcaatacagt | acaggcagca | cagagacccc | 2820 |
| cggaacaagc | ctaaaaattg | tttcaaaata | aaaaccaaga | agatgtcttc | acatattgta | 2880 |
| aaaaaaaaaa | aaaaaa | | | | | 2896 |

<210> SEQ ID NO 81
<211> LENGTH: 1119
<212> TYPE: DNA
<213> ORGANISM: Homo sapiens
<220> FEATURE:
<221> NAME/KEY: CXCL1
<222> LOCATION: (1)..(1119)

<400> SEQUENCE: 81

| | | | | | | |
|---|---|---|---|---|---|---|
| cacagagccc | gggccgcagg | cacctcctcg | ccagctcttc | cgctcctctc | acagccgcca | 60 |
| gacccgcctg | ctgagcccca | tggcccgcgc | tgctctctcc | gccgccccca | gcaatccccg | 120 |
| gctcctgcga | gtggcactgc | tgctcctgct | cctggtagcc | gctggccggc | cgcagcagg | 180 |
| agcgtccgtg | gccactgaac | tgcgctgcca | gtgcttgcag | accctgcagg | gaattcaccc | 240 |
| caagaacatc | caagtgtga | acgtgaagtc | ccccggaccc | cactgcgccc | aaaccgaagt | 300 |
| catagccaca | ctcaagaatg | gcggaaagc | ttgcctcaat | cctgcatccc | ccatagttaa | 360 |
| gaaaatcatc | gaaaagatgc | tgaacagtga | caaatccaac | tgaccagaag | ggaggaggaa | 420 |
| gctcactggt | ggctgttcct | gaaggaggcc | ctgcccttat | aggaacagaa | gaggaaagag | 480 |
| agacacagct | gcagaggcca | cctggattgt | gcctaatgtg | tttgagcatc | gcttaggaga | 540 |
| agtcttctat | ttatttattt | attcattagt | tttgaagatt | ctatgttaat | attttaggtg | 600 |
| taaataatt | aagggtatga | ttaactctac | ctgcacactg | tcctattata | ttcattcttt | 660 |
| ttgaaatgtc | aaccccaagt | tagttcaatc | tggattcata | tttaatttga | aggtagaatg | 720 |
| ttttcaaatg | ttctccagtc | attatgttaa | tatttctgag | gagcctgcaa | catgccagcc | 780 |
| actgtgatag | aggctggcgg | atccaagcaa | atggccaatg | agatcattgt | gaaggcaggg | 840 |
| gaatgtatgt | gcacatctgt | tttgtaactg | tttagatgaa | tgtcagttgt | tatttattga | 900 |
| aatgatttca | cagtgtgtgg | tcaacatttc | tcatgttgaa | actttaagaa | ctaaaatgtt | 960 |
| ctaaatatcc | cttggacatt | ttatgtcttt | cttgtaaggc | atactgcctt | gtttaatggt | 1020 |
| agttttacag | tgtttctggc | ttagaacaaa | ggggcttaat | tattgatgtt | ttcatagaga | 1080 |
| atataaaaat | aaagcactta | tagaaaaaaa | aaaaaaaa | | | 1119 |

<210> SEQ ID NO 82
<211> LENGTH: 1234
<212> TYPE: DNA
<213> ORGANISM: Homo sapiens
<220> FEATURE:
<221> NAME/KEY: CXCL2
<222> LOCATION: (1)..(1234)

<400> SEQUENCE: 82

| | | | | | |
|---|---|---|---|---|---|
| gagctccggg | aatttccctg | gcccgggact | ccgggctttc | cagccccaac | catgcataaa | 60 |
| aggggttcgc | cgttctcgga | gagccacaga | gcccgggcca | caggcagctc | cttgccagct | 120 |
| ctcctcctcg | cacagccgct | cgaaccgcct | gctgagcccc | atggcccgcg | ccacgctctc | 180 |
| cgccgccccc | agcaatcccc | ggctcctgcg | ggtggcgctg | ctgctcctgc | tcctggtggc | 240 |
| cgccagccgg | cgcgcagcag | gagcgcccct | ggccactgaa | ctgcgctgcc | agtgcttgca | 300 |
| gaccctgcag | ggaattcacc | tcaagaacat | ccaaagtgtg | aaggtgaagt | cccccggacc | 360 |
| ccactgcgcc | caaaccgaag | tcatagccac | actcaagaat | gggcagaaag | cttgtctcaa | 420 |
| ccccgcatcg | cccatggtta | agaaaatcat | cgaaaagatg | ctgaaaaatg | gcaaatccaa | 480 |
| ctgaccagaa | ggaaggagga | agcttattgg | tggctgttcc | tgaaggaggc | cctgccctta | 540 |
| caggaacaga | agaggaaaga | gagacacagc | tgcagaggcc | acctggattg | cgcctaatgt | 600 |
| gtttgagcat | cacttaggag | aagtcttcta | tttatttatt | tatttattta | tttgtttgtt | 660 |
| ttagaagatt | ctatgttaat | attttatgtg | taaaataagg | ttatgattga | atctacttgc | 720 |
| acactctccc | attatattta | ttgtttattt | taggtcaaac | ccaagttagt | tcaatcctga | 780 |
| ttcatattta | atttgaagat | agaaggtttg | cagatattct | ctagtcattt | gttaatattt | 840 |
| cttcgtgatg | acatatcaca | tgtcagccac | tgtgatagag | gctgaggaat | ccaagaaaat | 900 |
| ggccagtgag | atcaatgtga | cggcagggaa | atgtatgtgt | gtctattttg | taactgtaaa | 960 |
| gatgaatgtc | agttgttatt | tattgaaatg | atttcacagt | gtgtggtcaa | catttctcat | 1020 |
| gttgaagctt | taagaactaa | aatgttctaa | atatcccttg | gacattttat | gtctttcttg | 1080 |
| taaggcatac | tgccttgttt | aatgttaatt | atgcagtgtt | tccctctgtg | ttagagcaga | 1140 |
| gaggtttcga | tatttattga | tgttttcaca | agaacagga | aataaaata | tttaaaaata | 1200 |
| taaaaaaaaa | aaaaaaaaa | aaaaaaaaaa | aaaa | | | 1234 |

<210> SEQ ID NO 83
<211> LENGTH: 1166
<212> TYPE: DNA
<213> ORGANISM: Homo sapiens
<220> FEATURE:
<221> NAME/KEY: CXCL3
<222> LOCATION: (1)..(1166)

<400> SEQUENCE: 83

| | | | | | |
|---|---|---|---|---|---|
| gctccgggaa | tttccctggc | ccggccgctc | cgggctttcc | agtctcaacc | atgcataaaa | 60 |
| aggggttcgcc | gatcttgggg | agccacacag | cccgggtcgc | aggcacctcc | ccgccagctc | 120 |
| tcccgcttct | cgcacagctt | cccgacgcgt | ctgctgagcc | ccatggccca | cgccacgctc | 180 |
| tccgccgccc | ccagcaatcc | ccggctcctg | cgggtggcgc | tgctgctcct | gtcctggtg | 240 |
| gccgccagcc | ggcgcgcagc | aggagcgtcc | gtggtcactg | aactgcgctg | ccagtgcttg | 300 |
| cagacactgc | agggaattca | cctcaagaac | atccaaagtg | tgaatgtaag | gtcccccgga | 360 |
| ccccactgcg | cccaaaccga | agtcatagcc | acactcaaga | atgggaagaa | agcttgtctc | 420 |
| aaccccgcat | ccccccatggt | tcagaaaatc | atcgaaaaga | tactgaacaa | ggggagcacc | 480 |

```
aactgacagg agagaagtaa gaagcttatc agcgtatcat tgacacttcc tgcagggtgg      540
tccctgccct taccagagct gaaaatgaaa aagagaacag cagctttcta gggacagctg      600
gaaaggactt aatgtgtttg actatttctt acgagggttc tacttattta tgtatttatt      660
tttgaaagct tgtatttaa tattttacat gctgttattt aaagatgtga gtgtgtttca       720
tcaaacatag ctcagtcctg attatttaat tggaatatga tgggttttaa atgtgtcatt      780
aaactaatat ttagtgggag accataatgt gtcagccacc ttgataaatg acagggtggg      840
gaactggagg gtgggggat tgaaatgcaa gcaattagtg gatcactgtt agggtaaggg       900
aatgtatgta cacatctatt ttttatactt ttttttaaa aaagaatgt cagttgttat        960 ttattcaaat tatctcacat tatgtgttca acatttttat gctgaagttt cccttagaca     1020
ttttatgtct tgcttgtagg gcataatgcc ttgtttaatg tccattctgc agcgtttctc     1080
tttcccttgg aaaagagaat ttatcattac tgttacattt gtacaaatga catgataata     1140
aaagttttat gaaaaaaaaa aaaaaa                                          1166

<210> SEQ ID NO 84
<211> LENGTH: 476
<212> TYPE: DNA
<213> ORGANISM: Homo sapiens
<220> FEATURE:
<221> NAME/KEY: CXCL4
<222> LOCATION: (1)..(476)

<400> SEQUENCE: 84
ccatcgcact gagcactgag atcctgctgg aagctctgcc gcagcatgag ctccgcagcc       60
gggttctgcg cctcacgccc cgggctgctg ttcctggggt tgctgctcct gccacttgtg      120
gtcgccttcg ccagcgctga agctgaagaa gatgggacc tgcagtgcct gtgtgtgaag       180
accacctccc aggtccgtcc caggcacatc ccagcctgg aggtgatcaa ggccggaccc       240
cactgcccca ctgcccaact gatagccacg ctgaagaatg gaaggaaaat ttgcttggac      300
ctgcaagccc cgctgtacaa gaaaataatt aagaaacttt ggagagtta gctactagct      360 gcctacgtgt gtgcatttgc tatatagcat acttctttt tccagtttca atctaactgt       420
gaaagaactt ctgatatttg tgttatcctt atgattttaa ataaacaaaa taaatc          476

<210> SEQ ID NO 85
<211> LENGTH: 2475
<212> TYPE: DNA
<213> ORGANISM: Homo sapiens
<220> FEATURE:
<221> NAME/KEY: CXCL5
<222> LOCATION: (1)..(2475)

<400> SEQUENCE: 85
gtgcagaagg cacgaggaag ccacagtgct ccggatcctc caatcttcgc tcctccaatc       60
tccgctcctc cacccagttc aggaacccgc gaccgctcgc agcgctctct tgaccactat      120
gagcctcctg tccagccgcg cggcccgtgt cccggtcct tcgagctcct tgtgcgcgct       180
gttggtgctg ctgctgctgc tgacgcagcc agggcccatc gccagcgctg gtcctgccgc      240
tgctgtgttg agagagctgc gttgcgtttg tttacagacc acgcaaggag ttcatcccaa      300
aatgatcagt aatctgcaag tgttcgccat aggcccacag tgctccaagg tggaagtggt      360
agcctccctg aagaacggga aggaaatttg tcttgatcca gagcccctt ttctaaagaa       420 agtcatccag aaaattttgg acggtggaaa caaggaaaac tgattaagag aaatgagcac      480
gcatggaaaa gtttcccagt cttcagcaga gaagttttct ggaggtctct gaacccaggg     540
```

-continued

```
aagacaagaa ggaaagattt tgttgttgtt tgtttatttg tttttccagt agttagcttt      600
cttcctggat tcctcacttt gaagagtgtg aggaaaacct atgtttgccg cttaagcttt      660
cagctcagct aatgaagtgt ttagcatagt acctctgcta tttgctgtta ttttatctgc      720
tatgctattg aagttttggc aattgactat agtgtgagcc aggaatcact ggctgttaat      780 cttcaaagt  gtcttgaatt gtaggtgact attatatttc aagaaatat  tccttaagat      840 attaactgag aaggctgtgg atttaatgtg gaaatgatgt ttcataagaa ttctgttgat      900
ggaaatacac tgttatcttc acttttataa gaaataggaa atattttaat gtttcttggg      960
gaatatgtta gagaatttcc ttactcttga ttgtgggata ctatttaatt atttcacttt     1020
agaaagctga gtgtttcaca ccttatctat gtagaatata tttccttatt cagaatttct     1080
aaaagtttaa gttctatgag ggctaatatc ttatcttcct ataattttag acattcttta     1140
tctttttagt atggcaaact gccatcattt acttttaaac tttgatttta tatgctattt     1200
attaagtatt ttattaggag taccataatt ctggtagcta aatatatatt ttagatagat     1260
gaagaagcta gaaaacaggc aaattcctga ctgctagttt atagaaat   gtattctttt     1320 agttttaaa  gtaaaggcaa acttaacaat gacttgtact ctgaaagttt tggaaacgta     1380
ttcaaacaat ttgaatataa atttatcatt tagttataaa aatatatagc gacatcctcg     1440
aggccctagc atttctcctt ggataggga  ccagagagag cttggaatgt taaaaacaaa     1500 acaaacaaa  aaaaaacaag gagaagttgt ccaagggatg tcaattttt  atccctctgt     1560 atgggttaga ttttccaaaa tcataatttg aagaaggcca gcatttatgg tagaatatat     1620
aattatatat aaggtggcca cgctggggca agttccctcc ccactcacag ctttggcccc     1680
tttcacagag tagaacctgg gttagaggat tgcagaagac gagcggcagc ggggagggca     1740
gggaagatgc ctgtcgggtt tttagcacag ttcatttcac tgggattttg aagcatttct     1800
gtctgaatgt aaagcctgtt ctagtcctgg tgggacacac tggggttggg ggtgggggaa     1860
gatgcggtaa tgaaaccggt tagtcagtgt tgtcttaata tccttgataa tgctgtaaag     1920 tttatttta  caaatatttc tgtttaagct atttcacctt tgtttggaaa tccttccctt     1980
ttaaagagaa aatgtgacac ttgtgaaaag gcttgtagga aagctcctcc cttttttct      2040 ttaaaccttt aaatgacaaa cctaggtaat taatggttgt gaatttctat ttttgctttg     2100
tttttaatga acatttgtct ttcagaatag gattctgtga taatatttaa atggcaaaaa     2160
caaaacataa ttttgtgcaa ttaacaaagc tactgcaaga aaataaaac  atttcttggt     2220 aaaaacgtat gtatttatat attatatatt tatatataat atatattata tatttagcat     2280
tgctgagctt tttagatgcc tattgtgtat cttttaaagg ttttgaccat tttgttatga     2340
gtaattacat atatattaca ttcactatat taaaattgta cttttttact atgtgtctca     2400
ttggttcata gtctttattt tgtcctttga ataaacatta aagatttct  aaacttcaaa     2460 aaaaaaaaaa aaaaa                                                      2475
```

<210> SEQ ID NO 86
<211> LENGTH: 1677
<212> TYPE: DNA
<213> ORGANISM: Homo sapiens
<220> FEATURE:
<221> NAME/KEY: CXCL6
<222> LOCATION: (1)..(1677)

<400> SEQUENCE: 86

```
accccttctt tccacactgc ccctgagtt  cagggaattt ccccagcatc ccaaagcttg       60
```

```
agtttcctgc cagtcgggag ggatgaatgc agataaaggg agtgcagaag gcacgaggaa      120
accaaagtgc tctgtatcct ccagtctccg cgcctccacc cagctcagga acccgcgaac      180
cctctcttga ccactatgag cctcccgtcc agccgcgcgg cccgtgtccc gggtccttcg      240
ggctccttgt gcgcgctgct cgcgctgctg ctcctgctga cgccgccggg gcccctcgcc      300
agcgctggtc ctgtctctgc tgtgctgaca gagctgcgtt gcacttgttt acgcgttacg      360
ctgagagtaa accccaaaac gattggtaaa ctgcaggtgt tccccgcagg cccgcagtgc      420
tccaaggtgg aagtggtagc ctccctgaag aacgggaagc aagtttgtct ggacccggaa      480
gccccttttc taaagaaagt catccagaaa attttggaca gtggaaacaa gaaaaactga      540
gtaacaaaaa agaccatgca tcataaaatt gcccagtctt cagcggagca gttttctgga      600
gatccctgga cccagtaaga ataagaagga agggttggtt tttttccatt ttctacatgg      660
attccctact ttgaagagtg tggggaaag cctacgcttc tccctgaagt ttacagctca      720
gctaatgaag tactaatata gtatttccac tatttactgt tattttacct gataagttat      780 tgaaccettt ggcaattgac catattgtga gcaaagaatc actggttatt agtctttcaa      840
tgaatattga attgaagata actattgtat ttctatcata cattccttaa agtcttaccg      900
aaaaggctgt ggatttcgta tggaaataat gttttattag tgtgctgttg agggaggtat      960
cctgttgttc ttactcactc ttctcataaa ataggaaata ttttagttct gtttcttggg     1020
gaatatgtta ctctttaccc taggatgcta tttaagttgt actgtattag aacactgggt     1080
gtgtcatacc gttatctgtg cagaatatat ttccttattc agaatttcta aaaatttaag     1140
ttctgtaagg gctaatatat tctcttccta tggttttaga cgtttgatgt cttcttagta     1200
tggcataatg tcatgattta ctcattaaac tttgattttg tatgctattt tttcactata     1260
ggatgactat aattctggtc actaaatata cactttagat agatgaagaa gcccaaaaac     1320
agataaattc ctgattgcta atttacatag aaatgtattc tcttggtttt ttaaataaaa     1380
gcaaaattaa caatgatctg tgctctgaaa gttttgaaaa tatatttgaa caatttgaat     1440
ataaattcat catttagtcc tcaaaatata tatagcattg ctaagatttt cagatatcta     1500
ttgtggatct tttaaaggtt ttgaccattt tgttatgagg aattatacat gtatcacatt     1560
cactatatta aaattgcact tttatttttt cctgtgtgtc atgttggttt ttggtacttg     1620
tattgtcatt tggagaaaca ataaaagatt tctaaaccaa aaaaaaaaaa aaaaaaa       1677
```

<210> SEQ ID NO 87
<211> LENGTH: 1307
<212> TYPE: DNA
<213> ORGANISM: Homo sapiens
<220> FEATURE:
<221> NAME/KEY: CXCL7
<222> LOCATION: (1)..(1307)

<400> SEQUENCE: 87

```
acttatctgc agacttgtag gcagcaactc accctcactc agaggtcttc tggttctgga       60
aacaactcta gctcagcctt ctccaccatg agcctcagac ttgataccac cccttcctgt      120
aacagtgcga gaccacttca tgccttgcag gtgctgctgc ttctgtcatt gctgctgact      180
gctctggctt cctccaccaa aggacaaact aagagaaact ggcgaaagg caaagaggaa      240 agtctagaca gtgacttgta tgctgaactc cgctgcatgt gtataaagac aacctctgga      300
attcatccca aaaacatcca aagtttggaa gtgatcggga aggaaccca ttgcaaccaa      360 gtcgaagtga tagccacact gaaggatggg aggaaaatct gcctggaccc agatgctccc      420
agaatcaaga aaattgtaca gaaaaaattg gcaggtgatg aatctgctga ttaatttgtt      480
```

| | |
|---|---|
| ctgtttctgc caaacttctt taactcccag gaagggtaga attttgaaac cttgattttc | 540 |
| tagagttctc atttattcag gatacctatt cttactgtat taaaatttgg atatgtgttt | 600 |
| cattctgtct caaaaatcac attttattct gagaaggttg gttaaaagat ggcagaaaga | 660 |
| agatgaaaat aaataagcct ggtttcaacc ctctaattct tgcctaaaca ttggactgta | 720 |
| ctttgcattt ttttctttaa aaatttctat tctaacacaa cttggttgat ttttcctggt | 780 |
| ctactttatg gttattagac atactcatgg gtattattag atttcataat ggtcaatgat | 840 |
| aataggaatt acatggagcc caacagagaa tatttgctca atacatttt gttaatatat | 900 |
| ttaggaactt aatggagtct ctcagtgtct tagtcctagg atgtcttatt taaaatactc | 960 |
| cctgaaagtt tattctgatg tttatttag ccatcaaaca ctaaaataat aaattggtga | 1020 |
| atatgaatct tataaactgt ggttagctgg tttaaagtga atatatttgc cactagtaga | 1080 |
| acaaaaatag atgatgaaaa tgaattaaca tatctacata gttataattc tatcattaga | 1140 |
| atgagcctta taaataagta caatatagga cttcaacctt actagactcc taattctaaa | 1200 |
| ttctactttt ttcatcaaca gaactttcat tcattttta aaccctaaaa cttatacccca | 1260 |
| cactattctt acaaaaatat tcacatgaaa taaaaatttg ctattga | 1307 |

<210> SEQ ID NO 88
<211> LENGTH: 1718
<212> TYPE: DNA
<213> ORGANISM: Homo sapiens
<220> FEATURE:
<221> NAME/KEY: CXCL8
<222> LOCATION: (1)..(1718)

<400> SEQUENCE: 88

| | |
|---|---|
| gagggtgcat aagttctcta gtagggtgat gatataaaaa gccaccggag cactccataa | 60 |
| ggcacaaact ttcagagaca gcagagcaca caagcttcta ggacaagagc caggaagaaa | 120 |
| ccaccggaag gaaccatctc actgtgtgta aacatgactt ccaagctggc cgtggctctc | 180 |
| ttggcagcct tcctgatttc tgcagctctg tgtgaaggtg cagttttgcc aaggagtgct | 240 |
| aaagaactta gatgtcagtg cataaagaca tactccaaac ctttccaccc caaatttatc | 300 |
| aaagaactga gagtgattga gagtggacca cactgcgcca acacagaaat tattgtaaag | 360 |
| ctttctgatg gaagagagct ctgtctggac cccaaggaaa actgggtgca gaggggttgtg | 420 |
| gagaagtttt tgaagagggc tgagaattca taaaaaaatt cattctctgt ggtatccaag | 480 |
| aatcagtgaa gatgccagtg aaacttcaag caaatctact tcaacacttc atgtattgtg | 540 |
| tgggtctgtt gtagggttgc cagatgcaat acaagattcc tggttaaatt tgaatttcag | 600 |
| taaacaatga atagttttc attgtaccat gaaatatcca gaacatactt atatgtaaag | 660 |
| tattatttat ttgaatctac aaaaaacaac aaataatttt taaatataag gattttccta | 720 |
| gatattgcac gggagaatat acaaatagca aaattgaggc caagggccaa gagaatatcc | 780 |
| gaactttaat ttcaggaatt gaatgggttt gctagaatgt gatatttgaa gcatcacata | 840 |
| aaaatgatgg gacaataaat tttgccataa agtcaaattt agctggaaat cctggatttt | 900 |
| tttctgttaa atctggcaac cctagtctgc tagccaggat ccacaagtcc ttgttccact | 960 |
| gtgccttggt ttctccttta tttctaagtg gaaaaagtat tagccaccat cttacctcac | 1020 |
| agtgatgttg tgaggacatg tggaagcact ttaagttttt tcatcataac ataaattatt | 1080 |
| ttcaagtgta acttattaac ctatttatta tttatgtatt tatttaagca tcaaatattt | 1140 |
| gtgcaagaat ttggaaaaat agaagatgaa tcattgattg aatagttata aagatgttat | 1200 |

-continued

| | |
|---|---|
| agtaaattta ttttattta gatattaaat gatgttttat tagataaatt tcaatcaggg | 1260 |
| ttttagatt aaacaaacaa acaattgggt acccagttaa attttcattt cagataaaca | 1320 |
| acaaataatt tttagtata agtacattat tgtttatctg aaattttaat tgaactaaca | 1380 |
| atcctagttt gatactccca gtcttgtcat tgccagctgt gttggtagtg ctgtgttgaa | 1440 |
| ttacggaata atgagttaga actattaaaa cagccaaaac tccacagtca atattagtaa | 1500 |
| tttcttgctg gttgaaactt gtttattatg tacaaataga ttcttataat attatttaaa | 1560 |
| tgactgcatt tttaaataca aggctttata tttttaactt taagatgttt ttatgtgctc | 1620 |
| tccaaatttt ttttactgtt tctgattgta tggaaatata aaagtaaata tgaaacattt | 1680 |
| aaaatataat ttgttgtcaa agtaaaaaaa aaaaaaaa | 1718 |

<210> SEQ ID NO 89
<211> LENGTH: 2344
<212> TYPE: DNA
<213> ORGANISM: Homo sapiens
<220> FEATURE:
<221> NAME/KEY: CXCL16
<222> LOCATION: (1)..(2344)

<400> SEQUENCE: 89

| | |
|---|---|
| ggtgcgtccg cgggtggctg ccccgcaggt gcgcgcggcc ggggctggcg gcgactctct | 60 |
| ccaccgggcc gcccgggagg ctcatgcagc gcggctgggt cccgcggcgc ccggatcggg | 120 |
| gaagtgaaag tgcctcggag gaggagggcc ggtccggcag tgcagccgcc tcacaggtcg | 180 |
| gcggacgggc caggcgggcg gcctcctgaa ccgaaccgaa tcggctcctc gggccgtcgt | 240 |
| cctcccgccc ctcctcgccc gccgccggag ttttcttcg gtttcttcca agattcctgg | 300 |
| ccttccctcg acggagccgg gcccagtgcg gggcgcagg gcgcgggagc tccacctcct | 360 |
| cggcttttccc tgcgtccaga ggctggcatg gcgcgggccg agtactgagc gcacggtcgg | 420 |
| ggcacagcag ggccggggg tgcagctggc tcgcgcctcc tctccggccg ccgtctcctc | 480 |
| cggtccccgg cgaaagccat tgagacacca gctggacgtc acgcgccgga gcatgtctgg | 540 |
| gagtcagagc gaggtggctc catccccgca gagtccgcgg agccccgaga tgggacggga | 600 |
| cttgcggccc gggtcccgcg tgctcctgct cctgcttctg ctcctgctgg tgtacctgac | 660 |
| tcagccaggc aatggcaacg agggcagcgt cactggaagt tgttattgtg gtaaaagaat | 720 |
| ttcttccgac tccccgccat cggttcagtt catgaatcgt ctccggaaac acctgagagc | 780 |
| ttaccatcgg tgtctatact acacgaggtt ccagctcctt tcctggagcg tgtgtggggg | 840 |
| caacaaggac ccatgggttc aggaattgat gagctgtctt gatctcaaag aatgtggaca | 900 |
| tgcttactcg gggattgtgg cccaccgaaa gcatttactt cctaccagcc ccccaatttc | 960 |
| tcaggcctca gagggggcat cttcagatat ccacacccct gcccagatgc tcctgtccac | 1020 |
| cttgcagtcc actcagcgcc ccaccctccc agtaggatca ctgtcctcgg acaaagagct | 1080 |
| cactcgtccc aatgaaacca ccattcacac tgcgggccac agtctggcag ctgggcctga | 1140 |
| ggctggggag aaccagaagc agccggaaaa aaatgctggt cccacagcca ggacatcagc | 1200 |
| cacagtgcca gtcctgtgcc tcctggccat catcttcatc ctcaccgcag ccctttccta | 1260 |
| tgtgctgtgc aagaggagga gggggcagtc accgcagtcc tctccagatc tgccggttca | 1320 |
| ttatatacct gtggcacctg actctaatac ctgagccaag aatggaagct tgtgaggaga | 1380 |
| cggactctat gttgcccagg ctgttatgga actcctgagt caagtgatcc tcccaccttg | 1440 |
| gcctctgaag gtgcgaggat tataggcgtc acctaccaca tccagcctac acgtatttgt | 1500 |
| taatatctaa cataggacta accagccact gccctctctt aggcccctca tttaaaaacg | 1560 |

-continued

```
gttatactat aaaatctgct tttcacactg ggtgataata acttggacaa attctatgtg    1620
tattttgttt tgttttgctt tgctttgttt tgagacggag tctcgctctg tcatccaggc    1680
tggagtgcag tggcatgatc tcggctcact gcaaccccca tctcccaggt tcaagcgatt    1740
ctcctgcctc ctcctgagta gctgggacta caggtgctca ccaccacacc cggctaattt    1800
tttgtatttt tagtagagac ggggtttcac catgttgacc aggctggtct cgaactcctg    1860
acctggtgat ctgcccaccc aggcctccca aagtgctggg attaaaggtg tgagccacca    1920
tgcctggccc tatgtgtgtt ttttaactac taaaaattat ttttgtaatg attgagtctt    1980
ctttatggaa acaactggcc tcagcccttg cgcccttact gtgattcctg gcttcatttt    2040
ttgctgatgg ttcccccctcg tcccaaatct ctctcccagt acaccagttg ttcctccccc    2100
acctcagccc tctcctgcat cctcctgtac ccgcaacgaa ggcctgggct ttcccaccct    2160
ccctccttag caggtgccgt gctgggacac catacgggtt ggtttcacct cctcagtccc    2220
ttgcctaccc cagtgagagt ctgatcttgt ttttattgtt attgcttttta ttattattgc    2280 ttttattatc attaaaactc tagttcttgt tttgtctctc cgaaaaaaaa aaaaaaaaa     2340 aaaa                                                                 2344
```

<210> SEQ ID NO 90
<211> LENGTH: 2502
<212> TYPE: DNA
<213> ORGANISM: Homo sapiens
<220> FEATURE:
<221> NAME/KEY: CXCR1
<222> LOCATION: (1)..(2502)

<400> SEQUENCE: 90

```
tattcatcaa gtgccctcta gctgttaagt cactctgatc tctgactgca gctcctactg      60
ttggacacac ctggccggtg cttcagttag atcaaaccat tgctgaaact gaagaggaca     120
tgtcaaatat tacagatcca cagatgtggg attttgatga tctaaatttc actggcatgc     180
cacctgcaga tgaagattac agcccctgta tgctagaaac tgagacactc aacaagtatg     240
ttgtgatcat cgcctatgcc ctagtgttcc tgctgagcct gctgggaaac tccctggtga     300
tgctggtcat cttatacagc agggtcggcc gctccgtcac tgatgtctac ctgctgaacc     360
tggccttggc cgacctactc tttgccctga ccttgcccat ctgggccgcc tccaaggtga     420
atggctggat ttttggcaca ttcctgtgca aggtggtctc actcctgaag gaagtcaact     480
tctacagtgg catcctgctg ttggcctgca tcagtgtgga ccgttacctg gccattgtcc     540
atgccacacg cacactgacc cagaagcgtc acttggtcaa gtttgtttgt cttggctgct     600
ggggactgtc tatgaatctg tccctgccct tcttcctttt ccgccaggct taccatccaa     660
acaattccag tccagtttgc tatgaggtcc tgggaaatga cacagcaaaa tggcggatgg     720
tgttgcggat cctgcctcac acctttgct tcatcgtgcc gctgtttgtc atgctgttct     780
gctatggatt caccctgcgt acactgttta aggcccacat ggggcagaag caccgagcca     840
tgagggtcat ctttgctgtc gtcctcatct tcctgctttg ctggctgccc tacaacctgg     900
tcctgctggc agacaccctc atgaggaccc aggtgatcca ggagagctgt gagcgccgca     960
acaacatcgg ccgggccctg gatgccactg agattctggg attttctccat agctgcctca    1020 accccatcat ctacgccttc atcggccaaa attttcgcca tggattcctc aagatcctgg    1080
ctatgcatgg cctggtcagc aaggagttct tggcacgtca tcgtgttacc tcctacactt    1140
cttcgtctgt caatgtctct tccaacctct gaaaaccatc gatgaaggaa tatctcttct    1200
```

-continued

| | |
|---|---|
| cagaaggaaa gaataaccaa caccctgagg ttgtgtgtgg aaggtgatct ggctctggac | 1260 |
| aggcactatc tgggttttgg ggggacgcta taggatgtgg ggaagttagg aactggtgtc | 1320 |
| ttcaggggcc acaccaacct tctgaggagc tgttgaggta cctccaagga ccggcctttg | 1380 |
| cacctccatg gaaacgaagc accatcattc ccgttgaacg tcacatcttt aacccactaa | 1440 |
| ctggctaatt agcatggcca catctgagcc ccgaatctga cattagatga gagaacaggg | 1500 |
| ctgaagctgt gtcctcatga gggctggatg ctctcgttga ccctcacagg agcatctcct | 1560 |
| caactctgag tgttaagcgt tgagccacca agctggtggc tctgtgtgct ctgatccgag | 1620 |
| ctcagggggg tggttttccc atctcaggtg tgttgcagtg tctgctggag acattgaggc | 1680 |
| aggcactgcc aaaacatcaa cctgccagct ggccttgtga ggagctggaa acacatgttc | 1740 |
| cccttggggg tggtggatga acaaagagaa agagggtttg gaagccagat ctatgccaca | 1800 |
| agaacccect ttaccccat gaccaacatc gcagacacat gtgctggcca cctgctgagc | 1860 |
| cccaagtgga acgagacaag cagcccttag cccttcccct ctgcagcttc caggctggcg | 1920 |
| tgcagcatca gcatccctag aaagccatgt gcagccacca gtccattggg caggcagatg | 1980 |
| ttcctaataa agcttctgtt ccgtgcttgt ccctgtggaa gtatcttggt tgtgacagag | 2040 |
| tcaagggtgt gtgcagcatt gttggctgtt cctgcagtag aatgggggca gcacctccta | 2100 |
| agaaggcacc tctctgggtt gaagggcagt gttccctggg gctttaactc ctgctagaac | 2160 |
| agtctcttga ggcacagaaa ctcctgttca tgcccatacc cctggccaag aagatccct | 2220 |
| ttgtccacaa gtaaaggaa atgctcctcc agggagtctc agcttcaccc tgaggtgagc | 2280 |
| atcatcttct gggttaggcc ttgcctaggc atagccctgc ctcaagctat gtgagctcac | 2340 |
| cagtccctcc ccaaatgctt tccatgagtt gcagtttttt cctagtctgt tttccctcct | 2400 |
| tggagacagg gccctgtcgg tttattcact gtatgtcctt ggtgcctgga gcctactaaa | 2460 |
| tgctcaataa ataatgatca caggaaaaaa aaaaaaaaaa aa | 2502 |

<210> SEQ ID NO 91
<211> LENGTH: 2880
<212> TYPE: DNA
<213> ORGANISM: Homo sapiens
<220> FEATURE:
<221> NAME/KEY: CXCR2
<222> LOCATION: (1)..(2880)

<400> SEQUENCE: 91

| | |
|---|---|
| aggttcaaaa cattcagaga cagaaggtgg atagacaaat ctccaccttc agactggtag | 60 |
| gctcctccag aagccatcag acaggaagat gtgaaaatcc ccagcactca tcccagaatc | 120 |
| actaagtggc acctgtcctg ggccaaagtc ccaggacaga cctcattgtt cctctgtggg | 180 |
| aatacctccc caggagggca tcctggattt ccccccttgca acccaggtca gaagtttcat | 240 |
| cgtcaaggtt gtttcatctt ttttttcctg tctaacagct ctgactacca cccaaccttg | 300 |
| aggcacagtg aagacatcgg tggccactcc aataacagca ggtcacagct gctcttctgg | 360 |
| aggtgtccta caggtgaaaa gcccagcgac ccagtcagga tttaagttta cctcaaaaat | 420 |
| ggaagatttt aacatggaga gtgacagctt tgaagatttc tggaaaggtg aagatcttag | 480 |
| taattacagt tacagctcta ccctgccccc ttttctacta gatgccgccc catgtgaacc | 540 |
| agaatccctg gaaatcaaca agtatttgt ggtcattatc tatgccctgg tattcctgct | 600 |
| gagcctgctg ggaaactccc tcgtgatgct ggtcatctta tacagcaggg tcggccgctc | 660 |
| cgtcactgat gtctacctgc tgaacctagc cttggccgac ctactctttg ccctgaccct | 720 |
| gcccatctgg gccgcctcca aggtgaatgg ctggattttt ggcacattcc tgtgcaaggt | 780 |

```
ggtctcactc ctgaaggaag tcaacttcta tagtggcatc ctgctactgg cctgcatcag    840
tgtggaccgt tacctggcca ttgtccatgc cacacgcaca ctgacccaga agcgctactt    900
ggtcaaattc atatgtctca gcatctgggg tctgtccttg ctcctggccc tgcctgtctt    960
acttttccga aggaccgtct actcatccaa tgttagccca gcctgctatg aggacatggg   1020
caacaataca gcaaactggc ggatgctgtt acggatcctg ccccagtcct ttggcttcat   1080
cgtgccactg ctgatcatgc tgttctgcta cggattcacc ctgcgtacgc tgtttaaggc   1140
ccacatgggg cagaagcacc gggccatgcg ggtcatcttt gctgtcgtcc tcatcttcct   1200
gctctgctgg ctgccctaca acctggtcct gctggcagac accctcatga ggacccaggt   1260
gatccaggag acctgtgagc gccgcaatca catcgaccgg gctctggatg ccaccgagat   1320
tctgggcatc cttcacagct gcctcaaccc cctcatctac gccttcattg ccagaagtt   1380 tcgccatgga ctcctcaaga ttctagctat acatggcttg atcagcaagg actccctgcc   1440
caaagacagc aggccttcct ttgttggctc ttcttcaggg cacacttcca ctactctcta   1500
agacctcctg cctaagtgca gccccgtggg gttcctccct tctcttcaca gtcacattcc   1560
aagcctcatg tccactggtt cttcttggtc tcagtgtcaa tgcagccccc attgtggtca   1620
caggaagtag aggaggccac gttcttacta gtttcccttg catggtttag aaagcttgcc   1680
ctggtgcctc acccccttgcc ataattacta tgtcatttgc tggagctctg cccatcctgc   1740
ccctgagccc atggcactct atgttctaag aagtgaaaat ctacactcca gtgagacagc   1800
tctgcatact cattaggatg gctagtatca aagaaagaa atcaggctg ccaacgggg   1860 tgaaaccctg tctctactaa aaatacaaaa aaaaaaaaa attagccggg cgtggtggtg   1920
agtgcctgta atcacagcta cttgggaggc tgagatggga gaatcacttg aacccgggag   1980
gcagaggttg cagtgagccg agattgtgcc cctgcactcc agcctgagcg acagtgagac   2040
tctgtctcag tccatgaaga tgtagaggag aaactggaac tctcgagcgt tgctgggggg   2100
gattgtaaaa tggtgtgacc actgcagaag acagtatggc agctttcctc aaaacttcag   2160
acatagaatt aacacatgat cctgcaattc cacttatagg aattgaccca caagaaatga   2220
aagcagggac ttgaacccat atttgtacac caatattcat agcagcttat tcacaagacc   2280
caaaaggcag aagcaaccca aatgttcatc aatgaatgaa tgaatggcta agcaaaatgt   2340
gatatgtacc taacgaagta tccttcagcc tgaaagagga atgaagtact catacatgtt   2400
acaacacgga cgaaccttga aactttatg ctaagtgaaa taagccagac atcaacagat   2460
aaatagttta tgattccacc tacatgaggt actgagagtg aacaaattta cagagacaga   2520
aagcagaaca gtgattacca gggactgagg ggaggggagc atgggaagtg acggtttaat   2580
gggcacaggg tttatgttta ggatgttgaa aaagttctgc agataaacag tagtgatagt   2640
tgtaccgcaa tgtgacttaa tgccactaaa ttgacactta aaaatggttt aaatggtcaa   2700
ttttgttatg tatatttat atcaatttaa aaaaaacct gagccccaaa aggtatttta   2760
atcaccaagg ctgattaaac caaggctaga accacctgcc tatattttt gttaaatgat   2820 ttcattcaat atctttttt taataaacca tttttacttg ggtgtttata aaaaaaaaaa   2880
```

<210> SEQ ID NO 92
<211> LENGTH: 1912
<212> TYPE: DNA
<213> ORGANISM: Homo sapiens
<220> FEATURE:
<221> NAME/KEY: CXCR4a
<222> LOCATION: (1)..(1912)

<400> SEQUENCE: 92

```
tttttttct tccctctagt gggcggggca gaggagttag ccaagatgtg actttgaaac      60
cctcagcgtc tcagtgccct tttgttctaa acaaagaatt ttgtaattgg ttctaccaaa     120
gaaggatata atgaagtcac tatgggaaaa gatgggagg agagttgtag gattctacat      180
taattctctt gtgcccttag cccactactt cagaatttcc tgaagaaagc aagcctgaat     240
tggttttta aattgcttta aaatttttt ttaactgggt taatgcttgc tgaattggaa       300
gtgaatgtcc attcctttgc ctcttttgca gatatacact tcagataact acaccgagga    360
aatgggctca ggggactatg actccatgaa ggaaccctgt ttccgtgaag aaaatgctaa    420
tttcaataaa atcttcctgc ccaccatcta ctccatcatc ttcttaactg gcattgtggg    480
caatggattg gtcatcctgg tcatgggtta ccagaagaaa ctgagaagca tgacggacaa    540
gtacaggctg cacctgtcag tggccgacct cctctttgtc atcacgcttc ccttctgggc    600
agttgatgcc gtggcaaact ggtactttgg gaacttccta tgcaaggcag tccatgtcat    660
ctacacagtc aacctctaca gcagtgtcct catcctggcc ttcatcagtc tggaccgcta    720
cctggccatc gtccacgcca ccaacagtca gaggccaagg aagctgttgg ctgaaaaggt   780
ggtctatgtt ggcgtctgga tccctgccct cctgctgact attcccgact tcatctttgc   840
caacgtcagt gaggcagatg acagatatat ctgtgaccgc ttctacccca atgacttgtg   900
ggtggttgtg ttccagtttc agcacatcat ggttggcctt atcctgcctg gtattgtcat   960
cctgtcctgc tattgcatta tcatctccaa gctgtcacac tccaagggcc accagaagcg  1020
caaggccctc aagaccacag tcatcctcat cctggctttc ttcgcctgtt ggctgccta    1080
ctacattggg atcagcatcg actccttcat cctcctggaa atcatcaagc aagggtgtga  1140
gtttgagaac actgtgcaca gtggatttc catcaccgag gccctagctt tcttccactg   1200
ttgtctgaac cccatcctct atgctttcct tggagccaaa tttaaaacct ctgcccagca  1260
cgcactcacc tctgtgagca gagggtccag cctcaagatc ctctccaaag gaaagcgagg  1320
tggacattca tctgttttcca ctgagtctga gtcttcaagt tttcactcca gctaacacag 1380
atgtaaaaga ctttttttta tacgataaat aactttttt taagttacac attttttcaga  1440
tataaaagac tgaccaatat tgtacagttt ttattgcttg ttggattttt gtcttgtgtt   1500
tctttagttt ttgtgaagtt taattgactt atttatataa attttttttg tttcatattg  1560
atgtgtgtct aggcaggacc tgtggccaag ttcttagttg ctgtatgtct cgtggtagga  1620
ctgtagaaaa gggaactgaa cattccgag cgtgtagtga atcacgtaaa gctagaaatg  1680
atccccagct gtttatgcat agataatctc tccattcccg tggaacgttt ttcctgttct   1740
taagacgtga ttttgctgta gaagatggca cttataacca aagcccaaag tggtatagaa  1800
atgctggttt ttcagttttc aggagtgggt tgatttcagc acctacagtg tacagtcttg  1860
tattaagttg ttaataaaag tacatgttaa acttaaaaaa aaaaaaaaaa aa           1912
```

<210> SEQ ID NO 93
<211> LENGTH: 1691
<212> TYPE: DNA
<213> ORGANISM: Homo sapiens
<220> FEATURE:
<221> NAME/KEY: CXCR4b
<222> LOCATION: (1)..(1691)

<400> SEQUENCE: 93

```
aacttcagtt tgttggctgc ggcagcaggt agcaaagtga cgccgagggc ctgagtgctc     60
cagtagccac cgcatctgga gaaccagcgg ttaccatgga ggggatcagt atatacactt   120
```

```
cagataacta caccgaggaa atgggctcag gggactatga ctccatgaag gaaccctgtt    180
tccgtgaaga aaatgctaat ttcaataaaa tcttcctgcc caccatctac tccatcatct    240
tcttaactgg cattgtgggc aatggattgg tcatcctggt catgggttac cagaagaaac    300
tgagaagcat gacggacaag tacaggctgc acctgtcagt ggccgacctc ctctttgtca    360
tcacgcttcc cttctgggca gttgatgccg tggcaaactg gtactttggg aacttcctat    420
gcaaggcagt ccatgtcatc tacacagtca acctctacag cagtgtcctc atcctggcct    480
tcatcagtct ggaccgctac ctggccatcg tccacgccac caacagtcag aggccaagga    540
agctgttggc tgaaaaggtg gtctatgttg gcgtctggat ccctgccctc ctgctgacta    600
ttcccgactt catctttgcc aacgtcagtg aggcagatga cagatatatc tgtgaccgct    660
tctaccccaa tgacttgtgg gtggttgtgt tccagtttca gcacatcatg gttggcctta    720
tcctgcctgg tattgtcatc ctgtcctgct attgcattat catctccaag ctgtcacact    780
ccaagggcca ccagaagcgc aaggccctca agaccacagt catcctcatc ctggctttct    840
tcgcctgttg gctgccttac tacattggga tcagcatcga ctccttcatc ctcctggaaa    900
tcatcaagca agggtgtgag tttgagaaca ctgtgcacaa gtggatttcc atcaccgagg    960
ccctagcttt cttccactgt gtgctgaacc ccatcctcta tgctttcctt ggagccaaat   1020
ttaaaacctc tgcccagcac gcactcacct ctgtgagcag agggtccagc tcaagatcc   1080 tctccaaagg aaagcgaggt ggacattcat ctgtttccac tgagtctgag tcttcaagtt   1140
ttcactccag ctaacacaga gtaaaagac tttttttat acgataaata acttttttt    1200 aagttacaca ttttcagat ataaaagact gaccaatatt gtacagtttt tattgcttgt   1260 tggattttg tcttgtgttt ctttagtttt tgtgaagttt aattgactta tttatataa    1320 tttttttgt ttcatattga tgtgtgtcta ggcaggacct gtggccaagt tcttagttgc   1380
tgtatgtctc gtggtaggac tgtagaaaag ggaactgaac attccagagc gtgtagtgaa   1440
tcacgtaaag ctagaaatga tccccagctg tttatgcata gataatctct ccattcccgt   1500
ggaacgtttt tcctgttctt aagacgtgat tttgctgtag aagatggcac ttataaccaa   1560
agcccaaagt ggtatagaaa tgctggtttt tcagttttca ggagtgggtt gatttcagca   1620
cctacagtgt acagtcttgt attaagttgt taataaaagt acatgttaaa cttaaaaaaa   1680
aaaaaaaaaa a                                                         1691

<210> SEQ ID NO 94
<211> LENGTH: 1953
<212> TYPE: DNA
<213> ORGANISM: Homo sapiens
<220> FEATURE:
<221> NAME/KEY: CXCR6
<222> LOCATION: (1)..(1953)

<400> SEQUENCE: 94
gcagaccttg cttcatgagc aagctcatct ctggaacaaa ctggcaaagc atctctgctg     60
gtgttcatca gaacagacac catggcagag catgattacc atgaagacta tgggttcagc    120
agtttcaatg acagcagcca ggaggagcat caagacttcc tgcagttcag caaggtcttt    180 ctgcccctgca tgtacctggt ggtgtttgtc tgtggtctgg tggggaactc tctggtgctg    240
gtcatatcca tcttctacca taagttgcag agcctgacgg atgtgttcct ggtgaaccta    300 ccctgctg acctggtgtt tgtctgcact ctgccttct gggcctatgc aggcatccat    360
gaatgggtgt ttggccaggt catgtgcaag agcctactgg gcatctacac tattaacttc    420
```

| | |
|---|---|
| tacacgtcca tgctcatcct cacctgcatc actgtggatc gtttcattgt agtggttaag | 480 |
| gccaccaagg cctacaacca gcaagccaag aggatgacct ggggcaaggt caccagcttg | 540 |
| ctcatctggg tgatatccct gctggtttcc ttgccccaaa ttatctatgg caatgtcttt | 600 |
| aatctcgaca agctcatatg tggttaccat gacgaggcaa tttccactgt ggttcttgcc | 660 |
| acccagatga cactggggtt cttcttgcca ctgctcacca tgattgtctg ctattcagtc | 720 |
| ataatcaaaa cactgcttca tgctggaggc ttccagaagc acagatctct aaagatcatc | 780 |
| ttcctggtga tggctgtgtt cctgctgacc cagatgccct tcaacctcat gaagttcatc | 840 |
| cgcagcacac actgggaata ctatgccatg accagctttc actacaccat catggtgaca | 900 |
| gaggccatcg catacctgag ggcctgcctt aaccctgtgc tctatgcctt tgtcagcctg | 960 |
| aagtttcgaa agaacttctg gaaacttgtg aaggacattg gttgcctccc ttaccttggg | 1020 |
| gtctcacatc aatggaaatc ttctgaggac aattccaaga ctttttctgc ctcccacaat | 1080 |
| gtggaggcca ccagcatgtt ccagttatag gccttgccag ggtttcgaga agctgctctg | 1140 |
| gaatttgcaa gtcatggctg tgccctcttg atgtggtgag gcaggctttg tttatagctt | 1200 |
| gcgcattctc atggagaagt tatcagacac tctggctggt ttggaatgct tcttctcagg | 1260 |
| catgaacatg tactgttctc ttcttgaaca ctcatgctga aagcccaagt agggggtcta | 1320 |
| aaattttaa ggactttcct tcctccatct ccaagaatgc tgaaaccaag ggggatgaca | 1380 |
| tgtgactcct atgatctcag gttctccttg attgggactg gggctgaagg ttgaagaggt | 1440 |
| gagcacggcc aacaaagctg ttgatggtag gtggcacact gggtgcccaa gctcagaagg | 1500 |
| ctcttctgac tactgggcaa agagtgtaga tcagagcagc agtgaaaaca agtgctggca | 1560 |
| ccaccaggca cctcacagaa atgagatcag gctctgcctc accttggggc ttgacttttg | 1620 |
| tataggtaga tgttcagatt gctttgatta atccagaata actagcacca gggactatga | 1680 |
| atgggcaaaa ctgaattata agaggctgat aattccagtg gtccatggaa tgcttgaaaa | 1740 |
| atgtgcaaaa cagcgtttaa gactgtaatg aatctaagca gcatttctga agtggactct | 1800 |
| ttggtggctt tgcatttta aaatgaaatt ttccaatgtc tgccacacaa acgtatgtaa | 1860 |
| atgtatatac ccacacacat acacacatat gtcatatatt actagcatat gagtttcata | 1920 |
| gctaagaaat aaaactgtta aagtctccaa act | 1953 |

<210> SEQ ID NO 95
<211> LENGTH: 542
<212> TYPE: DNA
<213> ORGANISM: Homo sapiens
<220> FEATURE:
<221> NAME/KEY: CCL1
<222> LOCATION: (1)..(542)

<400> SEQUENCE: 95

| | |
|---|---|
| acagtggtga gctcttagct tcaccaggct catcaaagct gctccaggaa ggcccaagcc | 60 |
| agaccagaag acatgcagat catcaccaca gccctggtgt gcttgctgct agctgggatg | 120 |
| tggccggaag atgtggacag caagagcatg caggtaccct ctccagatg ttgcttctca | 180 |
| tttgcggagc aagagattcc cctgagggca atcctgtgtt acagaaatac cagctccatc | 240 |
| tgctccaatg agggcttaat attcaagctg aagagaggca agaggcctg cgccttggac | 300 |
| acagttggat gggttcagag gcacagaaaa atgctgaggc actgcccgtc aaaaagaaaa | 360 |
| tgagcagatt tctttccatt gtgggctctg gaaaccacat ggcttcacct gtccccgaaa | 420 |
| ctaccagccc tacaccattc cttctgccct gcttttgcta ggtcacagag gatctgcttg | 480 |
| gtcttgataa gctatgttgt tgcacttta acatttaaat tatacaatca tcaaccccca | 540 |

```
ac                                                                 542

<210> SEQ ID NO 96
<211> LENGTH: 760
<212> TYPE: DNA
<213> ORGANISM: Homo sapiens
<220> FEATURE:
<221> NAME/KEY: CCL2
<222> LOCATION: (1)..(760)

<400> SEQUENCE: 96
gaggaaccga gaggctgaga ctaacccaga aacatccaat tctcaaactg aagctcgcac     60
tctcgcctcc agcatgaaag tctctgccgc ccttctgtgc ctgctgctca tagcagccac    120
cttcattccc caagggctcg ctcagccaga tgcaatcaat gccccagtca cctgctgtta    180
taacttcacc aataggaaga tctcagtgca gaggctcgcg agctatagaa gaatcaccag    240
cagcaagtgt cccaaagaag ctgtgatctt caagaccatt gtggccaagg agatctgtgc    300
tgaccccaag cagaagtggg ttcaggattc catggaccac ctggacaagc aaacccaaac    360
tccgaagact tgaacactca ctccacaacc caagaatctg cagctaactt attttcccct    420
agctttcccc agacaccctg ttttatttta ttataatgaa ttttgtttgt tgatgtgaaa    480
cattatgcct taagtaatgt taattcttat ttaagttatt gatgttttaa gtttatcttt    540
catggtacta gtgttttta gatacagaga cttggggaaa ttgcttttcc tcttgaacca    600
cagttctacc cctgggatgt tttgagggtc tttgcaagaa tcattaatac aaagaatttt    660
ttttaacatt ccaatgcatt gctaaaatat tattgtggaa atgaatattt tgtaactatt    720
acaccaaata aatatatttt tgtacaaaaa aaaaaaaaa                          760

<210> SEQ ID NO 97
<211> LENGTH: 813
<212> TYPE: DNA
<213> ORGANISM: Homo sapiens
<220> FEATURE:
<221> NAME/KEY: CCL3
<222> LOCATION: (1)..(813)

<400> SEQUENCE: 97
agctggtttc agacttcaga aggacacggg cagcagacag tggtcagtcc tttcttggct     60
ctgctgacac tcgagcccac attccgtcac ctgctcagaa tcatgcaggt ctccactgct    120
gcccttgctg tcctcctctg caccatggct ctctgcaacc agttctctgc atcacttgct    180
gctgacacgc cgaccgcctg ctgcttcagc tacacctccc ggcagattcc acagaatttc    240
atagctgact actttgagac gagcagccag tgctccaagc ccgtgtgcat cttcctaacc    300
aagcgaagcc ggcaggtctg tgctgacccc agtgaggagt gggtccagaa atatgtcagc    360
gacctggagc tgagtgcctg aggggtccag aagcttcgag gcccagcgac ctcggtgggc    420
ccagtgggga ggagcaggag cctgagcctt gggaacatgc gtgtgacctc cacagctacc    480
tcttctatgg actggttgtt gccaaacagc cacactgtgg gactcttctt aacttaaatt    540
ttaatttatt tatactattt agttttgta atttatttc gatttcacag tgtgtttgtg    600
attgtttgct ctgagagttc ccctgtcccc tccccttcc ctcacaccgc gtctggtgac    660
aaccgagtgg ctgtcatcag cctgtgtagg cagtcatggc accaaagcca ccagactgac    720
aaatgtgtat cggatgcttt tgttcagggc tgtgatcggc ctggggaaat aataaagatg    780 ctctttaaa aggtaaaaaa aaaaaaaaaa aaa                                 813
```

```
<210> SEQ ID NO 98
<211> LENGTH: 667
<212> TYPE: DNA
<213> ORGANISM: Homo sapiens
<220> FEATURE:
<221> NAME/KEY: CCL4
<222> LOCATION: (1)..(667)

<400> SEQUENCE: 98
agcacaggac acagctgggt tctgaagctt ctgagttctg cagcctcacc tctgagaaaa      60
cctctttgcc accaatacca tgaagctctg cgtgactgtc ctgtctctcc tcatgctagt    120
agctgccttc tgctctccag cgctctcagc accaatgggc tcagaccctc ccaccgcctg    180
ctgcttttct tacactgcga ggaagcttcc tcgcaacttt gtggtagatt actatgagac    240
cagcagcctc tgctcccagc cagctgtggt attccaaacc aaaagaagca agcaagtctg    300
tgctgatccc agtgaatcct gggtccagga gtacgtgtat gacctggaac tgaactgagc    360
tgctcagaga caggaagtct tcagggaagg tcacctgagc ccggatgctt ctccatgaga    420
cacatctcct ccatactcag gactcctctc cgcagttcct gtcccttctc ttaatttaat    480
ctttttatg tgccgtgtta ttgtattagg tgtcatttcc attatttata ttagtttagc    540
caaaggataa gtgtcccta tggggatggt ccactgtcac tgtttctctg ctgttgcaaa    600
tacatggata acacatttga ttctgtgtgt tttcataata aaacttaaaa ataaaatgca    660
gacagtt                                                              667

<210> SEQ ID NO 99
<211> LENGTH: 1488
<212> TYPE: DNA
<213> ORGANISM: Homo sapiens
<220> FEATURE:
<221> NAME/KEY: CCL4L1
<222> LOCATION: (1)..(1488)

<400> SEQUENCE: 99
cctcacctct gagaaaacct ctttgccacc aataccatga agctctgcgt gactgtcctg      60
tctctcctcg tgctagtagc tgccttctgc tctctagcac tctcagcacc aagtaagtct    120
acttttgcag ctgctatttc gagtcaaggt gtaggcagag tcctttttc tagtcatggc    180
tggcaaacag tgggatctgg ggatgggaca aaaggcagct aggaagattg ccatgtagtc    240
tgctgctaaa tgtagagtct agtagatatt cagtaacatt caagttccta ttttcttaag    300
aattagcaac cagcagagga aaacgatggg ctggaagtca gactgttgaa ttggctctgc    360
ctttaattat ttgttcaagc aagcccctgt ccctctctgt gccttggttt ccccatctgt    420
catatgaagg gagtgcgatg tgttctgaga ctgaatccag ttccaatctt ctagatttct    480
ttctcgttct tctctgaaga tccactattc agaataagac tcctgctcat gttaggtggg    540
aatggataca agggaccata tttggggttc tggtagctcc acagggatgc tcaatgaaga    600
tgcaaaatta gaagtcaaaa taaacagctc ccatgggcag tgttgatctc accctggcct    660
ttcctttcag tgggctcaga ccctcccacc gcctgctgct tttcttacac cgcgaggaag    720
cttcctcgca actttgtggt agattactat gagaccagca gcctctgctc ccagccagct    780
gtggtgtgag tatcaacccc tggctgccct gggaggcaag ggtgagggct ggattttaa    840
agggggcctg ttttggggag ggggtgatga gcgctgggga ggcagctctc agggctgaag    900
ccttccctga cagcagtgag gtcacaggtc atgaactcac ttttcaagtg ctgaaggcgg    960
ctgagtggca gccgagacag aagggggttc ctggggagga agttattcag aggacaggga   1020
agcaggggaa ggcagacagg tcccatgaga tatggaccaa ttccttaaac catgctagaa   1080
```

| | | |
|---|---|---|
| aaacatgtgg aaaagtcact accaggctgg cagggaatgg ggcaatctat tcatactgat | 1140 | |
| tgcaatgccc actggttcct aatctgggca accctgggg cccacagcta atccagtga | 1200 | |
| gtggaagtta cagggagtct gcttccagtg ctgctcgagg aaggatccca tccaccagag | 1260 | |
| ctgccccaca tggaccatgg tcaggcagag gaagatgcct accacaggca agggataaag | 1320 | |
| ccagatgacc tcaaaggtcc catgggattc taatctgtct gctccttgtt ctacagattc | 1380 | |
| caaaccaaaa gaggcaagca agtctgcgct gaccccagtg agtcctgggt ccaggagtac | 1440 | |
| gtgtatgacc tggaactgaa ctgagctgct cagagacagg aagtcttc | 1488 | |

<210> SEQ ID NO 100
<211> LENGTH: 1237
<212> TYPE: DNA
<213> ORGANISM: Homo sapiens
<220> FEATURE:
<221> NAME/KEY: CCL5
<222> LOCATION: (1)..(1237)

<400> SEQUENCE: 100

| | | |
|---|---|---|
| gctgcagagg attcctgcag aggatcaaga cagcacgtgg acctcgcaca gcctctccca | 60 | |
| caggtaccat gaaggtctcc gcggcagccc tcgctgtcat cctcattgct actgccctct | 120 | |
| gcgctcctgc atctgcctcc ccatattcct cggacaccac accctgctgc tttgcctaca | 180 | |
| ttgcccgccc actgccccgt gcccacatca aggagtattt ctacaccagt ggcaagtgct | 240 | |
| ccaacccagc agtcgtcttt gtcacccgaa agaaccgcca agtgtgtgcc aacccagaga | 300 | |
| agaaatgggt tcgggagtac atcaactctt tggagatgag ctaggatgga gagtccttga | 360 | |
| acctgaactt acacaaattt gcctgttcct gcttgctctt gtcctagctt gggaggcttc | 420 | |
| ccctcactat cctaccccac ccgctccttg aagggcccag attctaccac acagcagcag | 480 | |
| ttacaaaaac cttccccagg ctggacgtgg tggctcacgc ctgtaatccc agcactttgg | 540 | |
| gaggccaagg tgggtggatc acttgaggtc aggagttcga gaccagcctg ccaacatga | 600 | |
| tgaaacccca tctctactaa aaatacaaaa aattagccgg gcgtggtagc gggcgcctgt | 660 | |
| agtcccagct actcgggagg ctgaggcagg agaatggcgt gaacccggga ggcggagctt | 720 | |
| gcagtgagcc gagatcgcgc cactgcactc cagcctgggc gacagagcga gactccgtct | 780 | |
| caaaaaaaaa aaaaaaaaa aaatacaaa attagccgg gcgtggtggc ccacgcctgt | 840 | |
| aatcccagct actcgggagg ctaaggcagg aaaattgttt gaacccagga ggtggaggct | 900 | |
| gcagtgagct gagattgtgc cacttcactc cagcctgggt gacaaagtga gactccgtca | 960 | |
| caacaacaac aacaaaaagc ttccccaact aaagcctaga agagcttctg aggcgctgct | 1020 | |
| ttgtcaaaag gaagtctcta ggttctgagc tctggctttg ccttggcttt gccagggctc | 1080 | |
| tgtgaccagg aaggaagtca gcatgcctct agaggcaagg aggggaggaa cactgcactc | 1140 | |
| ttaagcttcc gccgtctcaa cccctcacag gagcttactg gcaaacatga aaaatcggct | 1200 | |
| taccattaaa gttctcaatg caaccataaa aaaaaaa | 1237 | |

<210> SEQ ID NO 101
<211> LENGTH: 810
<212> TYPE: DNA
<213> ORGANISM: Homo sapiens
<220> FEATURE:
<221> NAME/KEY: CCL7
<222> LOCATION: (1)..(810)

<400> SEQUENCE: 101

| | | |
|---|---|---|
| agcagagggg ctgagaccaa accagaaacc tccaattctc atgtggaagc ccatgccctc | 60 | |

| | | |
|---|---|---|
| accctccaac atgaaagcct ctgcagcact tctgtgtctg ctgctcacag cagctgcttt | 120 |
| cagcccccag gggcttgctc agccagttgg gattaatact tcaactacct gctgctacag | 180 |
| atttatcaat aagaaaatcc ctaagcagag gctggagagc tacagaagga ccaccagtag | 240 |
| ccactgtccc cgggaagctg taatcttcaa gaccaaactg gacaaggaga tctgtgctga | 300 |
| ccccacacag aagtgggtcc aggactttat gaagcacctg gacaagaaaa cccaaactcc | 360 |
| aaagctttga acattcatga ctgaactaaa aacaagccat gacttgagaa acaaataatt | 420 |
| tgtataccct gtcctttctc agagtggttc tgaagattatt ttaatctaat tctaaggaat | 480 |
| atgagcttta tgtaataatg tgaatcatgg ttttttcttag tagattttaa aagttattaa | 540 |
| tatttttaatt taatcttcca tggattttggg tgggttttga acataaagcc ttggatgtat | 600 |
| atgtcatctc agtgctgtaa aaactgtggg atgctcctcc cttctctacc tcatgggggt | 660 |
| attgtataag tccttgcaag aatcagtgca aagatttgct ttaattgtta agatatgatg | 720 |
| tccctatgga agcatattgt tattatataa ttacatattt gcatatgtat gactcccaaa | 780 |
| ttttcacata aatagatttt ttgtaaaaaa | 810 |

```
<210> SEQ ID NO 102
<211> LENGTH: 1351
<212> TYPE: DNA
<213> ORGANISM: Homo sapiens
<220> FEATURE:
<221> NAME/KEY: CCL8
<222> LOCATION: (1)..(1351)

<400> SEQUENCE: 102
```

| | | |
|---|---|---|
| gtgatggaga gcaccagcaa agccttaggg cccatccctg gcctcctgtt acccacagag | 60 |
| gggtaggccc ttggctctct tccactatga cgtcagcttc cattcttcct ttcttataga | 120 |
| caattttcca tttcaaggaa atcagagccc ttaatagttc agtgaggtca ctttgctgag | 180 |
| cacaatccca tacccttcag cctctgctcc acagagccta agcaaaagat agaaactcac | 240 |
| aacttccttg ttttgttatc tggaaattat cccaggatct ggtgcttact cagcatattc | 300 |
| aaggaaggtc ttacttcatt cttccttgat tgtgaccatg cccaggctct ctgctcccta | 360 |
| taaaaggcag gcagagccac cgaggagcag agaggttgag aacaacccag aaaccttcac | 420 |
| ctctcatgct gaagctcaca cccttgccct ccaagatgaa ggtttctgca gcgcttctgt | 480 |
| gcctgctgct catggcagcc actttcagcc ctcagggact tgctcagcca gattcagttt | 540 |
| ccattccaat cacctgctgc tttaacgtga tcaataggaa aattcctatc cagaggctgg | 600 |
| agagctacac aagaatcacc aacatccaat gtcccaagga agctgtgatc ttcaagacca | 660 |
| aacgggcaa ggaggtctgt gctgacccca aggagagatg ggtcagggat tccatgaagc | 720 |
| atctggacca atatttcaa atctgaagc catgagcctt catacatgga ctgagagtca | 780 |
| gagcttgaag aaaagcttat ttattttccc caacctcccc caggtgcagt gtgacattat | 840 |
| tttattataa catccacaaa gagattattt ttaaataatt taaagcataa tatttcttaa | 900 |
| aaagtattta attatattta agttgttgat gttttaactc tatctgtcat acatcctagt | 960 |
| gaatgtaaaa tgcaaaatcc tggtgatgtg ttttttgttt ttgttttcct gtgagctcaa | 1020 |
| ctaagttcac ggcaaaatgt cattgttctc cctcctacct gtctgtagtg ttgtggggtc | 1080 |
| ctcccatgga tcatcaaggt gaaacacttt ggtattcttt ggcaatcagt gctcctgtaa | 1140 |
| gtcaaatgtg tgctttgtac tgctgttgtt gaaattgatg ttactgtata taactatgga | 1200 |
| attttgaaaa aaaatttcaa aaagaaaaaa atatatataa tttaaaacta aaaaaaaaaa | 1260 |

```
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa a                                  1351

<210> SEQ ID NO 103
<211> LENGTH: 925
<212> TYPE: DNA
<213> ORGANISM: Homo sapiens
<220> FEATURE:
<221> NAME/KEY: CCL11
<222> LOCATION: (1)..(925)

<400> SEQUENCE: 103
atgggcaaag gcttccctgg aatctcccac actgtctgct ccctataaaa ggcaggcaga    60
tgggccagag gagcagagag gctgagacca acccagaaac caccacctct cacgccaaag   120
ctcacacctt cagcctccaa catgaaggtc tccgcagcac ttctgtggct gctgctcata   180
gcagctgcct tcagccccca ggggctcgct gggccagctt ctgtcccaac cacctgctgc   240
tttaacctgg ccaataggaa atacccctt cagcgactag agagctacag gagaatcacc    300
agtggcaaat gtccccagaa agctgtgatc ttcaagacca aactggccaa ggatatctgt   360
gccgacccca agaagaagtg ggtgcaggat tccatgaagt atctggacca aaaatctcca   420
actccaaagc cataaataat caccattttt gaaaccaaac cagagcctga gtgttgccta   480
atttgttttc ccttcttaca atgcattctg aggtaacctc attatcagtc caagggcat    540 gggtttatt atatatatat attttttttt ttaaaaaaaa aacgtattgc atttaattta    600
ttgaggcttt aaaacttatc ctccatgaat atcagttatt tttaaactgt aaagctttgt   660
gcagattctt taccccctgg gagccccaat tcgatcccct gtcacgtgtg gcaatgttc    720 ccctctcct ctcttcctcc ctggaatctt gtaaaggtcc tggcaaagat gatcagtatg    780
aaaatgtcat tgttcttgtg aacccaaagt gtgactcatt aaatggaagt aaatgttgtt   840
ttaggaatac ataaagtatg tgcatatttt attatagtca ctagttgtaa ttttttttgtg  900 ggaaatccac actgagctga ggggg                                         925

<210> SEQ ID NO 104
<211> LENGTH: 861
<212> TYPE: DNA
<213> ORGANISM: Homo sapiens
<220> FEATURE:
<221> NAME/KEY: CCL13
<222> LOCATION: (1)..(861)

<400> SEQUENCE: 104
aaaaggccgg cggaacagcc agaggagcag agaggcaaag aaacattgtg aaatctccaa    60
ctcttaacct tcaacatgaa agtctctgca gtgcttctgt gcctgctgct catgacagca   120
gctttcaacc cccagggact tgctcagcca gatgcactca acgtcccatc tacttgctgc   180
ttcacattta gcagtaagaa gatctccttg cagaggctga gagctatgt gatcaccacc    240 agcaggtgtc cccagaaggc tgtcatcttc agaaccaaac tgggcaagga gatctgtgct   300
gacccaaagg agaagtgggt ccagaattat atgaaacacc tgggccggaa agctcacacc   360
ctgaagactt gaactctgct accctactg aaatcaagct ggagtacgtg aaatgacttt    420
tccattctcc tctggcctcc tcttctatgc tttggaatac ttctaccata attttcaaat   480
aggatgcatt cggttttgtg attcaaaatg tactatgtgt taagtaatat tggctattat   540
ttgacttgtt gctggtttgg agtttatttg agtattgctg atcttttcta aagcaaggcc   600
ttgagcaagt aggttgctgt ctctaagccc ccttccttc cactatgagc tgctggcagt    660
```

```
gggtttgtat tcggttccca ggggttgaga gcatgcctgt gggagtcatg gacatgaagg      720
gatgctgcaa tgtaggaagg agagctcttt gtgaatgtga ggtgttgcta aatatgttat      780
tgtggaaaga tgaatgcaat agtaggactg ctgacatttt gcagaaaata cattttattt      840
aaaatctcct aaaaaaaaaa a                                                861

<210> SEQ ID NO 105
<211> LENGTH: 506
<212> TYPE: DNA
<213> ORGANISM: Homo sapiens
<220> FEATURE:
<221> NAME/KEY: CCL14-1
<222> LOCATION: (1)..(506)

<400> SEQUENCE: 105
tttctcaaca attcctcacc gcaggagcct ctgaagctcc caccaggcca gctctcctcc       60
cacaacagct tcccacagca tgaagatctc cgtggctgcc attcccttct tcctcctcat      120
caccatcgcc ctagggacca agactgaatc ctcctcacgg ggaccttacc accccctcaga    180 gtgctgcttc acctacacta cctacaagat cccgcgtcag cggattatgg attactatga      240
gaccaacagc cagtgctcca gcccggaat tgtcttcatc accaaagggg ccattccgt       300 ctgtaccaac cccagtgaca gtgggtcca ggactatatc aaggacatga aggagaactg      360
agtgacccag aaggggtggc gaaggcacag ctcagagaca taaagagaag atgccaaggc      420
cccctcctcc acccaccgct aactctcagc cccagtcacc ctcttggagc ttccctgctt      480
tgaattaaag accactcatg ctcttc                                            506

<210> SEQ ID NO 106
<211> LENGTH: 579
<212> TYPE: DNA
<213> ORGANISM: Homo sapiens
<220> FEATURE:
<221> NAME/KEY: CCL14-2
<222> LOCATION: (1)..(579)

<400> SEQUENCE: 106
tttctcaaca attcctcacc gcaggagcct ctgaagctcc caccaggcca gctctcctcc       60
cacaacagct tcccacagca tgaagatctc cgtggctgcc attcccttct tcctcctcat      120
caccatcgcc ctagggacca agactgaatc ctcctcacaa actgggggga aaccgaaggt      180
tgttaaaata cagctaaagt tggtgggggg accttaccac ccctcagagt gctgcttcac      240
ctacactacc tacaagatcc gcgtcagcg gattatggat tactatgaga ccaacagcca      300
gtgctccaag cccggaattg tcttcatcac caaaggggc cattccgtct gtaccaaccc       360
cagtgacaag tgggtccagg actatatcaa ggacatgaag gagaactgag tgacccagaa      420
ggggtggcga aggcacagct cagagacata agagaagat gccaaggccc ctcctccac        480 ccaccgctaa ctctcagccc cagtcaccct cttggagctt ccctgctttg aattaaagac      540
cactcatgct cttcaaaaaa aaaaaaaaaa aaaaaaaa                               579

<210> SEQ ID NO 107
<211> LENGTH: 1080
<212> TYPE: DNA
<213> ORGANISM: Homo sapiens
<220> FEATURE:
<221> NAME/KEY: CCL15
<222> LOCATION: (1)..(1080)

<400> SEQUENCE: 107
tctcggtctc tcactctgcc ttatacccct cagttgaatt atttcttctg aggaggcaag       60
```

```
aactgaggct gctgcagact gatatggatt caccactgct aacacctcct ggttggaact    120
acaggaatag aactggaaag ggaaaaaagg cagcattcac cacatcccaa tcctgaatcc    180
aagagtctaa gatagtcccc cactcctatc tcaggcttag aggattagat taatctcctg    240
gagggaagac tcttccttga aacattttt tttatctgcc tgtagctatt gggataattc    300
gggaaatcca cagggacagt tcaagtcatc tttgtcctct actttctgtt gcactctcag    360
ccttgttctc ttttagaaa ctgcatggta actattatat agctaaagaa gagcattctg    420
acctctgccc tctgccctgg gacttcctgg atcctcctct tcttataaat acaagggcag    480
agctggtatc ccggggagcc aggaagcagt gagcccagga gtcctcggcc agccctgcct    540
gcccaccagg aggatgaagg tctccgtggc tgccctctcc tgcctcatgc ttgttgctgt    600
ccttggatcc caggcccagt tcataaatga tgcagagaca gagttaatga tgtcaaagct    660
tccactggaa aatccagtag ttctgaacag cttcactttt gctgctgact gctgcacctc    720
ctacatctca caaagcatcc cgtgttcact catgaaaagt tattttgaaa cgagcagcga    780
gtgctccaag ccaggtgtca tattcctcac caagaagggg cggcaagtct gtgccaaacc    840
cagtggtccg ggagttcagg attgcatgaa aaagctgaag ccctactcaa tataataata    900
aagagacaaa agaggccagc cacccacctc caacacctcc tgtgagtttc ttggtctgaa    960
atacttaaaa aatatatata ttgttgtgtc tggtaatgaa agtaatgcat ctaataaga   1020 gtattcaatt ttttaacttt gcttgagttt taagaggaaa taaactaata taaaactgaa   1080
```

<210> SEQ ID NO 108
<211> LENGTH: 1497
<212> TYPE: DNA
<213> ORGANISM: Homo sapiens
<220> FEATURE:
<221> NAME/KEY: CCL16
<222> LOCATION: (1)..(1497)

<400> SEQUENCE: 108

```
cggaccacca gcaacagaca acatcttcat tcggctctcc ctgaagctgt actgcctcgc     60
tgagaggatg aaggtctccg aggctgccct gtctctcctt gtcctcatcc ttatcattac    120
ttcggcttct cgcagccagc caaaagttcc tgagtgggtg aacacccat ccacctgctg    180 cctgaagtat tatgagaaag tgttgccaag gagactagtg gtgggataca gaaaggccct    240
caactgtcac ctgccagcaa tcatcttcgt caccaagagg aaccgagaag tctgcaccaa    300
ccccaatgac gactgggtcc aagagtacat caaggatccc aacctacctt gctgcctac    360 caggaacttg tccacggtta aaattattac agcaaagaat ggtcaacccc agctcctcaa    420
ctcccagtga tgaccaggct ttagtggaag cccttgttta cagaagagag gggtaaacct    480
atgaaaacag gggaagcctt attaggctga aactagccag tcacattgag agaagcagaa    540
caatgatcaa aataaaggag aagtatttcg aatatttct caatcttagg aggaaatacc    600
aaagttaagg gacgtgggca gaggtacgct cttttatttt tatatttata tttttatttt    660
tttgagatag gtcttactc tgtcacccag gctggagtgc agtggtgtga tcttggctca    720
cttgatcttg gctcactgta acctccacct cccaggctca agtgatcctc ccacccagc    780 ctcctgagta gctgggacta caggcttgcg ccaccacacc tggctaattt ttgtattttt    840
ggtagagacg ggattctacc atgttgccca ggctggtctc aaactcgtgt gcccaagcaa    900
tccacctgcc tcagccttcc aaaagtgctg gggattacagg cgtgagccac cacatccggc    960
cagtgcactc ttaatacaca gaaaaatata tttcacatcc ttctcctgct ctctttcaat   1020
```

```
tcctcacttc acaccagtac acaagccatt ctaaatactt agccagtttc cagccttcca    1080
gatgatcttt gccctctggg tcttgaccca ttaagagccc catagaactc ttgattttc     1140 ctgtccatct ttatggattt ttctggatct atattttctt caattattct ttcattttat    1200
aatgcaactt tttcatagga agtccggatg ggaatattca cattaatcat ttttgcagag    1260
actttgctag atcctctcat attttgtctt cctcagggtg gcaggggtac agagagtgcc    1320
tgattggaaa aaaaaaaaa agagagagag agagaagaag aagaagaaga gacacaaatc     1380
tctacctccc atgttaagct tgcaggaca gggaagaaa gggtatgaga cacggctagg      1440
ggtaaactct tagtccaaaa cccaagcatg caataaataa aactcccta tttgaca        1497
```

<210> SEQ ID NO 109
<211> LENGTH: 615
<212> TYPE: DNA
<213> ORGANISM: Homo sapiens
<220> FEATURE:
<221> NAME/KEY: CCL17
<222> LOCATION: (1)..(615)

<400> SEQUENCE: 109

```
gctcagagag aagtgactt gagctcacag tgtcaccgcc tgctgatggg agagctgaat      60
tcaaaaccag ggtgtctccc tgagcagagg gacctgcaca cagagactcc ctcctgggct    120
cctggcacca tggccccact gaagatgctg gccctggtca cctcctcct gggggcttct     180 ctgcagcaca tccacgcagc tcgagggacc aatgtgggcc gggagtgctg cctggagtac    240
ttcaagggag ccattcccct tagaaagctg aagacgtggt accagacatc tgaggactgc    300
tccagggatg ccatcgtttt tgtaactgtg cagggcaggg ccatctgttc ggaccccaac    360
aacaagagag tgaagaatgc agttaaatac ctgcaaagcc ttgagaggtc ttgaagcctc    420
ctcaccccag actcctgact gtctcccggg actacctggg acctccaccg ttggtgttca    480
ccgcccccac cctgagcgcc tgggtccagg ggaggccttc cagggacgaa gaagagccac    540
agtgagggag atcccatccc cttgtctgaa ctggagccat gggcacaaag ggcccagatt    600
aaagtcttta tcctc                                                    615
```

<210> SEQ ID NO 110
<211> LENGTH: 793
<212> TYPE: DNA
<213> ORGANISM: Homo sapiens
<220> FEATURE:
<221> NAME/KEY: CCL18
<222> LOCATION: (1)..(793)

<400> SEQUENCE: 110

```
aggagttgtg agtttccaag ccccagctca ctctgaccac ttctctgcct gcccagcatc     60
atgaagggcc ttgcagctgc cctccttgtc ctcgtctgca ccatggccct ctgctcctgt    120
gcacaagttg gtaccaacaa agagctctgc tgcctcgtct ataccctg gcagattcca      180 caaaagttca tagttgacta ttctgaaacc agccccagt gccccaagcc aggtgtcatc     240
ctcctaacca agagaggccg gcagatctgt gctgacccca taagaagtg ggtccagaaa     300 tacatcagcg acctgaagct gaatgcctga ggggcctgga agctgcgagg gcccagtgaa    360
cttggtgggc ccaggaggga acaggagcct gagccgggc aatggccctg ccaccctgga     420
ggccacctct tctaagagtc ccatctgcta tgcccagcca cattaactaa ctttaatctt    480
agtttatgca tcatatttca ttttgaaatt gatttctatt gttgagctgc attatgaaat    540
tagtattttc tctgacatct catgacattg tctttatcat cctttcccct ttcccttcaa    600
```

-continued

| | | |
|---|---|---|
| ctcttcgtac attcaatgca tggatcaatc agtgtgatta gctttctcag cagacattgt | 660 | |
| gccatatgta tcaaatgaca aatcttatt gaatggtttt gctcagcacc acctttaat | 720 | |
| atattggcag tacttattat ataaaaggta aaccagcatt ctcactgtga aaaaaaaaa | 780 | |
| aaaaaaaaaa aaa | 793 | |

<210> SEQ ID NO 111
<211> LENGTH: 684
<212> TYPE: DNA
<213> ORGANISM: Homo sapiens
<220> FEATURE:
<221> NAME/KEY: CCL19
<222> LOCATION: (1)..(684)

<400> SEQUENCE: 111

| | | |
|---|---|---|
| cattcccagc ctcacatcac tcacaccttg catttcaccc ctgcatccca gtcgccctgc | 60 | |
| agcctcacac agatcctgca cacacccaga cagctggcgc tcacacattc accgttggcc | 120 | |
| tgcctctgtt caccctccat ggccctgcta ctggccctca gctgctggt tctctggact | 180 | |
| tccccagccc caactctgag tggcaccaat gatgctgaag actgctgcct gtctgtgacc | 240 | |
| cagaaaccca tccctgggta catcgtgagg aacttccact accttctcat caaggatggc | 300 | |
| tgcagggtgc tgctgtagt gttcaccaca ctgaggggcc gccagctctg tgcaccccca | 360 | |
| gaccagccct gggtagaacg catcatccag agactgcaga ggacctcagc caagatgaag | 420 | |
| cgccgcagca gttaacctat gaccgtgcag agggagcccg gagtccgagt caagcattgt | 480 | |
| gaattattac ctaacctggg gaaccgagga ccagaaggaa ggaccaggct tccagctcct | 540 | |
| ctgcaccaga cctgaccagc caggacaggg cctggggtgt gtgtgagtgt gagtgtgagc | 600 | |
| gagagggtga gtgtggtcag agtaaagctg ctccaccccc agattgcaat gctaccaata | 660 | |
| aagccgcctg gtgtttacaa ctaa | 684 | |

<210> SEQ ID NO 112
<211> LENGTH: 851
<212> TYPE: DNA
<213> ORGANISM: Homo sapiens
<220> FEATURE:
<221> NAME/KEY: CCL20-1
<222> LOCATION: (1)..(851)

<400> SEQUENCE: 112

| | | |
|---|---|---|
| agaatataac agcactccca aagaactggg tactcaacac tgagcagatc tgttctttga | 60 | |
| gctaaaaacc atgtgctgta ccaagagttt gctcctggct gctttgatgt cagtgctgct | 120 | |
| actccacctc tgcggcgaat cagaagcagc aagcaacttt gactgctgtc ttggatacac | 180 | |
| agaccgtatt cttcatccta aatttattgt gggcttcaca cggcagctgg ccaatgaagg | 240 | |
| ctgtgacatc aatgctatca tctttcacac aaagaaaaag ttgtctgtgt gcgcaaatcc | 300 | |
| aaaacagact tgggtgaaat atattgtgcg tctcctcagt aaaaagtca agaacatgta | 360 | |
| aaaactgtgg cttttctgga atggaattgg acatagccca agaacagaaa gaaccttgct | 420 | |
| ggggttggag gtttcacttg cacatcatgg aggtttagt gcttatctaa tttgtgcctc | 480 | |
| actggacttg tccaattaat gaagttgatt catattgcat catagtttgc tttgtttaag | 540 | |
| catcacatta aagttaaact gtatttatg ttatttatag ctgtaggttt tctgtgttta | 600 | |
| gctatttaat actaattttc cataagctat tttggtttag tgcaaagtat aaaattatat | 660 | |
| ttgggggga ataagattat atggactttc tgcaagcaa caagctattt ttaaaaaaa | 720 | |
| actatttaac attctttgt ttatattgtt ttgtctccta aattgttgta attgcattat | 780 | |

| aaaataagaa aaatattaat aagacaaata ttgaaaataa agaaacaaaa agttcttctg | 840 |
| ttaaaaaaaa a | 851 |

<210> SEQ ID NO 113
<211> LENGTH: 848
<212> TYPE: DNA
<213> ORGANISM: Homo sapiens
<220> FEATURE:
<221> NAME/KEY: CCL20-2
<222> LOCATION: (1)..(848)

<400> SEQUENCE: 113

| agaatataac agcactccca aagaactggg tactcaacac tgagcagatc tgttctttga | 60 |
| gctaaaaacc atgtgctgta ccaagagttt gctcctggct gctttgatgt cagtgctgct | 120 |
| actccacctc tgcggcgaat cagaagcaag caactttgac tgctgtcttg gatacacaga | 180 |
| ccgtattctt catcctaaat ttattgtggg cttcacacgg cagctggcca atgaaggctg | 240 |
| tgacatcaat gctatcatct ttcacacaaa gaaaagttg tctgtgtgcg caaatccaaa | 300 |
| acagacttgg gtgaaatata ttgtgcgtct cctcagtaaa aaagtcaaga acatgtaaaa | 360 |
| actgtggctt ttctggaatg gaattggaca tagcccaaga acagaaagaa ccttgctggg | 420 |
| gttggaggtt tcacttgcac atcatggagg gtttagtgct tatctaattt gtgcctcact | 480 |
| ggacttgtcc aattaatgaa gttgattcat attgcatcat agtttgcttt gtttaagcat | 540 |
| cacattaaag ttaaactgta tttatgtta tttatagctg taggttttct gtgtttagct | 600 |
| atttaatact aattttccat aagctatttt ggtttagtgc aaagtataaa attatatttg | 660 |
| gggggaata agattatatg gactttcttg caagcaacaa gctattttt aaaaaaaact | 720 |
| atttaacatt cttttgttta tattgttttg tctcctaaat tgttgtaatt gcattataaa | 780 |
| ataagaaaaa tattaataag acaaatattg aaaataaga aacaaaaagt tcttctgtta | 840 |
| aaaaaaaa | 848 |

<210> SEQ ID NO 114
<211> LENGTH: 2933
<212> TYPE: DNA
<213> ORGANISM: Homo sapiens
<220> FEATURE:
<221> NAME/KEY: CCL22
<222> LOCATION: (1)..(2933)

<400> SEQUENCE: 114

| gcagacacct gggctgagac atacaggaca gagcatggat cgcctacaga ctgcactcct | 60 |
| ggttgtcctc gtcctccttg ctgtggcgct tcaagcaact gaggcaggcc cctacggcgc | 120 |
| caacatggaa gacagcgtct gctgccgtga ttacgtccgt taccgtctgc ccctgcgcgt | 180 |
| ggtgaaacac ttctactgga cctcagactc ctgcccgagg cctggcgtgg tgttgctaac | 240 |
| cttcagggat aaggagatct gtgccgatcc cagagtgccc tgggtgaaga tgattctcaa | 300 |
| taagctgagc caatgaagag cctactctga tgaccgtggc cttggctcct ccaggaaggc | 360 |
| tcaggagccc tacctccctg ccattatagc tgctccccgc cagaagcctg tgccaactct | 420 |
| ctgcattccc tgatctccat ccctgtggct gtcacccttg gtcacctccg tgctgtcact | 480 |
| gccatctcc ccctgacccc tctaacccat cctctgcctc cctccctgca gtcagagggt | 540 |
| cctgttccca tcagcgattc ccctgcttaa accttccat gactccccac tgccctaagc | 600 |
| tgaggtcagt ctcccaagcc tggcatgtgg ccctctggat ctgggttcca tctctgtctc | 660 |
| cagcctgccc acttcccttc atgaatgttg ggttctagct ccctgttctc caaacccata | 720 |

|             |             |             |             |             |      |
|-------------|-------------|-------------|-------------|-------------|------|
| ctacacatcc  | cacttctggg  | tctttgcctg  | ggatgttgct  | gacacccaga  | aagtcccacc | 780  |
| acctgcacat  | gtgtagcccc  | accagccctc  | caaggcattg  | ctcgcccaag  | cagctggtaa | 840  |
| ttccatttca  | tgtattagat  | gtcccctggc  | cctctgtccc  | ctcttaataa  | ccctagtcac | 900  |
| agtctccgca  | gattcttggg  | atttgggggt  | tttctccccc  | acctctccac  | tagttggacc | 960  |
| aaggtttcta  | gctaagttac  | tctagtctcc  | aagcctctag  | catagagcac  | tgcagacagg | 1020 |
| ccctggctca  | gaatcagagc  | ccagaaagtg  | gctgcagaca  | aaatcaataa  | aactaatgtc | 1080 |
| cctcccctct  | ccctgccaaa  | aggcagttac  | atatcaatac  | agagactcaa  | ggtcactaga | 1140 |
| aatgggccag  | ctgggtcaat  | gtgaagcccc  | aaatttgccc  | agattcacct  | tcttcccccc | 1200 |
| actcccttt   | tttttttttt  | tttgagatgg  | agtttcgctc  | ttgtcaccca  | cgctggagtg | 1260 |
| caatggtgtg  | gtcttggctt  | attgaagcct  | ctgcctcctg  | ggttcaagtg  | attctcttgc | 1320 |
| ctcagcctcc  | tgagtagctg  | ggattacagg  | ttcctgctac  | cacgcccagc  | taatttttgt | 1380 |
| atttttagta  | gagacgaggc  | ttcaccatgt  | tggccaggct  | ggtctcgaac  | tcctgtcctc | 1440 |
| aggtaatccg  | cccacctcag  | cctcccaaag  | tgctgggatt  | acaggcgtga  | gccacagtgc | 1500 |
| ctggcctctt  | ccctctcccc  | acccccccc   | caacttttt   | tttttttat   | ggcagggtct | 1560 |
| cactctgtcg  | cccaggctgg  | agtgcagtgg  | cgtgatctcg  | gctcactaca  | acctcgacct | 1620 |
| cctgggttca  | agcgattctc  | ccaccccagc  | ctcccaagta  | gctgggatta  | caggtgtgtg | 1680 |
| ccactacggc  | tggctaattt  | ttgtattttt  | agtagagaca  | ggtttcacca  | tattggccag | 1740 |
| gctggtcttg  | aactcctgac  | ctcaagtgat  | ccaccttcct  | tgtgctccca  | aagtgctgag | 1800 |
| attacaggcg  | tgagctatca  | cacccagcct  | ccccctttt  | ttcctaatag  | gagactcctg | 1860 |
| tacctttctt  | cgttttacct  | atgtgtcgtg  | tctgcttaca  | tttccttctc  | ccctcaggct | 1920 |
| tttttgggt   | ggtcctccaa  | cctccaatac  | ccaggcctgg  | cctcttcaga  | gtaccccca  | 1980 |
| ttccactttc  | cctgcctcct  | tccttaaata  | gctgacaatc  | aaattcatgc  | tatggtgtga | 2040 |
| aagactacct  | ttgacttggt  | attataagct  | ggagttatat  | atgtatttga  | aaacagagta | 2100 |
| aatacttaag  | aggccaaata  | gatgaatgga  | agaattttag  | gaactgtgag  | aggggggacaa | 2160 |
| ggtggagctt  | tcctggccct  | gggaggaagc  | tggctgtggt  | agcgtagcgc  | tctctctctc | 2220 |
| tgtctgtggc  | aggaggcaaa  | gagtagggtg  | taattgagtg  | aaggaatcct  | gggtagagac | 2280 |
| cattctcagg  | tggttgggcc  | aggctaaaga  | ctgggatttg  | ggtctatcta  | tgcctttctg | 2340 |
| gctgattttt  | gtagagacgg  | ggttttgcca  | tgttacccag  | gctggtctca  | aactcctggg | 2400 |
| ctcaagcgat  | cctcctggct  | cagcctccca  | aagtgctggg  | attacaggcg  | tgagtcactg | 2460 |
| cgcctggctt  | cctcttcctc  | ttgagaaata  | ttcttttcat  | acagcaagta  | tgggacagca | 2520 |
| gtgtcccagg  | taaaggacat  | aaatgttaca  | agtgtctggt  | cctttctgag  | ggaggctggt | 2580 |
| gccgctctgc  | agggtatttg  | aacctgtgga  | attggaggag  | gccatttcac  | tccctgaacc | 2640 |
| cagcctgaca  | aatcacagtg  | agaatgttca  | ccttataggc  | ttgctgtggg  | gctcaggttg | 2700 |
| aaagtgtggg  | gagtgacact  | gcctaggcat  | ccagctcagt  | gtcatccagg  | gcctgtgtcc | 2760 |
| ctcccgaacc  | cagggtcaac  | ctgcctacca  | caggcactag  | aaggacgaat  | ctgcctactg | 2820 |
| cccatgaacg  | gggccctcaa  | gcgtcctggg  | atctccttct  | ccctcctgtc  | ctgtccttgc | 2880 |
| ccctcaggac  | tgctggaaaa  | taaatccttt  | aaaatagtaa  | aaaaaaaaa   | aaa        | 2933 |

<210> SEQ ID NO 115
<211> LENGTH: 603
<212> TYPE: DNA
<213> ORGANISM: Homo sapiens
<220> FEATURE:

```
<221> NAME/KEY: CCL23-CKbeta8
<222> LOCATION: (1)..(603)

<400> SEQUENCE: 115
ctggcatccc gagaagccag gaagcagtga gcccaggagt cctcggccag ccctgcctgc      60
ccaccaggag gatgaaggtc tccgtggctg ccctctcctg cctcatgctt gttactgccc     120
ttggatccca ggcccgggtc acaaaagatg cagagacaga gttcatgatg tcaaagcttc     180
cattggaaaa tccagtactt ctggacagat tccatgctac tagtgctgac tgctgcatct     240
cctacacccc acgaagcatc ccgtgttcac tcctggagag ttactttgaa acgaacagcg     300
agtgctccaa gccgggtgtc atcttcctca ccaagaaggg gcgacgtttc tgtgccaacc     360
ccagtgataa gcaagttcag gtttgcgtga gaatgctgaa gctggacaca cggatcaaga     420
ccaggaagaa ttgaacttgt caaggtgaag ggacacaagt tgccagccac caactttctt     480
gcctcaacta ccttcctgaa ttatttttta aagaagcatt tattcttgtg ttctggattt     540
agagcaattc atctaataaa cagtttctca ctttaaaaaa aaaaaaaaaa aaaaaaaaa      600 aaa                                                                  603

<210> SEQ ID NO 116
<211> LENGTH: 641
<212> TYPE: DNA
<213> ORGANISM: Homo sapiens
<220> FEATURE:
<221> NAME/KEY: CCL23-CKbeta8-1
<222> LOCATION: (1)..(641)

<400> SEQUENCE: 116
ctggcatccc gagaagccag gaagcagtga gcccaggagt cctcggccag ccctgcctgc      60
ccaccaggag gatgaaggtc tccgtggctg ccctctcctg cctcatgctt gttactgccc     120
ttggatccca ggcccgggtc acaaaagatg cagagacaga gttcatgatg tcaaagcttc     180
cattggaaaa tccagtactt ctggacatgc tctggaggag aaagattggt cctcagatga     240 cccttctca tgctgcagga ttccatgcta ctagtgctga ctgctgcatc tcctacaccc      300
cacgaagcat cccgtgttca ctcctggaga gttactttga aacgaacagc gagtgctcca     360
agccgggtgt catcttcctc accaagaagg ggcgacgttt ctgtgccaac cccagtgata     420
agcaagttca ggtttgcgtg agaatgctga agctggacac acggatcaag accaggaaga     480
attgaacttg tcaaggtgaa gggacacaag ttgccagcca ccaactttct tgcctcaact     540
accttcctga attattttt aaagaagcat ttattcttgt gttctggatt tagagcaatt      600
catctaataa acagtttctc actttaaaaa aaaaaaaaa a                         641

<210> SEQ ID NO 117
<211> LENGTH: 360
<212> TYPE: DNA
<213> ORGANISM: Homo sapiens
<220> FEATURE:
<221> NAME/KEY: CCL24
<222> LOCATION: (1)..(360)

<400> SEQUENCE: 117
atggcaggcc tgatgaccat agtaaccagc cttctgttcc ttggtgtctg tgccaccac       60 atcatcccta cgggctctgt ggtcatcccc tctccctgct gcatgttctt tgtttccaag     120
agaattcctg agaaccgagt ggtcagctac cagctgtcca gcaggagcac atgcctcaag     180
gcaggagtga tcttcaccac caagaagggg cagcagttct gtggcgaccc caagcaggag     240
tgggtccaga ggtacatgaa gaacctggac gccaagcaga agaaggcttc cctagggcc      300
```

```
agggcagtgg ctgtcaaggg ccctgtccag agatatcctg caaccaaac cacctgctaa        360
```

<210> SEQ ID NO 118
<211> LENGTH: 1002
<212> TYPE: DNA
<213> ORGANISM: Homo sapiens
<220> FEATURE:
<221> NAME/KEY: CCL25-1
<222> LOCATION: (1)..(1002)

<400> SEQUENCE: 118

```
agatgggaca gcttggccta cagcccggcg ggcatcagct cccttgaccc agtggatatc         60
ggtggccccg ttattcgtcc aggtgcccag ggaggaggac ccgcctgcag catgaacctg        120
tggctcctgg cctgcctggt ggccggcttc ctgggagcct gggcccccgc tgtccacacc        180
caaggtgtct ttgaggactg ctgcctggcc taccactacc ccattgggtg ggctgtgctc        240
cggcgcgcct ggacttaccg gatccaggag gtgagcggga gctgcaatct gcctgctgcg        300
atattctacc tccccaagag acacaggaag gtgtgtggga accccaaaag cagggaggtg        360
cagagagcca tgaagctcct ggatgctcga aataaggttt ttgcaaagct ccaccacaac        420
acgcagacct tccaagcagg ccctcatgct gtaaagaagt tgagttctgg aaactccaag        480
ttatcatcgt ccaagtttag caatcccatc agcagcagta agaggaatgt ctccctcctg        540
atatcagcta attcaggact gtgagccggc tcatttctgg gctccatcgg cacaggaggg        600
gccggatctt tctccgataa aaccgtcgcc ctacagaccc agctgtcccc acgcctctgt        660
cttttgggtc aagtcttaat ccctgcacct gagttggtcc tccctctgca cccccaccac        720
ctcctgcccg tctggcaact ggaaagaggg agttggcctg attttaagcc ttttgccgct        780
ccggggacca gcagcaatcc tgggcagcca gtggctcttg tagagaagac ttaggatacc        840
tctctcactt tctgtttctt gccgtccacc ccgggccatg ccagtgtgtc cctctgggtc        900
cctccaaaac tctggtcagt tcaaggatgc ccctcccagg ctatgctttt ctataacttt        960
taaataaacc ttgggggtg atggagtcat tcctgcctgt ta                          1002
```

<210> SEQ ID NO 119
<211> LENGTH: 999
<212> TYPE: DNA
<213> ORGANISM: Homo sapiens
<220> FEATURE:
<221> NAME/KEY: CCL25-2
<222> LOCATION: (1)..(999)

<400> SEQUENCE: 119

```
agatgggaca gcttggccta cagcccggcg ggcatcagct cccttgaccc agtggatatc         60
ggtggccccg ttattcgtcc aggtgcccag ggaggaggac ccgcctgcag catgaacctg        120
tggctcctgg cctgcctggt ggccggcttc ctgggagcct gggcccccgc tgtccacacc        180
caaggtgtct ttgaggactg ctgcctggcc taccactacc ccattgggtg ggctgtgctc        240
cggcgcgcct ggacttaccg gatccaggag gtgagcggga gctgcaatct gcctgctgcg        300
atattctacc tccccaagag acacaggaag gtgtgtggga accccaaaag cagggaggtg        360
cagagagcca tgaagctcct ggatgctcga aataaggttt ttgcaaagct ccaccacaac        420
acgcagacct tccaaggccc tcatgctgta aagaagttga gttctggaaa ctccaagtta        480
tcatcgtcca agtttagcaa tcccatcagc agcagtaaga ggaatgtctc cctcctgata        540
tcagctaatt caggactgtg agccggctca tttctgggct ccatcggcac aggaggggcc        600
ggatctttct ccgataaaac cgtcgcccta cagacccagc tgtccccacg cctctgtctt        660
```

```
ttgggtcaag tcttaatccc tgcacctgag ttggtcctcc ctctgcaccc ccaccacctc    720
ctgcccgtct ggcaactgga agagggagt tggcctgatt ttaagccttt tgccgctccg    780
gggaccagca gcaatcctgg gcagccagtg gctcttgtag agaagactta ggatacctct    840
ctcactttct gtttcttgcc gtccaccccg ggccatgcca gtgtgtccct ctgggtccct    900
ccaaaactct ggtcagttca aggatgcccc tcccaggcta tgcttttcta taactttaa    960 ataaaccttg gggggtgatg gagtcattcc tgcctgtta                          999
```

<210> SEQ ID NO 120
<211> LENGTH: 562
<212> TYPE: DNA
<213> ORGANISM: Homo sapiens
<220> FEATURE:
<221> NAME/KEY: CCL26
<222> LOCATION: (1)..(562)

<400> SEQUENCE: 120

```
ctggaattga ggctgagcca agaccccag ggccgtctca gtctcataaa aggggatcag     60
gcaggaggag tttgggagaa acctgagaag ggcctgattt gcagcatcat gatgggcctc   120
tccttggcct ctgctgtgct cctggcctcc ctcctgagtc tccaccttgg aactgccaca   180
cgtgggagtg acatatccaa gacctgctgc ttccaataca gccacaagcc ccttccctgg   240
acctgggtgc gaagctatga attccaccagt aacagctgct cccagcgggc tgtgatattc   300
actaccaaaa gaggcaagaa agtctgtacc catccaagga aaaatgggt gcaaaaatac    360 atttctttac tgaaaactcc gaaacaattg tgactcagct gaattttcat ccgaggacgc    420
ttggaccccg ctcttggctc tgcagccctc tggggagcct gcggaatctt ttctgaaggc    480
tacatggacc cgctggggag gagagggtgt ttcctcccag agttacttta ataaaggttg    540
ttcatagagt tgacttgttc at                                            562
```

<210> SEQ ID NO 121
<211> LENGTH: 469
<212> TYPE: DNA
<213> ORGANISM: Homo sapiens
<220> FEATURE:
<221> NAME/KEY: CCL27
<222> LOCATION: (1)..(469)

<400> SEQUENCE: 121

```
cccagataaa aggtagggga ggaggagaga gagagaagga agagtctagg ctgagcaaca     60
tgaaggggcc cccaaccttc tgcagcctcc tgctgctgtc attgctcctg agcccagacc   120
ctacagcagc attcctactg ccacccagca ctgcctgctg tactcagctc taccgaaagc   180
cactctcaga caagctactg aggaaggtca tccaggtgga actgcaggag gctgacgggg   240
actgtcacct ccaggctttc gtgcttcacc tggctcaacg cagcatctgc atccaccccc   300
agaaccccag cctgtcacag tggtttgagc accaagagag aaagctccat gggactctgc   360
ccaagctgaa ttttgggatg ctaaggaaaa tgggctgaag cccccaatag ccaaataata   420
aagcagcatt ggataataat ttctgaaaaa aaaaaaaaaa aaaaaaaa               469
```

<210> SEQ ID NO 122
<211> LENGTH: 2689
<212> TYPE: DNA
<213> ORGANISM: Homo sapiens
<220> FEATURE:
<221> NAME/KEY: CCR2-A
<222> LOCATION: (1)..(2689)

<400> SEQUENCE: 122

```
tttattctct ggaacatgaa acattctgtt gtgctcatat catgcaaatt atcactagta    60
ggagagcaga gagtggaaat gttccaggta taaagaccca caagataaag aagctcagag   120
tcgttagaaa caggagcaga tgtacagggt ttgcctgact cacactcaag gttgcataag   180
caagatttca aaattaatcc tattctggag acctcaaccc aatgtacaat gttcctgact   240
ggaaaagaag aactatattt ttctgatttt tttttcaaa tctttaccat tagttgccct   300
gtatctccgc cttcactttc tgcaggaaac tttatttcct acttctgcat gccaagtttc   360
tacctctaga tctgtttggt tcagttgctg agaagcctga cataccagga ctgcctgaga   420
caagccacaa gctgaacaga gaaagtggat tgaacaagga cgcatttccc cagtacatcc   480
acaacatgct gtccacatct cgttctcggt ttatcagaaa taccaacgag agcggtgaag   540
aagtcaccac ctttttgat tatgattacg gtgctccctg tcataaattt gacgtgaagc   600
aaattggggc ccaactcctg cctccgctct actcgctggt gttcatcttt ggttttgtgg   660
gcaacatgct ggtcgtcctc atcttaataa actgcaaaaa gctgaagtgc ttgactgaca   720
tttacctgct caacctggcc atctctgatc tgcttttct tattactctc ccattgtggg   780
ctcactctgc tgcaaatgag tgggtctttg ggaatgcaat gtgcaaatta ttcacagggc   840
tgtatcacat cggttatttt ggcggaatct tcttcatcat cctcctgaca atcgatagat   900
acctggctat tgtccatgct gtgtttgctt taaaagccag gacggtcacc tttggggtgg   960
tgacaagtgt gatcacctgg ttggtggctg tgtttgcttc tgtcccagga atcatcttta  1020
ctaaatgcca gaaagaagat tctgtttatg tctgtggccc ttattttcca cgaggatgga  1080
ataatttcca cacaataatg aggaacattt tggggctggt cctgccgctg ctcatcatgg  1140
tcatctgcta ctcgggaatc ctgaaaaccc tgcttcggtg tcgaaacgag aagaagaggc  1200
ataggcagt gagagtcatc ttcaccatca tgattgttta ctttctcttc tggactccct  1260
ataatattgt cattctcctg aacaccttcc aggaattctt cggcctgagt aactgtgaaa  1320
gcaccagtca actggaccaa gccacgcagg tgacagagac tcttgggatg actcactgct  1380
gcatcaatcc catcatctat gccttcgttg gggagaagtt cagaagcctt tttcacatag  1440
ctcttggctg taggattgcc ccactccaaa aaccagtgtg tggaggtcca ggagtgagac  1500
caggaaagaa tgtgaaagtg actacacaag gactcctcga tggtcgtgga aaggaaagt   1560
caattggcag agcccctgaa gccagtcttc aggacaaaga aggagcctag agacagaaat  1620
gacagatctc tgctttggaa atcacacgtc tggcttcaca gatgtgtgat tcacagtgtg  1680
aatcttggtg tctacgttac caggcaggaa ggctgagagg agagagactc cagctgggtt  1740
ggaaaacagt atttttccaaa ctaccttcca gttcctcatt tttgaataca ggcatagagt  1800
tcagactttt tttaaatagt aaaaataaaa ttaaagctga aaactgcaac ttgtaaatgt  1860
ggtaaagagt tagtttgagt tactatcatg tcaaacgtga aaatgctgta ttagtcacag  1920
agataattct agctttgagc ttaagaattt tgagcaggtg gtatgtttgg gagactgctg  1980
agtcaaccca atagttgttg attggcagga gttggaagtg tgtgatctgt gggcacatta  2040
gcctatgtgc atgcagcatc taagtaatga tgtcgtttga atcacagtat acgctccatc  2100
gctgtcatct cagctggatc tccattctct caggcttgct gccaaaagcc ttttgtgttt  2160
tgttttgtat cattatgaag tcatgcgttt aatcacattc gagtgtttca gtgcttcgca  2220
gatgtccttg atgctcatat tgttccctat tttgccagtg ggaactccta atcaagttg    2280
gcttctaatc aaagcttta aaccctattg gtaaagaatg gaaggtggag aagctccctg  2340
```

| | |
|---|---|
| aagtaagcaa agactttcct cttagtcgag ccaagttaag aatgttctta tgttgcccag | 2400 |
| tgtgtttctg atctgatgca agcaagaaac actgggcttc tagaaccagg caacttggga | 2460 |
| actagactcc caagctggac tatggctcta ctttcaggcc acatggctaa agaaggtttc | 2520 |
| agaaagaagt ggggacagag cagaactttc accttcatat atttgtatga tcctaatgaa | 2580 |
| tgcataaaat gttaagttga tggtgatgaa atgtaaatac tgttttttaac aactatgatt | 2640 |
| tggaaaataa atcaatgcta taactatgtt gaaaaaaaaa aaaaaaaa | 2689 |

<210> SEQ ID NO 123
<211> LENGTH: 2335
<212> TYPE: DNA
<213> ORGANISM: Homo sapiens
<220> FEATURE:
<221> NAME/KEY: CCR2-B
<222> LOCATION: (1)..(2335)

<400> SEQUENCE: 123

| | |
|---|---|
| tttattctct ggaacatgaa acattctgtt gtgctcatat catgcaaatt atcactagta | 60 |
| ggagagcaga gagtggaaat gttccaggta taaagaccca caagataaag aagctcagag | 120 |
| tcgttagaaa caggagcaga tgtacagggt ttgcctgact cacactcaag gttgcataag | 180 |
| caagatttca aaattaatcc tattctggag acctcaaccc aatgtacaat gttcctgact | 240 |
| ggaaaagaag aactatattt ttctgatttt tttttcaaa tctttaccat tagttgccct | 300 |
| gtatctccgc cttcactttc tgcaggaaac tttatttcct acttctgcat gccaagtttc | 360 |
| tacctctaga tctgtttggt tcagttgctg agaagcctga cataccagga ctgcctgaga | 420 |
| caagccacaa gctgaacaga gaaagtggat tgaacaagga cgcatttccc cagtacatcc | 480 |
| acaacatgct gtccacatct cgttctcggt ttatcagaaa taccaacgag agcggtgaag | 540 |
| aagtcaccac cttttttgat tatgattacg gtgctccctg tcataaattt gacgtgaagc | 600 |
| aaattggggc ccaactcctg cctccgctct actcgctggt gttcatcttt ggttttgtgg | 660 |
| gcaacatgct ggtcgtcctc atcttaataa actgcaaaaa gctgaagtgc ttgactgaca | 720 |
| tttacctgct caacctggcc atctctgatc tgcttttttct tattactctc ccattgtggg | 780 |
| ctcactctgc tgcaaatgag tgggtctttg gaatgcaat gtgcaaatta ttcacagggc | 840 |
| tgtatcacat cggttatttt ggcggaatct tcttcatcat cctcctgaca atcgatagat | 900 |
| acctggctat tgtccatgct gtgtttgctt taaaagccag gacggtcacc tttggggtgg | 960 |
| tgacaagtgt gatcacctgg ttggtggctg tgtttgcttc tgtcccagga atcatcttta | 1020 |
| ctaaatgcca gaaagaagat tctgtttatg tctgtggccc ttattttcca cgaggatgga | 1080 |
| ataatttcca cacaataatg aggaacattt tggggctggt cctgccgctg ctcatcatgg | 1140 |
| tcatctgcta ctcgggaatc ctgaaaaccc tgcttcggtg tcgaaacgag aagaagaggc | 1200 |
| ataggggcagt gagagtcatc ttcaccatca tgattgttta cttctctcttc tggactccct | 1260 |
| ataatattgt cattctcctg aacaccttcc aggaattctt cggcctgagt aactgtgaaa | 1320 |
| gcaccagtca actggaccaa gccacgcagg tgacagagac tcttgggatg actcactgct | 1380 |
| gcatcaatcc catcatctat gccttcgttg gggagaagtt cagaaggtat ctctcggtgt | 1440 |
| tcttccgaaa gcacatcacc aagcgcttct gcaaacaatg tccagttttc tacagggaga | 1500 |
| cagtggatgg agtgacttca acaaacacgc cttccactgg ggagcaggaa gtctcggctg | 1560 |
| gtttataaaa cgaggagcag tttgattgtt gtttataaag ggagataaca atctgtatat | 1620 |
| aacaacaaac ttcaagggtt tgttgaacaa tagaaacctg taaagcaggt gcccaggaac | 1680 |
| ctcagggctg tgtgtactaa tacagactat gtcacccaat gcatatccaa catgtgctca | 1740 |

-continued

```
gggaataatc cagaaaaact gtgggtagag actttgactc tccagaaagc tcatctcagc    1800
tcctgaaaaa tgcctcatta ccttgtgcta atcctctttt tctagtcttc ataatttctt    1860
cactcaatct ctgattctgt caatgtcttg aaatcaaggg ccagctggag gtgaagaaga    1920
gaatgtgaca ggcacagatg aatgggagtg agggatagtg gggtcagggc tgagaggaga    1980
aggagggaga catgagcatg gctgagcctg gacaaagaca aggtgagca aagggctcac    2040 gcattcagcc aggagatgat actggtcctt agccccatct gccacgtgta tttaaccttg    2100
aagggttcac caggtcaggg agagtttggg aactgcaata acctgggagt tttggtggag    2160
tccgatgatt ctcttttgca taagtgcatg acatattttt gctttattac agtttatcta    2220
tggcacccat gcaccttaca tttgaaatct atgaaatatc atgctccatt gttcagatgc    2280
ttcttaggcc acatccccct gtctaaaaat tcagaaaatt tttgtttata aaaga         2335

<210> SEQ ID NO 124
<211> LENGTH: 1796
<212> TYPE: DNA
<213> ORGANISM: Homo sapiens
<220> FEATURE:
<221> NAME/KEY: CCR3-1
<222> LOCATION: (1)..(1796)

<400> SEQUENCE: 124
ctgatggtat ctctgtttca ggagtggtga cgcctaagct atcactggac atatcaagga      60
cttcactaaa ttagcaggta ccactggtct tcttgtgctt atccgggcaa gaacttatcg     120
aaatacaata gaagttttta cttagaagag attttcagca gatgagaagc tggtaacaga     180
gaccaaaata gtttggagac taaagaatca ttgcacattt cactgctgag ttgtattgga     240
gaagtgaaat gacaacctca ctagatacag ttgagacctt tggtaccaca tcctactatg     300
atgacgtggg cctgctctgt gaaaaagctg ataccagagc actgatggcc cagtttgtgc     360
ccccgctgta ctccctggtg ttcactgtgg gcctcttggg caatgtggtg gtggtgatga     420
tcctcataaa atacaggagg ctccgaatta tgaccaacat ctacctgctc aacctggcca     480
tttcggacct gctcttcctc gtcacccttc cattctggat ccactatgtc agggggcata     540
actgggtttt tggccatggc atgtgtaagc tcctctcagg gttttatcac acaggcttgt     600
acagcgagat cttttttcata atcctgctga caatcgacag gtacctggcc attgtccatg     660
ctgtgtttgc ccttcgagcc cggactgtca cttttggtgt catcaccagc atcgtcacct     720
ggggcctggc agtgctagca gctcttcctg aatttatctt ctatgagact gaagagttgt     780
ttgaagagac tctttgcagt gctctttacc cagaggatac agtatatagc tggaggcatt     840
tccacactct gagaatgacc atcttctgtc tcgttctccc tctgctcgtt atggccatct     900
gctacacagg aatcatcaaa acgctgctga ggtgccccag taaaaaaaag tacaaggcca     960
tccggctcat ttttgtcatc atggcggtgt tttcatttt ctggacaccc tacaatgtgg    1020
ctatccttct ctcttcctat caatccatct tatttggaaa tgactgtgag cggagcaagc    1080
atctggacct ggtcatgctg gtgacagagg tgatcgccta ctcccactgc tgcatgaacc    1140
cggtgatcta cgcctttgtt ggagagaggt tccggaagta cctgcgccac ttcttccaca    1200
ggcacttgct catgcacctg gcagatacat cccattcct tcctagtgag aagctggaaa    1260
gaaccagctc tgtctctcca tccacagcag agccggaact ctctattgtg ttttaggtca    1320
gatgcagaaa attgcctaaa gaggaaggac caaggagatg aagcaaacac attaagcctt    1380
ccacactcac ctctaaaaca gtccttcaaa cttccagtgc aacactgaag ctcttgaaga    1440
```

| | | |
|---|---|---|
| cactgaaaata tacacacagc agtagcagta gatgcatgta ccctaaggtc attaccacag | 1500 | |
| gccaggggct gggcagcgta ctcatcatca accctaaaaa gcagagcttt gcttctctct | 1560 | |
| ctaaaatgag ttacctacat tttaatgcac ctgaatgtta gatagttact atatgccgct | 1620 | |
| acaaaaaggt aaaactttt atattttata cattaacttc agccagctat tgatataaat | 1680 | |
| aaaacatttt cacacaatac aataagttaa ctattttatt ttctaatgtg cctagttctt | 1740 | |
| tccctgctta atgaaaagct tgttttttca gtgtgaataa ataatcgtaa gcaaca | 1796 | |

```
<210> SEQ ID NO 125
<211> LENGTH: 1786
<212> TYPE: DNA
<213> ORGANISM: Homo sapiens
<220> FEATURE:
<221> NAME/KEY: CCR3-2
<222> LOCATION: (1)..(1786)

<400> SEQUENCE: 125
```

| | | |
|---|---|---|
| ctgatggtat ctctgtttca ggagtggtga cgcctaagct atcactggac atatcaagga | 60 | |
| cttcactaaa ttagcaggta ccactggtct tcttgtgctt atccgggcaa gaacttatcg | 120 | |
| aaatacaata gaagttttta cttagaagag attttcagct gctgtggatt ggattatgcc | 180 | |
| atttggaata agaatgctgt taagagcaca caagccaggt tcctcaagga gaagtgaaat | 240 | |
| gacaacctca ctagatacag ttgagacctt tggtaccaca tcctactatg atgacgtggg | 300 | |
| cctgctctgt gaaaaagctg ataccagagc actgatggcc cagtttgtgc cccgctgta | 360 | |
| ctccctggtg ttcactgtgg gcctcttggg caatgtggtg gtggtgatga tcctcataaa | 420 | |
| atacaggagg ctccgaatta tgaccaacat ctacctgctc aacctggcca tttcggacct | 480 | |
| gctcttcctc gtcacccttc cattctggat ccactatgtc agggggcata actgggtttt | 540 | |
| tggccatggc atgtgtaagc tcctctcagg gttttatcac acaggcttgt acagcgagat | 600 | |
| cttttttcata atcctgctga caatcgcacg gtacctggcc attgtccatg ctgtgtttgc | 660 | |
| ccttcgagcc cggactgtca cttttggtgt catcaccagc atcgtcacct ggggcctggc | 720 | |
| agtgctagca gctcttcctg aatttatctt ctatgagact gaaagttgt ttgaagagac | 780 | |
| tctttgcagt gctctttacc cagaggatac agtatatagc tggaggcatt ccacactct | 840 | |
| gagaatgacc atcttctgtc tcgttctccc tctgctcgtt atggccatct gctacacagg | 900 | |
| aatcatcaaa acgctgctga ggtgccccag taaaaaaaag tacaaggcca tccggctcat | 960 | |
| ttttgtcatc atggcggtgt ttttcatttt ctggacaccc tacaatgtgg ctatccttct | 1020 | |
| ctcttcctat caatccatct tatttggaaa tgactgtgag cggagcaagc atctggacct | 1080 | |
| ggtcatgctg gtgacagagg tgatcgccta ctcccactgc tgcatgaacc cggtgatcta | 1140 | |
| cgcctttgtt ggagagaggt tccggaagta cctgcgccac ttcttccaca ggcacttgct | 1200 | |
| catgcacctg gcagatacat cccattcct tcctagtgag aagctggaaa gaaccagctc | 1260 | |
| tgtctctcca tccacagcag agccggaact ctctattgtg ttttaggtca gatgcagaaa | 1320 | |
| attgcctaaa gaggaaggac caaggagatg aagcaaacac attaagcctt ccacactcac | 1380 | |
| ctctaaaaca gtccttcaaa cttccagtgc aacactgaag ctcttgaaga cactgaaata | 1440 | |
| tacacacagc agtagcagta gatgcatgta ccctaaggtc attaccacag gccaggggct | 1500 | |
| gggcagcgta ctcatcatca accctaaaaa gcagagcttt gcttctctct ctaaaatgag | 1560 | |
| ttacctacat tttaatgcac ctgaatgtta gatagttact atatgccgct acaaaaaggt | 1620 | |
| aaaactttt atattttata cattaacttc agccagctat tgatataaat aaaacatttt | 1680 | |
| cacacaatac aataagttaa ctattttatt ttctaatgtg cctagttctt tccctgctta | 1740 | | atgaaaagct tgttttttca gtgtgaataa ataatcgtaa gcaaca 1786

<210> SEQ ID NO 126
<211> LENGTH: 1777
<212> TYPE: DNA
<213> ORGANISM: Homo sapiens
<220> FEATURE:
<221> NAME/KEY: CCR3-3
<222> LOCATION: (1)..(1777)

<400> SEQUENCE: 126

```
ctgatggtat ctctgtttca ggagtggtga cgcctaagct atcactggac atatcaagga    60
cttcactaaa ttagcaggta ccactggtct tcttgtgctt atccgggcaa gaacttatcg   120
aaatacaata gaagttttta cttagaagag attttcagct gctgtggatt ggattatgcc   180
atttggaata agaatgctgt taagagcaca caagccaggg agaagtgaaa tgacaacctc   240
actagataca gttgagacct tggtaccac atcctactat gatgacgtgg gcctgctctg    300
tgaaaaagct gataccagag cactgatggc ccagtttgtg cccccgctgt actccctggt   360
gttcactgtg ggcctcttgg gcaatgtggt ggtggtgatg atcctcataa aatacaggag   420
gctccgaatt atgaccaaca tctacctgct caacctggcc atttcggacc tgctcttcct   480
cgtcacccct tccattctgga tccactatgt caggggggcat aactgggttt ttggccatgg   540
catgtgtaag ctcctctcag ggttttatca cacaggcttg tacagcgaga tcttttttcat   600
aatcctgctg acaatcgaca ggtacctggc cattgtccat gctgtgtttg cccttcgagc   660
ccggactgtc acttttggtg tcatcaccag catcgtcacc tgggggcctgg cagtgctagc   720
agctcttcct gaatttatct ctatgagac tgaagagttg tttgaagaga ctctttgcag    780
tgctctttac ccagaggata cagtatatag ctggaggcat ttccacactc tgagaatgac   840
catcttctgt ctcgttctcc ctctgctcgt tatggccatc tgctacacag gaatcatcaa   900
aacgctgctg aggtgcccca gtaaaaaaaa gtacaaggcc atccggctca ttttttgtcat   960
catggcggtg tttttcattt tctggacacc ctacaatgtg gctatccttc tctcttccta  1020
tcaatccatc ttatttggaa atgactgtga gcggagcaag catctggacc tggtcatgct  1080
ggtgacagag gtgatcgcct actcccactg ctgcatgaac ccggtgatct acgcctttgt  1140
tggagagagg ttccggaagt acctgcgcca cttcttccac aggcacttgc tcatgcacct  1200
gggcagatac atcccattcc ttcctagtga gaagctggaa agaaccagct ctgtctctcc  1260
atccacagca gagccggaac tctctattgt gttttaggtc agatgcagaa aattgcctaa  1320
agaggaagga ccaaggagat gaagcaaaca cattaagcct tccacactca cctctaaaac  1380
agtccttcaa acttccagtg caacactgaa gctcttgaag acactgaaat atacacacag  1440
cagtagcagt agatgcatgt acctaaggt cattaccaca ggccaggggc tgggcagcgt   1500
actcatcatc aaccctaaaa agcagagctt tgcttctctc tctaaaatga gttacctaca  1560
ttttaatgca cctgaatgtt agatagttac tatatgccgc tacaaaaagg taaaacttttt  1620
tatatttat acattaactt cagccagcta ttgatataaa taaaacatttt tcacacaata  1680
caataagtta actattttat tttctaatgt gcctagttct ttccctgctt aatgaaaagc  1740
ttgtttttttc agtgtgaata aataatcgta agcaaca                           1777
```

<210> SEQ ID NO 127
<211> LENGTH: 1015
<212> TYPE: DNA
<213> ORGANISM: Homo sapiens
<220> FEATURE:

```
<221> NAME/KEY: CCR4
<222> LOCATION: (1)..(1015)

<400> SEQUENCE: 127
cctgaagggc ctccaaggga gacgcctaga agatggaggc ccagattctt gagacgtttc      60
tctttctgat ctagcaggag ggacaaagag ctcctccact ccctcattcc ccaagaaggc     120
ccccagccta cccagtttcc gtgaccattc cgccctggga aagcggcttc ccagacctcc     180
ttatctattt ttcttgaatc atgagagatg aaattgcaac aacagttttc tttgtcacaa     240
gattggtgaa aaaacatgat aaactaagta acagcaaat agaagacttt gcagaaaagc      300
tgatgacgat cttgtttgaa acatacagaa gtcactggca ctctgattgc ccttctaaag     360
ggcaagcctt caggtgcatc aggataaaca acaatcagaa taaagatccc attctagaaa     420
gggcatgtgt ggaaagtaat gtagattttt ctcacctggg acttccgaag gagatgacca     480
tatgggtaga tcccttgaa gtatgctgta ggtatggtga aaaaaccat ccatttacag        540 ttgcttcttt taaaggcaga tgggaggaat gggaactata tcaacaaatc agttatgccg     600
ttagtagagc ctcatcagac gtttcctctg gcacttcctg cgatgaagaa agttgtagca     660
aggaacctcg tgtcattcct aaagtcagca atccgaagag tatttatcag gttgaaaact     720
tgaaacagcc ctttcaatct tggttacaaa tccccgcaa aaagaatgtg gtggacggcc      780
gtgttggcct cctgggaaac acttaccatg gctcgcagaa gcatcctaag tgttacaggc     840
ctgctatgca ccggctggac agaattttat aacccacatc tgggaatgaa tttgcagcac     900
ctggtagaag aaggcacctt ggaaggcact gccttgggct tccatggcag gaagatgaga     960
agaaatcttc agggtgattt ctggagcctg aaaagaataa aaacaaaac caaaa          1015

<210> SEQ ID NO 128
<211> LENGTH: 3686
<212> TYPE: DNA
<213> ORGANISM: Homo sapiens
<220> FEATURE:
<221> NAME/KEY: CCR5
<222> LOCATION: (1)..(3686)

<400> SEQUENCE: 128
cttcagatag attatatctg gagtgaagaa tcctgccacc tatgtatctg gcatagtatt      60
ctgtgtagtg ggatgagcag agaacaaaaa caaaataatc cagtgagaaa agcccgtaaa     120
taaaccttca gaccagagat ctattctcta gcttatttta agctcaactt aaaaagaaga     180
actgttctct gattcttttc gccttcaata cacttaatga tttaactcca ccctccttca     240
aaagaaacag catttcctac ttttatactg tctatatgat tgatttgcac agctcatctg     300
gccgaaagag ctgagacatc cgttcccta caagaaactc tccccgggtg gaacaagatg      360
gattatcaag tgtcaagtcc aatctatgac atcaattatt atacatcgga gccctgccaa     420
aaaatcaatg tgaagcaaat cgcagcccgc ctcctgcctc cgctctactc actggtgttc     480
atctttggtt ttgtgggcaa catgctggtc atcctcatcc tgataaactg caaaaggctg     540
aagagcatga ctgacatcta cctgctcaac ctggccatct ctgacctgtt tttccttctt     600
actgtcccct ctgggctca ctatgctgcc gcccagtggg actttggaaa tacaatgtgt     660
caactcttga cagggctcta ttttataggc ttcttctctg gaatcttctt catcatcctc     720
ctgacaatcg ataggtacct ggctgtcgtc catgctgtgt ttgctttaaa agccaggacg     780
gtcacctttg ggtggtgac aagtgtgatc acttgggtgg tggctgtgtt tgcgtctctc     840
ccaggaatca tctttaccag atctcaaaaa gaaggtcttc attacacctg cagctctcat     900
```

```
tttccataca gtcagtatca attctggaag aatttccaga cattaaagat agtcatcttg    960
gggctggtcc tgccgctgct tgtcatggtc atctgctact cgggaatcct aaaaactctg   1020
cttcggtgtc gaaatgagaa gaagaggcac agggctgtga ggcttatctt caccatcatg   1080
attgtttatt ttctcttctg ggctccctac aacattgtcc ttctcctgaa cacccttccag  1140 gaattctttg gcctgaataa ttgcagtagc tctaacaggt tggaccaagc tatgcaggtg   1200
acagagactc ttgggatgac gcactgctgc atcaacccca tcatctatgc ctttgtcggg   1260
gagaagttca gaaactacct cttagtcttc ttccaaaagc acattgccaa acgcttctgc   1320
aaatgctgtt ctattttcca gcaagaggct cccgagcgag caagctcagt ttacacccga   1380
tccactgggg agcaggaaat atctgtgggc ttgtgacacg gactcaagtg ggctggtgac   1440
ccagtcagag ttgtgcacat ggcttagttt tcatacacag cctgggctgg gggtggggtg   1500
ggagaggtct tttttaaaag gaagttactg ttatagaggg tctaagattc atccatttat   1560
ttggcatctg tttaaagtag attagatctt ttaagcccat caattataga aagccaaatc   1620
aaaatatgtt gatgaaaaat agcaacctt ttatctcccc ttcacatgca tcaagttatt    1680
gacaaactct cccttcactc cgaaagttcc ttatgtatat ttaaaagaaa gcctcagaga   1740
attgctgatt cttgagttta gtgatctgaa cagaaatacc aaaattattt cagaaatgta   1800
caacttttta cctagtacaa ggcaacatat aggttgtaaa tgtgtttaaa acaggtctttt  1860 gtcttgctat ggggagaaaa gacatgaata tgattagtaa agaaatgaca cttttcatgt   1920
gtgatttccc ctccaaggta tggttaataa gtttcactga cttagaacca ggcgagagac   1980
ttgtggcctg ggagagctgg ggaagcttct taaatgagaa ggaatttgag ttggatcatc   2040
tattgctggc aaagacagaa gcctcactgc aagcactgca tgggcaagct ggctgtaga    2100 aggagacaga gctggttggg aagacatggg gaggaaggac aaggctagat catgaagaac   2160
cttgacggca ttgctccgtc taagtcatga gctgagcagg gagatcctgg ttggtgttgc   2220
agaaggttta ctctgtggcc aaaggagggt caggaaggat gagcatttag ggcaaggaga   2280
ccaccaacag ccctcaggtc agggtgagga tggcctctgc taagctcaag gcgtgaggat   2340
gggaaggagg gaggtattcg taaggatggg aaggaggag gtattcgtgc agcatatgag    2400
gatgcagagt cagcagaact ggggtggatt tgggttggaa gtgagggtca gagaggagtc   2460
agagagaatc cctagtcttc aagcagattg gagaaaccct tgaaaagaca tcaagcacag   2520
aaggaggagg aggaggttta ggtcaagaag aagatggatt ggtgtaaaag gatgggtctg   2580
gtttgcagag cttgaacaca gtctcaccca gactccaggc tgtctttcac tgaatgcttc   2640
tgacttcata gatttccttc ccatcccagc tgaaatactg aggggtctcc aggaggagac   2700
tagatttatg aatacacgag gtatgaggtc taggaacata cttcagctca cacatgagat   2760
ctaggtgagg attgattacc tagtagtcat ttcatgggtt gttgggagga ttctatgagg   2820
caaccacagg cagcatttag cacatactac acattcaata agcatcaaac tcttagttac   2880
tcattcaggg atagcactga gcaaagcatt gagcaaaggg gtcccataga ggtgagggaa   2940
gcctgaaaaa ctaagatgct gcctgcccag tgcacacaag tgtaggtatc attttctgca   3000
tttaaccgtc aataggcaaa gggggaagg gacatattca tttggaaata agctgccttg    3060
agccttaaaa cccacaaaag tacaatttac cagcctccgt atttcagact gaatgggggt   3120
ggggggggcg ccttaggtac ttattccaga tgccttctcc agacaaacca gaagcaacag   3180
aaaaaatcgt ctctccctcc ctttgaaatg aatatacccc ttagtgtttg ggtatattca   3240
tttcaaaggg agagagagag gttttttttct gttctgtctc atatgattgt gcacatactt   3300
```

-continued

| | |
|---|---|
| gagactgttt tgaatttggg ggatggctaa aaccatcata gtacaggtaa ggtgagggaa | 3360 |
| tagtaagtgg tgagaactac tcagggaatg aaggtgtcag aataataaga ggtgctactg | 3420 |
| actttctcag cctctgaata tgaacggtga gcattgtggc tgtcagcagg aagcaacgaa | 3480 |
| gggaaatgtc tttccttttg ctcttaagtt gtggagagtg caacagtagc ataggaccct | 3540 |
| accctctggg ccaagtcaaa gacattctga catcttagta tttgcatatt cttatgtatg | 3600 |
| tgaaagttac aaattgcttg aaagaaaata tgcatctaat aaaaaacacc ttctaaaata | 3660 |
| aaaaaaaaaa aaaaaaaaa aaaaaa | 3686 |

<210> SEQ ID NO 129
<211> LENGTH: 3693
<212> TYPE: DNA
<213> ORGANISM: Homo sapiens
<220> FEATURE:
<221> NAME/KEY: CCR6
<222> LOCATION: (1)..(3693)

<400> SEQUENCE: 129

| | |
|---|---|
| aactgtagtg cattttgcct tctttccttc ttagagtcac ctctactttc ctgctaccgc | 60 |
| tgcctgtgag ctgaaggggc tgaaccatac actcctttt ctacaaccag cttgcatttt | 120 |
| ttctgcccac aatgagcggg gtaagatttt tattttggc aaggggtata atttgggttc | 180 |
| actgtgctta cttgaacact acactgcagc taactctatc tttgtttcct ttccaggaat | 240 |
| caatgaattt cagcgatgtt ttcgactcca gtgaagatta ttttgtgtca gtcaatactt | 300 |
| catattactc agttgattct gagatgttac tgtgctcctt gcaggaggtc aggcagttct | 360 |
| ccaggctatt tgtaccgatt gcctactcct tgatctgtgt cttttggcctc ctggggaata | 420 |
| ttctggtggt gatcaccttt gctttttata agaaggccag gtctatgaca gacgtctatc | 480 |
| tcttgaacat ggccattgca gacatcctct ttgttcttac tctcccattc tgggcagtga | 540 |
| gtcatgccac tggtgcgtgg gttttcagca atgccacgtg caagttgcta aaaggcatct | 600 |
| atgccatcaa ctttaactgc gggatgctgc tcctgacttg cattagcatg gaccggtaca | 660 |
| tcgccattgt acaggcgact aagtcattcc ggctccgatc cagaacacta ccgcgcagca | 720 |
| aaatcatctg ccttgttgtg tgggggctgt cagtcatcat ctccagctca acttttgtct | 780 |
| tcaaccaaaa atacaacacc caaggcagcg atgtctgtga acccaagtac cagactgtct | 840 |
| cggagcccat caggtggaag ctgctgatgt tgggcttga gctactcttt ggtttctta | 900 |
| tccctttgat gttcatgata ttttgttaca cgttcattgt caaaaccttg gtgcaagctc | 960 |
| agaattctaa aaggcacaaa gccatccgtg taatcatagc tgtggtgctt tgtgtttctgg | 1020 |
| cttgtcagat tcctcataac atggtcctgc ttgtgacggc tgcaaatttg ggtaaaatga | 1080 |
| accgatcctg ccagagcgaa aagctaattg gctatacgaa aactgtcaca gaagtcctgg | 1140 |
| cttttcctgca ctgctgcctg aaccctgtgc tctacgcttt tattgggcag aagttcagaa | 1200 |
| actacttct gaagatcttg aaggacctgt ggtgtgtgag aggaagtac aagtcctcag | 1260 |
| gcttctcctg tgccgggagg tactcagaaa acatttctcg gcagaccagt gagaccgcag | 1320 |
| ataacgacaa tgcgtcgtcc ttcactatgt gatagaaagc tgagtctccc taaggcatgt | 1380 |
| gtgaaacata ctcatagatg ttatgcaaaa aaagtctat ggccaggtat gcatggaaaa | 1440 |
| tgtgggaatt aagcaaaatc aagcaagcct ctctcctgcg ggacttaacg tgctcatggg | 1500 |
| ctgtgtgatc tcttcagggt gggtggtct ctgataggta gcattttcca gcactttgca | 1560 |
| aggaatgttt tgtagctcta gggtatatat ccgcctggca tttcacaaaa cagccttgg | 1620 |
| gaaatgctga attaaagtga attgttgaca aatgtaaaca ttttcagaaa tattcatgaa | 1680 |

```
gcggtcacag atcacagtgt cttttggtta cagcacaaaa tgatggcagt ggtttgaaaa    1740
actaaaacag aaaaaaaaat ggaagccaac acatcactca ttttaggcaa atgtttaaac    1800
atttttatct atcagaatgt ttattgttgc tggttataag cagcaggatt ggccggctag    1860
tgtttcctct catttcccTt tgatacagtc aacaagcctg accctgtaaa atggaggtgg    1920
aaagacaagc tcaagtgttc acaacctgga agtgcttcgg aaagaagggg acaatggcag    1980
aacaggtgtt ggtgacaatt gtcaccaatt ggataaagca gctcaggttg tagtgggcca    2040
ttaggaaact gtcggtttgc tttgatttcc ctgggagctg ttctctgtcg tgagtgtctc    2100
ttgtctaaac gtccattaag ctgagagtgc tatgaagaca ggatctagaa taatcttgct    2160
cacagctgtg ctctgagtgc ctagcggagt tccagcaaac aaaatggact caagagagat    2220
ttgattaatg aatcgtaatg aagttggggt ttattgtaca gtttaaaatg ttagatgttt    2280
ttaatttttt aaataaatgg aatacttttt ttttttttta agaaagcaa ctttactgag     2340 acaatgtaga aagaagtttt gttccgtttc tttaatgtgg ttgaagagca atgtgtggct    2400
gaagactttt gttatgagga gctgcagatt agctagggga cagctggaat tatgctggct    2460
tctgataatt attttaaagg ggtctgaaat ttgtgatgga atcagatttt aacagctctc    2520
ttcaatgaca tagaaagttc atggaactca tgttttttaaa gggctatgta aatatatgaa    2580
cattagaaaa atagcaactt gtgttacaaa aatacaaaca catgttagga aggtactgtc    2640
atgggctagg catggtggct cacacctgta atcccagcat tttgggaagc taagatgggt    2700
ggatcacttg aggtcaggag tttgagacca gcctggccaa catggcgaaa cccctctcta    2760
ctaaaaatac aaaaatttgc caggcgtggt ggcgggtgcc tgtaatccca gctacttggg    2820
aggctgaggc aagagaatcg cttgaaccca ggaggcagag gttgcagtga gccgagatcg    2880
tgccattgca ctccagcctg ggtgacaaag cgagactcca tctcaaaaaa aaaaaaaaaa    2940
aaaaaaggaa agaactgtca tgtaaacata ccgacatgtt taaacctgac aatggtgtta    3000
tttgaaactt tatattgttc ttgtaagctt taactatatc tctctttaaa atgcaaaata    3060
atgtcttaag attcaaagtc tgtatttta aagcatggct ttggctttgc aaaataaaaa    3120
atgtgttttg tacatgaagt aggaatcgta tttcagcttc aaggttcaga ttgagggggcc    3180 cactgtttgg agaggatggt attcaggctt tctcatgtcc ttcaaatctg ttagcgtttg    3240
actctagaaa tcaaagcaaa ggagtggtta cccagacact tcttttggtg tgatcaatgc    3300
gctgatgtga tctatgaaga tgattcatgc ttgaaaacta gcacagaaac atcttgctta    3360
tttgccaaag ctgggagatg agcttctctg cataatttaa atgttcagat aaatgaagct    3420
gacttattta agcaataacc ttttaaacat tttagctaag atgtataaaa atgtttccaa    3480
aatataccac atactttatt tcttcttaaa tgtagtacat taggttacat catttttctt    3540
gctgtcttgg gcatcaaaac aggtgccatg gtaacctgac actctcagga gacattaaga    3600
tagaaggggc tgttcttcag tggttcccat tgattctccc catatctttt tgctctcagg    3660
ctctggccgt ctcttcctga gccttaactg tgt                                 3693
```

<210> SEQ ID NO 130  
<211> LENGTH: 1487  
<212> TYPE: DNA  
<213> ORGANISM: Homo sapiens  
<220> FEATURE:  
<221> NAME/KEY: CCR8  
<222> LOCATION: (1)..(1487)

<400> SEQUENCE: 130

```
tttgtagtgg gaggatacct ccagagaggc tgctgctcat tgagctgcac tcacatgagg      60
atacagactt tgtgaagaag gaattggcaa cactgaaacc tccagaacaa aggctgtcac     120
taaggtcccg ctgccttgat ggattataca cttgacctca gtgtgacaac agtgaccgac     180
tactactacc ctgatatctt ctcaagcccc tgtgatgcgg aacttattca gacaaatggc     240
aagttgctcc ttgctgtctt ttattgcctc ctgtttgtat tcagtcttct gggaaacagc     300
ctggtcatcc tggtccttgt ggtctgcaag aagctgagga gcatcacaga tgtataccctc    360 ttgaacctgg ccctgtctga cctgcttttt gtcttctcct tccccttttca gacctactat    420 ctgctggacc agtgggtgtt tgggactgta atgtgcaaag tggtgtctgg ctttttattac    480 attggcttct acagcagcat gttttttcatc accctcatga gtgtggacag gtacctggct    540
gttgtccatg ccgtgtatgc cctaaaggtg aggacgatca ggatgggcac aacgctgtgc    600
ctggcagtat ggctaaccgc cattatggct accatcccat tgctagtgtt ttaccaagtg     660
gcctctgaag atggtgttct acagtgttat tcattttaca atcaacagac tttgaagtgg    720
aagatcttca ccaacttcaa aatgaacatt ttaggcttgt tgatcccatt caccatcttt    780
atgttctgct acattaaaat cctgcaccag ctgaagaggg tcaaaaacca caacaagacc    840
aaggccatca ggttggtgct cattgtggtc attgcatctt tactttttctg ggtcccattc    900 aacgtggttc ttttcctcac ttccttgcac agtatgcaca tcttggatgg atgtagcata    960
agccaacagc tgacttatgc cacccatgtc acagaaatca tttcctttac tcactgctgt   1020
gtgaaccctg ttatctatgc ttttgttggg gagaagttca agaaacacct ctcagaaata   1080
tttcagaaaa gttgcagcca aatcttcaac tacctaggaa gacaaatgcc tagggagagc   1140
tgtgaaaagt catcatcctg ccagcagcac tcctcccgtt cctccagcgt agactacatt   1200
ttgtgaggat caatgaagac taaatataaa aaacattttc ttgaatggca tgctagtagc   1260
agtgagcaaa ggtgtgggtg tgaaaggttt ccaaaaaaag ttcagcatga aggatgccat   1320
atatgttgtt gccaacactt ggaacacaat gactaaagac atagttgtgc atgcctggca   1380
caacatcaag cctgtgattg tgtttattga tgatgttgaa caagtggtaa ctttaaagga   1440
ttctgtatgc caagtgaaaa aaaaagatgt ctgacctcct tacatat                 1487
```

<210> SEQ ID NO 131
<211> LENGTH: 2544
<212> TYPE: DNA
<213> ORGANISM: Homo sapiens
<220> FEATURE:
<221> NAME/KEY: CCR9A
<222> LOCATION: (1)..(2544)

<400> SEQUENCE: 131

```
gggtagctgc ctgctcagaa cccacaaagc ctgccctca tcccaggcag agagcaaccc      60 agctcttttcc ccagacactg agagctggtg gtgcctgctg tcccaggag agttgcatcg    120 ccctccacag agcaggcttg catctgactg acccaccatg acacccacag acttcacaag    180
ccctattcct aacatggctg atgactatgg ctctgaatcc acatcttcca tggaagacta    240
cgttaacttc aacttcactg acttctactg tgagaaaaac aatgtcaggc agtttgcgag    300
ccatttcctc ccacccttgt actggctcgt gttcatcgtg ggtgccttgg gcaacagtct    360
tgttatcctt gtctactggg tactgcacaag agtgaagacc atgaccgaca tgttcctttt    420
gaatttggca attgctgacc tcctctttct tgtcactctt cccttctggg ccattgctgc    480
tgctgaccag tggaagttcc agaccttcat gtgcaaggtg gtcaacagca tgtacaagat    540
gaacttctac agctgtgtgt tgctgatcat gtgcatcagc gtggacaggt acattgccat    600
```

```
tgcccaggcc atgagagcac atacttggag ggagaaaagg cttttgtaca gcaaaatggt    660
ttgctttacc atctgggtat tggcagctgc tctctgcatc ccagaaatct tatacagcca    720
aatcaaggag gaatccggca ttgctatctg caccatggtt taccctagcg atgagagcac    780
caaactgaag tcagctgtct tgaccctgaa ggtcattctg gggttcttcc ttcccttcgt    840
ggtcatggct tgctgctata ccatcatcat tcacaccctg atacaagcca agaagtcttc    900
caagcacaaa gccctaaaag tgaccatcac tgtcctgacc gtctttgtct tgtctcagtt    960
tccctacaac tgcattttgt tggtgcagac cattgacgcc tatgccatgt tcatctccaa   1020
ctgtgccgtt tccaccaaca ttgacatctg cttccaggtc acccagacca tcgccttctt   1080
ccacagttgc ctgaaccctg ttctctatgt ttttgtgggt gagagattcc gccgggatct   1140
cgtgaaaacc ctgaagaact ggggttgcat cagccaggcc cagtgggttt catttacaag   1200
gagagaggga agcttgaagc tgtcgtctat gttgctggag acaacctcag gagcactctc   1260
cctctgaggg gtcttctctg aggtgcatgg ttcttttgga agaaatgaga aatacagaaa   1320
cagtttcccc actgatggga ccagagagag tgaaagagaa aagaaaactc agaaagggat   1380
gaatctgaac tatatgatta cttgtagtca gaatttgcca aagcaaatat ttcaaaatca   1440
actgactagt gcaggaggct gttgattggc tcttgactgt gatgcccgca attctcaaag   1500
gaggactaag gaccggcact gtggagcacc ctggctttgc cactcgccgg agcatcaatg   1560
ccgctgcctc tggaggagcc cttggatttt ctccatgcac tgtgaacttc tgtggcttca   1620
gttctcatgc tgcctcttcc aaaagggac acagaagcac tggctgctgc tacagaccgc   1680
aaaagcagaa agtttcgtga aaatgtccat cttttgggaaa ttttctaccc tgctcttgag   1740
cctgataacc catgccaggt cttatagatt cctgatctag aacctttcca ggcaatctca   1800 gacctaatt ccttctgttc tccttgttct gttctgggcc agtgaaggtc cttgttctga   1860
ttttgaaacg atctgcaggt cttgccagtg aaccctggaa caactgacca cacccacaag   1920
gcatccaaag tctgttggct tccaatccat ttctgtgtcc tgctggaggt tttaacctag   1980
acaaggattc cgcttattcc ttggtatggt gacagtgtct ctccatggcc tgagcaggga   2040
gattataaca gctgggttcg caggagccag ccttggccct gttgtaggct tgttctgttg   2100
agtggcactt gctttgggtc caccgtctgt ctgctcccta gaaatgggc tggttctttt   2160 ggccctcttc tttctgaggc ccactttatt ctgaggaata cagtgagcag atatgggcag   2220
cagccaggta gggcaaaggg gtgaagcgca ggccttgctg gaaggctatt tacttccatg   2280
cttctccttt tcttactcta tagtggcaac attttaaaag cttttaactt agagattagg   2340
ctgaaaaaaa taagtaatgg aattcacctt tgcatctttt gtgtctttct tatcatgatt   2400
tggcaaaatg catcacccttt gaaaatattt cacatattgg aaaagtgctt tttaatgtgt   2460
atatgaagca ttaattactt gtcactttct ttaccctgtc tcaatatttt aagtgtgtgc   2520
aattaaagat caaatagata catt                                         2544
```

<210> SEQ ID NO 132
<211> LENGTH: 2462
<212> TYPE: DNA
<213> ORGANISM: Homo sapiens
<220> FEATURE:
<221> NAME/KEY: CCR9B
<222> LOCATION: (1)..(2462)

<400> SEQUENCE: 132

```
gccctcatc ccaggcagag agcaacccag ctctttcccc agacactgag agctggtggt     60
```

-continued

```
gcctgctgtc ccagggagag ttgcatcgcc ctccacaagc cctattccta acatggctga    120
tgactatggc tctgaatcca catcttccat ggaagactac gttaacttca acttcactga    180
cttctactgt gagaaaaaca atgtcaggca gtttgcgagc catttcctcc caccccttgta   240
ctggctcgtg ttcatcgtgg gtgccttggg caacagtctt gttatccttg tctactggta    300
ctgcacaaga gtgaagacca tgaccgacat gttccttttg aatttggcaa ttgctgacct    360
cctctttctt gtcactcttc ccttctgggc cattgctgct gctgaccagt ggaagttcca    420
gaccttcatg tgcaaggtgg tcaacagcat gtacaagatg aacttctaca gctgtgtgtt    480
gctgatcatg tgcatcagcg tggacaggta cattgccatt gcccaggcca tgagagcaca    540
tacttggagg gagaaaaggc ttttgtacag caaaatggtt tgctttacca tctgggtatt    600
ggcagctgct ctctgcatcc cagaaatctt atacagccaa atcaaggagg aatccggcat    660
tgctatctgc accatggttt accctagcga tgagagcacc aaactgaagt cagctgtctt    720
gacccctgaag gtcattctgg ggttcttcct tcccttcgtg gtcatggctt gctgctatac    780
catcatcatt cacaccctga tacaagccaa gaagtcttcc aagcacaaag ccctaaaagt    840
gaccatcact gtcctgaccg tctttgtctt gtctcagttt ccctacaact gcattttgtt    900
ggtgcagacc attgacgcct atgccatgtt catctccaac tgtgccgttt ccaccaacat    960
tgacatctgc ttccaggtca cccagaccat cgccttcttc cacagttgcc tgaaccctgt   1020
tctctatgtt tttgtgggtg agagattccg ccgggatctc gtgaaaaccc tgaagaactt   1080
gggttgcatc agccaggccc agtgggtttc atttacaagg agagagggaa gcttgaagct   1140
gtcgtctatg ttgctggaga caacctcagg agcactctcc ctctgagggg tcttctctga   1200
ggtgcatggt tcttttggaa gaaatgagaa atacagaaac agtttcccca ctgatgggac   1260
cagagagagt gaaagagaaa agaaaactca gaaagggatg aatctgaact atatgattac   1320
ttgtagtcag aatttgccaa agcaaatatt tcaaaatcaa ctgactagtg caggaggctg   1380
ttgattggct cttgactgtg atgcccgcaa ttctcaaagg aggactaagg accggcactg   1440
tggagcaccc tggctttgcc actcgccgga gcatcaatgc cgctgcctct ggaggagccc   1500
ttggattttc tccatgcact gtgaacttct gtggcttcag ttctcatgct gcctcttcca   1560
aaaggggaca cagaagcact ggctgctgct acagaccgca aaagcagaaa gtttcgtgaa   1620
aatgtccatc tttgggaaat tttctaccct gctcttgagc ctgataaccc atgccaggtc   1680
ttatagattc ctgatctaga acctttccag gcaatctcag acctaatttc cttctgttct   1740
ccttgttctg ttctgggcca gtgaaggtcc ttgttctgat tttgaaacga tctgcaggtc   1800
ttgccagtga accctggac aactgaccac acccacaagg catccaaagt ctgttggctt    1860
ccaatccatt tctgtgtcct gctggaggtt taacctaga caaggattcc gcttattcct    1920
tggtatggtg acagtgtctc tccatggcct gagcagggag attataacag ctgggttcgc   1980
aggagccagc cttggccctg ttgtaggctt gttctgttga gtggcacttg ctttgggtcc   2040
accgtctgtc tgctccctag aaaatgggct ggttcttttg gccctcttct ttctgaggcc   2100
cactttattc tgaggaatac agtgagcaga tatgggcagc agccaggtag ggcaaagggg   2160
tgaagcgcag gccttgctgg aaggctattt acttccatgc ttctccttttt cttactctat   2220
agtggcaaca ttttaaaagc ttttaactta gagattaggc tgaaaaaaat aagtaatgga   2280
attcaccttt gcatcttttg tgtctttctt atcatgattt ggcaaaatgc atcacctttg   2340
aaaatatttc acatattgga aaagtgcttt ttaatgtgta tatgaagcat taattacttg   2400
tcactttctt taccctgtct caatatttta agtgtgtgca attaaagatc aaatagatac   2460
```

| | |
|---|---:|
| at | 2462 |

<210> SEQ ID NO 133
<211> LENGTH: 1244
<212> TYPE: DNA
<213> ORGANISM: Homo sapiens
<220> FEATURE:
<221> NAME/KEY: CCR10
<222> LOCATION: (1)..(1244)

<400> SEQUENCE: 133

| | | | | | |
|---|---|---|---|---|---:|
| agagatgggg | acggaggcca | cagagcaggt | ttcctggggc | cattactctg | gggatgaaga | 60 |
| ggacgcatac | tcggctgagc | cactgccgga | gctttgctac | aaggccgatg | tccaggcctt | 120 |
| cagccgggcc | ttccaaccca | gtgtctccct | gaccgtggct | gcgctgggtc | tggccggcaa | 180 |
| tggcctggtc | ctggccaccc | acctggcagc | ccgacgcgca | gcgcgctcgc | ccacctctgc | 240 |
| ccacctgctc | cagctggccc | tggccgacct | cttgctggcc | ctgactctgc | ccttcgcggc | 300 |
| agcagggct | cttcagggct | ggagtctggg | aagtgccacc | tgccgcacca | tctctggcct | 360 |
| ctactcggcc | tccttccacg | ccggcttcct | cttcctggcc | tgtatcagcg | ccgaccgcta | 420 |
| cgtggccatc | gcgcgagcgc | tcccagccgg | gccgcggccc | tccactcccg | gccgcgcaca | 480 |
| cttggtctcc | gtcatcgtgt | ggctgctgtc | actgctcctg | gcgctgcctg | cgctgctctt | 540 |
| cagccaggat | gggcagcggg | aaggccaacg | acgctgtcgc | ctcatcttcc | ccgagggcct | 600 |
| cacgcagacg | gtgaagggg | cgagcgccgt | ggcgcaggtg | gccctgggct | tcgcgctgcc | 660 |
| gctgggcgtc | atggtagcct | gctacgcgct | tctgggccgc | acgctgctgg | ccgccagggg | 720 |
| gcccgagcgc | cggcgtgcgc | tgcgcgtcgt | ggtggctctg | gtggcggcct | tcgtggtgct | 780 |
| gcagctgccc | tacagcctcg | ccctgctgct | ggatactgcc | gatctactgg | ctgcgcgcga | 840 |
| gcggagctgc | cctgccagca | aacgcaagga | tgtcgcactg | ctggtgacca | gcggcttggc | 900 |
| cctcgccccgc | tgtggcctca | atcccgttct | ctacgccttc | ctgggcctgc | gcttccgcca | 960 |
| ggacctgcgg | aggctgctac | ggggtgggag | ctcgccctca | gggcctcaac | ccgccgcgg | 1020 |
| ctgcccccgc | cggccccgcc | tttcttcctg | ctcagctccc | acggagaccc | acagtctctc | 1080 |
| ctgggacaac | tagggctgcg | aatctagagg | agggggcagg | ctgagggtcg | tgggaagggg | 1140 |
| gagtaggtgg | gggaacactg | agaaagaggc | agggacctaa | agggactacc | tctgtgccttt | 1200 |
| gccacattaa | attgataaca | tggaaatgaa | aaaaaaaaaa | aaaa | | 1244 |

<210> SEQ ID NO 134
<211> LENGTH: 2224
<212> TYPE: DNA
<213> ORGANISM: Homo sapiens
<220> FEATURE:
<221> NAME/KEY: CCRL1
<222> LOCATION: (1)..(2224)

<400> SEQUENCE: 134

| | | | | | |
|---|---|---|---|---|---:|
| aaaagtagct | ggagttaggt | catttgattt | tatactctgt | actcaagact | gctcctctct | 60 |
| gccgactaca | acagattgga | gccatggctt | tggaacagaa | ccagtcaaca | gattattatt | 120 |
| atgaggaaaa | tgaaatgaat | ggcacttatg | actacagtca | atatgaactg | atctgtatca | 180 |
| aagaagatgt | cagagaattt | gcaaaagttt | tcctccctgt | attcctcaca | atagttttcg | 240 |
| tcattggact | tgcaggcaat | tccatggtag | tgcaattta | tgcctattac | aagaaacaga | 300 |
| gaaccaaaac | agatgtgtac | atcctgaatt | tggctgtagc | agatttactc | cttctattca | 360 |
| ctctgccttt | ttgggctgtt | aatgcagttc | atggtgggt | tttagggaaa | ataatgtgca | 420 |

| aataaacttc agccttgtac acactaaact ttgtctctgg aatgcagttt ctggcttgta | 480 |
| tcagcataga cagatatgtg gcagtaacta aagtccccag ccaatcagga gtgggaaaac | 540 |
| catgctggat catctgtttc tgtgtctgga tggctgccat cttgctgagc atacccagc | 600 |
| tggttttta tacagtaaat gacaatgcta ggtgcattcc catttccccc cgctacctag | 660 |
| gaacatcaat gaaagcattg attcaaatgc tagagatctg cattggattt gtagtaccct | 720 |
| ttcttattat gggggtgtgc tactttatca cagcaaggac actcatgaag atgccaaaca | 780 |
| ttaaaatatc tcgaccccta aaagttctgc tcacagtcgt tatagttttc attgtcactc | 840 |
| aactgcctta taacattgtc aagttctgcc gagccataga catcatctac tccctgatca | 900 |
| ccagctgcaa catgagcaaa cgcatggaca tcgccatcca agtcacagaa agcatcgcac | 960 |
| tctttcacag ctgcctcaac ccaatccttt atgtttttat gggagcatct ttcaaaaact | 1020 |
| acgttatgaa agtggccaag aaatatgggt cctggagaag acagagacaa agtgtggagg | 1080 |
| agtttccttt tgattctgag ggtcctacag agccaaccag tacttttagc atttaaaggt | 1140 |
| aaaactgctc tgccttttgc ttggatacat atgaatgatg ctttcccctc aaataaaaca | 1200 |
| tctgcattat tctgaaactc aaatctcaga cgccgtggtt gcaacttata taaagaatg | 1260 |
| ggttggggga agggggagaa ataaaagcca agaagaggaa acaagataat aaatgtacaa | 1320 |
| aacatgaaaa ttaaaatgaa caatatagga aaataattgt aacaggcata agtgaataac | 1380 |
| actctgctgt aacgaagaag agctttgtgg tgataatttt gtatcttggt tgcagtggtg | 1440 |
| cttatacaaa tctacacaag tgataaaatg acacagaact atatacacac attgtaccaa | 1500 |
| tttcaatttc ctggttttga cattatagta taattatgta agatggaacc attggggaaa | 1560 |
| actgggtgaa gggtacccag gaccactctg taccatcttt gtaacttcct gtgaatttat | 1620 |
| aataatttca aaataaaaca agttaaaaaa aaacccacta tgctataagt taggccatct | 1680 |
| aaaacagatt attaaagagg ttcatgttaa aaggcattta taattatttt taattatcta | 1740 |
| agttttaata caagaacgat ttccctgcat aattttagta cttgaataag tatgcagcag | 1800 |
| aactccaact atctttttc ctgtttttt taaatttgta agtaatttta taaaatccac | 1860 |
| ctcctccaaa aaagcaataa aaaaaaaaca aactataata agcttttctg attcttttca | 1920 |
| aaacattcct ggtaagttcc taaagacata atttgcttct atgatgtcaa ctttcttact | 1980 |
| aataactggt tatcatgaca aatgttaggt ttatcatata tagtctaggt gtaatcctca | 2040 |
| gactatcatt ttcatctggg ttccaatttc ttaacttcct aaagaattca tctgtttata | 2100 |
| caagtctacc actgccgatt gactaaaaaa tacattatcc catgcataaa atgtcctatt | 2160 |
| ttcatttaaa cactttattt ttgagtaata aaatatgta ccacaataaa ttattgttaa | 2220 |
| ttaa | 2224 |

<210> SEQ ID NO 135
<211> LENGTH: 1745
<212> TYPE: DNA
<213> ORGANISM: Homo sapiens
<220> FEATURE:
<221> NAME/KEY: CCRL2-1
<222> LOCATION: (1)..(1745)

<400> SEQUENCE: 135

| gaggaggaaa caacttcccg gttgctttca gacgcttcag agatcctctg gaggcctggg | 60 |
| ggagcttttg agtactttat ttcagttggt ccctgagctc ggtgagtggg gcgggtagag | 120 |
| ccaccagggg aatcaacagt ggtttctcgt gcccctcagg gtcaggagca gtctgatcaa | 180 |
| aaggagggca tccactgtcc ggggccattc ccacagctcc cggatgctgg gtctggaggc | 240 |

```
tgcgccctcc ccctgcagga gctcagccca gtgggcagtc tgaagatggc caattacacg    300
ctggcaccag aggatgaata tgatgtcctc atagaaggtg aactggagag cgatgaggca    360
gagcaatgtg acaagtatga cgcccaggca ctctcagccc agctggtgcc atcactctgc    420
tctgctgtgt tgtgatcgg tgtcctggac aatctcctgg ttgtgcttat cctggtaaaa     480
tataaaggac tcaaacgcgt ggaaaatatc tatcttctaa acttggcagt ttctaacttg    540
tgtttcttgc ttaccctgcc cttctgggct catgctgggg gcgatccat gtgtaaaatt     600 ctcattggac tgtacttcgt gggcctgtac agtgagacat ttttcaattg ccttctgact    660
gtgcaaaggt acctagtgtt tttgcacaag ggaaactttt tctcagccag gaggagggtg    720
ccctgtggca tcattacaag tgtcctggca tgggtaacag ccattctggc cactttgcct    780
gaattcgtgg tttataaacc tcagatgaa gaccagaaat acaagtgtgc atttagcaga     840
actcccttcc tgccagctga tgagacattc tggaagcatt ttctgacttt aaaaatgaac    900
atttcggttc ttgtcctccc cctatttatt tttacatttc tctatgtgca aatgagaaaa    960
acactaaggt tcaggagca gaggtatagc cttttcaagc ttgttttgc cataatggta     1020 gtcttccttc tgatgtgggc gccctacaat attgcattt tcctgtccac tttcaaagaa    1080
cacttctccc tgagtgactg caagagcagc tacaatctgg acaaaagtgt tcacatcact    1140
aaactcatcg ccaccaccca ctgctgcatc aaccctctcc tgtatgcgtt tcttgatggg    1200
acatttagca aatacctctg ccgctgtttc catctgcgta gtaacacccc acttcaaccc    1260
agggggcagt ctgcacaagg cacatcgagg gaagaacctg accattccac cgaagtgtaa    1320
actagcatcc accaaatgca agaagaataa acatggatt tcatctttct gcattatttc    1380
atgtaaattt tctacacatt tgtatacaaa tcggataca ggagaaaag ggagaggtga     1440 gctaacattt gctaagcact gaatttgtct caggcaccgt gcaaggctct ttacaaacgt    1500
gagctccttc gcctcctacc acttgtccat agtgtggata ggactagtct catttctctg    1560
agaagaaaac taaggcgcgg aaatttgtct aagatcacat aactaggaag tggcagaact    1620
gattctccag ccctggtagc atttgctcag agcctacgct tggtccagaa catcaaactc    1680
caaaccctgg ggacaaacga catgaaataa atgtatttta aacatctaa aaaaaaaaa     1740 aaaaa                                                                1745

<210> SEQ ID NO 136
<211> LENGTH: 1612
<212> TYPE: DNA
<213> ORGANISM: Homo sapiens
<220> FEATURE:
<221> NAME/KEY: CCRL2-2
<222> LOCATION: (1)..(1612)

<400> SEQUENCE: 136
gagcatggtt tcacttttgc aaacatttat ttatacccctt cgagagaaaa acgtctcagc    60
tgtcacagga agctgcttcg gggggtgagc aaacttttta aaatgcagaa attatgatct    120 acaccgttt cttaaaaggc agtctgaaga tggccaatta cacgctggca ccagaggatg    180
aatatgatgt ccctcataga agtgaactgg agagcgatga ggcagagcaa tgtgacaagt    240
atgacgccca ggcactctca gcccagctgg tgccatcact ctgctctgct gtgtttgtga    300
tcggtgtcct ggacaatctc ctggttgtgc ttatcctggt aaaatataaa ggactcaaac    360
gcgtggaaaa tatctatctt ctaaacttgg cagtttctaa cttgtgtttc ttgcttaccc    420
tgcccttctg ggctcatgct gggggcgatc ccatgtgtaa aattctcatt ggactgtact    480
```

-continued

| | |
|---|---|
| tcgtgggcct gtacagtgag acattttica attgccttct gactgtgcaa aggtacctag | 540 |
| tgttttgca aagggaaac ttttctcag ccaggaggag ggtgccctgt ggcatcatta | 600 |
| caagtgtcct ggcatgggta acagccattc tggccacttt gcctgaattc gtggtttata | 660 |
| aacctcagat ggaagaccag aaatacaagt gtgcatttag cagaactccc ttcctgccag | 720 |
| ctgatgagac attctggaag cattttctga cttaaaaat gaacatttcg gttcttgtcc | 780 |
| tcccctatt tattttaca tttctctatg tgcaaatgag aaaaacacta aggttcaggg | 840 |
| agcagaggta tagccttttc aagcttgttt ttgccataat ggtagtcttc cttctgatgt | 900 |
| gggcgcccta caatattgca tttttcctgt ccactttcaa agaacacttc tccctgagtg | 960 |
| actgcaagag cagctacaat ctggacaaaa gtgttcacat cactaaactc atcgccacca | 1020 |
| cccactgctg catcaaccct ctcctgtatg cgtttcttga tgggacattt agcaaatacc | 1080 |
| tctgccgctg tttccatctg cgtagtaaca ccccacttca acccagggg cagtctgcac | 1140 |
| aaggcacatc gagggaagaa cctgaccatt ccaccgaagt gtaaactagc atccaccaaa | 1200 |
| tgcaagaaga ataaacatgg attttcatct ttctgcatta tttcatgtaa attttctaca | 1260 |
| catttgtata caaaatcgga tacaggaaga aaagggagag gtgagctaac atttgctaag | 1320 |
| cactgaattt gtctcaggca ccgtgcaagg ctctttacaa acgtgagctc cttcgcctcc | 1380 |
| taccacttgt ccatagtgtg gataggacta gtctcatttc tctgagaaga aaactaaggc | 1440 |
| gcggaaattt gtctaagatc acataactag gaagtggcag aactgattct ccagccctgg | 1500 |
| tagcatttgc tcagagccta cgcttggtcc agaacatcaa actccaaacc ctggggacaa | 1560 |
| acgacatgaa ataaatgtat tttaaaacat ctaaaaaaaa aaaaaaaaa aa | 1612 |

<210> SEQ ID NO 137
<211> LENGTH: 1367
<212> TYPE: DNA
<213> ORGANISM: Homo sapiens
<220> FEATURE:
<221> NAME/KEY: XCL1
<222> LOCATION: (1)..(1367)

<400> SEQUENCE: 137

| | |
|---|---|
| taagaaaaat aaaagcatca gtattgcaaa gactttccat gatcctacac ccacctcgaa | 60 |
| agcccctct caccacagga agtgcactga ccactggagg cataaaagag gtcctcaaag | 120 |
| agcccgatcc tcactctcct tgcacagctc agcaggacct cagccatgag acttctcatc | 180 |
| ctggccctcc ttggcatctg ctctctcact gcatacattg tggaaggtgt agggagtgaa | 240 |
| gtctcagata agaggacctg tgtgagcctc actacccagc gactgccggt tagcagaatc | 300 |
| aagacctaca ccatcacgga aggctccttg agacagtaa ttttattac caaacgtggc | 360 |
| ctaaaagtct gtgctgatcc acaagccaca tgggtgagag acgtggtcag gagcatggac | 420 |
| aggaaatcca acaccagaaa taacatgatc cagaccaagc caacaggaac ccagcaatcg | 480 |
| accaatacag ctgtgactct gactggctag tagtctctgg caccctgtcc gtctccagcc | 540 |
| agccagctca tttcactta cacgctcatg gactgagttt atactcacct tttatgaaag | 600 |
| cactgcatga ataaaattat tcctttgtat tttactttt aaatgtcttc tgtattcact | 660 |
| tatatgttct aattaataaa ttatttatta ttaagaatag ttccctagtc tattcattat | 720 |
| atttagggaa aggtagtgta tcattgttgt ttgattctg accttgtacc tctctttgat | 780 |
| ggtaaccata atggaagaga ttctggctag tgtctatcag aggtgaaagc tatatcaatc | 840 |
| tctcttagag tccagcttgt aatggttctt tacacatcag tcacaagtta cagctgtgac | 900 |
| aatggcaaca atttgagatg tatttcaact tgtctctata atagaattct gtttatagaa | 960 |

```
taagggagaa aataatccag tcttcactgg gttcccattc tgagggtcca ctactcaaaa    1020
atttgcttca ctcaattttt ttcacctctt tgtgttttat tttggtgtcc tattaaagga    1080
ataaaatgac acaacttgtc ccttttttgt cccattagca aaattagaa tttttggtata    1140 aagaaacttt attcaagtaa aaatcaatac cctttgaatt ggacaataat ctcactacct    1200
tattaggatt tctgtatttg ccattacgct agttatcatg catgttatgc tttactgcga    1260
ataagctttt aatgctccaa atgctgaccc atgcaatatt tcctcatgtg atcacaattt    1320 gcagtaaaact tttaattaaa tgctcatctg gtaactcaac accccag                 1367

<210> SEQ ID NO 138
<211> LENGTH: 1373
<212> TYPE: DNA
<213> ORGANISM: Homo sapiens
<220> FEATURE:
<221> NAME/KEY: XCR1
<222> LOCATION: (1)..(1373)

<400> SEQUENCE: 138
ctttaagtga aatatgaaac agagaagcac catttctgcc tcaagacgca tgtaaagagg      60
tgtagattca ggttggagtg cagtggcatg atcacagctc tctgcagtct cgccctcctg    120
ggctcaagca atctttcccc accccccggt ttcctgagta gctgggacta taggcatgcg    180
ccaccacacc cggatgctct aaacgtccct gccatctggt ccagatggag tcctcaggca    240
acccagagag caccaccttt ttttactatg accttcagag ccagccgtgt gagaaccagg    300
cctgggtctt tgctacccct gccaccactg tcctatactg cctggtgttt ctcctcagcc    360
tagtgggcaa cagcctggtc ctgtgggtcc tggtgaagta tgagagcctg gagtccctca    420
ccaacatctt catcctcaac ctgtgcctct cagacctggt gttcgcctgc ttgttgcctg    480
tgtggatctc cccataccac tggggctggg tgctgggaga cttcctctgc aaactcctca    540
atatgatctt ctccatcagc ctctacagca gcatcttctt cctgaccatc atgaccatcc    600
accgctacct gtcggtagtg agccccctct ccaccctgcg cgtccccacc ctccgctgcc    660
gggtgctggt gaccatggct gtgtgggtag ccagcatcct gtcctccatc ctcgacacca    720
tcttccacaa ggtgctttct tcgggctgtg attattccga actcacgtgg tacctcacct    780
ccgtctacca gcacaacctc ttcttcctgc tgtccctggg gattatcctg ttctgctacg    840
tggagatcct caggaccctg ttccgctcac gctccaagcg gcgccaccgc acggtcaagc    900
tcatcttcgc catcgtggtg gcctacttcc tcagctgggg tccctacaac ttcaccctgt    960
ttctgcagac gctgtttcgg acccagatca tccggagctg cgaggccaaa cagcagctag   1020
aatacgccct gctcatctgc cgcaacctcg ccttctccca ctgctgcttt aacccggtgc   1080
tctatgtctt cgtggggggtc aagttccgca cacacctgaa acatgttctc cggcagttct   1140
ggttctgccg gctgcaggca cccagcccag cctcgatccc ccactcccct ggtgccttcg   1200
cctatgaggg cgcctccttc tactgagggg cctgtggcgg tgcaggcgca ggtgcaggtg   1260
gacagggact ggaatggggg tcatggagaa gcgggcctgg aaggagcatt gcagaacaca   1320
gcagggtgga gacgtctcct ccgctgcagg cgtgcagtga aggtcattca tta          1373

<210> SEQ ID NO 139
<211> LENGTH: 3160
<212> TYPE: DNA
<213> ORGANISM: Homo sapiens
<220> FEATURE:
<221> NAME/KEY: CX3CR1a
<222> LOCATION: (1)..(3160)
```

<400> SEQUENCE: 139

```
gggcgggcc gtgcttacca ggccgtggac ttaaaccagg atgagagaac ccctggaggc    60
gtttaagttg gcagacttgg atttcaggaa gagctctctg gcttctgggt ggagaatggc   120
cagtgggcc ttcaccatgg atcagttccc tgaatcagtg acagaaaact ttgagtacga   180
tgatttggct gaggcctgtt atattgggga catcgtggtc tttgggactg tgttcctgtc   240
catattctac tccgtcatct ttgccattgg cctggtggga aatttgttgg tagtgtttgc   300
cctcaccaac agcaagaagc ccaagagtgt caccgacatt tacctcctga acctggcctt   360
gtctgatctg ctgtttgtag ccactttgcc cttctggact cactatttga taaatgaaaa   420
gggcctccac aatgccatgt gcaaattcac taccgccttc ttcttcatcg gcttttttgg   480
aagcatattc ttcatcaccg tcatcagcat tgataggtac ctggccatcg tcctggccgc   540
caactccatg aacaaccgga ccgtgcagca tggcgtcacc atcagcctag gcgtctgggc   600
agcagccatt ttggtggcag caccccagtt catgttcaca aagcagaaag aaaatgaatg   660
ccttggtgac taccccgagg tcctccagga atctggcccc gtgctccgca atgtggaaac   720
aaattttctt ggcttcctac tcccctgct cattatgagt tattgctact tcagaatcat   780
ccagacgctg ttttcctgca agaaccacaa gaaagccaaa gccattaaac tgatccttct   840
ggtggtcatc gtgttttttcc tcttctggac ccctacaac gttatgattt tcctggagac   900
gcttaagctc tatgacttct ttcccagttg tgacatgagg aaggatctga ggctggccct   960
cagtgtgact gagacggttg catttagcca ttgttgcctg aatcctctca tctatgcatt  1020
tgctggggag aagttcagaa gatacctta ccacctgtat gggaaatgcc tggctgtcct  1080
gtgtgggcgc tcagtccacg ttgatttctc ctcatctgaa tcacaaagga gcaggcatgg  1140
aagtgttctg agcagcaatt ttacttacca cacgagtgat ggagatgcat tgctccttct  1200
ctgaagggaa tcccaaagcc ttgtgtctac agagaacctg gagttcctga acctgatgct  1260
gactagtgag gaaagatttt tgttgttatt tcttacaggc acaaaatgat ggacccaatg  1320
cacacaaaac aaccctagag tgttgttgag aattgtgctc aaaatttgaa gaatgaacaa  1380
attgaactct ttgaatgaca aagagtagac atttctctta ctgcaaatgt catcagaact  1440
ttttggtttg cagatgacaa aaattcaact cagactagtt tagttaaatg agggtggtga  1500
atattgttca tattgtggca caagcaaaag ggtgtctgag ccctcaaagt gaggggaaac  1560
cagggcctga gccaagctag aattccctct ctctgactct caaatctttt agtcattata  1620
gatcccccag actttacatg acacagcttt atcaccagag agggactgac acccatgttt  1680
ctctggcccc aagggcaaaa ttcccaggga agtgctctga taggccaagt ttgtatcagg  1740
tgcccatccc tggaaggtgc tgttatccat ggggaaggga tatataagat ggaagcttcc  1800
agtccaatct catggagaag cagaaataca tatttccaag aagttggatg ggtgggtact  1860
attctgatta cacaaaacaa atgccacaca tcacccttac catgtgcctg atccagcctc  1920
tccccctgatt acaccagcct cgtcttcatt aagccctctt ccatcatgtc cccaaacctg  1980
caagggctcc ccactgccta ctgcatcgag tcaaaactca aatgcttggc ttctcatacg  2040
tccaccatgg ggtcctacca atagattccc cattgcctcc tccttcccaa aggactccac  2100
ccatcctatc agcctgtctc ttccatatga cctcatgcat ctccacctgc tcccaggcca  2160
gtaagggaaa tagaaaaacc ctgcccccaa ataagaaggg atggattcca accccaactc  2220
cagtagcttg ggacaaatca agcttcagtt tcctggtctg tagaagaggg ataaggtacc  2280
tttcacatag agatcatcct ttccagcatg aggaactagc caccaactct tgcaggtctc  2340
```

```
aacccttttg tctgcctctt agacttctgc tttccacacc tggcactgct gtgctgtgcc    2400
caagttgtgg tgctgacaaa gcttggaaga gcctgcaggt gctgctgcgt ggcatagccc    2460
agacacagaa gaggctggtt cttacgatgg cacccagtga gcactcccaa gtctacagag    2520
tgatagcctt ccgtaaccca actctcctgg actgccttga atatcccctc ccagtcacct    2580
tgtggcaagc ccctgcccat ctgggaaaat accccatcat tcatgctact gccaacctgg    2640
ggagccaggg ctatgggagc agcttttttt tcccccctag aaacgtttgg aacaatctaa    2700
aagtttaaag ctcgaaaaca attgtaataa tgctaaagaa aaagtcatcc aatctaacca    2760
catcaatatt gtcattcctg tattcacccg tccagacctt gttcacactc tcacatgttt    2820
agagttgcaa tcgtaatgta cagatggttt tataatctga tttgttttcc tcttaacgtt    2880
agaccacaaa tagtgctcgc tttctatgta gtttggtaat tatcattttta gaagactcta    2940 ccagactgtg tattcattga agtcagatgt ggtaactgtt aaattgctgt gtatctgata    3000
gctctttggc agtctatatg tttgtataat gaatgagaga ataagtcatg ttccttcaag    3060
atcatgtacc ccaatttact tgccattact caattgataa acatttaact tgtttccaat    3120
gtttagcaaa tacatatttt atagaacttc caaaaaaaaa                          3160
```

<210> SEQ ID NO 140
<211> LENGTH: 3108
<212> TYPE: DNA
<213> ORGANISM: Homo sapiens
<220> FEATURE:
<221> NAME/KEY: CX3CR1b
<222> LOCATION: (1)..(3108)

<400> SEQUENCE: 140

```
gaaatactcg tctctggtaa agtctgagca ggacagggtg gctgactggc agatccagag      60
gttcccttgg cagtccacgc caggccttca ccatggatca gttccctgaa tcagtgacag     120
aaaactttga gtacgatgat ttggctgagg cctgttatat tggggacatc gtggtctttg     180
ggactgtgtt cctgtccata ttctactccg tcatctttgc cattggcctg gtgggaaatt     240
tgttggtagt gtttgccctc accaacagca agaagcccaa gagtgtcacc gacatttacc     300
tcctgaacct ggccttgtct gatctgctgt ttgtagccac tttgcccttc tggactcact     360
atttgataaa tgaaagggc ctccacaatg ccatgtgcaa attcactacc gccttcttct     420
tcatcggctt ttttggaagc atattcttca tcaccgtcat cagcattgat aggtacctgg     480
ccatcgtcct ggccgccaac tccatgaaca accggaccgt gcagcatggc gtcaccatca    540
gcctaggcgt ctgggcagca gccatttttgg tggcagcacc ccagttcatg ttcacaaagc     600
agaaagaaaa tgaatgcctt ggtgactacc ccgaggtcct ccaggaaatc tggcccgtgc     660
tccgcaatgt ggaaacaaat tttcttggct tcctactccc cctgctcatt atgagttatt     720
gctacttcag aatcatccag acgctgtttt cctgcaagaa ccacaagaaa gccaaagcca     780
ttaaactgat ccttctggtg gtcatcgtgt ttttcctctt ctggacaccc tacaacgtta    840 tgatttcct ggagacgctt aagctctatg acttctttcc cagttgtgac atgaggaagg     900
atctgaggct ggccctcagt gtgactgaga cggttgcatt tagccattgt tgcctgaatc     960
ctctcatcta tgcatttgct ggggagaagt tcagaagata cctttaccac ctgtatggga    1020
aatgcctggc tgtcctgtgt gggcgctcag tccacgttga tttctcctca tctgaatcac    1080
aaaggagcag gcatgaagt gttctgagca gcaatttttac ttaccacacg agtgatggag    1140
atgcattgct ccttctctga agggaatccc aaagccttgt gtctacagag aacctggagt    1200
```

```
tcctgaacct gatgctgact agtgaggaaa gattttgtt gttatttctt acaggcacaa    1260
aatgatggac ccaatgcaca caaaacaacc ctagagtgtt gttgagaatt gtgctcaaaa   1320
tttgaagaat gaacaaattg aactctttga atgacaaaga gtagacattt ctcttactgc   1380
aaatgtcatc agaactttt ggtttgcaga tgacaaaaat tcaactcaga ctagtttagt    1440
taaatgaggg tggtgaatat tgttcatatt gtggcacaag caaaagggtg tctgagccct   1500
caaagtgagg gaaaccagg gcctgagcca agctagaatt ccctctctct gactctcaaa    1560
tcttttagtc attatagatc ccccagactt tacatgacac agctttatca ccagagaggg   1620
actgacaccc atgtttctct ggccccaagg gcaaaattcc cagggaagtg ctctgatagg   1680
ccaagtttgt atcaggtgcc catccctgga aggtgctgtt atccatgggg aagggatata   1740
taagatggaa gcttccagtc caatctcatg gagaagcaga atacatatt tccaagaagt    1800
tggatgggtg ggtactattc tgattacaca aaacaaatgc cacacatcac ccttaccatg   1860
tgcctgatcc agcctctccc ctgattacac cagcctcgtc ttcattaagc cctcttccat   1920
catgtcccca aacctgcaag ggctccccac tgcctactgc atcgagtcaa aactcaaatg   1980
cttggcttct catacgtcca ccatggggtc ctaccaatag attccccatt gcctcctcct   2040
tcccaaagga ctccacccat cctatcagcc tgtctcttcc atatgacctc atgcatctcc   2100
acctgctccc aggccagtaa gggaaataga aaaccctgc ccccaaataa gaagggatgg    2160
attccaaccc caactccagt agcttgggac aaatcaagct tcagtttcct ggtctgtaga   2220
agagggataa ggtacctttc acatagagat catcctttcc agcatgagga actagccacc   2280
aactcttgca ggtctcaacc cttttgtctg cctcttagac ttctgctttc cacacctggc   2340
actgctgtgc tgtgcccaag ttgtggtgct gacaaagctt ggaagagcct gcaggtgctg   2400
ctgcgtggca tagcccagac acagaagagg ctggttctta cgatggcacc cagtgagcac   2460
tcccaagtct acagagtgat agccttccgt aacccaactc tcctggactg ccttgaatat   2520
cccctcccag tcaccttgtg gcaagcccct gcccatctgg gaaaatacc catcattcat    2580
gctactgcca acctggggag ccagggctat gggagcagct tttttttccc ccctagaaac   2640
gtttggaaca atctaaaagt ttaaagctcg aaaacaattg taataatgct aaagaaaaag   2700
tcatccaatc taaccacatc aatattgtca ttcctgtatt cacccgtcca gaccttgttc   2760
acactctcac atgtttagag ttgcaatcgt aatgtacaga tggttttata atctgatttg   2820
ttttcctctt aacgttagac cacaaatagt gctcgctttc tatgtagttt ggtaattatc   2880
attttagaag actctaccag actgtgtatt cattgaagtc agatgtggta actgttaaat   2940
tgctgtgtat ctgatagctc tttggcagtc tatatgtttg tataatgaat gagagaataa   3000
gtcatgttcc ttcaagatca tgtaccccaa tttacttgcc attactcaat tgataaacat   3060
ttaacttgtt tccaatgttt agcaaataca tattttatag aacttcca              3108
```

<210> SEQ ID NO 141
<211> LENGTH: 3304
<212> TYPE: DNA
<213> ORGANISM: Homo sapiens
<220> FEATURE:
<221> NAME/KEY: CX3CL1
<222> LOCATION: (1)..(3304)

<400> SEQUENCE: 141

```
ctgagctctg ccgcctggct ctagccgcct gcctggcccc cgccgggact cttgcccacc     60
ctcagccatg gctccgatat ctctgtcgtg gctgctccgc ttggccacct tctgccatct    120
gactgtcctg ctggctggac agcaccacgg tgtgacgaaa tgcaacatca cgtgcagcaa    180
```

```
gatgacatca aagatacctg tagctttgct catccactat caacagaacc aggcatcatg    240
cggcaaacgc gcaatcatct tggagacgag acagcacagg ctgttctgtg ccgacccgaa    300
ggagcaatgg gtcaaggacg cgatgcagca tctggaccgc caggctgctg ccctaactcg    360
aaatggcggc accttcgaga agcagatcgg cgaggtgaag cccaggacca cccctgccgc    420
cgggggaatg gacgagtctg tggtcctgga gcccgaagcc acaggcgaaa gcagtagcct    480
ggagccgact ccttcttccc aggaagcaca gagggccctg ggacctccc cagagctgcc    540
gacgggcgtg actggttcct cagggaccag gctccccccg acgccaaagg ctcaggatgg    600
agggcctgtg ggcacggagc ttttccgagt gcctcccgtc tccactgccg ccacgtggca    660
gagttctgct ccccaccaac ctgggcccag cctctgggct gaggcaaaga cctctgaggc    720
cccgtccacc caggacccct ccacccaggc ctccactgcg tcctccccag ccccagagga    780
gaatgctccg tctgaaggcc agcgtgtgtg gggtcaggga cagagcccca ggccagagaa    840
ctctctggag cgggaggaga tgggtcccgt gccagcgcac acggatgcct tccaggactg    900
ggggcctggc agcatggccc acgtctctgt ggtccctgtc tcctcagaag gaccccccag    960
cagggagcca gtggcttcag gcagctggac ccctaaggct gaggaaccca tccatgccac   1020
catggacccc cagaggctgg gcgtccttat cactcctgtc cctgacgccc aggctgccac   1080
ccggaggcag gcggtggggc tgctggcctt ccttggcctc ctcttctgcc tggggggtgc   1140
catgttcacc taccagagcc tccagggctg ccctcgaaag atggcaggag agatggcgga   1200
gggccttcgc tacatccccc ggagctgtgg tagtaattca tatgtcctgg tgcccgtgtg   1260
aactcctctg gcctgtgtct agttgtttga ttcagacagc tgcctgggat ccctcatcct   1320
catacccacc cccacccaag ggcctggcct gagctgggat gattggaggg gggaggtggg   1380
atcctccagg tgcacaagct ccaagctccc aggcattccc caggaggcca gccttgacca   1440
ttctccacct tccagggaca gagggggtgg cctcccaact caccccagcc ccaaaactct   1500
cctctgctgc tggctggtta gaggttccct ttgacgccat cccagcccca atgaacaatt   1560
atttattaaa tgcccagccc cttctgaccc atgctgccct gtgagtacta cagtcctccc   1620
atctcacaca tgagcatcag gccaggccct ctgcccactc cctgcaacct gattgtgtct   1680
cttggtcctg ctgcagttgc cagtcacccc ggccacctgc ggtgctatct cccccagccc   1740
catcctctgt acagagccca cgcccccact ggtgacatgt cttttcttgc atgaggctag   1800
tgtggtgttt cctggcactg cttccagtga ggctctgccc ttggttaggc attgtgggaa   1860
ggggagataa gggtatctgg tgactttcct ctttggtcta cactgtgctg agtctgaagg   1920
ctgggttctg atcctagttc caccatcaag ccaccaacat actcccatct gtgaaaggaa   1980
agagggaggt aaggaatacc tgtcccctg acaacactca ttgacctgag gcccttctct   2040
ccagcccctg gatgcagcct cacagtcctt accagcagag caccttagac agtccctgcc   2100
aatggactaa cttgtctttg gaccctgagg cccagagggc ctgcaaggga gtgagttgat   2160
agcacagacc ctgccctgtg ggcccccaaa tggaaatggg cagagcagag accatccctg   2220
aaggccccgc ccaggcttag tcactgagac agcccgggct ctgcctccca tcacccgcta   2280
agagggaggg agggctccag acacatgtcc aagaagccca ggaaaggctc caggagcagc   2340
cacattcctg atgcttcttc agagactcct gcaggcagcc aggccacaag accttgtgg   2400
tcccacccca cacacgccag attctttcct gaggctgggc tccttccca cctctctcac   2460
tccttgaaaa cactgttctc tgccctccaa gaccttctcc ttcacctttg tccccaccgc   2520
agacaggacc agggatttcc atgatgtttt ccatgagtcc cctgtttgtt tctgaaaggg   2580
```

```
acgctacccg ggaaggggge tgggacatgg gaaaggggaa gttgtaggca taaagtcagg  2640
ggttcccttt tttggctgct gaaggctcga gcatgcctgg atggggctgc accggctggc  2700 ctggccctc  agggtccctg gtggcagctc acctctccct tggattgtcc ccgacccttg  2760
ccgtctacct gagggcctc  ttatgggctg ggttctaccc aggtgctagg aacactcctt  2820
cacagatggg tgcttggagg aaggaaaccc agctctggtc catagagagc aagacgctgt  2880
gctgccctgc ccacctggcc tctgcactcc cctgctgggt gtggcgcagc atattcagga  2940
agctcagggc ctggctcagg tggggtcact ctggcagctc agagagggtg ggagtgggtc  3000
caatgcactt tgttctggct cttccaggct gggagagcct ttcaggggtg ggacaccctg  3060
tgatggggcc ctgcctcctt tgtgaggaag ccgctggggc cagttggtcc cccttccatg  3120
gactttgtta gtttctccaa gcaggacatg gacaaggatg atctaggaag actttggaaa  3180
gagtaggaag actttggaaa gacttttcca accctcatca ccaacgtctg tgccattttg  3240
tattttacta ataaaattta aaagtcttgt gaaaaaaaaa aaaaaaaaaa aaaaaaaaa   3300 aaaa                                                              3304
```

US 8,563,476 B2

ANTI-CXCL9, ANTI-CXCL10, ANTI-CXCL11, ANTI-CXCL13, ANTI-CXCR3 AND ANTI-CXCR5 AGENTS FOR INFLAMMATORY DISORDERS

This application is a Continuation-In-Part of U.S. patent application Ser. No. 13/105,335, filed on May 11, 2011, which is a continuation application of U.S. patent application Ser. No. 10/712,393, filed on Nov. 14, 2003, now U.S. Pat. No. 7,964,194, which claims priority of U.S. Provisional Application No. 60/426,350, filed on Nov. 15, 2002.

FIELD

This application generally relates to detection of inflammatory diseases. In particular, the application relates to a method for detecting inflammatory diseases using anti-chemokine and/or anti-chemokine receptor detection reagents.

BACKGROUND

Despite recent advances in studies related to the inflammation process, methods for diagnosing and treating chronic inflammatory diseases have remained largely elusive. This is perhaps a result of the many and complex factors in the host that initiate and maintain inflammatory conditions. Current therapies have disadvantages associated with them, including the suppression of the immune system that can render the host more susceptible to bacterial, viral and parasitic infections. For example, use of steroids is a traditional approach to chronic inflammation treatment. Such treatment can lead to changes in weight and suppression of protective immunity. Advances in biotechnology have promoted the development of targeted biologicals with fewer side effects. To improve inflammatory disease treatment, technologies that alter and control the factors generated by cells of both innate and adaptive immunity systems need to be developed.

Host cells have surface receptors that associate with ligands to signal and regulate host cell activities. Administration of anti-TNF-α antibody or soluble TNF-α receptor has been shown to inhibit inflammatory diseases. Unfortunately, the side effects associated with this treatment can result in an increased risk of infections (e.g., tuberculosis) and other adverse reactions by mechanisms not fully understood. Similarly, antibody therapies focused on membrane bound molecules like CD40 have a propensity for inhibiting inflammation and graft-host diseases. While other targeted host cell therapies to prevent inflammatory diseases are being developed, there is no known single surface or secreted factor that will stop all inflammatory diseases. Consequently, the development of therapies to exploit newly identified specific host cell targets is required.

A variety of pathogens or toxins activate macrophages, neutrophils, T cells, B cells, monocytes, NK cells, Paneth and crypt cells, as well as epithelial cells shortly after entry into the mucosa. Chemokines represent a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein-coupled receptors. Chemokines can mediate the growth and migration of host cells that express their receptors. The cellular mechanisms responsible for the function of chemokines are often, but not entirely, $Ca^{2+}$ flux dependent and pertussis toxin-sensitive. However, the precise mechanisms for chemokine-mediated events are not known.

SUMMARY

One aspect of the present application relates to an isolated anti-CXCL9, anti-CXCL10, anti-CXCL11, anti-CXCL13, anti-CXCR3 or anti-CXCR5 agent having binding affinity with Kd value in the range of 0.01 pM to 1 uM for inflammatory disorder. In one embodiment, the present application directs to a method for detecting an inflammatory disease in a subject. The method comprises the steps of (a) detecting a level of expression of one or more inflammatory disease markers in a biological sample obtained from the subject; and (b) comparing the level of expression of said one or more inflammatory disease markers in the biological sample to a normal level of expression of the one or more inflammatory disease markers, wherein a higher than normal level of expression of one or more of the plurality of inflammatory disease markers in the biological sample is indicative of the presence of an inflammatory disease in the subject, wherein the normal levels of expression of said plurality of inflammatory disease markers is a predetermined value, and wherein the one or more inflammatory disease markers comprise one or more markers selected from the group consisting of CXCL9, CXCL10, CXCL11, CXCL13, CXCR3 and CXCR5.

Another aspect of the present application relates to a method for monitoring the course of treatment for an inflammatory disease in a subject. The method comprises the steps of determining the expression levels of one or more inflammatory disease markers in one or more biological samples obtained from the subject during or after the treatment, and comparing the level of expression of the one or more inflammatory disease markers in the one or more biological samples to a control level of expression of the one or more inflammatory disease markers, wherein the control level of the one or more inflammatory disease markers is a pre-treatment level of the one or more inflammatory disease markers in the subject or a predetermined reference level, wherein the treatment is deemed efficacious if the levels of expression of the one or more inflammatory disease markers in the one or more biological samples obtained from the subject during or after the treatment are similar to, or lower than, the control level, wherein the one or more inflammation markers comprise one or more inflammatory disease markers selected from the group consisting of CXCL9, CXCL10, CXCL11, CXCL13, CXCR3 and CXCR5.

Another aspect of the present application relates to a kit for detecting an inflammatory disease in a subject. The kit comprises reagents for determining expression of one or more inflammatory disease markers selected from the group consisting of CXCL9, CXCL10, CXCL11, CXCL13, CXCR3 and CXCR5; reagents for determining expression of one or more inflammatory disease markers selected from the group consisting of leptin, tumor necrosis factor α (TNFα), interferon-γ (IF-γ), interleukin-1α (IL-1α), IL-1β, IL-6, IL-12, IL-17, and IL-23 in a biological sample; and instructions for how to use said reagents.

DETAILED DESCRIPTION

Figure 1:
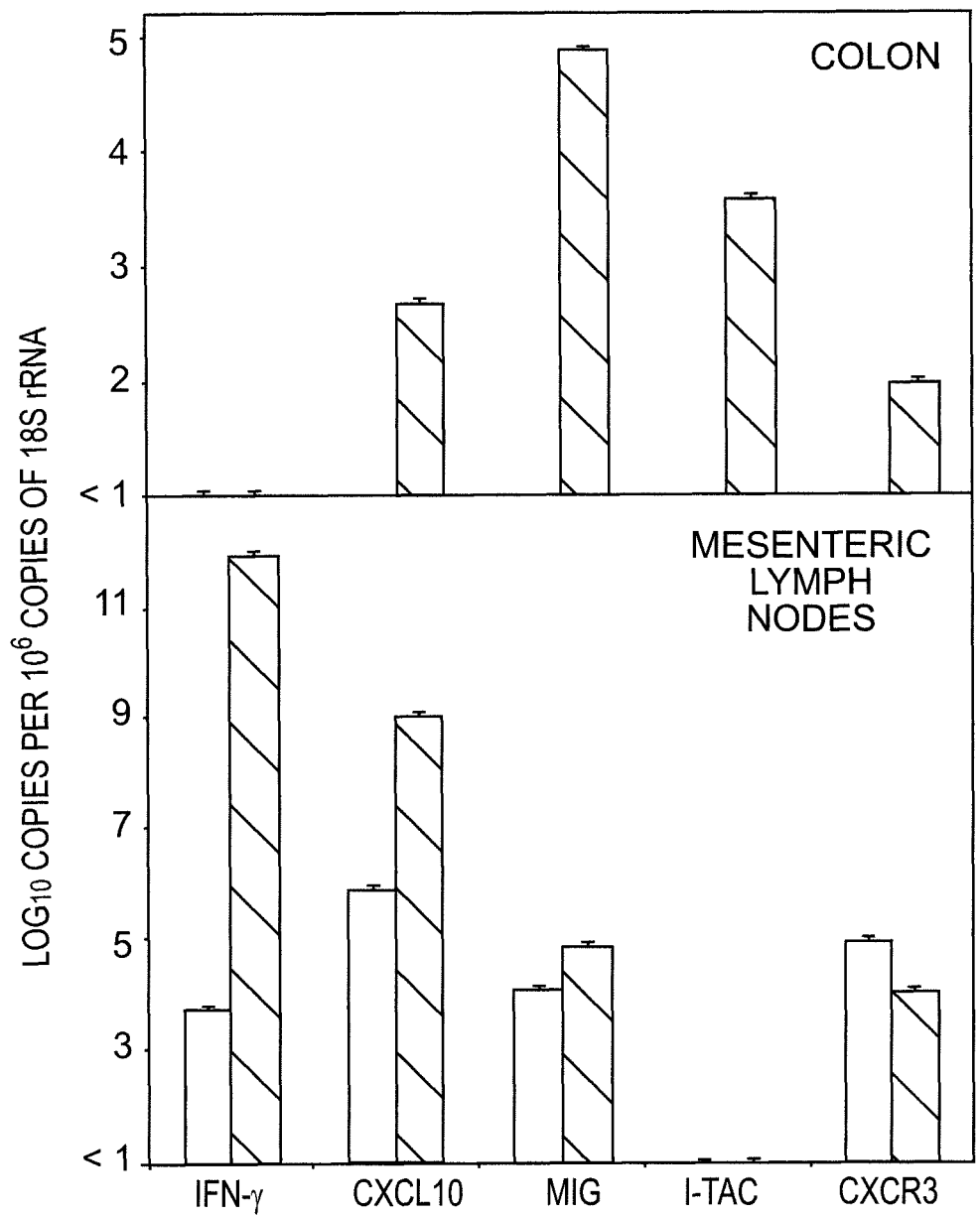
FIG. 1 shows IFN-γ, IP-10, MIG, I-TAC, and CXCR3 mRNA expression during murine colitis.

The following detailed description is presented to enable any person skilled in the art to make and use the present application. For purposes of explanation, specific nomenclature is set forth to provide a thorough understanding of the present application. However, it will be apparent to one skilled in the art that these specific details are not required to practice the present application. Descriptions of specific applications are provided only as representative examples. The present application is not intended to be limited to the embodiments shown, but is to be accorded the widest possible scope consistent with the principles and features disclosed herein.

Unless otherwise defined, scientific and technical terms used in connection with the present application shall have the meanings that are commonly understood by those of ordinary skill in the art. Further, unless otherwise required by context, singular terms shall include pluralities and plural terms shall include the singular.

DEFINITIONS

As used herein, the following terms shall have the following meanings:

The term "biological sample" refers to material of a biological origin, which may be a body fluid or body product such as blood, plasma, urine, saliva, cerebral fluid, synovial fluid, spinal fluid, stool, lymph, sweat, nipple aspirate or breath. A biological sample may include tissue samples, cell samples, or combination thereof. A "tissue sample" includes a portion, piece, part, segment, or fraction of a tissue which is obtained or removed from an intact tissue of a subject, preferably a human subject. The biological sample may be obtained in the form of a tissue biopsy obtained from any bodily tissue as described herein. The biopsy may be an aspiration biopsy, a brush biopsy, a surface biopsy, a needle biopsy, a punch biopsy, an excision biopsy, an open biopsy, an incision biopsy, an endoscopic biopsy or any other type of biopsy known to those skilled in the art.

The terms "inflammation marker levels" and "expression levels" are used interchangeably with reference to a quantitative measure of the amount of an inflammation marker (e.g., mRNA, protein), the activity of an inflammation marker, or combinations thereof.

As used herein, the term "antibody" refers to immunoglobulin molecules and immunologically active portions of immunoglobulin (Ig) molecules, i.e., molecules that contain an antigen binding site or epitope binding domain that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies), and antibody fragments (e.g., Fc fragments and single chain Fc (scFc) fragments) so long as they exhibit specific binding to a target antigen. By "specifically bind" or "immunoreacts with" is meant that the antibody reacts with one or more antigenic determinants of the desired antigen and does not react (i.e., bind) with other polypeptides or binds at much lower affinity with other polypeptides.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. Methods for making humanized and other chimeric antibodies are known in the art.

"Bispecific antibodies" are antibodies that have binding specificities for at least two different antigens.

The use of "heteroconjugate antibodies" "aptamers" and "synbodies" are also within the scope of the present application.

Heteroconjugate antibodies are composed of two covalently joined antibodies. It is contemplated that the antibodies can be prepared in vitro using known methods in synthetic protein chemistry, including those involving the use of crosslinking agents. Alternatively, they may be prepared by fusing two antibodies or fragments thereof by recombinant DNA techniques known to those of skill in the art.

Aptamers are oligonucleic acid or peptide molecules that bind to a specific target molecule. Aptamers are usually created by selecting them from a large random sequence pool, but natural aptamers also exist in riboswitches. Aptamers can be combined with ribozymes to self-cleave in the presence of their target molecule. Aaptamers include DNA or RNA aptamers, as well as peptide aptamers.

Synbodies are synthetic protein molecules that mimic the functionality of monoclonal antibodies using small affinity peptides. Synbodies may be produced from libraries comprised of strings of random peptides screened for binding to target proteins of interest. In some embodiments, a synbody is composed of 2 or more peptides linked by a scaffold of variable composition and length to create a multivalent binding agent.

As used herein, the term "nucleic acid" refers to a polydeoxyribonucleotide (DNA or an analog thereof) or polyribonucleotide (RNA or an analog thereof) made up of at least two, and preferably ten or more bases linked by a backbone structure. In DNA, the common bases are adenine (A), guanine (G), thymine (T) and cytosine (C), whereas in RNA; the common bases are A, G, C and uracil (U, in place of T), although nucleic acids may include base analogs (e.g., inosine) and abasic positions (i.e., a phosphodiester backbone that lacks a nucleotide at one or more positions). Exemplary nucleic acids include single-stranded (ss), double-stranded (ds), or triple-stranded polynucleotides or oligonucleotides of DNA and RNA.

The term "polynucleotide" refers to nucleic acids containing more than 10 nucleotides.

The term "oligonucleotide" refers to a single stranded nucleic acid containing between about 5 to about 100 nucleotides.

The term "inflammatory bowel disease" or "IBD" refers to the group of disorders that cause the intestines to become inflamed, generally manifested with symptoms including abdominal cramps and pain, diarrhea, weight loss and intestinal bleeding. The main forms of IBD are ulcerative colitis (UC) and Crohn's disease.

The term "ulcerative colitis" or "UC" is a chronic, episodic, inflammatory disease of the large intestine and rectum characterized by bloody diarrhea. Ulcerative colitis is characterized by chronic inflammation in the colonic mucosa and can be categorized according to location: "proctitis" involves only the rectum, "proctosigmoiditis" affects the rectum and sigmoid colon, "left-sided colitis" encompasses the entire left side of the large intestine, "pancolitis" inflames the entire colon.

The term "Crohn's disease," also called "regional enteritis," is a chronic autoimmune disease that can affect any part of the gastrointestinal tract but most commonly occurs in the ileum (the area where the small and large intestine meet). Crohn's disease, in contrast to ulcerative colitis, is characterized by chronic inflammation extending through all layers of the intestinal wall and involving the mesentery as well as regional lymph nodes. Whether or not the small bowel or colon is involved, the basic pathologic process is the same.

Ulcerative colitis and Crohn's disease can be distinguished from each other clinically, endoscopically, pathologically, and serologically in more than 90% of cases; the remainder are considered to be indeterminate IBD.

The term "mucosal tissue" refers to any tissue in which mucosal cells are found, such tissues, include, for example, gastro-intestinal tissues (e.g., stomach, small intestine, large intestine, rectum), uro-genital tissue (e.g., vaginal tissue, penile tissue, urethra), nasal-larynx tissue (e.g., nasal tissue, larynx tissue), mouth (buccal tissue) to name a few. Other mucosal tissues are known and easily identifiable by one of skill in the art.

The terms "binding agent," "binding ligand," "capture binding ligand," "capture probe" or grammatical equivalents are used interchangeably with reference to a compound or large molecule that is used to detect the presence of or to quantify, relatively or absolutely, a target analyte, target species or target sequence (all used interchangeably) corresponding to the inflammation marker. Generally, the binding agent or capture probe allows the attachment of a target species or target sequence to a solid support for the purposes of detection as further described herein. Attachment of the target species to the binding agent may be direct or indirect. In exemplary embodiments, the target species is an inflammation marker. As will be appreciated by those in the art, the composition of the binding agent will depend on the composition of the inflammation marker.

The term "host proteins" refers to proteins that are expressed endogenouly in a host.

The term "normal level of expression" of an inflammatory marker refers to the expression level or levels of the inflammatory marker in a subject or subjects who is/are free from the inflammatory diseases associated with the inflammatory marker.

The term "increased level" refers to a level that is higher than a normal or control level customarily defined or used in the relevant art. For example, an increased level of immunostaining in a tissue is a level of immunostaining that would be considered higher than the level of immunostaining in a control tissue by a person of ordinary skill in the art.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

Detection of Inflammatory Diseases

CXCL9, CXCL10, and CXCL11 chemokines are ligands for the CXCR3 chemokine receptor. CXCL1 chemokines are ligands for the CXCR5 chemokine receptor. Each of these chemokine ligands and their receptor are locally upregulated and play a role in various inflammatory diseases, including inflammatory bowel diseases. Additionally, CXCL9, CXCL10, CXCL11 and CXCL13 chemokines enhance inflammation both in vivo and in vitro. CXCR3 and CXCR5 are members of the chemokine receptor family of G protein coupled receptors (GPCRs). Interaction of CXCR3 with CXCL9, CXCL10, and CXCL11 and interaction of CXCR5 with CXCL13 activate inflammation.

One aspect of the present application relates to methods for detecting an inflammatory disease in a subject. The method comprises the steps of (a) detecting a level of expression of one or more inflammatory disease markers in a biological sample obtained from said subject; and (b) comparing the level of expression of said one or more inflammatory disease markers in said biological sample to a normal level of expression of said one or more inflammatory disease markers, wherein a higher than normal level of expression of one or more of said plurality of inflammatory disease markers in said biological sample is indicative of the presence of an inflammatory disease in said subject, wherein said normal levels of expression of said plurality of inflammatory disease markers is a predetermined value, and wherein said one or more inflammatory disease markers comprise one or more markers selected from the group consisting of CXCL9, CXCL10, CXCL11, CXCL13, CXCR3 and CXCR5.

In some embodiments, the one or more inflammatory disease markers further comprise one or more markers selected from the group consisting of CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, XCL1, CX3CL1, CCR1, CCR2, CCR3, CCR4, CCR5, CCR6, CCR8, CCR9, CCR10, CXCR1, CXCR2, CXCR4, XCR1.

In other embodiments, the one or more inflammatory disease markers further comprise one or more markers selected from the group consisting of leptin, tumor necrosis factor α (TNFα), interferon-γ (IF-γ), interleukin-1α (IL-1α), IL-β, IL-6, IL-12, IL-17, and IL-23.

In yet other embodiments, the one or more inflammatory disease markers further comprise one or more antibodies directed against, and/or one or more antigens derived from, inflammation-related microorganisms selected from the group consisting of *Mycobacterium, Bacteroides, Brucella, Campylobacter, Escherichia coli, Saccharomyces cerevisiae, Klebsiella, Yersinia pseudotuberculosis, Clostridium, Enterococcus, Eubacterium, Listeria monocytogenes, Peptostreptococcus, Helicobacter, Haemophilus influenzae, Pseudomanas fluorescens, Salmonella, Chlamydia*, human hepatitis virus, human rhinovirus.

In certain embodiments, the one or more inflammatory disease markers are detected using one or more binding agents that bind specifically to the one or more inflammatory disease markers. In some embodiments, the binding agents are antibodies that bind to target molecules with Kds of between $10^{-8}$ M to $10^{-14}$ M and that bind to non-target molecules with Kds of greater than $10^{-7}$ M.

Inflammatory Diseases

The inflammatory disease detectable by the methods of the present application include, but are not limited to, anaphylaxis, septic shock, septic arthritis, rheumatoid arthritis, psoriatic arthritis, asthma, delayed type hypersensitivity, dermatitis, diabetes mellitus, juvenile onset diabetes, graft rejection, inflammatory bowel diseases, Crohn's disease, ulcerative colitis, enteritis, interstitial cystitis, multiple sclerosis, myasthemia gravis, Grave's disease, Hashimoto's thyroiditis, pneumonitis, nephritis, pneumonitis, chronic obstructive pulmonary disease, chronic bronchitis, chronic bronchitis rhinitis, spondyloarthropathies, scleroderma, and systemic lupus erythematosus, and chronic hepatitis.

The Binding Agents

Binding agents for inflammation markers are known or can be readily found using known techniques. For example, where the inflammation marker is a protein, the binding ligands include proteins (particularly including antibodies or fragments thereof (Fabs, etc.) as discussed further below) or small molecules. The binding agent may also have cross-reactivity with proteins of other species. Antigen-antibody pairs, receptor-ligands, and carbohydrates and their binding partners are also suitable analyte-binding ligand pairs. In other embodiments, the binding agent may be a nucleic acid binding agent. Nucleic acid binding agents also find particular use when nucleic acids are the binding targets. Aptamers can be developed for binding to virtually any inflammation marker.

The binding agents can be engineered to bind to target inflammatory markers with Kds of between $10^{-5}$ to $10^{-14}$ M. In some embodiments, the binding agents bind to the target molecule with Kds of less than $10^{-5}$ M, less than $10^{-6}$ M, less than $10^{-7}$ M, less than $10^{-8}$ M, less than $10^{-9}$ M, less than $10^{-19}$ M, or less than $10^{-12}$ M. In one embodiments, the binding agents bind to target molecules with Kds of between $10^{-6}$ M to $10^{-14}$ M. In one embodiments, the binding agents bind to target molecules with Kds of between $10^{-7}$ M to $10^{-14}$ M. In other embodiments, the binding agents bind to target molecules with Kds of between $10^{-8}$ M to $10^{-14}$ M. In other embodiments, the binding agents bind to target molecules with Kds of between $10^{-8}$ M to $10^{-14}$ M and bind to non-target molecules with Kds of greater than $10^{-7}$ M. In some embodiment, In some embodiments, the binding agents are antibodies having above-described Kd ranges. In some embodiments, the antibodies have kd value in the range of 0.01 pM to 10 μM, 0.01 pM to 1 μM, 0.01 pM to 100 nM, 0.01 pM to 10 nM, 0.01 pM to 1 nM, 0.1 pM to 10 μM, 0.1 pM to 1 μM, 0.1 pM to 100 nM, 0.1 pM to 10 nM, 0.1 pM to 1 nM, 1 pM to 10 μM, 1 pM to 1 μM, 1 pM to 100 nM, 1 pM to 10 nM, 1 pM to 1 nM, 10 pM to 10 μM, 10 pM to 1 μM, 10 pM to 100 nM, 10 pM to 10 nM, 10 pM to 1 nM, 100 pM to 10 μM, 100 pM to 1 μM and 100 pM to 100 nM.

In various exemplary embodiments, the binding agent is an antibody. These embodiments are particularly useful for the detection of the protein form of an inflammation marker. Conversely, in other embodiments, the binding agent is an antigen, which can be particularly useful for the detection of the antibody form of an inflammation marker.

Inflammatory Disease Markers

Inflammatory disease markers may originate from epidemiological studies, animal studies, pathophysiological considerations and end-organ experiments. Ideally, a inflammatory disease marker will have a high predictive value for a meaningful outcome measure, can be or is validated in appropriately designed prospective trials, reflects therapeutic success by corresponding changes in the surrogate marker results, and should be easy to assess in clinical practice. Inflammatory disease markers can be used in conjunction with other diagnostic tools or used alone.

In various embodiments, the inflammatory disease marker may be used to assess a pathological state. Measurements of the inflammatory disease marker may be used alone or combined with other data obtained regarding a subject in order to determine the state of the subject. In some embodiments, the inflammatory disease markers allow the detection of asymptomatic risk.

Typically an inflammatory disease marker for use in the present application will be over-expressed (over-abundant) in a subject suffering from an inflammatory disease. However, in some embodiments, the inflammatory disease marker may be under-expressed (under abundant) relative to a control. An inflammatory disease marker may be determined to be "differentially present," for example, between different phenotypic statuses, if the mean or median level (particularly the expression level of the associated mRNAs as described below) of the inflammatory disease marker in different phenotypic statuses is statistically significant. Common tests for statistical significance include, among others, t-test, ANOVA, Kruskal-Wallis, Wilcoxon, Mann-Whitney and odds ratio.

In various embodiments, the inflammatory disease markers used in the present application can be detected either as proteins (e.g. chemokines) or as nucleic acids (e.g., mRNA or cDNA transcripts) in any combination. In various embodiments, the protein form of a inflammatory disease marker is measured. As will be appreciated by those in the art, protein assays may be done using standard techniques such as ELISA assays. In various embodiments, the nucleic acid form of an inflammatory disease marker (e.g., the corresponding mRNA) is measured. In various exemplary embodiments, one or more inflammatory disease markers from a particular panel are measured using a protein assay and one or more inflammatory disease markers from the same panel are measured using a nucleic acid assay.

As will be appreciated by those in the art, there are a large number of possible protein and/or nucleic acid inflammatory disease markers that may be detected using the present application. In other embodiments, variants of the inflammatory markers described herein, including proteins, nucleic acids, splice variants, variants comprising a deletion, addition and/or substitution, fragments of proteins or nucleic acid, preproprotein, processed preproprotein (e.g., without a signaling peptide), processed preprotein (e.g., resulting in an active form). Nonhuman proteins, nonhuman nucleic acids and variants thereof may also be used as inflammatory disease markers.

In some embodiments, the inflammatory disease markers include, but are not limited to, CXCL9, CXCL10, CXCL11, CXCR3, CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, CXCL13, XCL1, CX3CL1, CCR1, CCR2, CCR3, CCR4, CCR5, CCR6, CCR8, CCR9, CCR10, CXCR1, CXCR2, CXCR4, CXCR5, XCR1; leptin, tumor necrosis factor α (TNFα), interferon-γ (IF-γ), interleukin-1α (IL-1α), IL-1β, IL-6, IL-12, IL-17, IL-23, and antibody directed against, or antigens derived from, an inflammation-related microorganism selected from the group consisting of Mycobacterium, Bacteroides, Brucella, Campylobacter, Escherichia coli, Saccharomyces cerevisiae, Klebsiella, Yersinia pseudotuberculosis, Clostridium, Enterococcus, Eubacterium, Listeria monocytogenes, Peptostreptococcus, Helicobacter, Haemophilus influenzae, Pseudomanas fluorescens, Salmonella, Chlamydia, human hepatitis virus, and human rhinovirus.

In other embodiments, the inflammatory disease marker is a nucleic acid encoding CXCL9, CXCL10, CXCL11, CXCR3, CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, CXCL13, XCL1, CX3CL1, CCR1, CCR2, CCR3, CCR4, CCR5, CCR6, CCR8, CCR9, CCR10, CXCR1, CXCR2, CXCR4, CXCR5, XCR1; leptin, tumor necrosis factor α (TNFα), interferon-γ (IF-γ), interleukin-1α (IL-1α), IL-1β, IL-6, IL-12, IL-17 or IL-23.

Protein and cDNA sequences, respectively, from NIH-NCBI Genbank are described in Table 1.

TABLE 1

| Chemokine/Receptor | Protein Accession No. | SEQ ID NO: | cDNA Accession NO: | SEQ ID NO: |
| --- | --- | --- | --- | --- |
| CXCL9 | NP_002407 | 1 | NM_002416 | 72 |
| CXCL10 | NP_001556 | 2 | NM_001565 | 73 |
| CXCL11 | NP_005400 | 3 | NM_005409 | 74 |
| CXCL12 | NP_000600 | 4 | NM_000609 | 75 |
| CXCL13 | NP_006410 | 5 | NM_006419 | 76 |
| CXCR3-1 | NP_001495 | 6 | NM_001504 | 77 |
| CXCR3-2 | NP_001136269 | 7 | NM_001142797 | 78 |
| CXCR5-1 | NP_001707 | 8 | NM_001716 | 79 |
| CXCR5-2 | NP_116743 | 9 | NM_032966 | 80 |
| CXCL1 | NP_001502 | 10 | NM_001511 | 81 |
| CXCL2 | NP_002080 | 11 | NM_002089 | 82 |
| CXCL3 | NP_002081 | 12 | NM_002090 | 83 |
| CXCL4 | NP_002610 | 13 | NM_002619 | 84 |
| CXCL5 | NP_002985 | 14 | NM_002994 | 85 |
| CXCL6 | NP_002984 | 15 | NM_002993 | 86 |
| CXCL7 | NP_002695 | 16 | NM_002704 | 87 |
| CXCL8 | NP_000575 | 17 | NM_000584 | 88 |
| CXCL16 | NP_071342 | 18 | NM_022059 | 89 |
| CXCR1 | NP_000625 | 19 | NM_000634 | 90 |
| CXCR2 | NP_001548 | 20 | NM_001557 | 91 |
| CXCR4a | NP_001008540 | 21 | NM_001008540 | 92 |
| CXCR4b | NP_003458 | 22 | NM_003467 | 93 |
| CXCR6 | NP_006555 | 23 | NM_006564 | 94 |
| CCL1 | NP_002972 | 24 | NM_002981 | 95 |
| CCL2 | NP_002973 | 25 | NM 002982 | 96 |
| CCL3 | NP_002974 | 26 | NM 002983 | 97 |
| CCL4 | NP_002975 | 27 | NM 002984 | 98 |
| CCL4L1 | NP_001001435 | 28 | AY079147 | 99 |
| CCL5 | NP_002976 | 29 | NM 002985 | 100 |
| CCL7 | NP_006264 | 30 | NM 006273 | 101 |
| CCL8 | NP_005614 | 31 | NM 005623 | 102 |
| CCL11 | CAG33702 | 32 | NM_002986 | 103 |
| CCL13 | NP_005399 | 33 | NM_005408 | 104 |
| CCL14-1 | NP_116739 | 34 | NM 032963 | 105 |
| CCL14-2 | NP_116738 | 35 | NM 032962 | 106 |
| CCL15 | NP_116741 | 36 | NM_032965 | 107 |
| CCL16 | NP 004581 | 37 | NM 004590 | 108 |
| CCL17 | NP_002978 | 38 | NM_002987 | 109 |
| CCL18 | NP_002979 | 39 | NM_002988 | 110 |
| CCL19 | NP_006265 | 40 | NM 006274 | 111 |
| CCL20-1 | NP_004582 | 41 | NM 004591 | 112 |
| CCL20-2 | NP_001123518 | 42 | NM_001130046 | 113 |
| CCL22 | NP_002981 | 43 | NM_002990 | 114 |
| CCL23-1 | NP_665905 | 44 | NM_145898 | 115 |
| CCL23-2 | NP_005055 | 45 | NM_005064 | 116 |
| CCL24 | NP_002982 | 46 | NM 002991 | 117 |
| CCL25-1 | NP 005615 | 47 | NM 005624 | 118 |

TABLE 1-continued

| Chemokine/Receptor | Protein Accession No. | SEQ ID NO: | cDNA Accession NO: | SEQ ID NO: |
|---|---|---|---|---|
| CCL25-2 | NP 683686 | 48 | NM_001201359 | 119 |
| CCL25-3 | EAW68951 | 49 | | |
| CCL26 | NP_006063 | 50 | NM 006072 | 120 |
| CCL27 | NP_006655 | 51 | NM_006664 | 121 |
| CCR2-A | NP_001116513 | 52 | NM_001123041 | 122 |
| CCR2-B | NP_001116868 | 53 | NM_001123396 | 123 |
| CCR3-1 | NP_847899 | 54 | NM_001837 | 124 |
| CCR3-2 | NP_847898 | 55 | NM_178328 | 125 |
| CCR3-3 | NP_001158152 | 56 | NM_001164680 | 126 |
| CCR4 | NP_005499 | 57 | NM_005508 | 127 |
| CCR5 | AAB57793 | 58 | NM 000579 | 128 |
| CCR6 | NP_004358 | 59 | U45984 | 129 |
| CCR8 | NP_005192 | 60 | NM_005201 | 130 |
| CCR9A | NP_112477 | 61 | AF145439 | 131 |
| CCR9B | NP_006632 | 62 | AF145440 | 132 |
| CCR10 | NP_057686 | 63 | AF215981 | 133 |
| CCRL1 | NP 057641 | 64 | NM 016557 | 134 |
| CCRL2-1 | NP_003956 | 65 | NM 003965 | 135 |
| CCRL2-2 | NP_001124382 | 66 | NM_001130910 | 136 |
| XCL1 | AAH69817 | 67 | NM_002995 | 137 |
| XCR1 | NP_005274 | 68 | NM_005283 | 138 |
| CX3CR1a | NP_001164645 | 69 | NM_001171174 | 139 |
| CX3CR1b | NP 001328 | 70 | NM 001337 | 140 |
| CX3CL1 | NP 002987 | 71 | NM 002996 | 141 |

The inflammatory disease markers of the present application show a statistically significant difference in inflammatory disease diagnosis. In various embodiments, detection tests that use these inflammatory disease markers alone or in combination show a sensitivity and specificity of at least about 80%, at least about 85%, at least about 90%, at least about 95%, at least about 98% and about 100%.

Inflammatory Disease Marker Panels

In some embodiments, the one or more inflammatory disease markers in step (a) comprises a panel of inflammatory disease markers. Any combination of binding agents described herein may be used to assemble an inflammatory disease marker panel for measuring inflammatory disease marker levels as described herein. As is generally understood in the art, a combination may refer to an entire set or any subset or subcombination thereof. The term "inflammatory disease marker panel," "inflammatory disease marker profile," or "inflammatory disease marker fingerprint" refers to a set of inflammatory disease markers. As used herein, these terms can also refer to any form of the inflammatory disease marker that is measured. Thus, if CXCL10 is part of a inflammatory disease marker panel, then either CXCL10 mRNA or CXCL10 protein could be considered to be part of the panel.

While individual inflammatory disease markers are useful as diagnostics, combination of inflammatory disease markers can sometimes provide greater value in determining a particular status than single inflammatory disease markers alone. Specifically, the detection of a plurality of inflammatory disease markers in a sample can increase the sensitivity and/or specificity of the test. Thus, in various embodiments, an inflammatory disease marker panel may include 1, 2, 3, 4, 5, 5-10, 10-20, 10-50, 10-100, 100-1,000 or more inflammatory disease markers. In various exemplary embodiments, the inflammatory disease marker panel consists of a minimum number of inflammatory disease markers to generate a maximum amount of information. Thus, in various embodiments, the inflammatory disease marker panel consists of at least 1, at least 2, at least 3, at least 5, at least 8, at least 10, at least 20, at least 50, at least 100, at least 500, and at least 1,000. Where an inflammatory disease marker panel "consists of a set of inflammatory disease markers, no inflammatory disease markers other than those of the set are present.

In exemplary embodiments, the inflammatory disease marker panel includes (1) 2, 3, 4, 5 or 6 inflammatory disease markers selected from the group consisting of CXCL9, CXCL10, CXCL11, CXCL13, CXCR3 and CXCR5, and one or more inflammatory disease markers selected from the group consisting of CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, XCL1, CX3CL1, CCR1, CCR2, CCR3, CCR4, CCR5, CCR6, CCR8, CCR9, CCR10, CXCR1, CXCR2, CXCR4, XCR1; leptin, tumor necrosis factor α (TNFα), interferon-γ (IF-γ), interleukin-1α (IL-1α), IL-1β, IL-6, IL-12, IL-17 and IL-23.

Using any of the methods and compositions described herein, a sample can be assayed to determine expression levels or relative activities for a plurality of inflammatory disease markers in an inflammatory disease marker panel. Thus, in one aspect, the present application provides a method of assaying a sample from a patient to determine concentrations of an inflammatory disease marker panel in the sample. In some embodiments, the method comprises contacting the sample with a composition comprising a solid support comprising a binding agent or capture probe for each inflammatory disease marker in an inflammatory disease marker panel.

The quantity or activity measurements of an inflammatory disease marker panel can be compared to a reference value or control value obtained from a control sample of known normal non-inflammatory cells of the same origin or type as the biological sample. Differences in the measurements of inflammatory disease markers in the subject sample compared to the reference value are then identified. In exemplary embodiments, the reference value is given by a risk category as described further below.

In various embodiments, the reference value is a baseline value. A baseline value is a composite sample of an effective amount of inflammatory disease markers from one or more subjects who do not have a disease, who are asymptomatic for a disease or who have a certain level of a disease. A baseline value can also comprise the amounts of inflammatory disease markers in a sample derived from a subject who has shown an improvement in risk factors of a disease as a result of treatments or therapies. In these embodiments, to make comparisons to the subject-derived sample, the amounts of inflammatory disease markers are similarly calculated. A reference value can also comprise the amounts of inflammatory disease markers derived from subjects who have a disease confirmed by an invasive or non-invasive technique, or are at high risk for developing a disease. Optionally, subjects identified as having a disease, or being at increased risk of developing a disease are chosen to receive a therapeutic regimen to slow the progression of a disease, or decrease or prevent the risk of developing a disease. A disease is considered to be progressive (or, alternatively, the treatment does not prevent progression) if the amount of inflammatory disease marker increases over time relative to the reference value, whereas a disease is not progressive if the amount of inflammatory disease markers decreases or remains constant over time (relative to the reference population, or "constant" as used herein). The term "constant" as used in the context of the present application is construed to include changes over time with respect to the reference value.

The inflammatory disease markers of the present application can be used to generate a "reference inflammatory disease marker profile" of those subjects who do not have a disease according to a certain threshold, are not at risk of having a disease or would not be expected to develop a disease. The inflammatory disease markers disclosed herein can also be used to generate a "subject inflammatory disease marker profile" taken from subjects who have a disease or are at risk for having a disease. The subject inflammatory disease marker profiles can be compared to a reference inflammatory disease marker profile to diagnose or identify subjects at risk for developing a disease, to monitor the progression of disease, as well as the rate of progression of disease, and to monitor the effectiveness of disease treatment modalities. The reference and subject inflammatory disease marker profiles of the present application can be contained in a machine-readable medium, such as but not limited to, analog tapes like those readable by a VCR; optical media such as CD-ROM, DVD-ROM and the like; and solid state memory, among others.

Measurements of the inflammatory disease marker panels of the present application can lead a practitioner to select a therapy with respect to a subject. Measurement of inflammatory disease marker levels further allows for the course of treatment of a disease to be monitored as further described herein. The effectiveness of a treatment regimen for a disease can be monitored by detecting one or more inflammatory disease markers in an effective amount from samples obtained from a subject over time and comparing the amount of inflammatory disease markers detected. For example, a first sample can be obtained prior to the subject receiving treatment and one or more subsequent samples are taken before, during and/or after treatment of the subject, wherein changes in inflammatory disease marker levels across the samples may provide an indication as to the effectiveness of the therapy.

The choice of inflammatory disease markers will depend on the inflammatory disease to be detected. Table 1 shows some chemokines that are associated with inflammatory diseases. By exposing patient tissue samples to antibodies against each of the chemokines and evaluating the amount of antibody/chemokine binding, it is possible to evaluate the level of expression for each chemokine to enable diagnosis and monitoring of the inflammatory disease.

TABLE 2

| Chemokine, Chemokine Receptor and Inflammatory Disease Association (dependent of stage of disease) | | |
|---|---|---|
| Disease | Chemokine | Chemokine Receptor |
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CXCL9, CXCL10, CXCL11, CCL3, CCL4, CCL5, CCL7, CCL8, CCL11, CCL15, CCL17, CCL22, CCL24, CCL26, | CXCR3 CCR3, CCR4, CCR5, |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
| | CCL20 | CCR6 |
| | XCL1 | XCR1 |
| | CX3CL1 | CX3CR1 |
| Osteoarthritis | CXCL1, CXCL2, CXCL3, CXCL5, CXCL6, CXCL7, CXCL8, CXCL12, CXCL13, CCL2, CCL3, CCL4, CCL7, CCL8, CCL13, CCL5, CCL18 | CXCR1, CXCR2, CCR2, CCR5 |
| Atherosclerosis | CXCL1, CXCL2, CXCL3, CXCL4, CXCL5, CXCL8 | CXCR1, CXCR2 |
| | CCL2, CCL3, CCL4, CCL8, CCL12, CCL13, CCL17, CCL22 | CCR2, CCR8 |
| | CX3CL1 | CX3CR1 |
| Dermatitis & Delayed-Typed Hypersensitivity | CXCL9, CXCL10, CXCL11, CCL2, CCL3, CCL4, CCL5, CCL17, CCL20, CCL22, CCL27 | CXCR3 CCR4, CCR5, CCR6, CCR10 |
| Diabetes | CXCL9, CXCL10, CXCL11, CCL2, CCL9 | CXCR3 CCR2, CCR4 |
| | CX3CL1 | CX3CR1 |
| Graft rejection | CXCL9, CXCL10, CXCL11, CCL3, CCL4, CCL5 | CXCR3 CCR5 |
| | XCL1 | XCR1 |
| Inflammatory Bowel Diseases | CXCL9, CXCL10, CXCL11, CCL3, CCL4, CCL5 | CXCR3 CCR5 |
| Interstitial Cystitis | CXCL9, CXCL10, CXCL11, CCL3, CCL4, CCL5 | CXCR3 CCR5 |
| Multiple Sclerosis | CXCL9, CXCL10, CXCL11, CCL3, CCL4, CCL5, CCL7, CCL14, CCL15, CCL23 | CXCR3 CCR1, CCR5 |
| Myasthemia gravis, Grave's disease, & Hashimoto thyroiditis | CXCL9, CXCL10, CXCL11, CCL3, CCL4, CCL5 | CXCR3 CCR5 |
| | XCL1 | XCR1 |

TABLE 2-continued

Chemokine, Chemokine Receptor and Inflammatory
Disease Association (dependent of stage of disease)

| Disease | Chemokine | Chemokine Receptor |
|---|---|---|
| Nephritis & Systemic Lupus Erthematosus | CXCL9, CXCL10, CXCL11, CXCL13 | CXCR3, CXCR5 |
| | CCL2, CCL3, CCL4, CCL5, CCL8, CCL12, CCL13, CX3CL1 | CCR2, CCR4 CX3CR1 |
| Pneumonitis, Chronic Obstructive Pulmonary Disease, & Chronic Bronchitis | CXCL1, CXCL2, CXCL3, CXCL5, CXCL7, CXCL8, CXCL10, CXCL11 | CXCR2, CXCR3 |
| | CCL3, CCL5, CCL7, CCL8, CCL11, CCL13, CCL24, CCL26. | CCR3 |

In one embodiment, an inflammatory disease marker panel for Crohn's disease, ulcerative colitis, enteritis, inflammatory bowel disorders, and/or interstitial cystitis comprises (1) one or more members from the group consisting of CXCL9, CXCL10, CXCL11, CXCL13, CXCR3 and CXCR5, and (2) one or more members from the group consisting of CCL3, CCL4, CCL5, and CCR5.

In another embodiment, an arthritis marker panel comprises (1) one or more members from the group consisting of CXCL9, CXCL10, CXCL11, CXCL13, CXCR3 and CXCR5, and (2) one or more inflammatory disease markers selected from the group consisting of CXCL12, CCL20, XCL1, CX3CL1, CXCR4, CCR6, XCR1, CX3CR1.

In another embodiment, an asthma marker panel comprises (1) one or more members from the group consisting of CXCL9, CXCL10, CXCL11, CXCL13, CXCR3 and CXCR5, and (2) one or more inflammatory disease markers selected from the group consisting of CCL3, CCL4, CCL5, CCL7, CCL8, CCR3, CCR4, CCR5, CCL11, CCL15, CCL17, CCL22, CCL24, and CCL26.

In another embodiment, a septic shock or anaphylaxis marker panel comprises (1) one or more members from the group consisting of CXCL9, CXCL10, CXCL11, CXCL13, CXCR3 and CXCR5, and (2) one or more inflammatory disease markers selected from the group consisting of CXCL1, CXCL2, CXCL3, CXCL5, CXCL6, CXCL7, CXCL8, CCL5, CXCR1, and CXCR2.

In another embodiment, a diabetes marker panel comprises (1) one or more members from the group consisting of CXCL9, CXCL10, CXCL11, CXCL13, CXCR3 and CXCR5, and (2) one or more inflammatory disease markers selected from the group consisting of CCL2, CCL9, CX3CL1, CCR2, CCR4, and CX3CR1.

In another embodiment, a dermatitis or delayed-type hypersensitivity marker panel comprises (1) one or more members from the group consisting of CXCL9, CXCL10, CXCL11, CXCL13, CXCR3 and CXCR5, and (2) one or more inflammatory disease markers selected from the group consisting of CCL2, CCL3, CCL4, CCL5, CCL17, CCL29, CCL22, CCL27, CCR4, CCR5, CCR6, and CCR10.

In another embodiment, a graft rejection marker panel comprises (1) one or more members from the group consisting of CXCL9, CXCL10, CXCL11, CXCL13, CXCR3 and CXCR5, and (2) one or more inflammatory disease markers further comprises one or more inflammatory disease markers selected from the group consisting of CCL3, CCL4, CCL5, XCL1, CCR5, and XCR1.

In another embodiment, an interstitial cystitis marker panel comprises (1) one or more members from the group consisting of CXCL9, CXCL10, CXCL11, CXCL13, CXCR3 and CXCR5, and (2) one or more inflammatory disease markers further comprises one or more inflammatory disease markers selected from the group consisting of CCL3, CCL4, CCL5, and CCR5.

In another embodiment, a multiple sclerosis marker panel comprises (1) one or more members from the group consisting of CXCL9, CXCL10, CXCL11, CXCL13, CXCR3 and CXCR5, and (2) one or more inflammatory disease markers further comprises one or more inflammatory disease markers selected from the group consisting of CCL3, CCL4, CCL5, CCL7, CCL14, CCL15, CCL23, CCR1, and CCR5.

In another embodiment, a mysasthemia gravis, Grave's disease or Hashimoto thyroiditis marker panel comprises (1) one or more members from the group consisting of CXCL9, CXCL10, CXCL11, CXCL13, CXCR3 and CXCR5, and (2) one or more inflammatory disease markers selected from the group consisting of CCL3, CCL4, CCL5, XCL1, CCR5, and XCR1.

In another embodiment, a nephritis or systemic lupus ethematosus marker panel comprises (1) one or more members from the group consisting of CXCL9, CXCL10, CXCL11, CXCL13, CXCR3 and CXCR5, and (2) one or more inflammatory disease markers selected from the group consisting of CCL2, CCL3, CCL4, CCL5, CCL8, CCL12, CCL13, CX3CL1, CCR2, CCR4, and CX3CR1.

In another embodiment, a pneumonitis, chronic obstructive pulmonary disease (COPD) or chronic bronchitis marker panel comprises (1) one or more members from the group consisting of CXCL9, CXCL10, CXCL11, CXCL13, CXCR3 and CXCR5, and (2) one or more inflammatory disease markers selected from the group consisting of CXCL1, CXCL2, CXCL3, CXCL5, CXCL7, CXCL8, CCL3, CCL5, CCL7, CCL8, CCL11, CCL13, CCL24, CCL26, CXCR2, CCR3.

In some embodiments, the above described marker panels may further comprise one or more inflammatory disease markers selected from the group consisting of leptin, tumor necrosis factor α (TNFα), interferon-γ interleukin-1α (IL-1α), IL-1β, IL-6, IL-12, IL-17 and IL-23.

Detection Methods

The expression levels of the inflammatory disease marker(s) can be determined at the transcription level (i.e., the amount of mRNA) or the translation level (i.e., the amount of protein or antibody). As used herein the terms "inflammatory disease marker levels" and "expression levels" are used interchangeably with reference to a quantitative measure of product amount, product activity, or combinations thereof. In certain embodiments, expression of the inflammatory disease marker(s) is determined at the mRNA level by quantitative RT-PCR, Northern blot or other methods known to a person of ordinary skill in the art. In other embodiments, the expression of the inflammatory disease marker(s) is determined at the protein level by ELISA, Western blot or other types of immuno-detection methods using anti-inflammatory disease marker antibodies, such as anti-CXCL9, anti-CXCL10, anti-CXCL11, anti-CXCL13, anti-CXCR3 and anti-CXCR5 antibodies and the like. In yet other embodiments, the expression level is determined at the inflammatory disease marker activity level.

Inflammatory disease markers generally can be measured and detected through a variety of assays, methods and detection systems known to one of skill in the art. The term "measuring," "detecting," or "taking a measurement" refers to a quantitative or qualitative determination of a property of an entity, for example, quantifying the amount or concentration of a molecule or the activity level of a molecule. The term "concentration" or "level" can refer to an absolute or relative quantity. Measuring a molecule may also include determining the absence or presence of the molecule.

In addition to the above, the detection methods may further include, but are not limited to, refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance. In this regard, inflammatory disease markers can be measured using the above-mentioned detection methods, or other methods known to the skilled artisan. Other inflammatory disease markers can be similarly detected using reagents that are specifically designed or tailored to detect them.

Assays may be done in a solution format or on a solid support. The term "solid support" or "substrate" refers to any material that can be modified to contain discrete individual sites appropriate for the attachment or association of a binding agent. Suitable substrates include metal surfaces such as gold, electrodes, glass and modified or functionalized glass, plastics (including acrylics, polystyrene and copolymers of styrene and other materials, polypropylene, polyethylene, polybutylene, polycarbonate, polyurethanes, Teflon, derivatives thereof, etc.), polysaccharides, nylon or nitrocellulose, resins, mica, silica or silica-based materials including silicon and modified silicon, carbon, metals, inorganic glasses, fiberglass, ceramics, GETEK (a blend of polypropylene oxide and fiberglass) and a variety of other polymers.

Different types of inflammatory disease markers and their measurements can be combined in the compositions and methods of the present application. In some embodiments, the protein form of the inflammatory disease markers is measured. In other embodiments, the nucleic acid form of the inflammatory disease markers is measured, such as DNA or mRNA. In some embodiments, measurements of protein inflammatory disease markers is used in conjunction with measurements of nucleic acid inflammatory disease markers.

Detection of a target species in some embodiments requires a "label" or "detectable marker" (as described below) that can be incorporated in a variety of ways. Thus, in various embodiments, the composition comprises a "label" or a "detectable marker." In one embodiment, the target species (or target analyte or target sequence) is labeled; binding of the target species thus provides the label at the surface of the solid support.

In embodiments finding particular use herein, a sandwich format is utilized, in which target species are unlabeled. In these embodiments, a "capture" or "anchor" binding ligand is attached to the detection surface as described herein, and a soluble binding ligand (frequently referred to herein as a "signaling probe," "label probe" or "soluble capture ligand") binds independently to the target species and either directly or indirectly comprises at least one label or detectable marker.

By "label" or "labeled" herein is meant that a compound has at least one molecule, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) enzymes; although labels include particles such as magnetic particles as well. The dyes may be chromophores or phosphors but are preferably fluorescent dyes, which due to their strong signals provide a good signal-to-noise ratio for decoding. Suitable dyes for use in the present application include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes, and the like.

In various embodiments, a secondary detectable label is used. A secondary label is one that is indirectly detected; for example, a secondary label can bind or react with a primary label for detection, can act on an additional product to generate a primary label (e.g., enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc. Secondary labels can also include additional labels.

In various embodiments, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (Fabs, etc.); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, for example, biotin (or imino-biotin) and streptavidin.

In the sandwich formats of the present application, an enzyme serves as the secondary label, bound to the soluble capture ligand. Of particular use in some embodiments is the use of horseradish peroxidase, which when combined with 3,3',5,5'-tetramethylbenzidine (TMB) forms a colored precipitate which is then detected. In some cases, the soluble capture ligand comprises biotin, which is then bound to a enzyme-streptavidin complex and forms a colored precipitate with the addition of TMB.

In various embodiments, the label or detectable marker is a conjugated enzyme (for example, horseradish peroxidase). In various embodiments, the system relies on detecting the precipitation of a reaction product or on a change in, for example, electronic properties for detection. In various embodiments, none of the compounds comprises a label.

As used herein, the term "fluorescent signal generating moiety" or "fluorophore" refers to a molecule or part of a molecule that absorbs energy at one wavelength and re-emits energy at another wavelength. Fluorescent properties that can be measured include fluorescence intensity, fluorescence lifetime, emission spectrum characteristics, energy transfer, and the like.

Signals from single molecules can be generated and detected by a number of detection systems, including, but not limited to, scanning electron microscopy, near field scanning optical microscopy (NSOM), total internal reflection fluorescence microscopy (TIRFM), and the like. Applying such techniques for analyzing and detecting nanoscale structures on surfaces is well known to those skilled in the art.

A detection system for fluorophores may include any device that can be used to measure fluorescent properties as discussed above. In various embodiments, the detection system comprises an excitation source, a fluorophore, a wavelength filter to isolate emission photons from excitation photons and a detector that registers emission photons and produces a recordable output, in some embodiments as an electrical signal or a photographic image. Examples of detection devices include without limitation spectrofluorometers and microplate readers, fluorescence microscopes, fluorescence scanners (including e.g., microarray readers) and flow cytometers.

In various exemplary embodiments, the binding of the inflammatory disease marker to the binding ligand is specific or selective, and the binding ligand is part of a binding pair. By "specifically bind" or "selectively bind" or "selective for" an inflammatory disease marker herein is meant that the ligand binds the inflammatory disease marker with specificity sufficient to differentiate between the inflammatory disease marker and other components or contaminants of the test sample.

Nucleic Acid Detection

Methods for detecting mRNA, such as RT-PCR, real time PCR, branch DNA, NASBA and others, are well known in the art. Using sequence information corresponding to database entries for the inflammatory disease marker sequences, expression of the inflammatory disease marker sequences can be detected (if present) and measured using techniques well known to one of ordinary skill in the art. For example, sequences in the sequence database entries can be used to construct probes for detecting inflammatory disease marker RNA sequences in, e.g., Northern blot hybridization analyses or methods which specifically, and, preferably, quantitatively amplify specific nucleic acid sequences. As another example, the sequences can be used to construct primers for specifically amplifying the inflammatory disease marker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

Detecting or measuring the level (e.g., the transcription level) of an inflammatory disease marker involves binding of the inflammatory disease marker to a binding agent serving as a "capture probe" when the mRNA of the inflammatory disease marker is to be detected on a solid support. In that sense, the inflammatory disease marker is a target sequence. The term "target sequence" or "target nucleic acid" or grammatical equivalents herein means a nucleic acid sequence that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. In some embodiments, measuring a nucleic acid can thus refer to measuring the complement of the nucleic acid. It may be any length, with the understanding that longer sequences are more specific.

The target sequence may also comprise different target domains; for example, a first target domain of the sample target sequence may hybridize to a first capture probe, a second target domain may hybridize to a label probe (e.g., a "sandwich assay" format), etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the target sequence, the first target domain may be located either 5' to the second domain, or 3' to the second domain.

When nucleic acids are used as the target analyte, the assays of the present application can take on a number of embodiments. In one embodiment, the assays are done in solution format, using any number of solution based formats. In one embodiment, end-point or real time PCR formats are used, as are well known in the art. These assays can be done either as a panel, microarray, or multiplex assay or in individual tubes or wells, using sets of primers and different labels within a single tube or well. In addition to PCR-based solution formats, other formats can be utilized, including, but not limited to for example ligation based assays utilizing FRET dye pairs. In this embodiment, only upon ligation of two (or more) probes hybridized to the target sequence is a signal generated.

In one embodiment, the target sequence comprises a detectable label, which may be added, for example, to the target sequence during amplification of the target in one of two ways: either labeled primers are utilized during the amplification step or labeled dNTPs are used, both of which are well known in the art. The label can either be a primary or secondary label as discussed herein. For example, in one embodiment, the label on the primer and/or a dNTP is a primary label such as a fluorophore. Alternatively, the label may be a secondary label such as biotin or an enzyme; for example, in one embodiment, the primers or dNTPs are labeled with biotin, and then a streptavidin/label complex is added. In one embodiment, the streptavidin/label complex contains a label such as a fluorophore. In an alternative embodiment, the streptavidin/label complex comprises an enzymatic label. For example, the complex can comprise horseradish peroxidase, and upon addition of TMB, the action of the horseradish peroxidase causes the TMB to precipitate, causing an optically detectable event. This has a particular benefit in that the optics for detection does not require the use of a fluorometer.

For labeling of nucleic acids, especially DNA or RNA, a variety of methodologies are known to those skilled in the art. For example, the labeling of the nucleic acids is performed by primer extension, in vitro transcription, biotin-streptavidin-labeling, isothermal Klenow fragment-based labeling or direct nucleic amplification labeling, preferably by direct PCR labeling. A preferred labeling method involves the use of fluorescence dyes, especially Cy5.

Amplified labeled nucleic acids may be applied to a microarray with or without a purification or washing step after the nucleic acid amplification reaction. In one embodiment, DNA or RNA is subjected to multiplex PCR, fluorescence labeling (Cy5-dCTP) by a primer extension step and subsequent microarray hybridization.

In some embodiments, the solid phase assay relies on the use of a labeled soluble capture ligand, sometimes referred to as a "label probe" or "signaling probe" when the target analyte is a nucleic acid. In this format, the assay is a "sandwich" type assay, where the capture probe binds to a first domain of the target sequence and the label probe binds to a second domain. In this embodiment, the label probe can also be either a primary (e.g., a fluorophore) or a secondary (biotin or enzyme) label. In one embodiment, the label probe comprises biotin, and a streptavidin/enzyme complex is used, as discussed herein. As above, for example, the complex can comprise horseradish peroxidase, and upon addition of TMB, the action of the horseradish peroxidase causes the TMB to precipitate, causing an optically detectable event.

In other embodiments, the assays are done on a solid support, utilizing a capture probe associated with the surface. As discussed herein, the capture probes (or binding agents, as they are sometimes referred to) can be covalently attached to the surface, for example using capture probes terminally modified with functional groups, for example amino groups, that are attached to modified surfaces such as silanized glass. Alternatively, non-covalent attachment, such as electrostatic, hydrophobic/hydrophilic adhesion can be utilized. As is appreciated by those in the art and discussed herein, a large number of attachments are possible on a wide variety of surfaces.

Immunodetection

Those skilled in the art will be familiar with numerous additional immunoassay formats and variations thereof which are useful for detecting proteins or antibodies. Examples of suitable immunoassays include immunoblotting, immunofluorescence methods, immunoprecipitation, chemiluminescence methods, electrochemiluminescence (ECL) or enzyme-linked immunoassays. In general, immunoassays carried out in accordance with the present application may be homogeneous assays or heterogeneous assays.

In a homogeneous assay the immunological reaction usually involves a specific antibody (e.g., anti-inflammatory disease marker protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. Antibodies can be conjugated to a solid support suitable for a diagnostic assay (e.g., beads such as protein A or protein G agarose, microspheres, plates, slides or wells formed from materials such as latex or polystyrene), and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. Antibodies as described herein may be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques. If the antigen to be detected contains a second binding site, an antibody which binds to that site can be conjugated to a detectable group and added to the liquid phase reaction solution before the separation step. The presence of the detectable group on the solid support indicates the presence of the antigen in the test sample.

In certain embodiments, the inflammatory disease markers are detected using enzyme-linked immunosorbent assay (ELISA) which is typically carried out using antibody coated assay plate or wells. Commonly used ELISA assay employs either a sandwich immunoassay or a competitive binding immunoassay.

Briefly, a sandwich immunoassay is a method using two antibodies, which bind to different sites on the antigen or ligand. The primary antibody, which is highly specific for the antigen, is attached to a solid surface. The antigen is then added followed by addition of a second antibody referred to as the detection antibody. The detection antibody binds the antigen to a different epitope than the primary antibody. As a result the antigen is 'sandwiched' between the two antibodies. The antibody binding affinity for the antigen is usually the main determinant of immunoassay sensitivity. As the antigen concentration increases the amount of detection antibody increases leading to a higher measured response. The standard curve of a sandwich-binding assay has a positive slope. To quantify the extent of binding different reporters can be used. Typically an enzyme is attached to the secondary antibody which must be generated in a different species than primary antibodies (i.e., if the primary antibody is a rabbit antibody than the secondary antibody would be an anti-rabbit from goat, chicken, etc., but not rabbit). The substrate for the enzyme is added to the reaction that forms a colorimetric readout as the detection signal. The signal generated is proportional to the amount of target antigen present in the sample.

The antibody linked reporter used to measure the binding event determines the detection mode. A spectrophotometric plate reader may be used for colorimetric detection. Several types of reporters have been recently developed in order to increase sensitivity in an immunoassay. For example, chemiluminescent substrates have been developed which further amplify the signal and can be read on a luminescent plate reader. Also, a fluorescent readout where the enzyme step of the assay is replaced with a fluorophor tagged antibody is becoming quite popular. This readout is then measured using a fluorescent plate reader.

A competitive binding assay is based upon the competition of labeled and unlabeled ligand for a limited number of antibody binding sites. Competitive inhibition assays are often used to measure small analytes. These assays are also used when a matched pair of antibodies to the analyte does not exist. Only one antibody is used in a competitive binding ELISA. This is due to the steric hindrance that occurs if two antibodies would attempt to bind to a very small molecule. A fixed amount of labeled ligand (tracer) and a variable amount of unlabeled ligand are incubated with the antibody. According to law of mass action the amount of labeled ligand is a function of the total concentration of labeled and unlabeled ligand. As the concentration of unlabeled ligand is increased, less labeled ligand can bind to the antibody and the measured response decreases. Thus the lower the signal, the more unlabeled analyte there is in the sample. The standard curve of a competitive binding assay has a negative slope.

In certain embodiments, the inflammatory disease markers are detected using antibody coated microbeads. In some embodiments, the microbeads are magnetic beads. In other embodiments, the beads are internally color-coded with fluorescent dyes and the surface of the bead is tagged with an anti-inflammatory disease marker antibody (e.g., an anti-CXCL9, anti-CXCL10, anti-CXCL11, anti-CXCL13, anti-CXCR3 or anti-CXCR5 antibody) that can bind a inflammatory disease marker in a test sample. The inflammatory disease marker, in turn, is either directly labeled with a fluorescent tag or indirectly labeled with an anti-marker antibody conjugated to a fluorescent tag. Hence, there are two sources of color, one from the bead and the other from the fluorescent tag. Alternatively, the beads can be internally coded by different sizes.

By using a blend of different fluorescent intensities from the two dyes, as well as beads of different sizes, the assay can measure up to hundreds of different inflammatory disease markers. During the assay, a mixture containing the color/size-coded beads, fluorescence labeled anti-marker antibodies, and the sample are combined and injected into an instrument that uses precision fluidics to align the beads. The beads then pass through a laser and, on the basis of their color or size, either get sorted or measured for color intensity, which is processed into quantitative data for each reaction.

When samples are directly labeled with fluorophores, the system can read and quantitate only fluorescence on beads without removing unbound fluorophores in solution. The assays can be multiplexed by differentiating various colored or sized beads. Real time measurement is achievable when a sample is directly required for unlabeled samples. Standard assay steps include incubation of a sample with anti-marker antibody coated beads, incubation with biotin or fluorophore-labeled secondary antibody, and detection of fluorescence signals. Fluorescent signals can be developed on bead (by adding streptavidin-fluorophore conjugates for biotinylated secondary antibody) and read out by a bead analyzer. Depending on the anti-marker immobilized on the bead surface, a bead-based immunoassay can be a sandwich type or a competitive type immunoassay.

Biochips and Microarrays

In one embodiment, the method is carried out using one or more biochip or microarray assays. The terms "biochip", "chip" and "microarray" are used interchangeably with reference to a composition comprising a solid support or substrate to which a binding agent (or when nucleic acid is measured, a capture probe) is attached for binding to proteins, nucleic acids or combinations thereof. Generally, where a biochip is used for measurements of protein and nucleic acid inflammatory disease markers, the protein inflammatory disease markers are measured on a chip separate from that used to measure the nucleic acid inflammatory disease markers. For nonlimiting examples of additional platforms and methods useful for measuring nucleic acids, see Publications US/2006/0275782, and US/2005/0064469. In various embodiments, inflammatory disease markers are measured on the same platform, such as on one chip. In various embodiments, inflammatory disease markers are measured using different platforms and/or different experimental runs.

Frequently, the surface of a biochip comprises a plurality of addressable locations, each of which comprises a binding agent. An "array location," "addressable location," "pad" or "site" herein means a location on the substrate that comprises a covalently attached binding agent. An "array" herein means a plurality of binding agents in a regular, ordered format, such as a matrix. The size of the array will depend on the composition and end use of the array. Arrays containing from about two or more different binding agents to many thousands can be made. The array may include controls, replicates of the markers and the like. Exemplary ranges are from about 3 to 10, to about 100, from about 100 to about 1000, and from about 1,000 to about 10,000 or more.

In some embodiments, an in vivo persistent infection can be identified through the use of a reverse transcriptase polymerase chain reaction (RT-PCR) to demonstrate the presence of 16S rRNA transcripts in bacterially infected cells after treatment with one or more antibiotics as previously described (*Antimicrob. Agents Chemother.* 12:3288-3297, 2000). For example, in some embodiments, Group III microbial inflammatory disease markers corresponding to microbial organisms can be detected and/or quantitated by 16S rRNA profiling.

In one embodiment, this method comprises the additional steps of: (a) amplifying DNA or RNA from a biological sample; (b) amplifying DNA or RNA from a control sample of known normal non-inflammatory cells of the same origin or type as the biological sample; (c) contacting the amplified nucleic acids in steps (a) and (b) with a microarray comprising on defined areas on the microarray's surface immobilized probes for microbial DNA encoding 16S or 18S rRNA from microbial pathogens; (d) detecting the binding of one or more species of the labeled amplified nucleic acids to a probe by detecting an amplified nucleic acid specifically bound to the microarray; and (e) identifying one or more microbial organisms in the sample associated with the subject having the inflammatory disease.

The DNA can be amplified by known methods, such as for example, the PCR method. In PCR, preferably a primer would be directed towards a conserved region to ensure that the largest population of micro flora DNA is amplified, while the area amplified includes a less conserved region, thereby allowing a broad polymorphic analysis. Suitable examples might, for example, include the 16S rRNA gene, 23S rRNA gene or the region between the 16S and 23S rRNA genes. Any form of polymorphic analysis is suitable. The more variable products that are detectable, the more determinate the analysis will be. For example, a restriction fragment length polymorphism analysis could be performed over the variable region of the 16S rRNA gene.

In a preferred embodiment, the 16S rRNA profiling is carried out in a microarray in the form of a DNA biochip comprising oligonucleotide capture probes for the relevant microbial targets, which may represent genus groups or individual species. Thus, a microarray may include, for example, 25 different microbes, including a wide variety of gram positive and gram negative organisms. Such a microarray can enable the detection and/or relative quantitation of microorganisms within a short time frame, e.g., within 6 hours, enabling rapid diagnosis of pathogens from biological samples at the genus and/or species level and providing important conclusions for therapeutic treatments.

Preferably, the nucleic acid amplification reaction on the microbial DNA encoding 16S or 18S rRNA is performed by a PCR reaction. The amplification reaction can be performed by e.g., Multiplex-PCR, however, according to the present application reduction in primer number for the nucleic acid amplification has proven to be advantageous. Therefore, in the method according to the present application the nucleic acid amplification reaction on the microbial DNA encoding 16S or 18S rRNA is preferably performed with universal primers for the microbial DNA encoding 16S or 18S rRNA, preferably with not more than eight (4 forward, 4 reverse) primers, more preferred with not more than six (3 forward, 3 reverse) primers, preferably with not more than four (2 forward, 2 reverse) primers.

In some embodiments, the amplified labeled nucleic acids are directly applied to a microarray without a purification or washing step after the nucleic acid amplification reaction.

In some embodiments, the microarray includes immobilized probes for microbial DNA encoding 16S or 18S rRNA from at least ten, preferably at least 15, especially at least 20, of the following microbial pathogens: Mycobacterium (tuberculosis, avium paratuberculosis), Bacteroides, Brucella, Campylobacter (concisus, hominus, upsaliensis and C. ureolyticus), Escherichia coli (including adhesive-invasive E. coli (AIEC)), Saccharomyces cerevisiae, Klebsiella, Yersinia pseudotuberculosis, Clostridium (difficile), Enterococcus faecalis, Enterococcus faecium, Eubacterium, Listeria monocytogenes, Peptostreptococcus, Helicobacter(hepaticus), Pseudomanas fluorescens, Salmonella, Chlamydia, and the like.

The microarray may comprise at least 10 different species and/or genera, preferably of at least 15 different species/genera, especially of at least 20 different species/genera.

In some embodiments, the microarray comprises immobilized probes which are multispecific. As used herein, the term "multispecific" refers to a binding specificity for a plurality of different microbial species in a genus or for a plurality of different microbial species across a plurality of microbial genera.

The microarray may comprise the probes as spots on the surface, preferably in each of the spots only one species of probes is present. The probes of the present application are nucleic acid molecules, especially DNA molecules which bind to nucleic acids amplified according to the present application, i.e., specific for microbial DNA or RNA corresponding to 16S or 18S rRNA.

Preferably, the microarray according to the present application comprises at least 5, preferably at least 10, 15, 20, 30, 40 or more specific and/or multispecific immobilized probes. In specific embodiments, the microarray may comprise a portion of at least 5%, 10%, 20%, 30%, 40% or 50% multispecific probes of the total number of probes immobilized on the microarray.

In other embodiments, the inflammatory disease markers are detected by a protein microarray containing immobilized inflammatory disease marker-specific antibodies on its surface. The microarray can be used in a "sandwich" assay in which the antibody on the microarray captures a inflammatory disease marker in the test sample and the captured marker is detected by a labeled secondary antibody that specifically binds to the captured marker. In a preferred embodiment, the secondary antibody is biotinylated or enzyme-labeled. The detection is achieved by subsequent incubation with a streptavidin-fluorophore conjugate (for fluorescence detection) or an enzyme substrate (for colorimetric detection).

Typically, a microarray assay contains multiple incubation steps, including incubation with the samples and incubation with various reagents (e.g., primary antibodies, secondary antibodies, reporting reagents, etc.). Repeated washes are also needed between the incubation steps. In one embodiment, the microarray assays is performed in a fast assay mode that requires only one or two incubations. It is also conceivable that the formation of a detectable immune complex (e.g., a captured inflammatory disease marker/anti-marker antibody/label complex) may be achieved in a single incubation step by exposing the protein microarray to a mixture of the sample and all the necessary reagents. In one embodiment, the primary and secondary antibodies are the same antibody.

In another embodiment, the protein microarray provides a competitive immunoassay. Briefly, a microarray comprising immobilized anti-marker antibodies is incubated with a test sample in the presence of a labeled inflammatory disease marker standard. The labeled inflammatory disease marker competes with the unlabeled inflammatory disease marker in the test sample for the binding to the immobilized antigen-specific antibody. In such a competitive setting, an increased concentration of the specific inflammatory disease marker in the test sample would lead to a decreased binding of the labeled inflammatory disease marker standard to the immobilized antibody and hence a reduced signal intensity from the label.

The microarray can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.) or Assay 1200™ Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up the whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

Accordingly, in one aspect, the present application provides a composition comprising a solid support comprising a plurality of binding agents for inflammatory disease markers in an inflammatory disease marker panel. In some embodiments, the capture ligand is a nucleic acid probe. In other embodiments, the binding agent is an antibody or antibody-binding protein. In further embodiments, the composition further comprises soluble binding ligand for each inflammatory disease marker of an inflammatory disease marker panel.

A number of different biochip array platforms as known in the art may be used. For example, the compositions and methods of the present application can be implemented with array platforms such as GeneChip® (Affymetrix), CodeLink™ Bioarray (Amersham), Expression Array System (Applied Biosystems), SurePrint microarrays (Agilent), Sentrix® LD BeadChip or Sentrix® Array Matrix (Illumina), Verigene (Nanosphere), and ClonDiag ArrayTube (AT) (Alere Technologies GmbH, Jena, Germany).

In some embodiments, detection and measurement of inflammatory disease markers utilizes colorimetric methods and systems in order to provide an indication of binding of a target analyte or target species. In colorimetric methods, the presence of a bound target species such as an inflammatory disease marker will result in a change in the absorbance or transmission of light by a sample or substrate at one or more wavelengths. Detection of the absorbance or transmission of light at such wavelengths thus provides an indication of the presence of the target species.

A detection system for colorimetric methods includes any device that can be used to measure colorimetric properties as discussed above. Generally, the device is a spectrophotometer, a colorimeter or any device that measures absorbance or transmission of light at one or more wavelengths. In various embodiments, the detection system comprises a light source; a wavelength filter or monochromator; a sample container such as a cuvette or a reaction vial; a detector, such as a photoresistor, that registers transmitted light; and a display or imaging element.

Test Stick

In some other embodiments, the inflammatory disease markers in a liquid sample are detected using a test stick. The test stick typically contains a fluid impermeable housing and a fluid permeable "stick" having one or more detection zones. In one embodiment, each detection zone contains a dried binding reagent that binds to a inflammatory disease marker in the biological sample. In another embodiment, the dried binding reagent is a labeled binding reagent. In another embodiment, the test stick may further comprise a control zone to indicate that the assay test has been carried out satisfactorily, namely the reagents were present in the test stick and that they become mobilized during running the test and have been transported along the flow path. The control zone can also indicate that the reagents within the device are capable of immunochemical interactions, confirming the chemical integrity of the device. This is important when considering the storage and shipment of the device under desiccated conditions within a certain temperature range. The control zone is typically positioned downstream from the detection zone(s) and may, for example, comprise an immobilized binding reagent for a labeled binding reagent. The labeled binding reagent may be present in a mobilizable form upstream from the control zone and detection zone. The labeled binding reagent may be the same or different to the labeled binding reagent for the inflammatory disease marker.

In one embodiment, the test stick comprise a porous sample receiver in fluid connection with and upstream from one or more flow-paths. The porous sample receiver may be common to all assays. Thus a fluid sample applied to the common sample application region of the device is able to travel along the one or more flow-paths to the respective detection zones. The porous sample receiver may be provided within a housing or may at least partially extend out of the housing and may serve for example to collect a body fluid. The porous sample receiver may also act as a fluid reservoir. The porous sample receiving member can be made from any bibulous, porous or fibrous material capable of absorbing liquid rapidly. The porosity of the material can be unidirectional (i.e., with pores or fibers running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fiber.

If desired, an absorbent "sink" can be provided at the distal end of the carrier material. The absorbent sink may comprise, for example, Whatman 3 MM chromatography paper, and should provide sufficient absorptive capacity to allow any unbound labeled binding reagent to wash out of the detection zone(s). As an alternative to such a sink it can be sufficient to have a length of porous solid phase material which extends beyond the detection zone(s).

Following the application of a binding reagent to a detection zone, the remainder of the porous solid phase material may be treated to block any remaining binding sites. Blocking can be achieved by treatment for example with protein (e.g., bovine serum albumin or milk protein), or with polyvinyl alcohol or ethanolamine, or combinations thereof. To assist the free mobility of the labeled binding reagent when the porous carrier is moistened with the sample, the porous carrier may further comprise a sugar such as sucrose or lactose and/or other substances, such as polyvinyl alcohol (PVA) or polyvinyl pyrrolidone (PVP). Such material may be deposited, for example, as an aqueous solution in the region to which the labeled binding reagent is to be applied. Such materials could be applied to the porous carrier as a first application followed by the application of the label; alternatively, such materials could be mixed with the label and applied to the porous carrier or combinations of both. Such material may be deposited upstream from or at the labeled binding reagent.

Alternatively, the porous carrier may not be blocked at the point of manufacture; instead the means for blocking the porous carrier are included in a material upstream from the porous carrier. On wetting the test strip, the means for blocking the porous carrier are mobilized and the blocking means flow into and through the porous carrier, blocking as the flow progresses. The blocking means include proteins such as BSA and casein as well as polymers such as PVP, PVA as well as sugars and detergents such as Triton-X100. The blocking means could be present in the macroporous carrier material.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimize non-specific binding and to facilitate free movement of the labeled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastic materials such as polyethylene and polypropylene, or other materials such as paper or glass-fiber. In the case that the labeled binding reagent is labeled with a detectable particle, the macroporous body may have a pore size at least ten times greater than the maximum particle size of the particle label. Larger pore sizes give better release of the labeled reagent. As an alternative to a macroporous carrier, the labeled binding reagent may be provided on a non-porous substrate provided upstream from the detection zone, the non-porous substrate forming part of the flow-path.

In another embodiment, the test stick may further comprise a sample receiving member for receiving the fluid sample. The sample receiving member may extend from the housing.

The housing may be constructed of a fluid impermeable material. The housing will also desirably exclude ambient light. The housing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively, the aperture may serve to allow a porous sample receiver to extend from the housing to a position external from the housing.

Implantable Biosensors

In other embodiments, the inflammatory disease markers are detected using implantable biosensors. Biosensors are electronic devices that produce electronic signals as the result of biological interactions. In one embodiment, the biosensors use antibodies, receptors, nucleic acids, or other members of a binding pair to bind with a inflammatory disease marker, which is typically the other member of the binding pair. Biosensors may be used with a blood sample to determine the presence of a inflammatory disease marker without the need for sample preparation and/or separation steps typically required for the automated immunoassay systems.

In one embodiment, the sensor is a nanoscale device. The sensor system includes a biological recognition element attached to a nanowire and a detector that is capable of determining a property associated with the nanowire. The biological recognition element is one member of a binding pair (e.g., a receptor of the inflammatory disease marker or an anti-inflammatory disease marker antibody) where the inflammatory disease marker being measured is the other member of the binding pair. Preferably, the nanowire sensor includes a semiconductor nanowire with an exterior surface formed thereon to form a gate electrode and a first end in electrical contact with a conductor to form a source electrode and a second end in contact with a conductor to form a drain electrode. In one embodiment the sensor is a field effect transistor comprising a substrate formed of an insulating material, a source electrode, a drain electrode and a semiconductor nanowire disposed there between with a biological recognition element attached on a surface of the nanowire. When a binding event occurs between the biological recognition element and its specific binding partner, a detectable change is caused in a current-voltage characteristic of the field effect transistor.

In another embodiment, the sensor system includes an array of sensors. One or more of the sensors in the array is associated with a protective member that prevents the associated sensor from interacting with the surrounding environment. At a selected time, the protective member may be disabled, thereby allowing the sensor to begin operating to interact with the surrounding fluid or tissue so that the biological recognition element can interact with the other member of its binding pair if that pair member is present.

In another embodiment, the protective member is formed of a conductive material that can oxidize, is biocompatible, bio-absorbable, and that may be dissolved in solution such as blood upon application of an electric potential. For example, a sensor may be formed within a well of a substrate that is capped by a conductive material such as a biocompatible metal or an electrically-erodible polymer. In another embodiment, the protective member is formed using a material that dissolves over a predetermined period of time.

Mass Spectrometry

In other embodiments, the inflammatory disease markers are detected using mass spectrometry (MS) such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.).

Mass spectrometry methods are well known in the art and have been used to quantify and/or identify biomolecules, such as proteins. Further, mass spectrometric techniques have been developed that permit at least partial de novo sequencing of isolated proteins. In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. In SELDI, the substrate surface is modified so that it is an active participant in the desorption process. In one embodiment, the surface is derivatized with adsorbent and/or capture reagents that selectively bind the protein of interest. In another embodiment, the surface is derivatized with energy absorbing molecules that are not desorbed when struck with the laser. In another embodiment, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 (Hutchens & Yip) and WO 98/59361 (Hutchens & Yip). The two methods can be combined by, for example, using a SELDI affinity surface to capture an analyte and adding matrix-containing liquid to the captured analyte to provide the energy absorbing material.

Detection of the presence of a inflammatory disease marker will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

A person skilled in the art understands that any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g., $^{13}C$) thereby permitting the test sample to be mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more inflammatory disease markers present in a first or second sample is determined, in part, by executing an algorithm with a computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the inflammatory disease marker that is present in the first and second samples. A standard containing a known amount of a inflammatory disease marker can be analyzed as the second sample to better quantify the amount of the biomolecule present in the first sample. In certain embodiments, the identity of the inflammatory disease markers in the first and second sample can also be determined.

Determination of Standard Value, Specificity and Sensitivity

In the present application, the standard expression level of a inflammatory disease marker, such as the blood concentration of CXCL10, can be determined statistically. For example, the blood concentration of CXCL10 in healthy individuals can be measured to determine the standard blood concentration of CXCL10 statistically. When a statistically sufficient population can be gathered, a value in the range of twice or three times the standard deviation (S.D.) from the mean value is often used as the standard value. Therefore, values corresponding to the mean value+2×.S.D. or mean value+3×S.D. may be used as standard values. The standard values set as described theoretically comprise 90% and 99.7% of healthy individuals, respectively.

Alternatively, standard values can also be set based on the actual expression level (e.g., blood concentration of CXCR3) in the subject. Generally, standard values set this way minimize the percentage of false positives, and are selected from a range of values satisfying conditions that can maximize detection sensitivity. Herein, the percentage of false positives refers to a percentage, among healthy individuals, of patients whose blood concentration of CXCR3 is judged to be higher than a standard value. On the contrary, the percentage, among healthy individuals, of patients whose blood concentration of CXCR3 is judged to be lower than a standard value indicates specificity. That is, the sum of the false positive percentage and the specificity is always 1. The detection sensitivity refers to the percentage of patients whose blood concentration of CXCR3 is judged to be higher than a standard value, among all patients within a population of individuals for whom diagnosis of the inflammatory disease has been confirmed.

As used herein, the term "test sensitivity" is the ability of a screening test to identify true disease, also characterized by being a test with high sensitivity has few false negatives, additionally a test independent of disease prevalence. The test sensitivity is calculated as true positive tests per total affected patients tested, expressed as a percentage.

The term "Test Specificity" is a screening test which is correctly negative in the absence of disease, has high specificity and few false positives, is independent of disease prevalence. The test specificity is calculated as true negative tests per unaffected individual s tested, expressed as a percentage.

The term "PPV" (Positive Predictive Value) is the percent of patients with positive test having disease, and thus assesses reliability of positive test. Calculation:

1. PPV=(True positive)/(True+False positives).

The term "NPV" (Negative Predictive Value) refers to patients with negative test that do not have disease, and assesses reliability of negative test. Calculation:

2. NPV=(True negative)/(true and false negatives).

As the relationship shown above indicates, each of the values for sensitivity, specificity, positive predictive value, and negative predictive value, which are indexes for evaluating the diagnostic accuracy, varies depending on the standard value for judging the level of the blood concentration of one or more inflammatory disease markers.

A standard value is usually set such that the false positive ratio is low and the sensitivity is high. However, as also apparent from the relationship shown above, there is a trade-off between the false positive ratio and sensitivity. That is, if the standard value is decreased, the detection sensitivity increases. However, since the false positive ratio also increases, it is difficult to satisfy the conditions to have a "low false positive ratio". Considering this situation, for example, values that give the following predicted results may be selected as the preferable standard values in the present application: (1) standard values for which the false positive ratio is 50% or less (that is, standard values for which the specificity is not less than 50%) and (2) standard values for which the sensitivity is not less than 20%.

The standard values can be set using receiver operating characteristic (ROC) curve. An ROC curve is a graph that shows the detection sensitivity on the vertical axis and the false positive ratio (that is, "1-specificity") on the horizontal axis. A ROC curve can be obtained by plotting the changes in the sensitivity and the false positive ratio, which were obtained after continuously varying the standard value for determining the high/low degree of the blood concentration of a inflammatory disease marker, such as CXCL10.

The "standard value" for obtaining the ROC curve is a value temporarily used for the statistical analyses. The "standard value" for obtaining the ROC curve can generally be continuously varied within a range that allows to cover all selectable standard values. For example, the standard value can be varied between the smallest and largest measured blood CXCL10 values in an analyzed population.

Based on the obtained ROC curve, a preferable standard value to be used in the present application can be selected from a range that satisfies the above-mentioned conditions. Alternatively, a standard value can be selected based on a ROC curve produced by varying the standard values from a range that comprises most of the measured blood CXCL10.

Monitoring the Course of Inflammatory Disease Treatment

In certain embodiments, the levels of one or more inflammatory disease markers are used to monitor the course of inflammatory disease treatment. In this method, a biological sample is provided from a subject undergoing treatment for an inflammatory disease. Preferably, multiple test biological samples are obtained from the subject at various time points before, during or after the treatment. The expression level of the cancer marker in the post-treatment sample may then be compared with the level of the inflammatory disease marker in the pre-treatment sample or, alternatively, with a reference sample (e.g., a normal control level). For example, if the post-treatment marker level is lower than the pre-treatment marker level, one can conclude that the treatment was efficacious. Likewise, if the post-treatment marker level is similar to, or the same as, the normal control marker level, one can also conclude that the treatment was efficacious.

An "efficacious" treatment is one that leads to a reduction in the level of an inflammatory disease marker or a decrease in the inflammatory disease symptoms in a subject. When a treatment is applied prophylactically, "efficacious" means that the treatment retards or prevents occurrence of cancer or alleviates a clinical symptom of the inflammatory disease. The assessment of inflammatory disease can be made using standard clinical protocols. Furthermore, the efficaciousness of a treatment can be determined in association with any known method for diagnosing or treating an inflammatory disease.

In one embodiment, the inflammatory disease marker levels in the biological sample are compared with their corresponding inflammatory disease marker levels associated with a reference sample, such as normal control samples. The phrase "normal control level" refers to the level of an inflammatory disease marker typically found in a biological sample of a population not suffering from the inflammatory disease. The reference sample is preferably of a similar nature to that of the test sample. For example, if the test sample comprises patient serum, the reference sample should also be serum. The inflammatory disease marker levels in the biological samples from control and test subjects may be determined at the same time or, alternatively, the normal control level may be determined by a statistical method based on the results obtained by analyzing the level of the cancer marker in samples previously collected from a control group.

Kits for Detecting Inflammatory Diseases or Monitoring disease Progression

Another aspect of the present application relates to a kit for detecting an inflammatory disease or monitoring inflammatory disease progression. In one embodiment, the kit includes reagents for determining expression of CXCL9, CXCL10, CXCL11, CXCL13, CXCR3 and/or CXCR5 in a biological sample, and instructions for how to use the reagents, wherein the reagents include a plurality of binding agents or probes directed against CXCL9, CXCL10, CXCL11, CXCL13, CXCR3 and/or CXCR5. The kit may further include a variety of Group II, Group III, Group IV, and/or other inflammatory disease markers and detection formats as described above.

The kit may additionally comprise a carrier, such as a box, carton, tube or the like, having in close confinement therein one or more containers, such as vials, tubes, ampoules, bottles, pouches, envelopes and the like. In various embodiments, the kits comprise one or more components selected from one or more media or media ingredients and reagents for the measurement of the various inflammatory disease markers and inflammatory disease marker panels disclosed herein. For example, kits of the present application may also comprise, in the same or different containers, one or more DNA polymerases, one or more primers, one or more suitable buffers, one or more nucleotides (such as deoxynucleoside triphosphates (dNTPs) and preferably fluorescently labeled dNTPs) and labeling components. The one or more components may be contained within the same container, or may be in separate containers to be admixed prior to use. The kits of the present application may also comprise one or more instructions or protocols for carrying out the methods of the present application. The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of inflammatory disease markers as provided herein. In various embodiments, the kit comprises an inflammatory disease marker assay involving a lateral-flow-based point-of-care rapid test with detection of risk thresholds, or a biochip with quantitative assays for the constituent inflammatory disease markers.

The present application is further illustrated by the following examples that should not be construed as limiting. The contents of all references, patents, and published patent applications cited throughout this application, as well as the Figures and Tables, are incorporated herein by reference.

Example 1

Upregulation of Chemokines and Their Receptors in Inflammatory Diseases

Materials and Methods

The protein sequences of the chemokines used herein are recorded in NIH-NCBI GenBank as: (1) CXCR1 (ACCESSION# NP 000625), (2) CXCR2(ACCESSION# NP 001548), (3) CXCL1 (ACCESSION# NP 001502), (4) CXCL2 (ACCESSION# NP 002080), (5) CXCL3 (ACCESSION# NP 002081), (6) CXCL5 (ACCESSION# NP 002985), (7) CXCL6 (ACCESSION# NP 002984), (8) CXCL7 (ACCESSION# NP 002695), (9) CXCL8 (IL-8, ACCESSION# NP 000575), (10) CXCR4 (ACCESSION# NP 003458), (11) CXCL12 (ACCESSION# NP 000600), (12) CXCR5A (ACCESSION# NP 116743), (13) CXCR5B (ACCESSION# NP 001707), (14) CXCL13 (ACCESSION# NP 006410), (15) CXCR6 (ACCESSION# NP 006555), (16) CXCL16 (ACCESSION# NP 071342), (17) CCL16 (ACCESSION# NP 004581), (18) CCL25 (ACCESSION# NP_005616.2), (19) CCL25-1 (ACCESSION# NP 005615), (20) CCL25-2 (ACCESSION# NP 683686), (21) CX3CR1 (ACCESSION# NP 001328), and (22) CX3CL1 (ACCESSION# NP 002987).

The cDNA sequences are known and are available in NIH-NCBI GenBank under the following accession numbers: (23) CXCR1 (ACCESSION# NM 000634), (24) CXCR2(ACCESSION# NM 001557), (25) CXCL1 (ACCESSION# NM 001511), (26) CXCL2 (ACCESSION# NM 002089), (27) CXCL3 (ACCESSION# NM 002090), (28) CXCL5 (ACCESSION# NM 002994), (29) CXCL6 (ACCESSION# NM 002993), (30) CXCL7 (ACCESSION# NM 002704), (31) CXCL8 (IL-8, ACCESSION# NM 000584), (32) CXCR4 (ACCESSION# NM 003467), (33) CXCL12 (ACCESSION# NM 000609), (34) CXCR5A (ACCESSION# NM 032966), -(35) CXCR5B (ACCESSION# NM 001716) (36) CXCL13 (ACCESSION# NM 006419), (37) CXCR6 (ACCESSION# NM 006564), (38) CXCL16 (ACCESSION# NM 022059), (39) CCL16 (ACCESSION# NM 004590), (40) CCL25 (ACCESSION# NM_005624.3), (41) CCL25-1 (ACCESSION# NM 005624), (42) CCL25-2 (ACCESSION# NM 148888), (43) CX3CR1 (ACCESSION# NM 001337), and (44) CX3CL1 (ACCESSION# NM 002996).

Primer Design. Messenger RNA sequences for CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were obtained from the NIH-NCBI gene bank database. Primers were designed using the BeaconJ 2.0 computer program. Thermodynamic analysis of the primers was conducted using computer programs: Primer PremierJ and MIT Primer 3. The resulting primer sets were compared against the entire human genome to confirm specificity.

Real Time PCR Analysis. Lymphocytes or inflamed tissues were cultured in RMPI-1640 containing 10% fetal calf serum, 2% human serum, supplemented with non-essential amino acids, L-glutamate, and sodium pyruvate (complete media). Additionally, primary inflammatory and normal-paired matched tissues were obtained from clinical isolates (Clinomics Biosciences, Frederick, Md. and UAB Tissue Procurement, Birmingham, Ala.). Messenger RNA (mRNA) was isolated from $10^6$ cells using TriReagent (Molecular Research Center, Cincinnati, Ohio) according to manufacturers protocols. Potential genomic DNA contamination was removed from these samples by treatment with 10 U/µl of RNase free DNase (Invitrogen, San Diego, Calif.) for 15 minutes at 37° C. RNA was then precipitated and resuspended in RNA Secure (Ambion, Austin, Tex.). cDNA was generated by reverse transcribing approximately 2 µg of total RNA using Taqman7 reverse transcription reagents (Applied-Biosystems, Foster City, Calif.) according to manufacturers protocols. Subsequently, cDNAs were amplified with specific human cDNA primers, to CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2, using SYBR7 Green PCR master mix reagents (Applied Biosystems) according to manufacturers protocol. The level of copies of mRNA of these targets were evaluated by real-time PCR analysis using the BioRad Icycler and software (Hercules, Calif.).

Anti-sera preparation. The 15 amino acid peptides from chemokines CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were synthesized (Sigma Genosys, The Woodlands, Tex.) and conjugated to hen egg lysozyme (Pierce, Rockford, Ill.) to generate the antigens for subsequent immunizations for anti-sera preparation or monoclonal antibody generation. The endotoxin levels of chemokine peptide conjugates were quantified by the chromogenic *Limulus amebocyte* lysate assay (Cape Cod, Inc., Falmouth, Miss.) and shown to be <5 EU/mg. 100 µg of the antigen was used as the immunogen together with complete Freund's adjuvant Ribi Adjuvant system (RAS) for the first immunization in a final volume of 1.0 ml. This mixture was administered in 100 ml aliquots on two sites of the back of the rabbit subcutaneously and 400 ml intramuscularly in each hind leg muscle. Three to four weeks later, rabbits received 100 µg of the antigen in addition to incomplete Freund's adjuvant for 3 subsequent immunizations. Anti-sera were collected when antibody titers reached 1:1,000,000. Subsequently, normal or anti-sera were heat-inactivated and diluted 1:50 in PBS.

Monoclonal Antibody Preparation. The 15 amino acid peptides from chemokines CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were synthesized (Sigma Genosys) and conjugated to hen egg lysozyme (Pierce) to generate the Antigen@ for subsequent immunizations for anti-sera preparation or monoclonal antibody generation. The endotoxin levels of chemokine peptide conjugates were quantified by the chromogenic *Limulus amebocyte* lysate assay (Cape Cod, Inc., Falmouth, Miss.) and shown to be <5 EU/mg. 100 ng of the antigen was used as the immunogen together with complete Freund's adjuvant Ribi Adjuvant system (RAS) for the first immunization in a final volume of 200 µl. This mixture was subcutaneously administered in 100 µl aliquots at two sites of the back of a rat, mouse, or immunoglobulin-humanized mouse. Two weeks later, animals received 100 µg of the antigen in addition to incomplete Freund's adjuvant for 3 subsequent immunizations. Serum were collected and when anti-CXCL9, -CXCL10, -CXCL11, -CCRL1, -CCRL2, -CCR5, -CCL1, -CCL2, -CCL3, -CCL4, -CCL4L1, -CCL5, -CCL7, -CCL8, -CCL14-1, -CCL14-2, -CCL14-3, -CCL15-1, -CCL15-2, -CCL16, -CCL19, -CCL23-1, -CCL23-2, —CCL24, -CCL26, —CCR6, -CCL20, and -CCL25, -CCL25-1, -CCL25-2 antibody titers reached 1:2,000,000, hosts were sacrificed and splenocytes were isolated for hybridoma generation.

B cells from the spleen or lymph nodes of immunized hosts were fused with immortal myeloma cell lines (e.g., YB2/0). Hybridomas were next isolated after selective culturing conditions (i.e., HAT-supplemented media) and limiting dilution methods of hybridoma cloning. Cells that produce antibodies with the desired specificity were selected using ELISA. Hybridomas from normal rats or mice were humanized with molecular biological techniques in common use. After cloning a high affinity and prolific hybridoma, antibodies were isolated from ascites or culture supernatants and adjusted to a titer of 1:2,000,000 and diluted 1:50 in PBS.

Anti-Sera or Monoclonal Antibody Treatment. Knockout or transgenic mice (8 to 12 weeks old, Charles River Laboratory, Wilmington, Mass.) that spontaneous—or when treated—develop inflammatory diseases were treated with 200 µl intraperitoneal injections of either anti-sera or monoclonal antibodies specific for each of the chemokines every three days. The inflammatory disease state of the host was next monitored for progression or regression of disease.

Cytokine Analysis by ELISA. The serum level of IL-2, —IL-6, -TNF-α, and -IFN-γ were determined by ELISA, following the manufacturers instructions (E-Biosciences, San Diego, Calif.). Plates were coated with 100 µl of the respective capture antibody in 0.1 M bicarbonate buffer (pH 9.5) and incubated O/N at 4° C. After aspiration and washing with wash buffer, the wells were blocked with assay diluent for 1 hour at RT. Samples and standards were added and incubated for 2 hours at RT. Next, 100 µl of detection antibody solutions were added and incubated for 1 hour. 100 µl of avidin-HRP solution was added and incubated for 30 minutes. Subsequently, 100 µl Tetramethylbenzidine (TMB) substrate solution was added and allowed to react for 20 minutes. 50 µl of the stop solution was added and plates were read at 450 nm. The cytokine ELISA assays were capable of detecting >15 pg/ml for each assay.

Cytokine Analysis by Multiplex Cytokine ELISA. The T helper cell derived cytokines, IL-1α, IL-1β, IL-2, IL-12, IFN-γ, TNF-α, in serum were also determined by Beadlyte mouse multi-cytokine detection system kit provided by BioRad, following manufacturer instructions. Filter bottom plates were rinsed with 100 µl of bio-plex assay buffer and removal using a Millipore Multiscreen Separation Vacuum Manifold System (Bedford, Mass.), set at 5 in Hg. IL-1α, IL-1β, IL-2; IL-12, IFN-γ, TNF-α beads in assay buffer were added into wells. Next, 50 µl of serum or standard solution were added and the plates were incubated for 30 minutes at RT with continuous shaking (setting 3) using a Lab-Line Instrument Titer Plate Shaker (Melrose, Ill.), after sealing the plates. The filter bottom plates were washed 2 times, as before, and centrifuged at 300×g for 30 seconds. Subsequently, 50 µl of anti-mouse IL-1α, IL-1β, IL-2, IL-12, IFN-γ, TNF-α antibody-biotin reporter solution was added in each well followed by incubation with continuous shaking for 30 minutes followed by centrifugation at 300×g for 30 seconds. The plates were washed 3 times with 100 µl of bio-plex assay buffer as before. Next, 50 µl streptavidin-phycoerythrin solution was added to each well and incubated with continuous shaking for 10 minute at RT. 125 µl of bio-plex assay buffer was added and Beadlyte readings were measured using a Luminexl instrument (Austin, Tex.). The resulting data was collected and calculated using Bio-plexl software (Bio-Rad). The cytokine Beadlyte assays were capable of detecting >5 pg/ml for each analyte.

Serum Amyloid Protein A (BAA) ELISA. The SAA levels were determined by ELISA using a kit supplied by Biosource International, (Camarillo, Calif.). Briefly, 50 µl of SAA-specific monoclonal antibody solution was used to coat microtiter strips to capture SAA. Serum samples and standards were added to wells and incubated for 2 hours at RT. After washing in the assay buffer, the HRP-conjugated anti-SAA monoclonal antibody solution was added and incubated for 1 hour at 37° C. After washing, 100 µl Tetramethylbenzidine (TMB) substrate solution was added and the reaction was stopped after incubation for 15 minutes at RT. After the stop solution was added, the plates were read at 450 nm.

Histology and Pathology Scoring. Fixed tissues were sectioned at 6 µm, and stained with hematoxylin and eosin for light microscopic examination. The intestinal lesions were multi-focal and of variable severity, the grades given to any section of intestine took into account the number of lesions as well as their severity. A score (0 to 4) was given, based on the following criteria: (Grade 0) no change from normal tissue. (Grade 1) 1 or a few multi-focal mononuclear cell infiltrates, minimal hyperplasia and no depletion of mucus. (Grade 2) lesions tended to involve more of the mucosa and lesions had several multi-focal, yet mild, inflammatory cell infiltrates in the lamina propria composed of mononuclear cells, mild hyperplasia, epithelial erosions were occasionally present, and no inflammation was noticed in the sub-mucosa. (Grade 3) lesions involved a large area of mucosa or were more frequent than Grade 2, where inflammation was moderate and often involved in the sub-mucosa as well as moderate epithelial hyperplasia, with a mixture of mononuclear cells and neutrophils. (Grade 4) lesions usually involved most of the section and were more severe than Grade 3 lesions. Additionally, Grade 4 inflammations were more severe and included mononuclear cell and neutrophils; epithelial hyperplasia was marked with crowding of epithelial cells in elongated glands. The summation of these score provide a total inflammatory disease score per mouse. The disease score could range from 0 (no change in any segment) to a maximum of 12 with Grade 4 lesions of segments.

Data Analysis. SigmaStat 2000 (Chicago, Ill.) software was used to analyze and confirm the statistical significance of data. The data were subsequently analyzed by the Student's t-test, using a two-factor, unpaired test. In this analysis, treated samples were compared to untreated controls. The significance level was set at $p<0.05$.

Results

Semiquantitative RT-PCR Identification of Molecular Targets. RT-PCR products obtained using CXCL9-, CXCL10-, CXCL11-, CCRL1-, CCRL2-, CCR5-, CCL1-, CCL2-, CCL3-, CCL4-, CCL4L1-, CCL5-, CCL7-, CCL8-, CCL14-1-, CCL14-2-, CCL14-3-, CCL15-1-, CCL15-2-, CCL16-, CCL19-, CCL23-1-, CCL23-2-, CCL24-, CCL26-, CCR6-, CCL20-, and CCL25-, CCL25-1-, CCL25-2-specific primer sets did not cross react with other gene targets due to exclusion of primers that annealed to host sequences. The primers used produced different size amplicon products relative the polymorphisms that resulted in CCL4 versus CCL4L1, CCL14-1, CCL14-2, versus CCL14-3, CCL15-1 versus CCL15-2, CCL23-1 versus CCL23-2, and CCL25, CCL25-1, versus CCL25-2. To this end, RT-PCR analysis of tissue from subjects exhibiting anaphylaxis, arthritis (e.g., rheumatoid, psoriatic), asthma, allergies (e.g., drug, insect, plant, food), atherosclerosis, delayed type hypersensitivity, dermatitis, diabetes (e.g., mellitus, juvenile onset), graft rejection, inflammatory bowel diseases (e.g., Crohn's disease, ulcerative colitis, enteritis), multiple sclerosis, myasthenia gravis, pneumonitis, psoriasis, nephritis, rhinitis, spondyloarthropathies, scheroderma, systemic lupus, or thyroiditis revealed that CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, and CCL25, CCL25-1, CCL25-2 were differentially expressed by inflammatory host cells.

In vivo Inflammatory Disease Inhibition. Mammals that develop anaphylaxis, septic shock, arthritis (e.g., rheumatoid, psoriatic), asthma, allergies (e.g., drug, insect, plant, food), atherosclerosis, bronchitis, chronic pulmonary obstructive disease, delayed type hypersensitivity, dermatitis, diabetes (e.g., mellitus, juvenile onset), graft rejection, Grave's disease, Hashimoto's thyroiditis, inflammatory bowel diseases (e.g., Crohn's disease, ulcerative colitis, enteritis), interstitial cystitis, multiple sclerosis, myasthemia gravis, pneumonitis, psoriasis, nephritis, rhinitis, spondyloarthropathies, scleroderma, systemic lupus erythematosus, or thyroiditis were allowed to develop the inflammatory disease of interest. Antibodies directed against CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, or CCL25, CCL25-1, CCL25-2 differentially affected the progression and regression of inflammatory disease as determined by histological scoring and comparing pre- and post-treatment serum levels of IFN-γ, IL-1α, IL-1β, IL-6, IL-12, TNF-α, amyloid protein A. Antibodies directed towards CXCL9, CXCL10, CXCL11, CCRL1, CCRL2, CCR5, CCL1, CCL2, CCL3, CCL4, CCL4L1, CCL5, CCL7, CCL8, CCL14-1, CCL14-2, CCL14-3, CCL15-1, CCL15-2, CCL16, CCL19, CCL23-1, CCL23-2, CCL24, CCL26, CCR6, CCL20, or CCL25, CCL25-1, CCL25-2 effectively lead to the both regression and impeding progression of inflammatory disease as determined by histological scoring and comparing pre- and post-treatment serum levels of IFN-γ, IL-1α, IL-1β, IL-6, IL-12, TNF-α, amyloid protein A.

As indicated previously, the chemokines used in the methods of the present application are known. Their accession numbers for the protein sequences are identified in Table 2.

As shown in the Table 1, the particular chemokines which give rise to inflammatory diseases differ with the disease. They also differ among individuals. Hence, it is wise, when treating an individual, to identify the particular chemokines which are increased in the tissues of the patient. Using the antibodies produced against each of the chemokines and exposing the tissue samples from the patient to the particular antibodies, then evaluating the amount of antibody/chemokine binding, it is possible to evaluate the level of expression for each chemokine and to administer to the patient the particular antibodies that will bind the excessive chemokine. This tailored approach to treatment of inflammatory disease is novel, and a particularly valuable aspect of the present application.

Example 2 mRNA Expression of IFN-γ, CXCL10, MIG, I-TAC, CXCR3 in Murine Colitis

FIG. 1 shows mRNA expression of IFN-γ, CXCL10, MIG, I-TAC, and CXCR3 during murine colitis. Laminar flow barriers were removed from the housing cages of IL-10$^{-/-}$ mice, on C57BL/6 background, for the spontaneous development of colitis. Following sacrifice, total RNA was isolated from the colon or mesenteric lymph nodes from mice before the onset of colitis (sterile conditions, open squares) and after the development of colitis (closed squares). The levels of IFN-γ, IP-10, MIG, I-TAC, and CXCR3 mRNA expression were ascertained after RT-PCR analysis that was capable of detecting >20 copies of transcribed cDNA. In FIG. 1, the Log$_{10}$ copies of transcripts are expressed relative to actual copies of 18S rRNA.

As shown in FIG. 1, a significant increase in CXCR3 and CXCL10 expression was observed in inflamed colons of IL-10$^{-/-}$ mice developing colitis. In addition, a significant increase in CXCL10 expression was observed in mesenteric lymph nodes of the IL-10$^{-/-}$ mice developing colitis.

Example 3

Figure 2A:
FIG. 2 shows histological analysis of IBD in TCR βxδ$^{-/-}$ mice that received CD45RB$^{HI}$ or CXCR3$^+$ CD4$^+$ T cells by adoptive transfer.
Figure 2B:
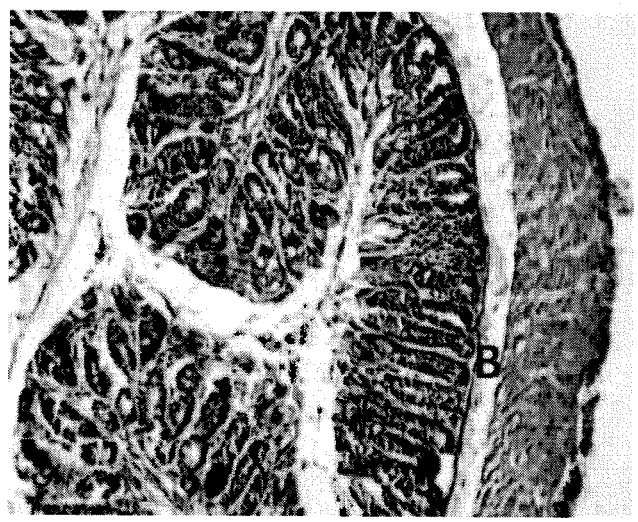
Figure 2C:
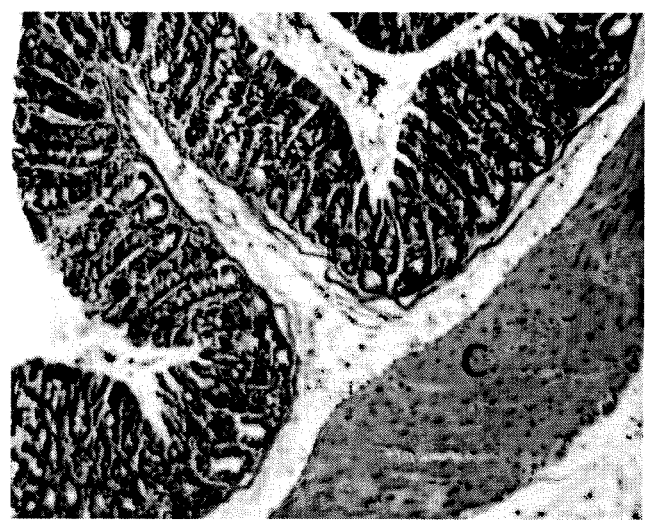

Histological Analysis of IBD in TCR βxδ$^{-/-}$ Mice that Received CD45RB$^{HI}$ or CXCR3$^+$ CD4$^+$ T Cells by Adoptive Transfer FIG. 2 shows histological analysis of IBD in TCR ⊖xδ$^{-/-}$ mice that received CD45RB$^{HI}$ or CXCR3$^+$ CD4$^+$ T cells by adoptive transfer. 60x magnification of intestinal inflammation in TCR βxδ$^{-/-}$ mice that received CD45RB$^{Lo}$-(Panel A), CD45RB$^{Hi}$-(Panel B), or CXCR3$^+$-CD4$^+$ T cells (Panel C) from normal C57BL/6 mice. Cross sections of intestines demonstrate the differences in wall thickness, enlargement of mucosal layer, crypt malformation, and leukocyte infiltration using hematoxylin-eosin staining of 6 μm paraffin sections.

This analysis shows that CXCR3$^+$ CD4$^+$ T cells, which consisted of both CD45RB populations induced induction of colitis in TCR βxδ$^{-/-}$ mice (Panel C).

Example 4

SAA Levels and the Development of Colitis in IL-10$^{-/-}$ Mice

Figure 3:
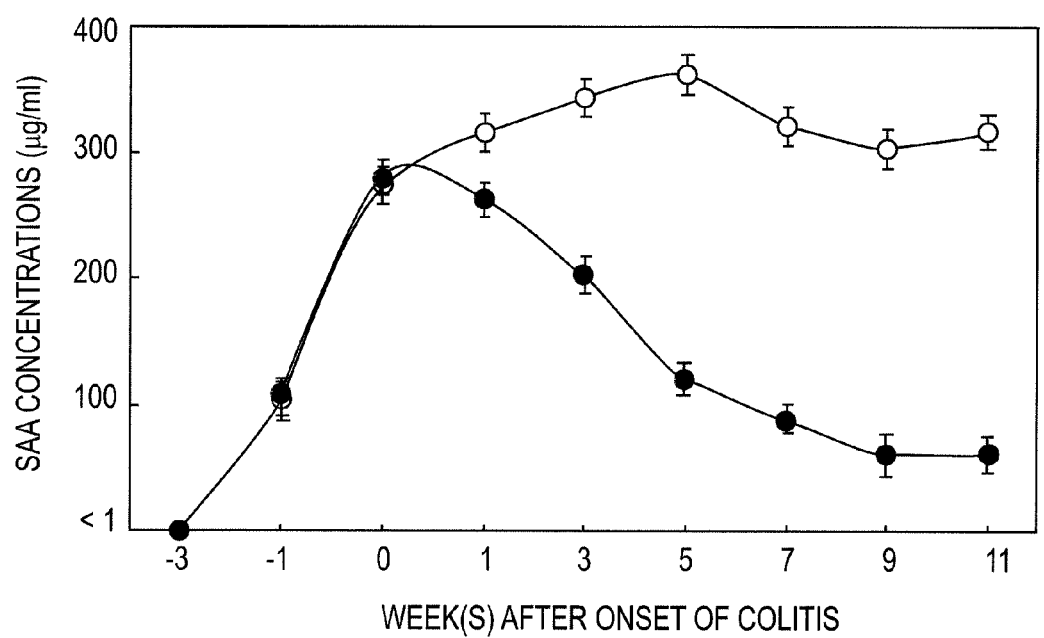
FIG. 3 shows SAA levels and the development of colitis in IL-10$^{-/-}$ mice. SAA concentrations >200 µg/ml were associated with the onset of asymptomatic colitis at week 0.

FIG. 3 shows serum amyloid A (SAA) levels and the development of colitis in IL-10$^{-/-}$ mice. SAA concentrations >200 μg/ml were associated with the onset of asymptomatic colitis at week 0. Mice received 200 μl of pre-immune- (open circles) or anti-mouse CXCL10 (closed circles) Ab solutions every 3 days. Sera were collected every 2 weeks and the data presented are the mean SAA concentrations±SEM.

The results in FIG. 3 show that CXCL10 blockage with anti-mouse CXCL10 antibodies inhibited the elevated SAA levels that are associated with IBD.

Example 5

Changes in Body Weight of IL-10$^{-/-}$ Mice

Figure 4:
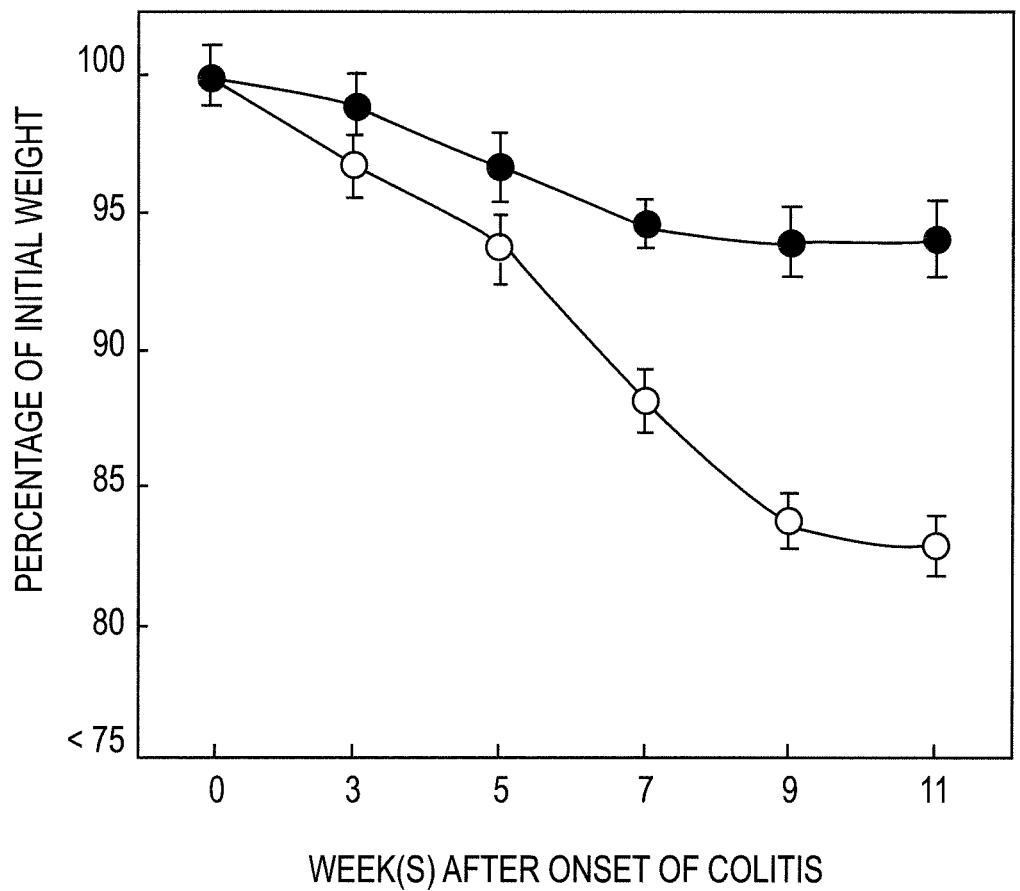
FIG. 4 shows changes in body weight of IL-10$^{-/-}$ mice.

FIG. 4 shows changes in body weight of IL-10$^{-/-}$ mice. The wasting disease associated with murine CD was observed by monitoring the change in initial body mass at week 0. IL-10$^{-/-}$ mice received 200 μl of pre-immune- (open circles) or anti-mouse CXCL10 (closed circles) Ab solutions every 3 days. Body masses were recorded every 2 weeks and the change from initial body mass was expressed as a percentage: weight at week 0 minus weight at week 1, 3, 5, 7, 9, or 11 divided by the weight at week 0.

The results in FIG. 4 show that CXCL10 blockage with anti-mouse CXCL10 antibodies inhibited the weight loss associated with IBD.

Example 6

Association of Serum IL-6 and SAA Levels with Murine Colitis

Figure 5:
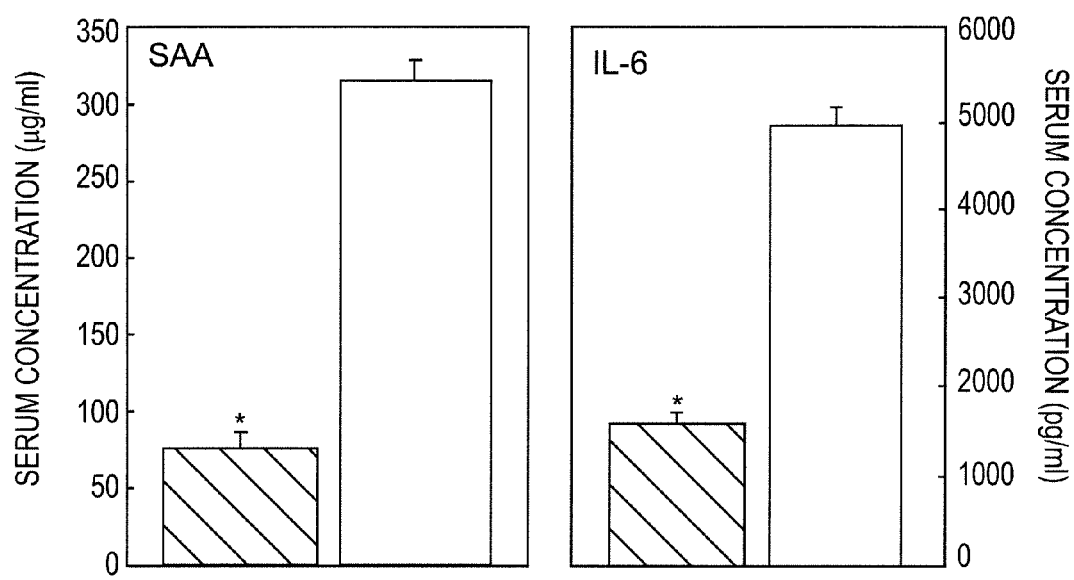
FIG. 5 shows association of serum IL-6 and SAA levels with murine colitis.

FIG. 5 shows association of serum IL-6 and SAA levels with murine colitis. IL-10$^{-/-}$ mice received 200 μl of pre-immune- (open boxes) or anti-mouse CXCL10 (closed boxes) Ab solutions every 3 days. The levels of SAA and serum IL-6, at week 11, were determined by ELISA. The data presented are the mean SAA or IL-6 concentrations±SEM.

The results in FIG. 5 show that CXCL10 blockage with anti-mouse CXCL10 antibodies significantly reduced SAA and IL-6 serum concentrations as compared with control mice. The results further suggest a utility of using SAA levels as an indicator for the switch from acute (i.e., asymptomatic) to chronic colitis in this murine model of CD.

Example 7

Total fecal and serum Ab levels in IL-10$^{-/-}$ mice

Figure 6:
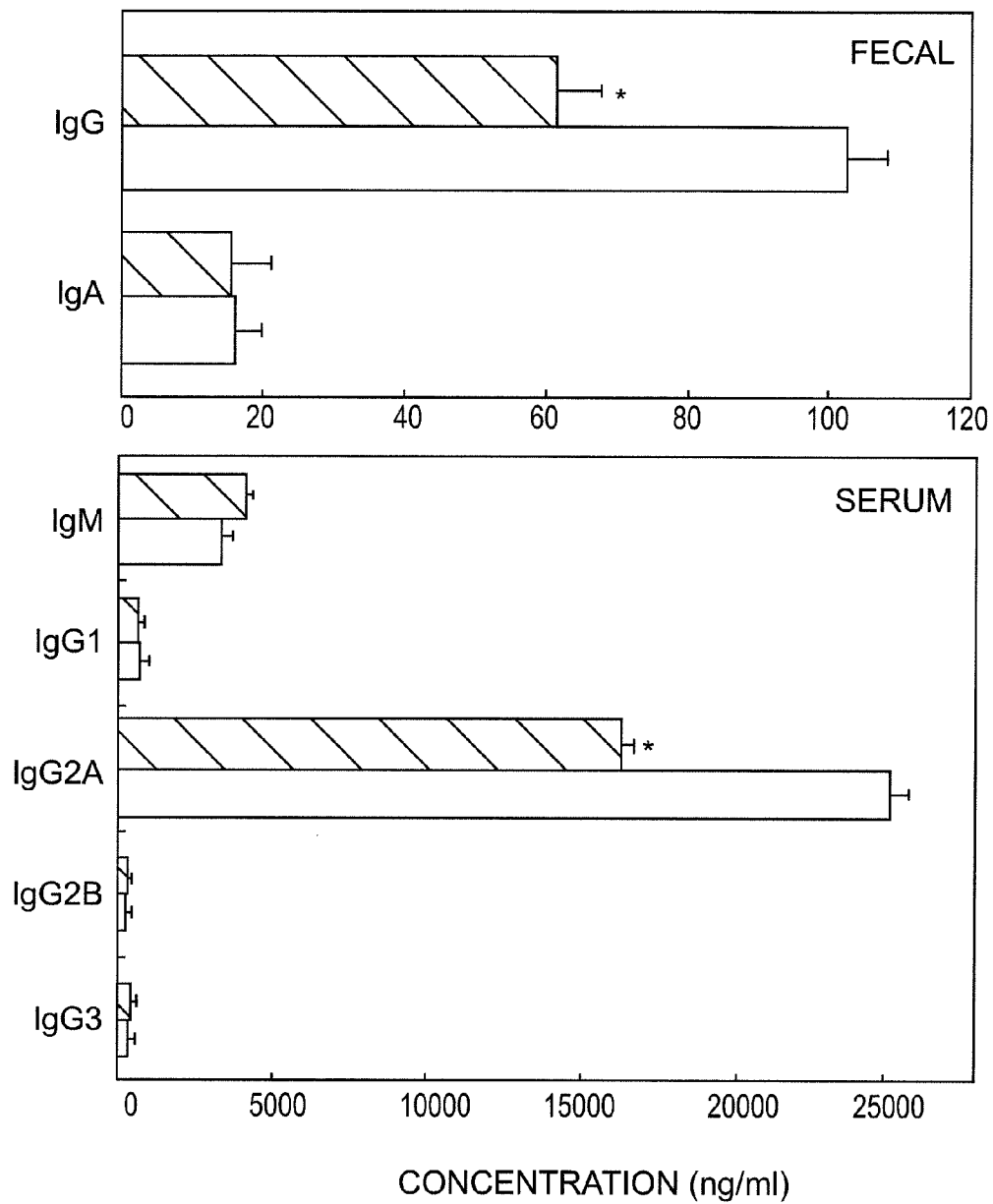
FIG. 6 shows total fecal and serum Ab levels in IL-10$^{-/-}$ mice.

FIG. 6 shows total fecal and serum Ab levels in IL-10$^{-/-}$ mice. Groups of 5 IL-10-/- mice received 200 μl of either pre-immune- (open squares) or anti-mouse IP-10-(closed squares) Ab solutions every 3 days. The data presented are the mean concentration of total Ig Abs (ng/ml)±SEM. Total IgA and IgG Abs in fecal extracts or IgM, IgG1, IgG2a, IgG2b, and IgG3 Abs in serum were collected at week 11 and levels determined by ELISA. Asterisk(s) indicate statistically significant differences, i.e., p<0.05 (*), between the 2 groups.

Total fecal IgG and IgA levels were determined to correlate changes in intestinal Abs during CD. As shown in FIG. 6, IgA Ab levels in fecal extracts was relatively constant. A significant decline in fecal IgG Abs was observed in IL-10$^{-/-}$ mice that received the IP-10 Ab solution (FIG. 6). These results indicate that blockade of IP-10 attenuated the excretion of IgG Abs from the periphery to the lumen of the intestinal mucosa during murine CD. In addition, total IgG1, IgG2a, IgG2b, IgG3, and IgM antibody levels were compared between the sera of control mice and those treated with anti-CXCL10 Abs. Control and CXCL10 Ab-treated mice had similar levels of IgM, IgG1, IgG2b, and IgG3 Abs. However, total serum IgG2a levels were significantly higher in mice with active colitis, as compared with anti-CXCL10 Ab-treated mice (FIG. 6). The results indicate that blockade of CXCL10 attenuated total IgG2a levels and the excretion of IgG Abs during CD, consistent with the predicted imbalance of Th1>>Th2 cytokine levels during CD.

Example 8

Figure 7:
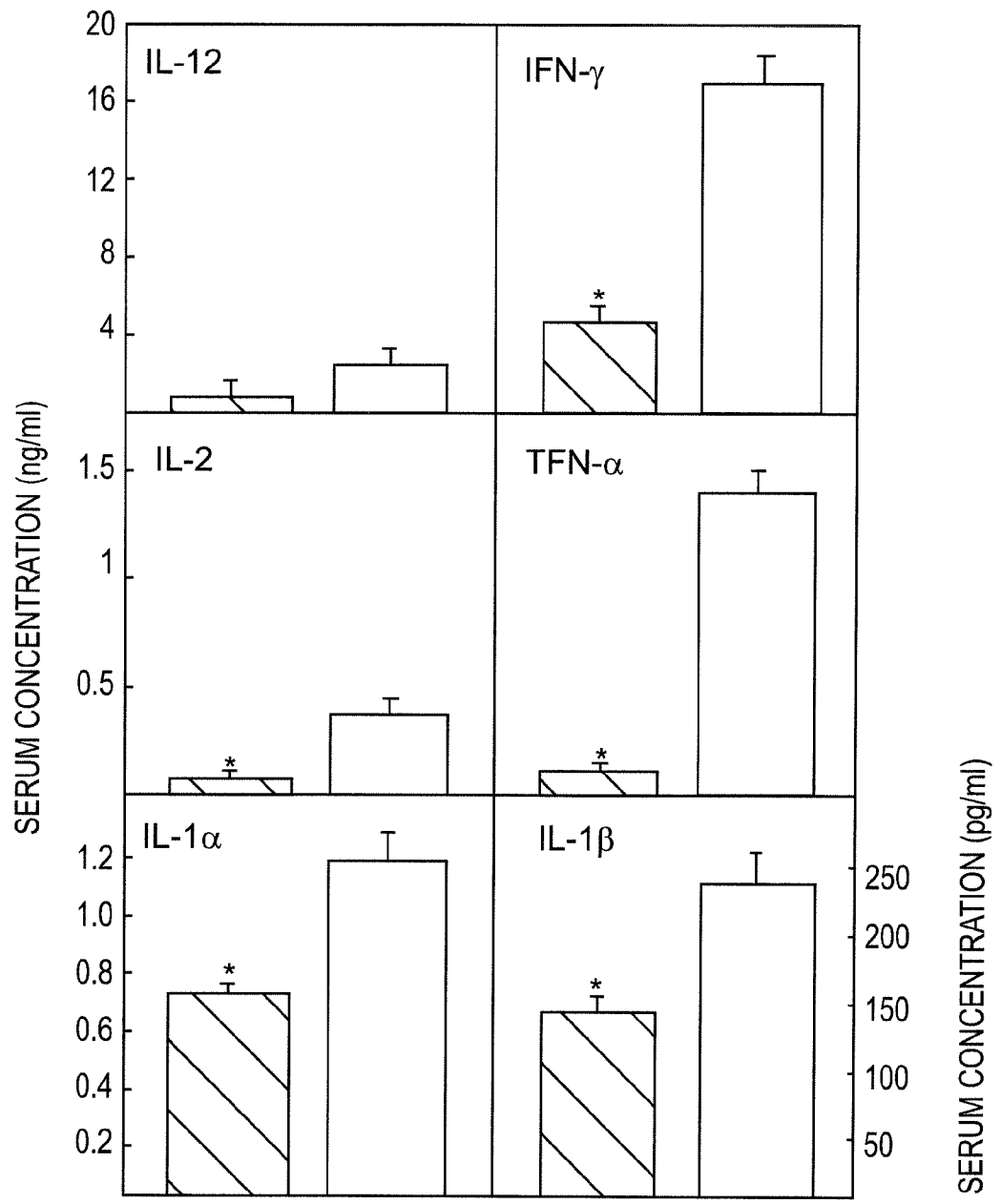
FIG. 7 shows serum IL-12, IFN-γ, IL-2, TNF-α, IL-1α, and IL-1β levels in IL-10$^{-/-}$ mice with IBD.
Figure 8A:
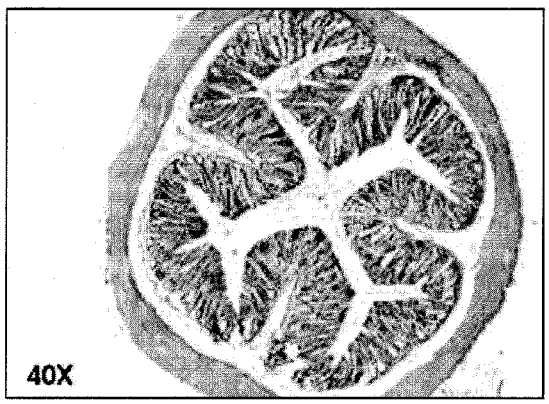
FIG. 8 shows histological characteristics of colitis presented by IL-10$^{-/-}$ mice.
Figure 8B:
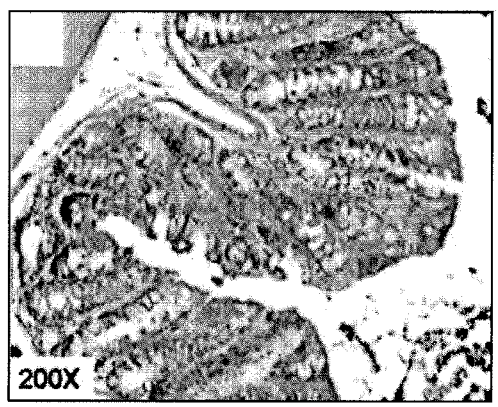
Figure 8C:
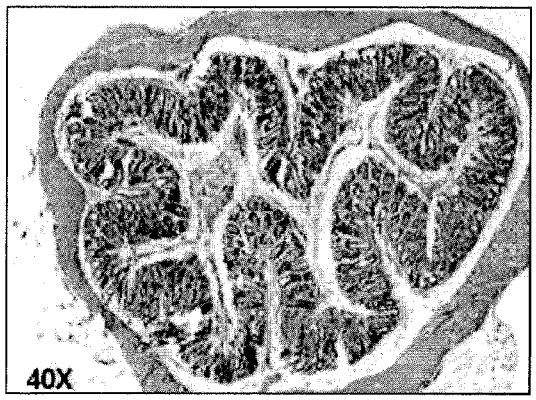
Figure 8D:
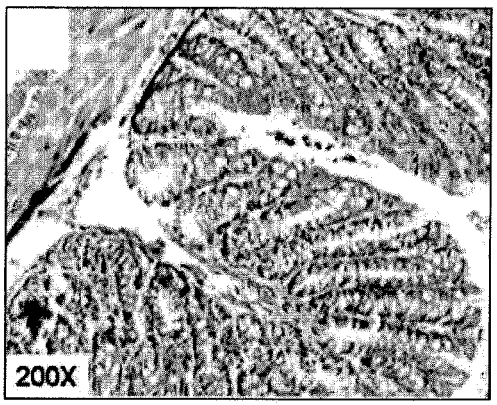

Serum IL-12, IFN-γ, IL-2, TNF-α, IL-1α, and IL-1β Levels in IL-10$^{-/-}$ Mice with IBD FIG. 7 shows serum IL-12, IFN-γ, IL-2, TNF-α, IL-1α, and IL-1β levels in IL-10$^{-/-}$ mice with IBD. IL-10$^{-/-}$ mice received 200 μl of either pre-immune- (open squares) or anti-mouse IP-10- (closed squares) Ab solutions every 3 days. Serum cytokines, at week 11, levels were determined by ELISA. The data presented are the mean cytokine concentrations±SEM (ng/ml).

Control groups showed moderately higher levels of serum IL-12 p40, compared with IP-10 Ab-treated mice (FIG. 7). In contrast, anti-CXCL10 Ab therapy dramatically decreased IFN-γ levels in IL-10$^{-/-}$ mice, as well as the levels of IL-2, TNF-α, IL-1α, and IL-1β levels. Overproduction of IL-2, IL-12, TNF-α, IL-1α, and IL-1β during IBD has been well documented. The significant decreases in serum IL-2, TNF-α, IL-1α, and IL-1β levels by CXCL10 blockade (FIG. 7) is consistent with the inflammatory state of the host with active colitis being significantly reduced by anti-CXCL10 Ab treatment.

Example 9

Histological Characteristics of Colitis Presented by IL-10$^{-/-}$ Mice

FIG. 8 shows histological characteristics of colitis presented by IL-10$^{-/-}$ mice. Changes in mice that received 200 μl of either pre-immune- (C or D) or anti-mouse IP-10- (A or B) Ab solutions every 3 days. Following sacrifice at week 11, the intestines were fixed, sectioned at 6 μm, and stained. Sections were examined microscopically at a magnification view of 40× (A and C) or 200× (B and D).

Observed pathologic changes included small multifocal infiltrates in the lamina propria of the ascending and transverse colon. These infiltrates consisted of lymphocytes and occasional small numbers of neutrophils. Epithelial cells were not hypertrophied in the IP-10-inhibited group. Multinucleated, enlarged epithelial, and elongated glandular cells were also present in control mice. However, colitis progression was more aggressive in control groups, as noted by multifocal lesions in all regions of the large intestine, especially in colon. The results show a marked improvement in colitis associated with CXCL10 blockade.

Example 10

Anti-CXCL10 Antibody Abrogates Severe Colitis

Figure 9A:
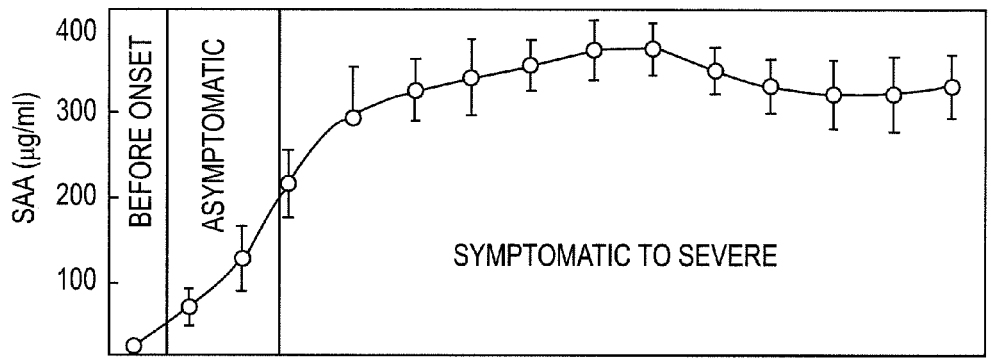
FIG. 9 shows that anti-CXCL10 antibody abrogates severe colitis.

FIG. 9 shows that anti-CXCL10 antibody abrogates severe colitis. IL-10$^{-/-}$ mice received 200 μl of control Ab (open circles) or anti-mouse CXCL10 Ab (closed circles) every 3 days starting 14 weeks after the onset of symptomatic colitis, when mice had lost about 10 to 15% of their initial body weight and attained a peak in SAA levels, and continued until the mice were sacrificed at week 26. The level of SAA±SEM and body weight of the IL-10$^{-/-}$ mice were recorded every week, and the change from initial body weight was expressed as a percentage of the weight before the onset of colitis (week −2) minus the weight at subsequent weeks divided by the weight before the onset of colitis (±SEM). Data represents the mean of three independent experiments involving 5 mice per groups. Asterisks indicate statistically significant differences (p<0.01) between anti-CXCL10 Ab- and control Ab-treated groups.

Figure 9B:
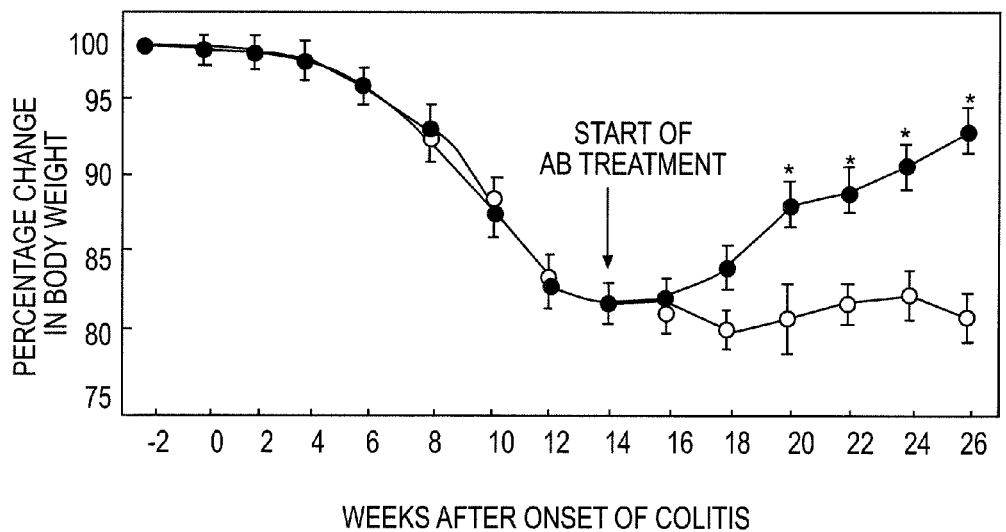

Chronic colitis in the IL-10$^{-/-}$ mice corresponded with an increase in SAA levels (>300 μg/mL)(FIG. 9A) and with a 10%-15% reduction in the body weight of the mice compared with their initial body weight (FIG. 9B). CXCL10 blockade in mice with chronic colitis alleviated weight loss when compared with the weight loss experienced by IL-10$^{-/-}$ mice with chronic colitis treated with control Ab.

Example 11

Figure 10:
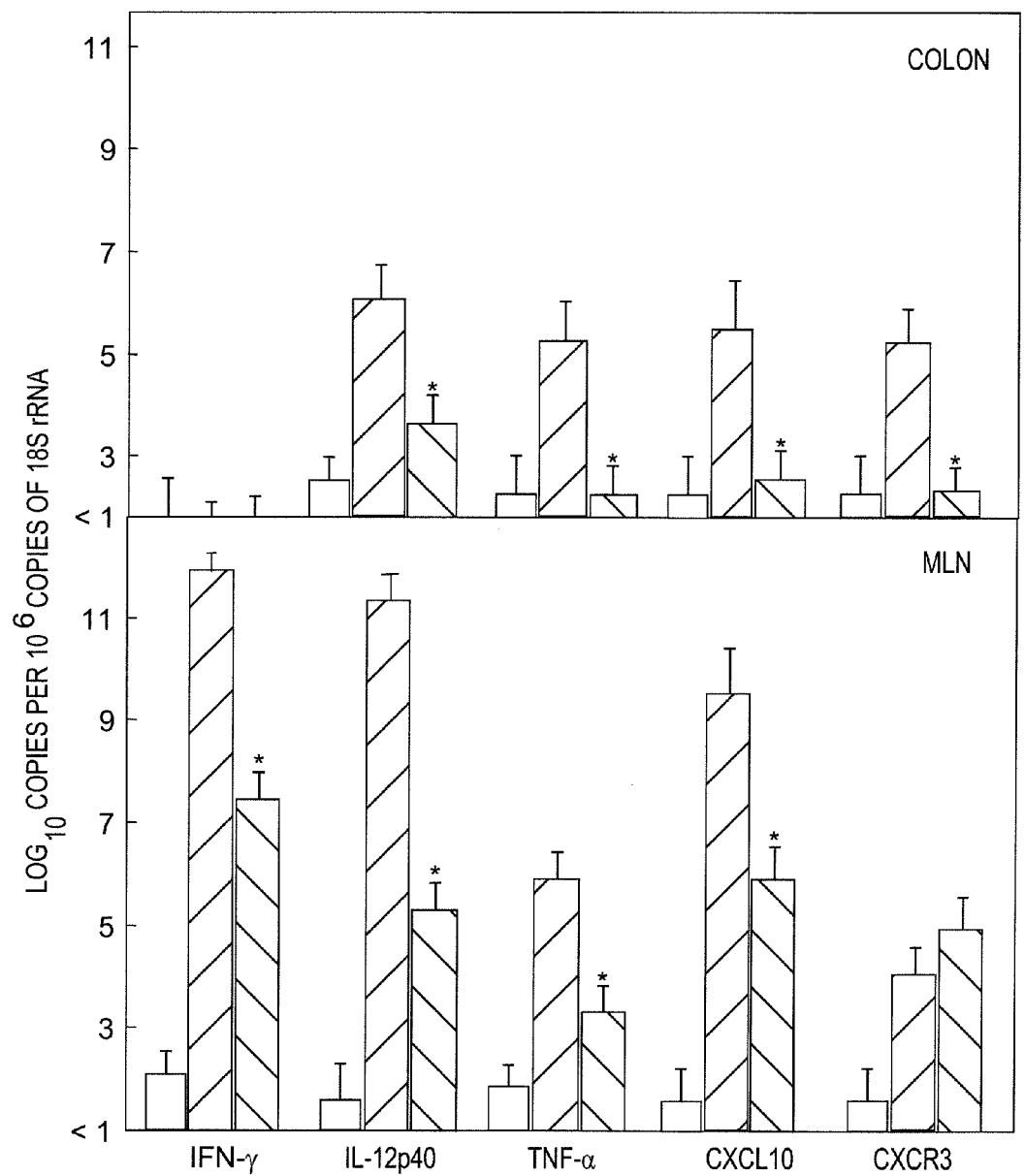
FIG. 10 shows Th1 cytokine, CXCL10 and CXCR3 mRNA expression in mucosal tissue during severe colitis.

Th1 Cytokine, CXCL10 and CXCR3 mRNA Expression in Mucosal Tissue During Severe Colitis FIG. 10 shows Th1 cytokine, CXCL10 and CXCR3 mRNA expression in mucosal tissue during severe colitis. After chronic development of colitis, mice received 200 μl of either control Ab (solid bars), or anti-CXCL10 Ab (hashed bars) or normal WT mice (open bars), every 3 days starting 14 weeks after the onset of symptomatic colitis, when mice had lost about 15% of their initial body weight. Following sacrifice of the mice, total RNA was isolated from the colons and mesenteric lymph nodes (MLNs) of mice treated with either control Ab, wild type or anti-CXCL10 Ab. The levels of IFN-γ, CXCL10, TNF-α, IL-12p40, and CXCR3 mRNA expression were ascertained by an RT-PCR analysis capable of detecting >20 copies of transcribed cDNA. Log$_{10}$ copies of transcripts are expressed relative to actual copies of 18S rRNA±SEM in FIG. 10. Data represents the mean of three independent experiments involving 5 mice per group. Asterisks indicate statistically significant differences (p<0.01) between anti-CXCL10 and control Ab-treated groups.

As shown in FIG. 10, significant increases in the expression of TNF-α and IL-12p40 mRNA were noted in the MLNs and colons of IL-10$^{-/-}$ mice with chronic colitis compared with anti-CXCL10 Ab-treated mice. CXCL10 mRNA expression by the colon and MLNs was also significantly elevated during chronic colitis in IL-10$^{-/-}$ mice treated with control Ab compared with anti-CXCL10 Ab-treated mice. IFN-γ Levels were reduced in the MLNs of mice with severe colitis following anti-CXCL10 Ab treatment compared with control Ab treatment; however, this Th1-associated cytokine was below detectable levels in the colons of both groups. CXCR3 mRNA expression was significantly reduced in the colons of IL-10$^{-/-}$ mice with colitis after CXCL10 inhibition, but its level in MLNs was not diminished during the same treatment compared with control Ab-treated mice.

Example 12

Th1 and Inflammatory Cytokine Levels in Serum During Severe Colitis Progression

Figure 11:
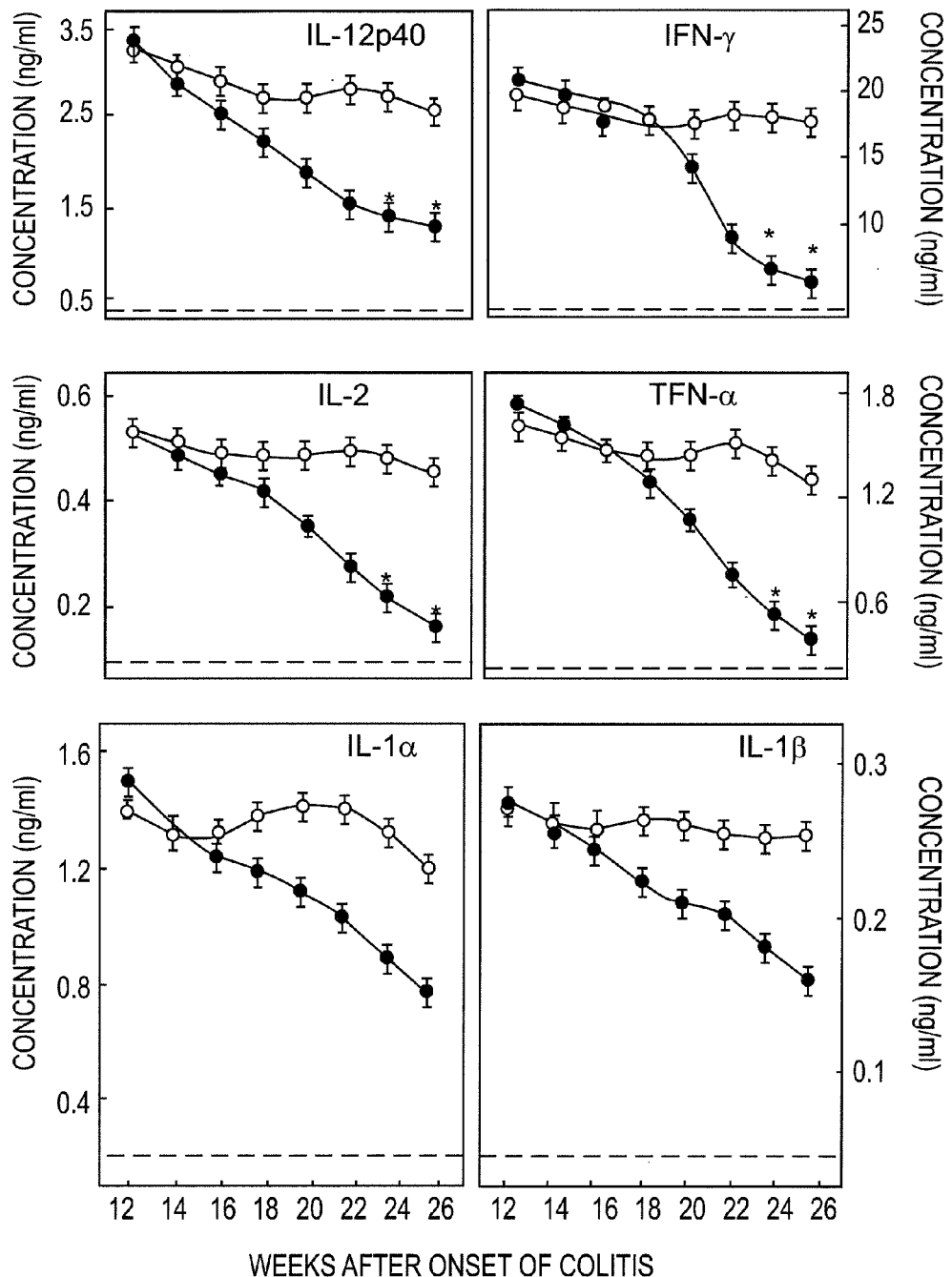
FIG. 11 shows Th1 and inflammatory cytokine levels in serum during severe colitis progression.
Figure 12A:
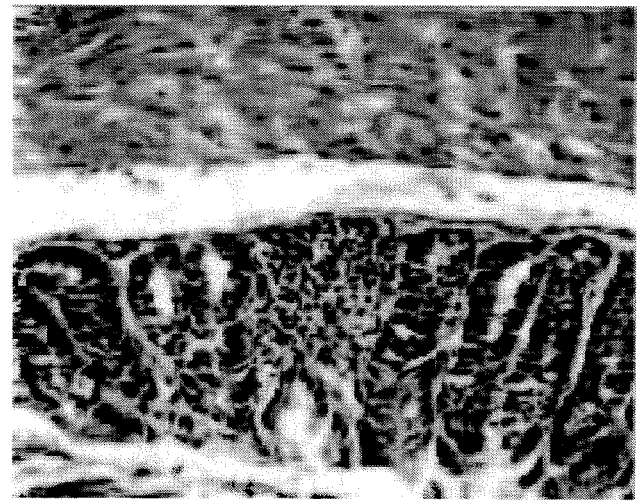
FIG. 12 shows anti-CXCL10 antibody effects on colitis pathology.
Figure 12B:
Figure 12C:
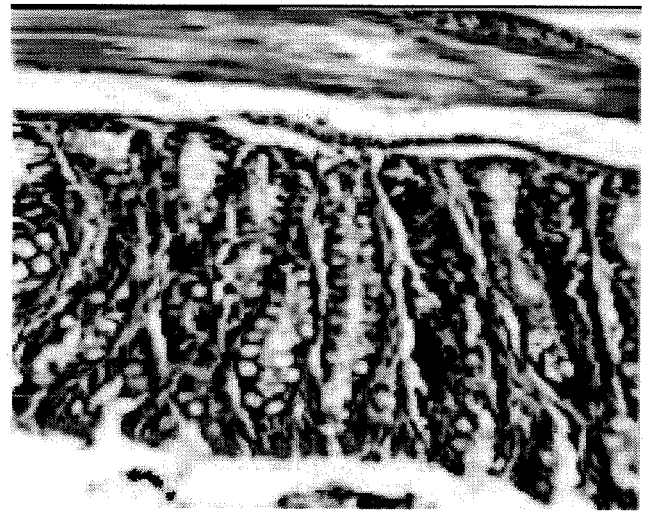
Figure 12D:
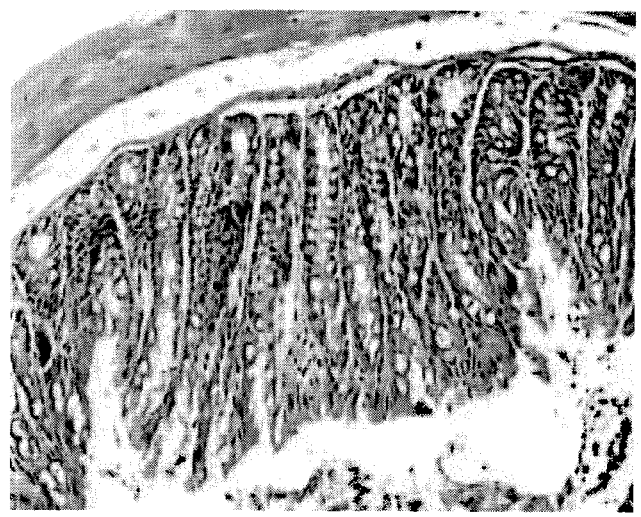

FIG. 11 shows Th1 and inflammatory cytokine levels in serum during severe colitis progression. IL-10$^{-/-}$ mice, received 200 μl of either control Ab (open circles) or anti-CXCL10 Ab (closed circles) every 3 days, starting 14 weeks after the onset of symptomatic colitis, which continued through week 26. Before sacrifice, levels of serum cytokines at week 26 were determined by an ELISA capable of detecting >10 μg/ml of IL-12p40, IL-2, TNF-α, IFN-γ, IL-1α, and IL-1β. The data presented are the mean concentrations±SEM. Asterisk (s) indicate statistically significant differences, i.e., p<0.01 (*), between the two groups. Experimental groups consisted of 5 mice, and experiments were repeated 3 times. Data represents the mean of 3 independent experiments.

Consistent with the RT-PCR analysis in FIG. 10, anti-CXCL10 Ab treatment decreased IFN-γ and IL-12p40 serum levels in IL-10$^{-/-}$ mice with chronic colitis (FIG. 11). Serum IL-2, TNF-α, IL-1α, and IL-1β levels also declined after CXCL10 blockade in IL-10$^{-/-}$ mice with chronic colitis compared with the control Ab-treated mice. These data indicate that CXCL10 blockade caused the reduction of SAA, IL-6, IL-12p40, IFN-γ, IL-2, TNF-α, IL-1α, and IL-1β serum levels of the IL-10$^{-/-}$ mice with chronic colitis.

Example 13

Anti-CXCL10 Antibody Effects on Colitis Pathology

FIG. 12 shows anti-CXCL10 antibody effects on colitis pathology. Histopathology of the colons from IL-10$^{-/-}$ mice with chronic colitis that were treated with either control Ab, (Panels A and B) or anti-CXCL10 Ab (panels C-D) as before. Sections were examined by light microscopy. Experimental groups consisted of 5 mice and were repeated 3 times.

The mice that received anti-CXCL10 Ab showed a significant reduction in intestinal inflammation. An increase in leukocyte infiltrates (FIG. 12A) and distortion of glandular architecture (FIG. 12B) were observed in the intestines during chronic colitis. Anti-CXCL10 Ab reduced the lymphocyte infiltration and partially restored the glandular and goblet cell architecture (FIG. 12C), which also coincided with lengthening of intestinal crypts FIG. 12D). In addition, the mean histologic scores of IL-10$^{-/-}$ mice with severe colitis that received control Ab were significantly higher than the scores of mice treated with anti-CXCL10 Ab (data not shown). Similarly, SAA levels correlated with the severity of colitis as determined by histologic analysis. Pathologic changes included leukocyte infiltrates in the LP of the colon of control Ab-treated IL-10$^{-/-}$ mice, with the number of these infiltrates being reduced after CXCL10 blockade. Taken together, the results show a marked improvement in the characteristic intestinal inflammation associated with chronic colitis after CXCL10 blockade.

Example 14

Figure 13:
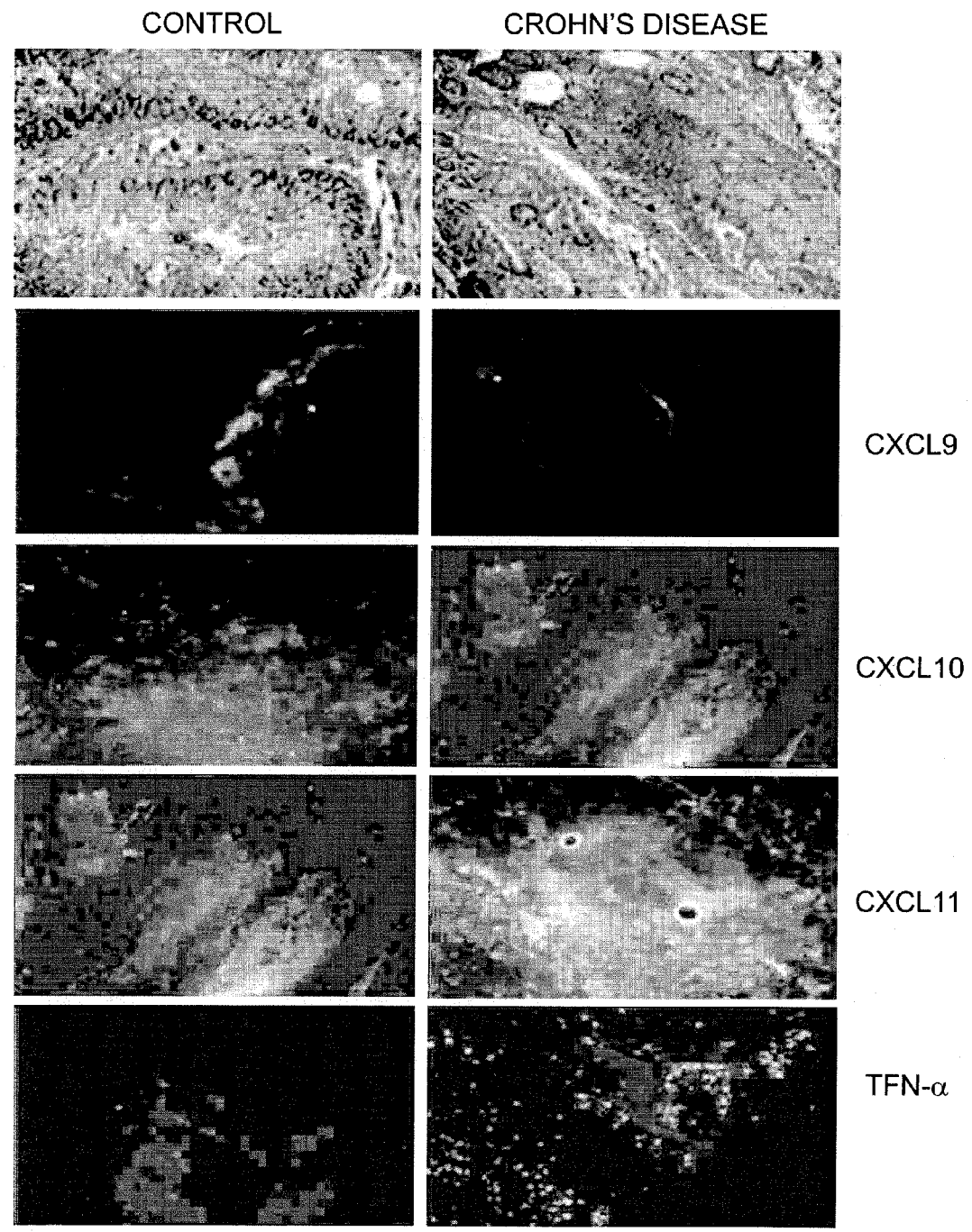
FIG. 13 shows histological and immunofluorescence localization of CXCL9, CXCL10, CXCL11, and TNF-α in the colon of CD patients.

Histological and Immunofluorescence Localization of CXCL9, CXCL10, CXCL11, and TNF-α in the Colon of CD Patients FIG. 13 shows histological and immunofluorescence localization of CXCL9, CXCL10, CXCL11, and TNF-α in the colon of CD patients. Histopathology of colonic changes in the intestines of CD patients and normal control were fixed, sectioned at 6 μm, and stained with hematoxylin and eosin or anti-CXCL9, CXCL10, CXCL11 or TNF-α antibodies. Sections were examined at a magnification view of 130×. The inflamed colon demonstrates the differences in mucosal wall thickness, crypt malformation, leukocyte infiltration, and glandular elongation between normal and CD patients.

The colon pathology of control samples showed hypertrophied epithelial layers at multiple sites, with only a few inflammatory infiltrates and low expression of CXCL9, CXCL10, CXCL11 and CXCR3 (FIG. 13). In contrast, CD patients with high levels of serum CXCL9, CXCL10, and CXCL11 also expressed significant levels of CXCL11 and CXCL9 with modest increases in CXCL10 in the colon.

Example 15

Figure 14:
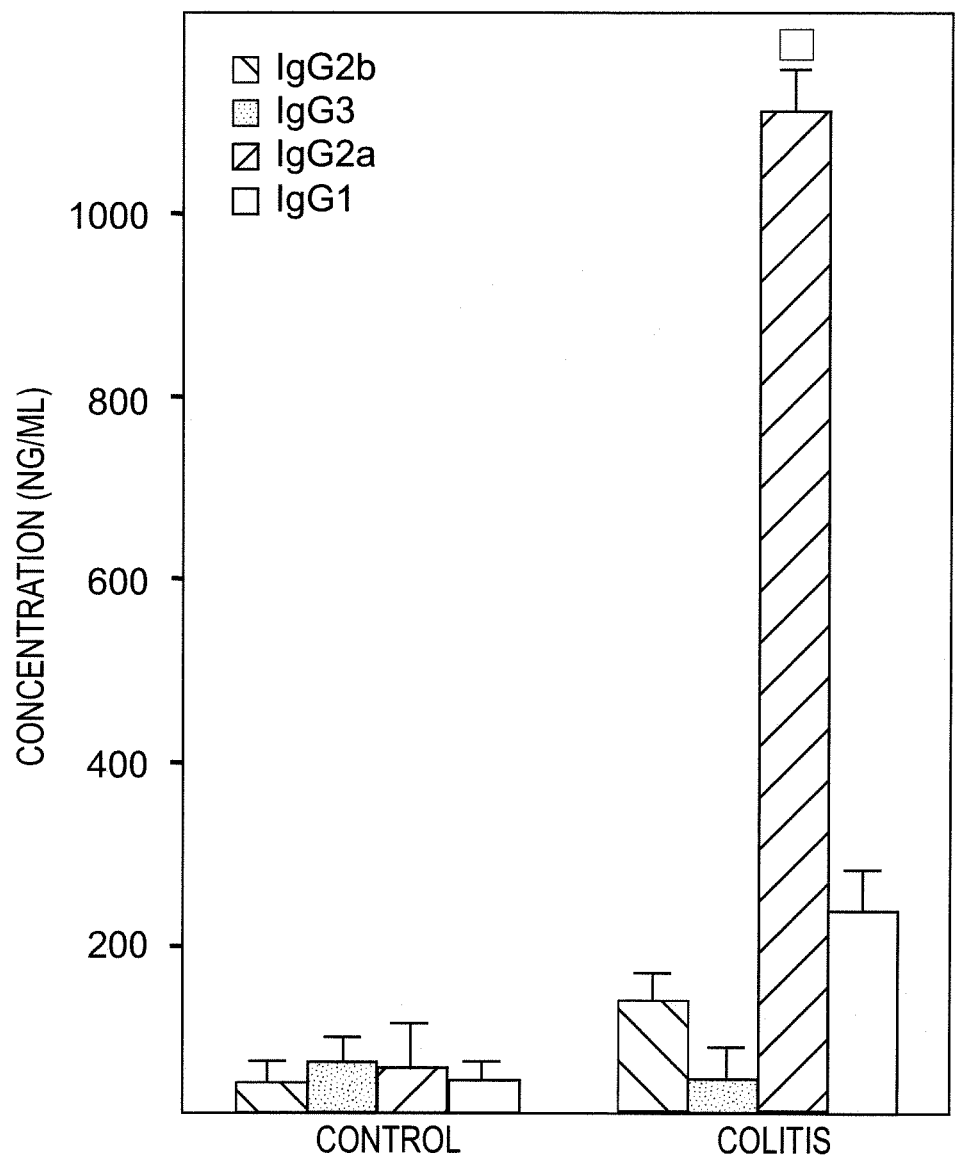
FIG. 14 shows *M. avium* subsp. *paratuberculosis* (MAP)-specific serum Ab responses in IL-10$^{-/-}$ mice during spontaneous colitis.

MAP-Specific Serum Ab Responses in IL-10$^{-/-}$ Mice During Spontaneous Colitis FIG. 14 shows *M. avium* subsp. *paratuberculosis* (MAP)-specific serum Ab responses in IL-10$^{-/-}$ mice during spontaneous colitis. The data presented are the mean±SD concentration (ng/ml) of MAP-specific IgG subclasses from three separate experiments. Asterisks (*) indicate statistically significant differences, i.e., p<0.01, compared to controls. Mice experimental groups consisted of 15 mice. Assays were repeated 3 times.

FIG. 14 shows that MAP-specific IgG2a Ab responses were significantly higher in mice with spontaneous colitis, kept under conventional housing, than in similar control mice without disease, which were housed under germfree conditions. This is consistent with the previously described imbalance of cytokine levels (Th1>Th2) during colitis, suggesting there is a Th1-biased humoral response associated with the progression of colitis.

Example 16

Histological Characteristics of IL-10$^{-/-}$ Mice Challenged with MAP

Figure 15:
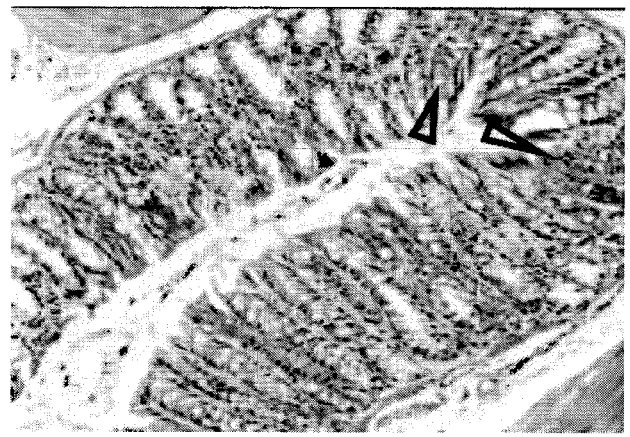
FIG. 15 shows histological characteristics of IL-10$^{-/-}$ mice challenged with *M. avium* subsp. *paratuberculosis* (MAP).
Figure 15:
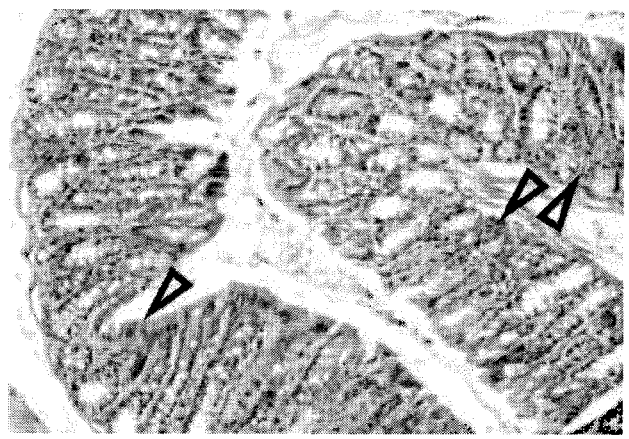
Figure 15:
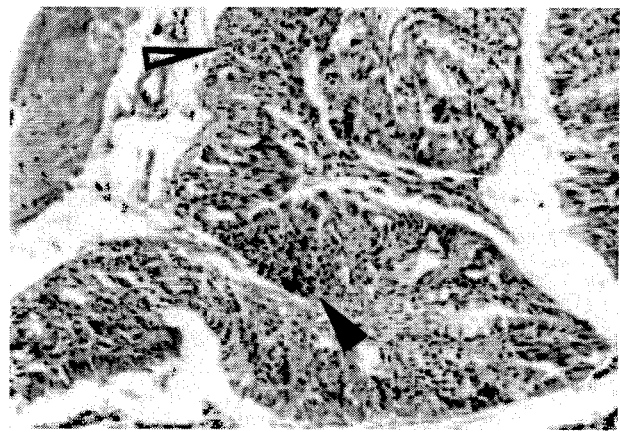

FIG. 15 shows histological characteristics of IL-10$^{-/-}$ mice challenged with MAP. 14 weeks post challenge, histopathologies of colons from IL-10$^{-/-}$ mice that received a single dose of 200 μl of control vehicle (cream only), 10$^4$ CFU of live MAP in cream, or 10$^4$ CFU of heat-killed MAP in cream by gavage and maintained under otherwise germ-free conditions were fixed, sectioned at 6 μm, and stained with hematoxylin and eosin. Mild (open triangles) and heavy (solid triangles) cellular infiltrates were noted in groups (i.e., live MAP>>heat-killed MAP>controls). In live MAP challenged mice, aggregates of cellular infiltrates were typically associated with focal lesions and hypertrophied epithelial cells with reduced crypt lengths. Sections were examined by light microscopy (40× magnification). Experimental groups consisted of 15 mice. Representative samples are shown.

FIG. 15 shows that the intestinal tissues of mice challenged with live *M. avium* subsp. *paratuberculosis* exhibited increased levels of cellular infiltrates, which consisted of lymphocytes and, occasionally, polymorphonuclear cells. The colitis progression was more aggressive in mice that received live *M. avium* subsp. *paratuberculosis*, as noted by multifocal lesions, or aggregates of cellular infiltrates, in all regions of their large intestines. In addition, epithelial cells in mice challenged with live *M. avium* subsp. *paratuberculosis* were hypertrophied, the intestinal crypt length was decreased, and elongated glandular cells were also present in both the mucosa and the submucosa.

Example 17

Changes in Body Weight of IL-10$^{-/-}$ Mice After MAP Challenge

Figure 16:
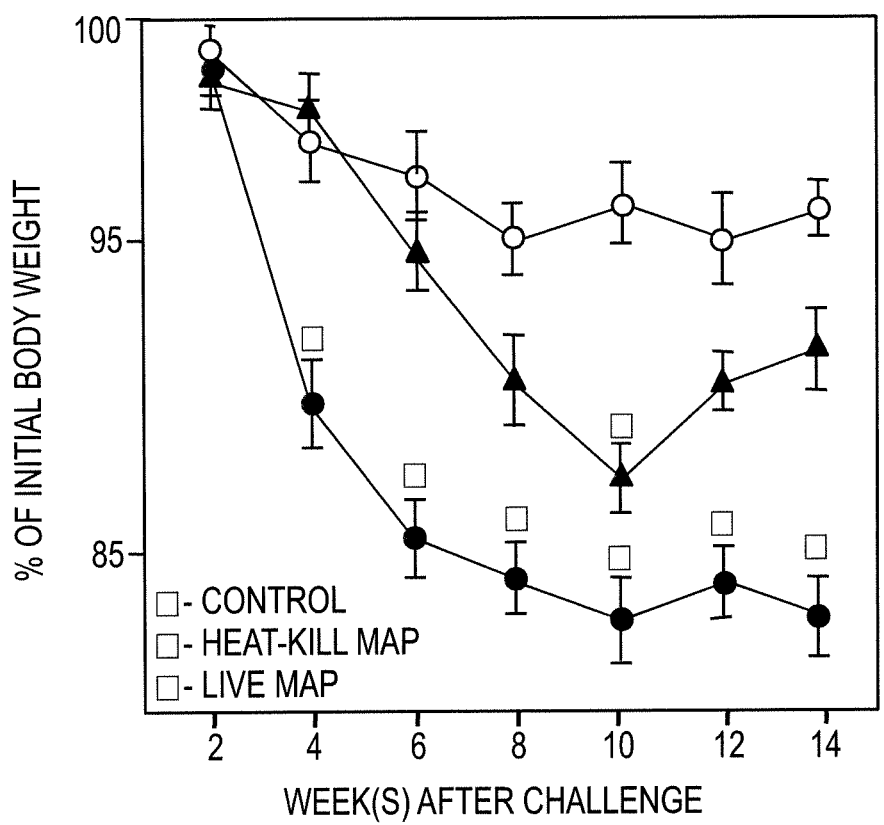
FIG. 16 shows changes in body weight of IL-10$^{-/-}$ mice after MAP challenge.

FIG. 16 shows changes in body weight of IL-10$^{-/-}$ mice after MAP challenge. The wasting disease associated with murine colitis was observed by monitoring the body weight during colitis progression. IL-10$^{-/-}$ mice on B6 background, received a single dose of 200 μl normal control (cream, open circles), 10$^4$ CFUs of live MAP in cream (solid circles) or 10$^4$ CFUs of pasteurized MAP in cream (triangles) and maintained under otherwise germ-free conditions. Percentage of initial body weight of IL-10$^{-/-}$ mice was recorded biweekly. The data presented are the mean±SD of 3 separate experiments. Asterisks (*) indicate statistically significant differences, i.e., p<0.01, compared to controls. Experimental groups consisted of 15 mice and assays were repeated 3 times.

FIG. 16 shows that mice challenged with *M. avium* subsp. *paratuberculosis* and housed under otherwise germfree conditions lost more body weight and experienced higher SAA levels than did similar mice challenged with heat-killed *M.*

*avium* subsp. *paratuberculosis* or given the control vehicle. Mice exposed to heat-killed *M. avium* subsp. *paratuberculosis* had less weight loss than those exposed to live *M. avium* subsp. *paratuberculosis* but had only a marginal increase in the SAA level. The results indicate that mice challenged with live *M. avium* subsp. *paratuberculosis* show rapid colitis progression associated with elevated SAA levels and reductions in body weight compared with the control group.

Example 18

Serum Cytokine Levels in IL-10$^{-/-}$ Mice after MAP Challenge

Figure 17:
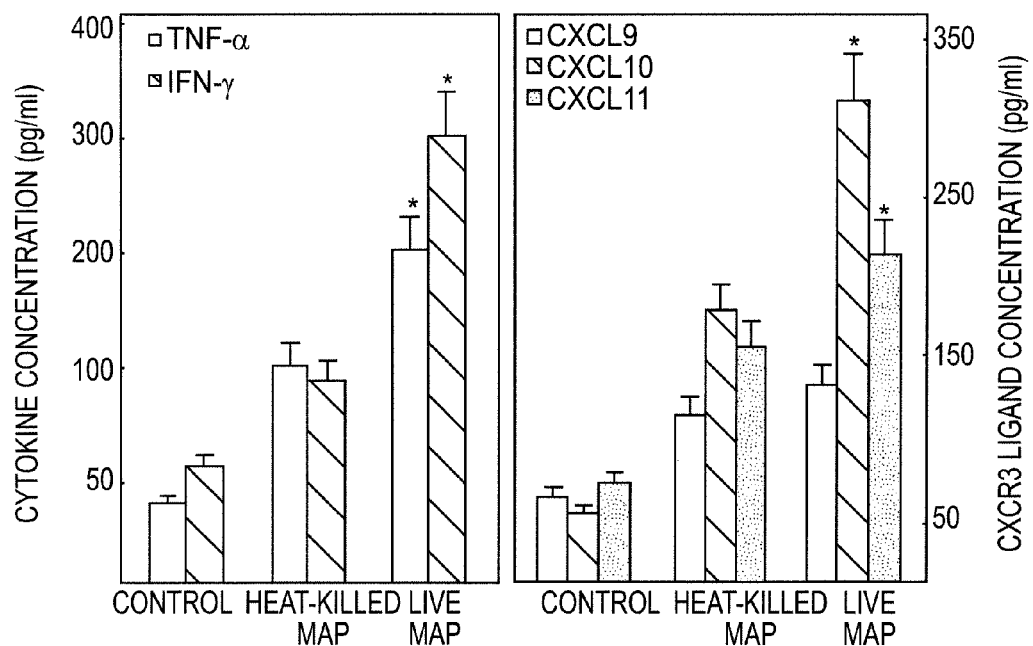
FIG. 17 shows serum cytokine levels in IL-10$^{-/-}$ mice after MAP challenge.

FIG. 17 shows serum cytokine levels in IL-10$^{-/-}$ mice after MAP challenge. IL-10$^{-/-}$ mice, on a B6 background, received a single dose of 200 µl of the control vehicle (i.e., cream), 10$^4$ CFUs of live MAP in cream, or 10$^4$ CFUs heat-killed MAP in cream by gavage and maintained under otherwise germ-free conditions. The levels of serum TNF-α and IFN-γ and CXCL9, CXCL10, and CXCL11 14 weeks after challenge were determined by ELISA, capable of detecting >10 pg/ml TNF-α, IFN-γ or CXCR3 ligand. The data presented are the mean TNF-α, IFN-γ, and CXCR3 ligand concentrations±SD (ng/ml). Asterisks (*) indicate statistically significant differences, i.e., $p<0.01$, compared to controls. Experimental groups consisted of 15 mice. Assays were repeated 3 times.

Following *M. avium* subsp. *paratuberculosis* challenge, IFN-γ and TNF-α levels were significantly higher (~6-fold) in sera of IL-10$^{-/-}$ mice challenged with live *M. avium* subsp. *paratuberculosis* than in control mice; mice exposed to heat-killed *M. avium* subsp. *paratuberculosis* had ~2-fold greater TNF-α and IFN-γ responses than those of controls, but these differences were not significant (FIG. 17). Serum levels of CXCL10 and CXCL11, but not CXCL9, were significantly increased in mice challenged with live or heat-killed *M. avium* subsp. *paratuberculosis* compared with those for mice in the control group. These results indicate that exposure to *M. avium* subsp. *paratuberculosis* increased the production of systemic IFN-γ, TNF-α, CXCL10, and CXCL11.

Example 19

Figure 18:
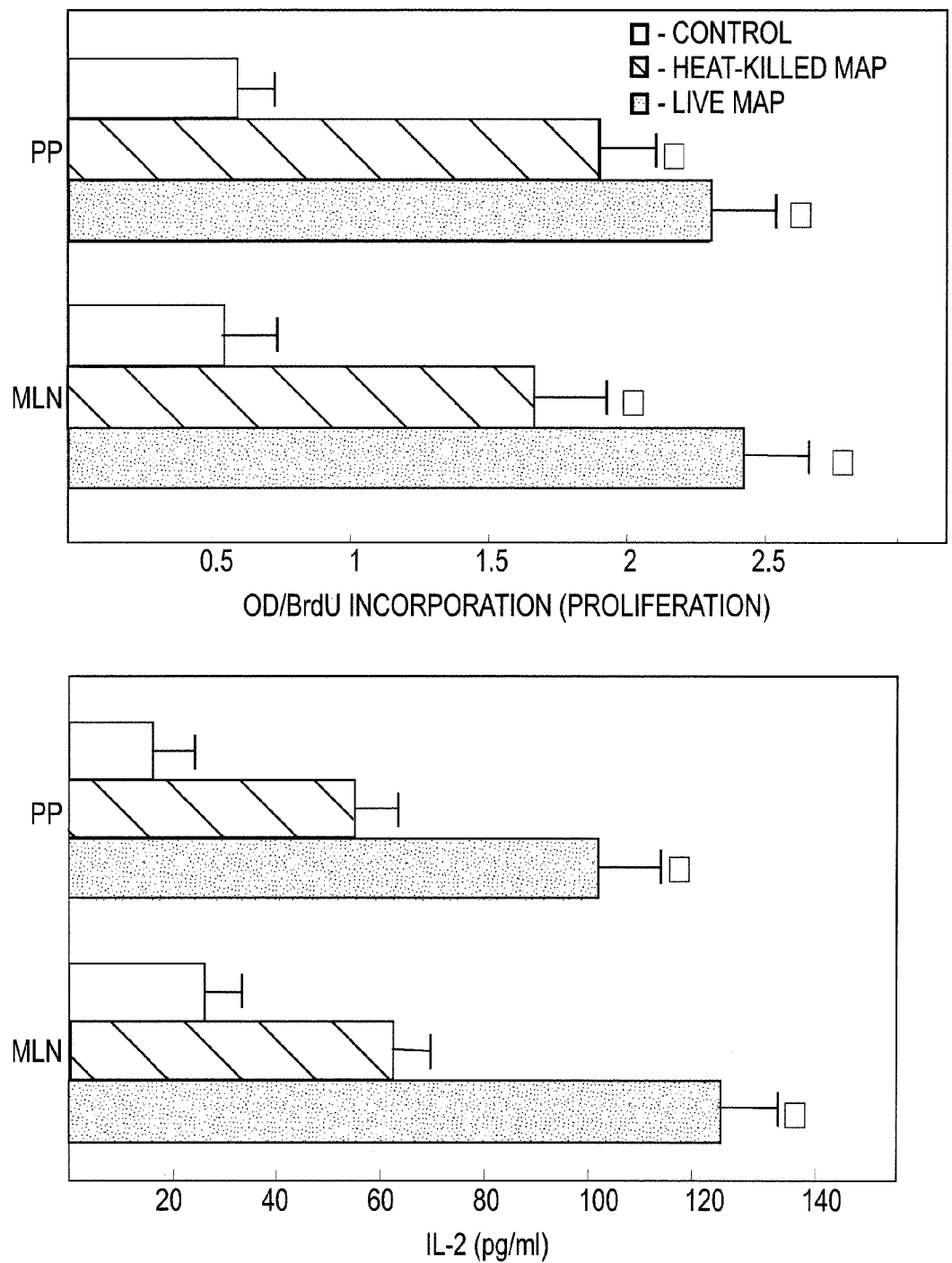
FIG. 18 shows anti-peptide #25 Ag (from MPT59)-induced proliferation and IL-2 production by CD4$^+$ T cells from IL-10$^{-/-}$ mice.

Anti-Peptide #25 Ag (from MPT59)-Induced Proliferation and IL-2 Production by CD4$^+$ T cells from IL-10$^{-/-}$ Mice FIG. 18 shows anti-peptide #25 Ag (from MPT59)-induced proliferation and IL-2 production by CD4$^+$ T cells from IL-10$^{-/-}$ mice. IL-10$^{-/-}$ mice, on B6 background, received a single dose of 200 µl of control vehicle (open bars, cream only), 10$^4$ CFUs of live MAP in cream (hatched bars), or 10$^4$ CFUs of heat-killed MAP in cream (solid bars) and maintained under otherwise germ-free conditions. CD4$^+$ lymphocytes derived from the MLN, and PPs of the mice were purified and cultured at density of 5×10$^6$ cells/ml with peptide #25 (1 µg/ml) for 3 days with γ-irradiated APCs (10$^6$ Cytokines present in culture supernatants were determined ELISA. Proliferation was measured by BrdU incorporation. The data presented are the mean OD$_{450}$ for proliferative responses or the mean of IL-2 secretion (pg/ml)±SD of quadruplicate cultures. Asterisks (*) indicate statistically significant differences, i.e., $p<0.01$, compared to controls. Experimental groups consisted of 15 mice and experiments were repeated three times.

FIG. 18 shows that peptide 25-stimulated CD4$^+$ T cells from the MLN and PP of mice previously challenged with either live or heat-killed *M. avium* subsp. *paratuberculosis* exhibited marked increases in BrdU incorporation compared with similar CD4$^+$ T cells from mice challenged with cream alone. These results suggest that Ag restimulation after exposure to *M. avium* subsp. *paratuberculosis* enhances CD4$^+$ T-cell proliferation.

Example 20

Serum CXCR3 Ligands and Mycobacterial-Specific Ab Responses in IBD Patients

Figure 19:
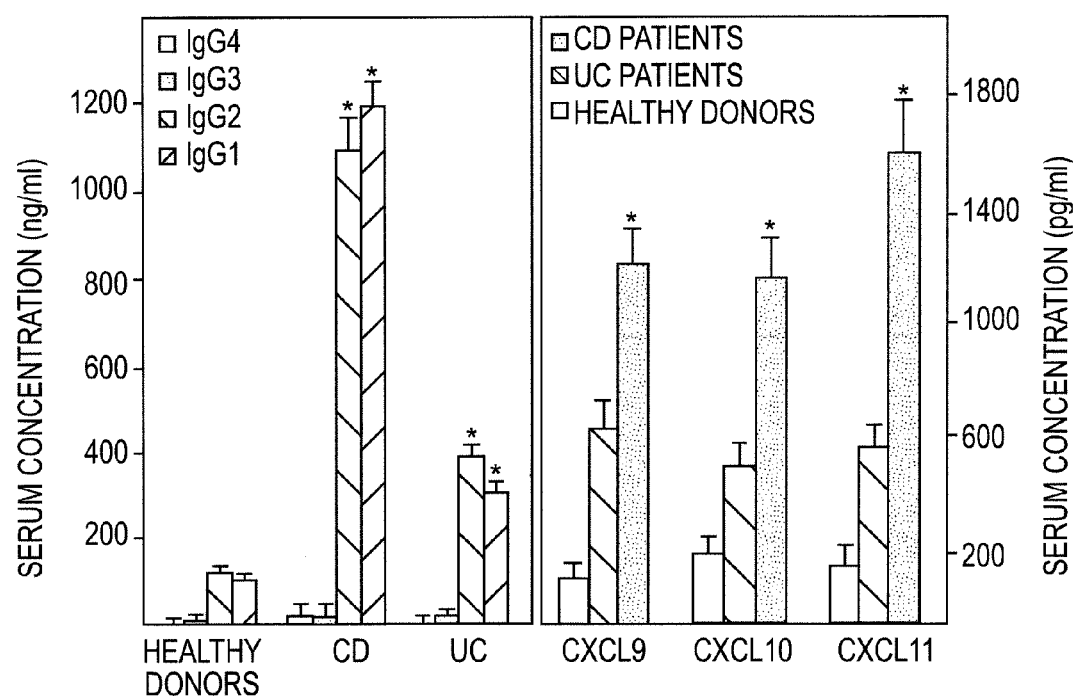
FIG. 19 shows serum CXCR3 ligands and mycobacterial-specific Ab responses in IBD patients.

FIG. 19 shows serum CXCR3 ligands and mycobacterial-specific Ab responses in IBD patients. Sera from 62 CD and 88 UC female patients and 32 normal healthy female donors, not undergoing any treatment, were isolated and evaluated for the presence of CXCR3 ligands (i.e., CXCL9, CXCL10, and CXCL11) and mycobacterial-specific IgG1, IgG2, IgG3 and IgG4 Abs. These levels were determined by ELISAs capable of detecting 10>pg/ml of these ligands. The data presented are concentrations±SEM. Asterisk(s) indicate statistically significant differences, i.e., $p<0.01$, between healthy donors and IBD patients.

While total IgG1, IgG2, IgG3, and IgG4 subclass Abs were significantly higher in the sera of IBD patients compared to healthy donors (data not shown), the profile of the IgG humoral response in IBD patients also revealed increases in *Mycobacteria*-specific IgG1 and IgG2 Abs (FIG. 19). These responses in CD patients were significantly higher than in UC patients or normal healthy donors. CXCR3 ligands were also increased in these samples than compared to healthy donors. These results suggest that IBD patients have higher CXCL9, CXCL10, and CXCL11 levels and *Mycobacteria*-specific IgG1 and IgG2 Ab responses. Moreover, these findings correlate with previous findings showing higher levels of *Mycobacteria*-specific IgG2a and CXCR3 ligands during spontaneous colitis in IL-10$^{-/-}$ mice under conventional housing.

Example 21

Figure 20:
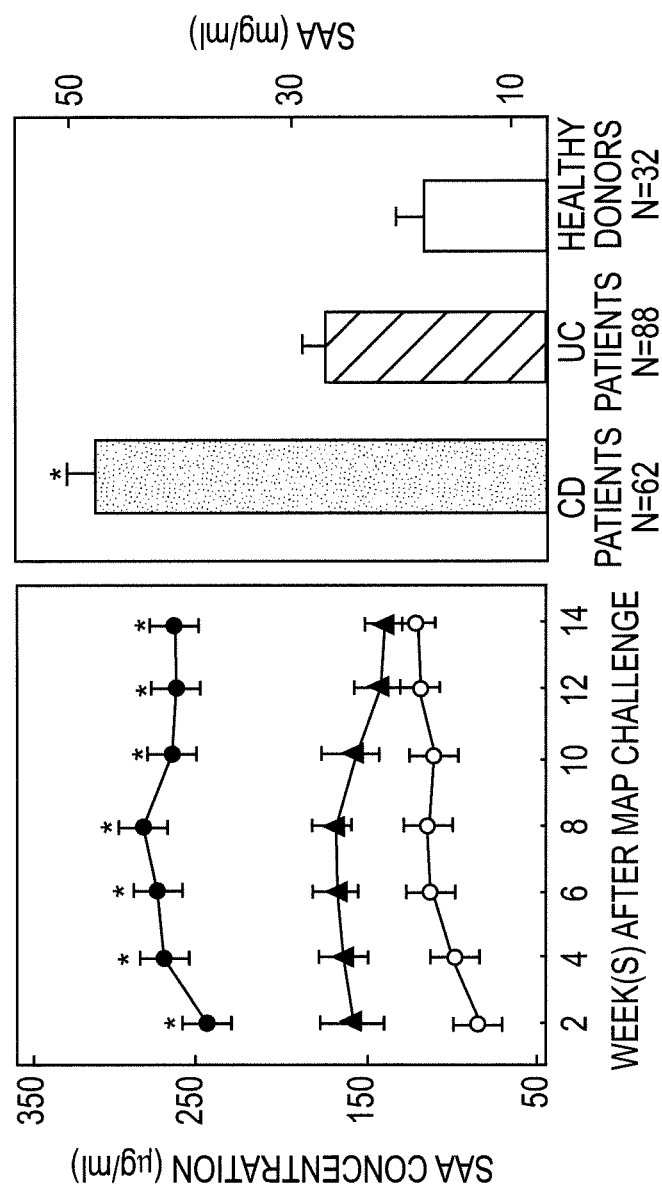
FIG. 20 shows changes in SAA levels in IBD patients and in IL-10$^{-/-}$ mice after mycobacterial challenge.

Changes in SAA Levels in IBD Patients and in IL-10$^{-/-}$ Mice after Mycobacterial Challenge FIG. 20 shows changes in SAA levels in IBD patients and in IL-10$^{-/-}$ mice after mycobacterial challenge. IL-10$^{-/-}$ mice on B6 background, received 200 µl of cream milk alone (open circles; control) or cream milk containing 10$^4$ CFU of live (closed circles) or heat-killed (closed triangles) *M. avium paratuberculosis*. SAA levels during *Mycobacteria*-enhanced colitis as well as IBD patients and healthy donors were measured by ELISA. Experimental groups consisted of 5 mice, and experiments were repeated 3 times. The data presented are the mean±SEM concentration of SAA. Asterisks indicate statistically significant differences, i.e., $p<0.01$, between control and *Mycobacteria*-treated groups or healthy donors and IBD patients.

The results in FIG. 20 show that mice challenged with live *Mycobacteria* in otherwise specific pathogen-free conditions experienced a significant rise in SAA levels when compared to similar mice challenged with heat-killed *Mycobacteria* or control mice.

Example 22

Intestinal Histological Characteristics of IL-10$^{-/-}$ Mice Challenged with *Mycobacteria*

Figure 21:
FIG. 21 shows intestinal histological characteristics of IL-10$^{-/-}$ mice challenged with *Mycobacteria*.
Figure 21:
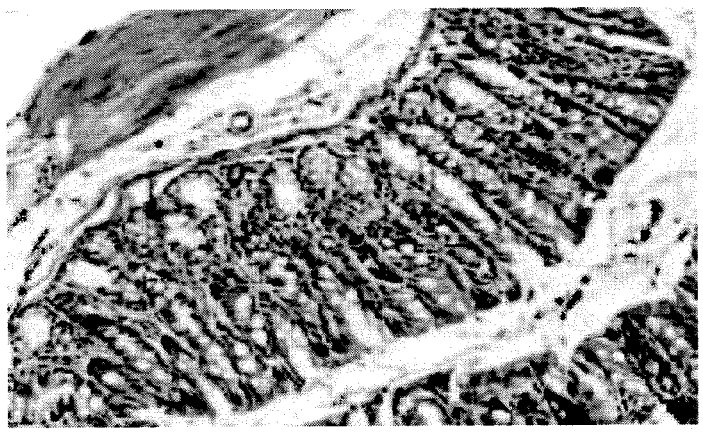
Figure 21:

FIG. 21 shows intestinal histological characteristics of IL-10$^{-/-}$ mice challenged with *Mycobacteria*. IL-10$^{-/-}$ mice on B6 background, received 200 μl of cream milk alone ((open circles; control) or cream milk containing 10⁴ CFU of live (closed circles) or heat-killed (closed triangles) *M. avium paratuberculosis*. After sacrifice, intestines were fixed, sectioned at 6 μm, and stained with hematoxylin and eosin. Sections were examined by light microscopy. Experimental groups consisted of 5 mice and experiments were repeated 3 times.

The intestinal tissues of mice challenged with *Mycobacteria* showed higher increases in leukocyte infiltrates, which consisted of lymphocytes and occasionally polymorphonuclear cells as well as a higher frequency of lymphoid follicles in live versus heat-killed *Mycobacteria*-challenged groups (FIG. 21). Moreover, colitis was more aggressive in mice that received live *Mycobacteria*, as noted by multi-focal lesions and aggregates of leukocyte infiltrates in the large intestines, than compared to control mice.

Example 23

Serum CXCL9, CXCL10 and CXCL11 Concentrations in IC Patients

FIG. 22 shows serum CXCL9, CXCL10 and CXCL11 concentrations in IC patients. Panel A: Sera from IC patients (n=32) and normal, healthy donors (n=16) were isolated and evaluated for the presence of CXCR3 ligands by ELISA, capable of detecting >10 pg/ml of each CXCR3 ligand. The data presented are the mean CXCL9, CXCL10, and CXCL11 of IC patient and normal healthy donors concentrations±SEM. Asterisks (*) indicate statistically significant differences, i.e., p<0.01, between the healthy donors and IC patients. Panel B: Control or anti-CXCL10 Ab solutions were administered 2 days prior to CYP challenge and every 2 days thereafter. Five days after CYP administration, the serum levels of CXCL9, CXCL10, and CXCL11 were determined by ELISA. The data presented are the mean concentrations±SEM in each group. Asterisks (*) indicate statistically significant (p<0.01) differences between unaffected and CYP-induced groups. Triangles indicate statistically significant (p<0.01) differences between control Ab- and anti-CXCL10 Ab-treated groups administered CYP.

Figure 22A:
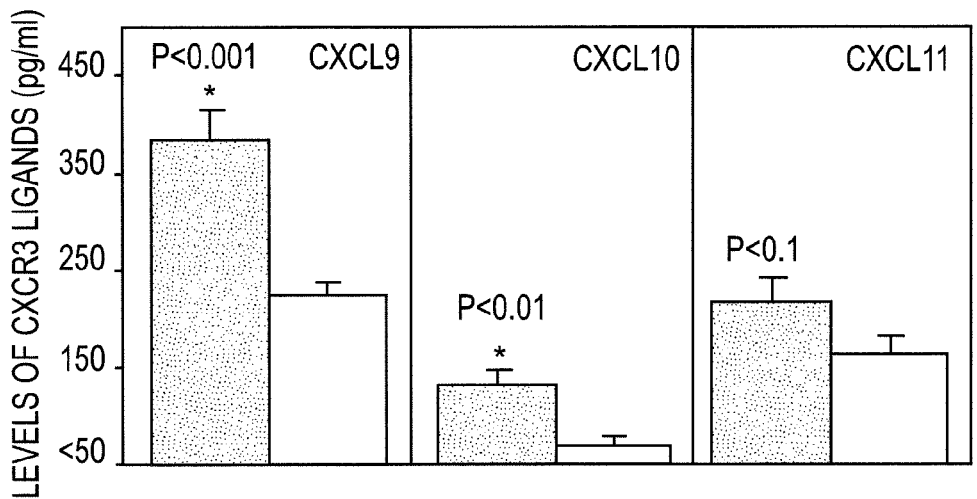
FIG. 22 shows serum CXCL9, CXCL10 and CXCL11 concentrations in IC patients.

As shown in FIG. 22A, the serum levels of CXCL9 and CXCL10 in IC patients were significantly higher than levels in unaffected healthy donors. In particular, the difference in serum levels between IC patients and healthy donors were greatest for CXCL9 (p<0.001), followed by CXCL10 (p<0.01) and CXCL11 (p>0.1). These CXCR3 ligand levels also correlated (although not statistically significant) with disease severity as manifested by pathological reports for each individual patient (data not shown). Further, these patients showed multiple pathological features of tissue damage that frequently included urothelium denudation, mucosal edema, and/or leukocyte infiltration.

Figure 22B:
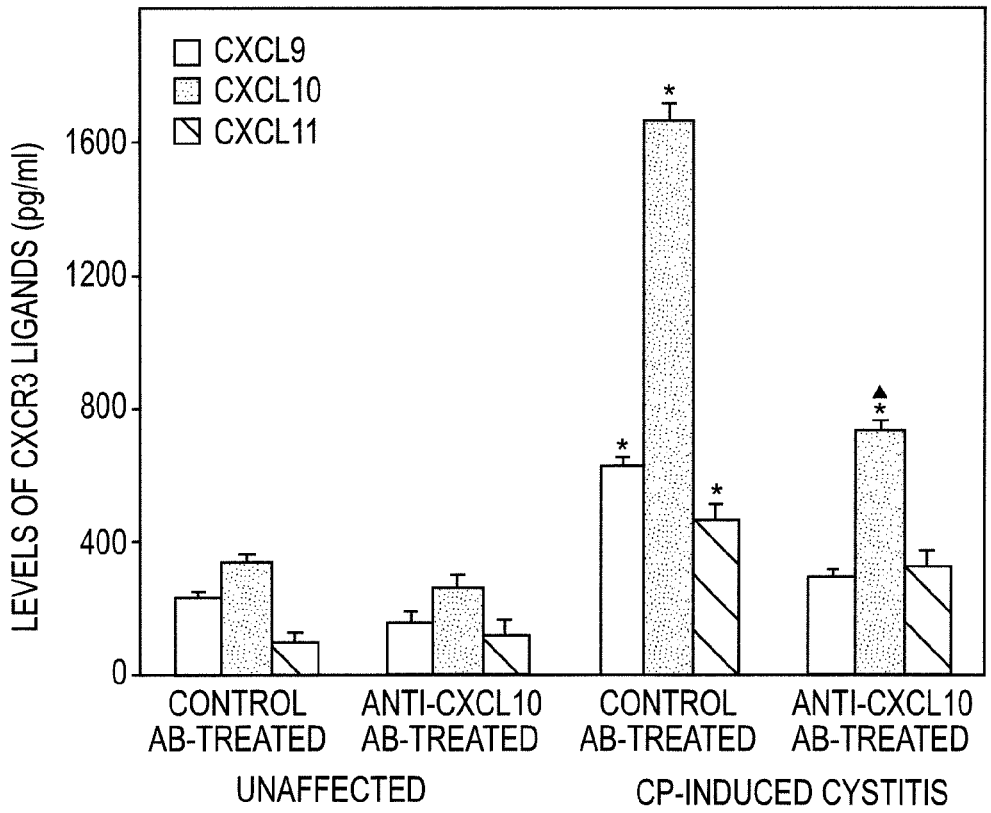
Figure 23A:
FIG. 23 shows histological changes after CYP-induced cystitis.
Figure 23B:
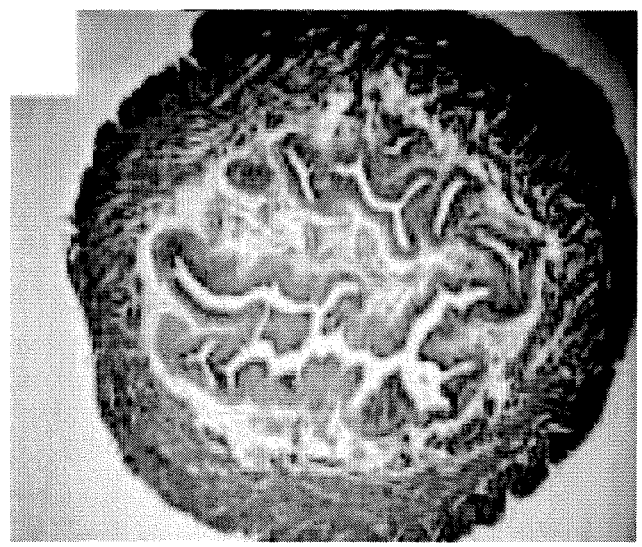
Figure 23C:
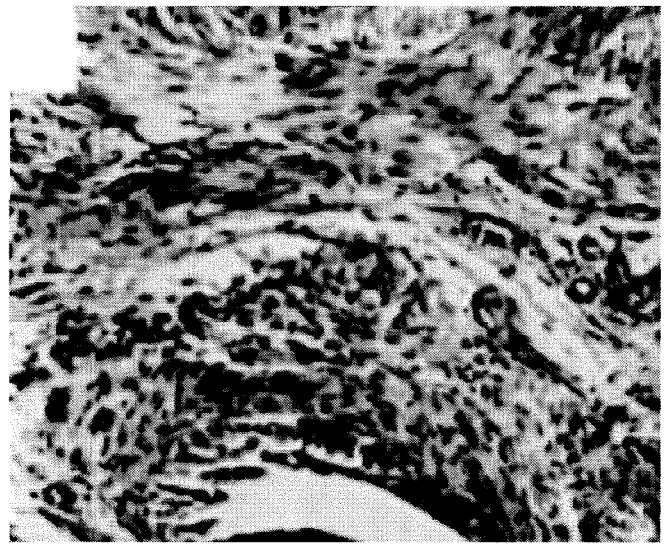
Figure 23D:
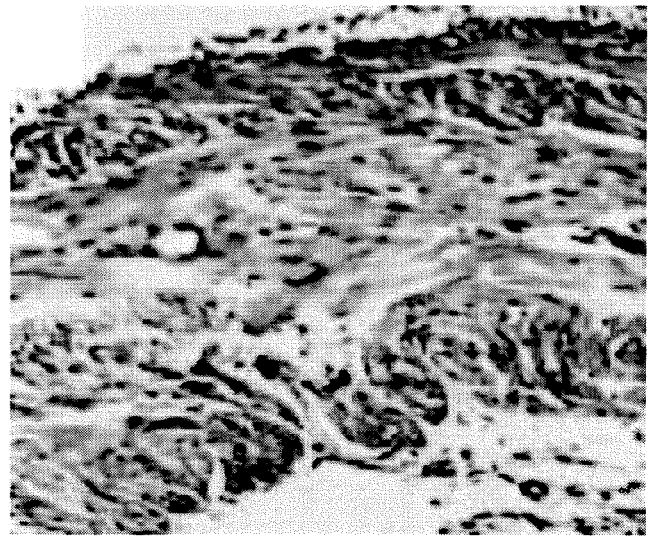

CYP-induced cystitis in mice led to substantial increases in serum levels of CXCL10>>CXCL9 when compared with the levels in unaffected controls (FIG. 22B). In confirmation with serum CXCR3 ligand levels in IC patients, murine CXCL11 levels did not significantly change in groups induced with CYP. In summary, mice with CYP-induced cystitis expressed higher serum CXCL10>CXCL9 than unaffected controls, while IC patients displayed higher CXCL9>CXCL10 serum levels than unaffected individuals.

Example 24

Histological Changes After CYP-Induced Cystitis

FIG. 23 shows histological changes after CYP-induced cystitis. Control or anti-mouse CXCL10 Ab solutions were administered 2 days prior to CYP treatment and every 2 days thereafter. Five days after CYP administration, the urinary bladders of the mice were fixed, sectioned at 6 μm, and stained with hematoxylin and eosin. The sections were examined microscopically at magnification views of 10× and 100×. Panels A and C show the magnified sections from control Ab-treated mice, while Panels B and D display similar sections from anti-CXCL10 Ab-treated mice given CYP to illustrate inflamed bladders and characterized differences in mucosal wall thickness, enlargement of mucosal layer, leukocyte infiltration, and glandular elongation.

Control Ab-treated mice given CYP showed pathological signs of cystitis (i.e., urinary bladder inflammation, discontinuous uroepitheium). However, affected mice treated with anti-CXCL10 Ab displayed a reduction in cystitis, as noted by a decrease in urinary bladder leukocyte infiltrates (FIG. 23). Histological differences between control Ab- and anti-CXCL10 Ab-treated mice with CYP-induced cystitis were considered significant and showed that CXCL10 blockade significantly reduced CYP-induced cystitis.

Example 25

CXCR3, -9, -10, and -11 mRNA Expression in CYP-Treated Mice

Figure 24:
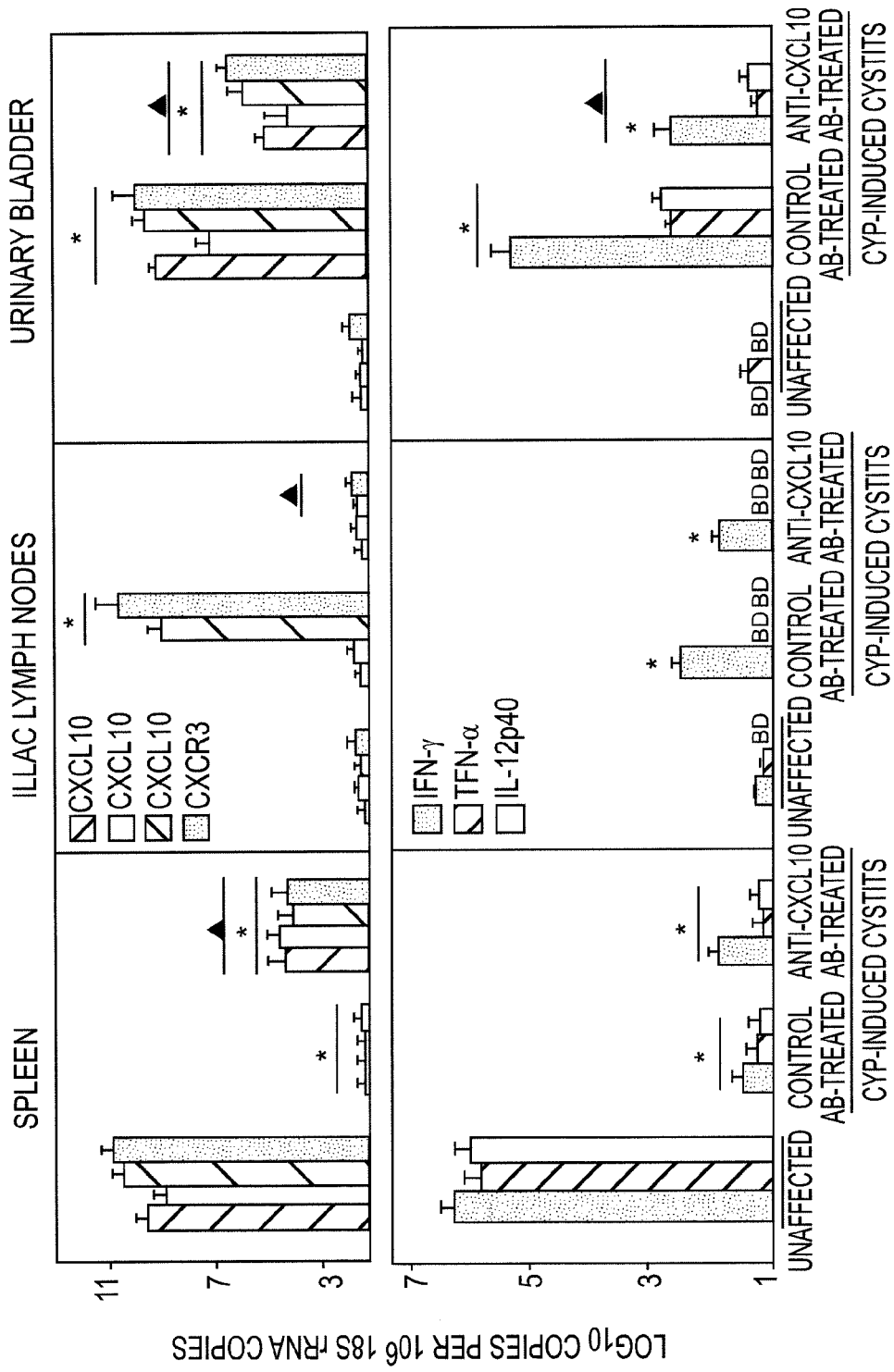
FIG. 24 shows CXCR3, CXCL9, CXCL10, and CXCL11 mRNA expression in CYP-treated mice.

FIG. 24 shows CXCR3, CXCL9, CXCL10, and CXCL11 mRNA expression in CYP-treated mice. Control or anti-mouse CXCL10 Ab solutions were administered 2 days prior to CYP treatment and every 2 days thereafter. Five days after CYP administration, total RNA was isolated from the spleen, iliac lymph nodes, or urinary bladder of the mice. Panel A: RT-PCR analysis of CXCR3, CXCL9, CXCL10, or CXCL11 mRNA expression was performed. Panel B: RT-PCR analysis of IFN-γ, IL-12 p40, or TNF-α mRNA expression was performed. $Log_{10}$ copies of transcripts±SEM are expressed relative to actual copies of 18S rRNA. Asterisks (*) indicate statistically significant (p<0.01) differences between unaffected and CYP-induced groups. Triangles indicate statistically significant (p<0.01) differences between control Ab- and anti-CXCL10 Ab-treated groups administered CYP.

As shown in FIG. 24A, CYP-induced cystitis in mice led to substantial increases in the expression of CXCL10, CXCL11, and CXCR3 mRNA by urinary bladder leukocytes as well as modest increases in the expression of CXCL9 and CXCR3 transcripts by iliac lymph node lymphocytes than compared to normal, untreated mice. In contrast, the expression of these IFN-γ—and nuclear factor kappa B (NFκB)-inducible chemokines and CXCR3 mRNAs were significantly diminished in splenocytes from CYP-treated mice than compared to similar cells from control mice. Anti-CXCL10 Ab treatment significantly decreased the expression of CXCL9 and CXCR3 mRNAs by iliac lymph node leukocytes and reduced the production of CXCL9, CXCL10, CXCL11, and CXCR3 mRNAs by urinary bladder leukocytes.

To investigate local and peripheral changes in Th1 and inflammatory cytokine expression during CYP-induced cystitis, the levels of IFN-γ, IL-12p40, and TNF-α mRNAs expressed by leukocytes isolated from the spleen, iliac lymph nodes and urinary bladder were measured by quantitative RT-PCR analysis. CYP-induced mice receiving control Ab exhibited substantial decreases in the expression of IFN-γ, IL-12p40, and TNF-α mRNAs by splenocytes; however, this treatment significantly increased the expression of cytokines by urinary bladder leukocytes than compared to unaffected mice (FIG. 24B). Mice with CYP-induced cystitis exhibited increased IFN-γ mRNA expression by iliac lymph node lymphocytes compared to similar cells from unaffected mice. However, the expression of IFN-γ, IL-12p40, and TNF-α mRNAs by urinary bladder lymphocytes from mice with cystitis were significantly decreased following anti-CXCL10 Ab treatment than compared to similar cells from CYP-induced mice treated with control Ab.

Example 26

Serum CXCL10 Concentrations During Active Crohn's Disease (CD)

Figure 25A:
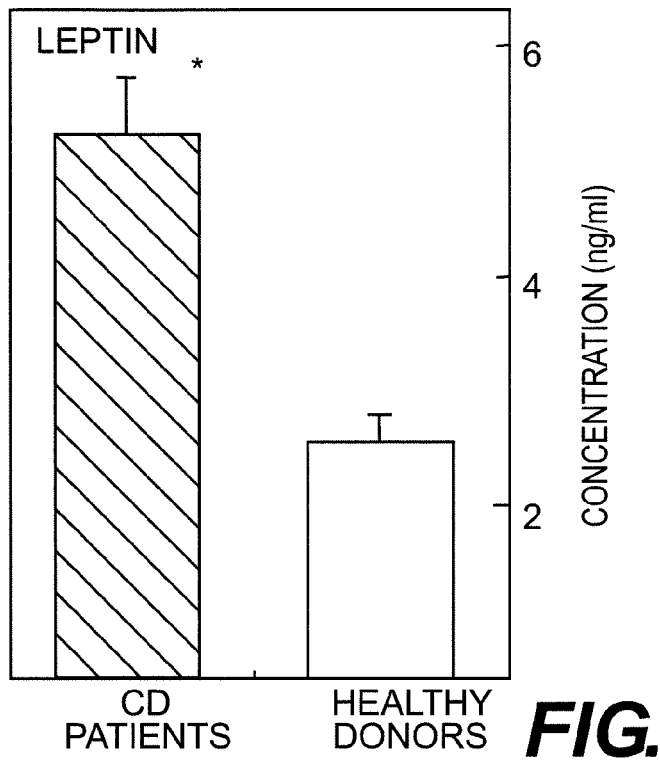
FIG. 25 shows upregulated CXCL10 expression during active CD.
Figure 25B:
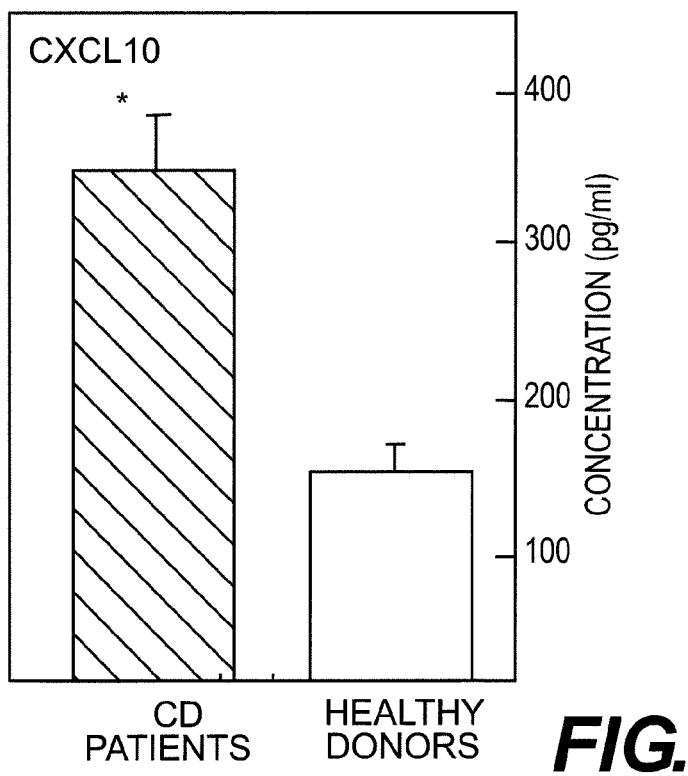

FIG. 25 shows upregulated CXCL10 expression during active CD. Sera from CD patients (n=120) and normal healthy donors (n=30), not undergoing treatment, were isolated and evaluated for the presence of CXCL10. The levels of CXCL10 were determined by an ELISA assay capable of detecting >20 pg/ml of CXCL10. The data presented are the mean CXCL10 concentrations±SEM in CD patients and healthy donors. Asterisk(s) indicate statistically significant differences, i.e., $p<0.05$ (*), between the 2 groups.

The results in FIG. 25 show that CD patients exhibited significant increases in leptin and CXCL10 compared to healthy donors.

Example 27

Serum CXCL11 and CXCL9 Concentrations During Active Crohn's Disease

Figure 26A:
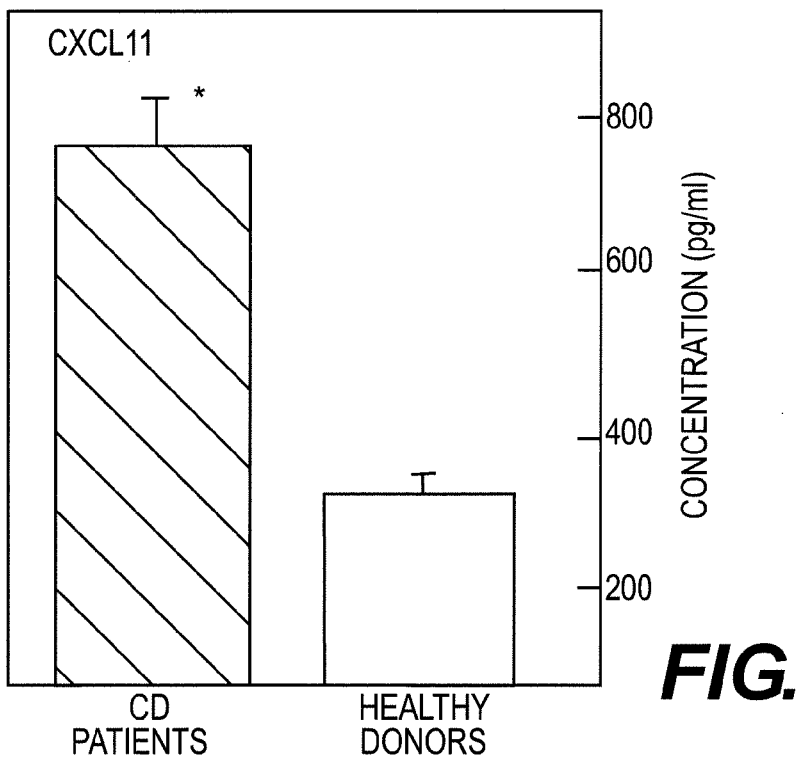
FIG. 26 shows upregulated expression of CXCL11 and CXCL9 during active CD.
Figure 26B:
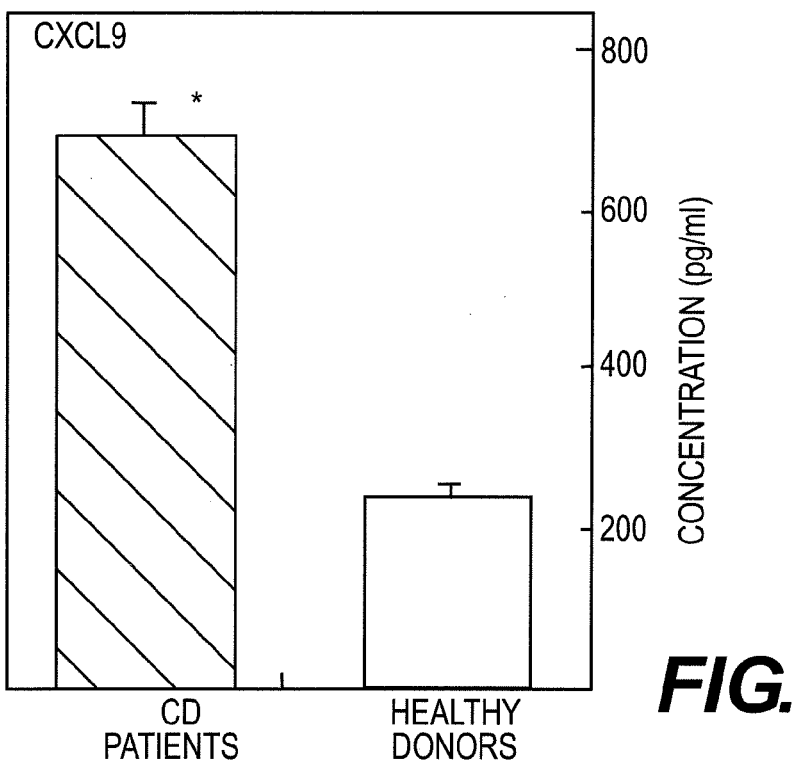

FIG. 26 shows upregulated expression of CXCL11 and CXCL9 during active CD. Sera from CD patients (n=120) and normal healthy donors (n=30), not undergoing treatment, were isolated and evaluated for the presence of CXCL11 and CXCL9. The levels of serum CXCL11 and CXCL9 were determined by ELISA that was capable of detecting >20 pg/ml of each Th1 cytokine. The data presented are mean CXCL11 (FIG. 26A) and CXCL9 (FIG. 26B) concentrations±SEM in CD patients and healthy donors. Asterisk(s) indicate statistically significant differences, i.e., $p<0.05$ (*), between the 2 groups.

The results in FIG. 26 show that CD patients exhibited significant increases in leptin and CXCL11 and CXCL9 compared to healthy donors.

Example 28

Figure 27A:
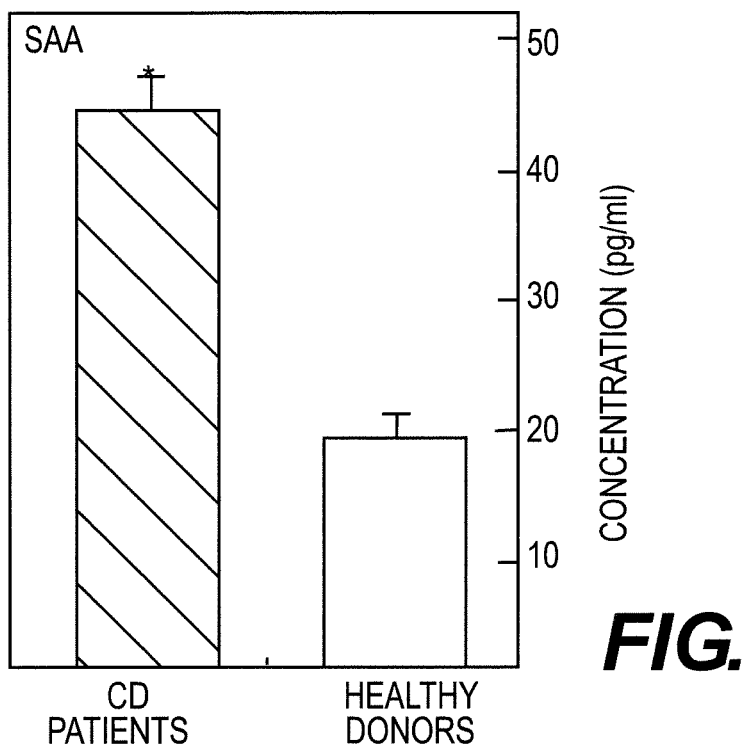
FIG. 27 shows upregulated serum concentrations of serum amyloid A (SAA) and IL-6 in CD patients.
Figure 27B:
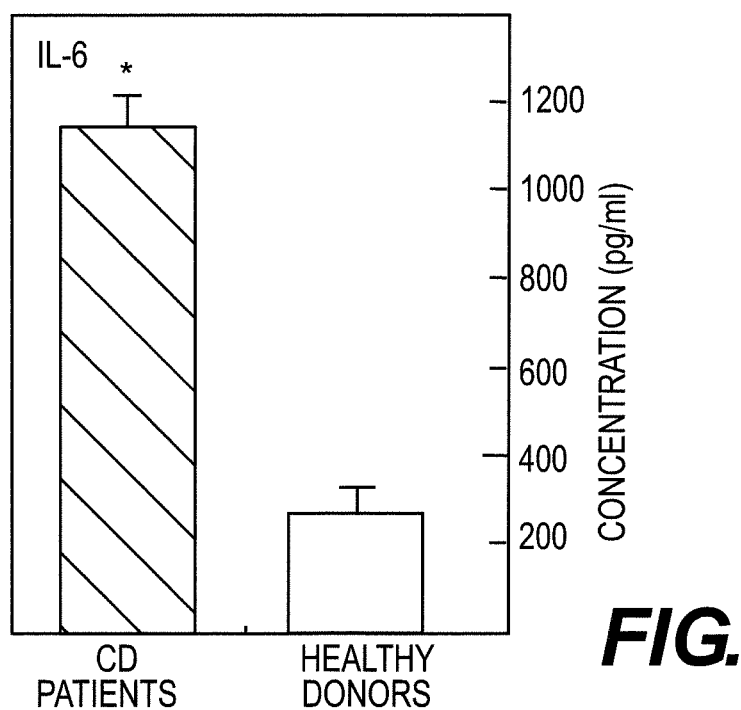

Serum Amyloid Protein A (SAA) and IL-6 Concentrations During Active Crohn's Disease FIG. 27 shows upregulated serum concentrations of serum amyloid A (SAA) and IL-6 in CD patients. Sera from CD patients (n=120) and normal healthy donors (n=30), not undergoing treatment, were isolated and evaluated for the presence of SAA and IL-6 levels. The levels of serum SAA and IL-6 were determined by ELISA that was capable of detecting 20>pg/ml of the SAA and IL-6 concentration. The data presented are the mean of SAA (FIG. 27A) and IL-6 (FIG. 27B) concentrations±SEM in CD patients and healthy donors. Asterisk(s) indicate statistically significant differences, i.e., $p<0.05$ (*), between the 2 groups. This data is consistent with elevated SAA and serum IL-6 levels corresponding with the severity of CD.

The results in FIG. 27 show that CD patients exhibited significant increases in SAA and IL-6 compared to healthy donors.

Example 29

Serum IL-12p40 and IFN-γ Levels Correlate During Active Crohn's Disease

Figure 28A:
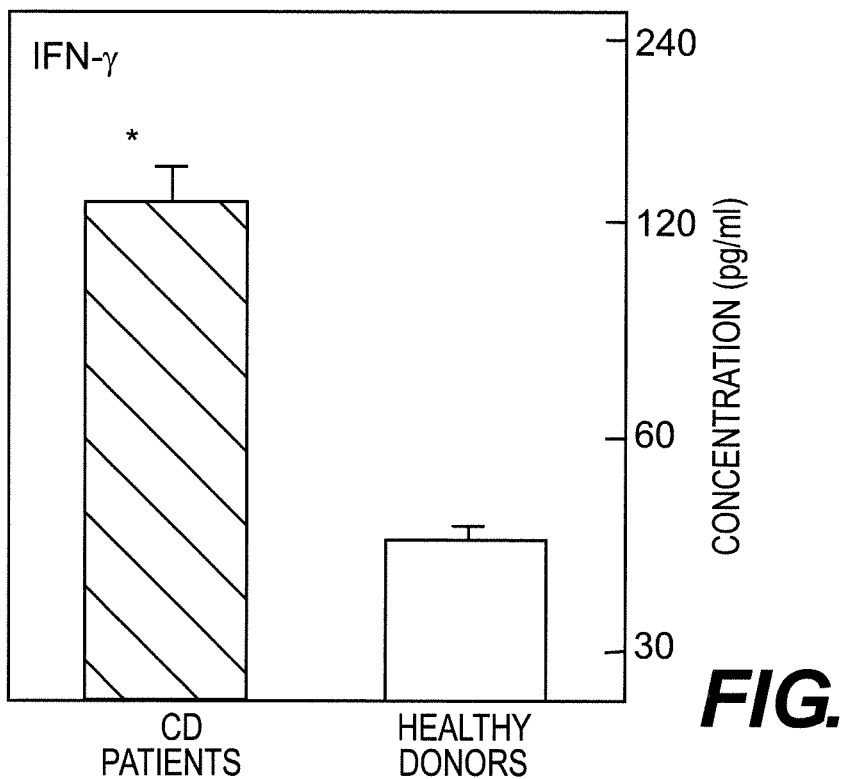
FIG. 28 shows serum IL-12p40 and IFN-γ levels correlate during CD.
Figure 28B:
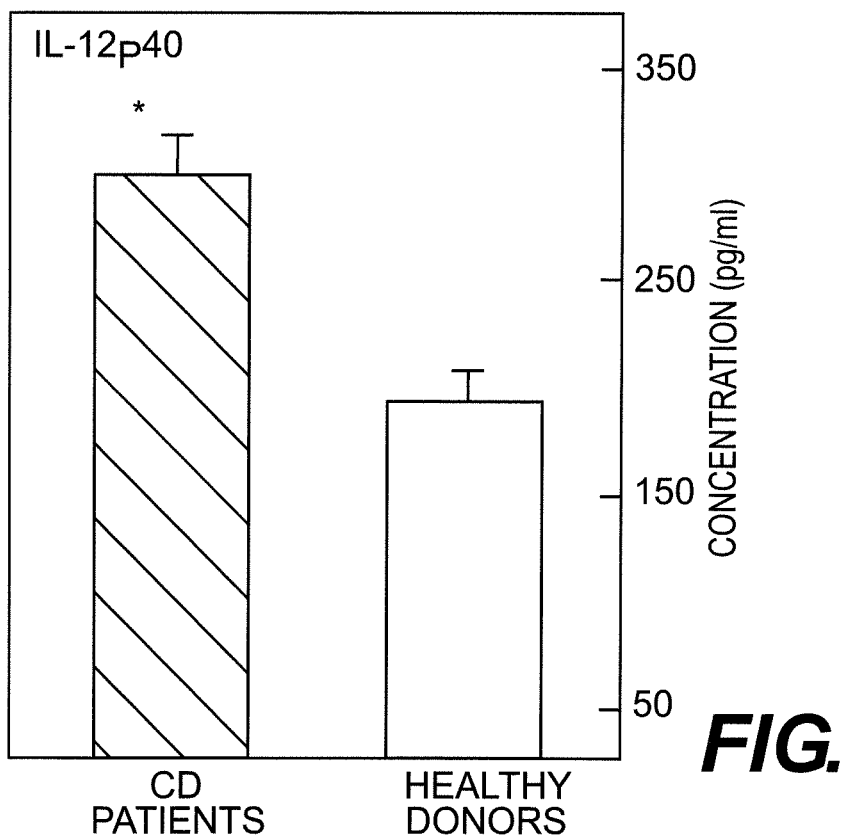

FIG. 28 shows serum IL-12p40 and IFN-γ levels correlate during CD. Sera from CD patients (n=120) and normal healthy donors (n=30), not undergoing treatment, were isolated and evaluated for the presence of IL-12p40 and IFN-γ. The levels of serum IFN-γ and IL-12p40 were determined by ELISA that was capable of detecting >20 pg/ml of each cytokine. The data presented are the mean IL-12p40 (FIG. 28A) and IFN-γ (FIG. 28B) concentrations±SEM from the serum of CD patients and healthy donors. Asterisk(s) indicate statistically significant differences, i.e., $p<0.05$ (*), between the 2 groups.

The results in FIG. 28 show that CD patients exhibited significant increases in IFN-γ and IL-12p40 compared to healthy donors.

Example 30

Inflammatory Cytokine Levels During Active Crohn's Disease

Figure 29A:
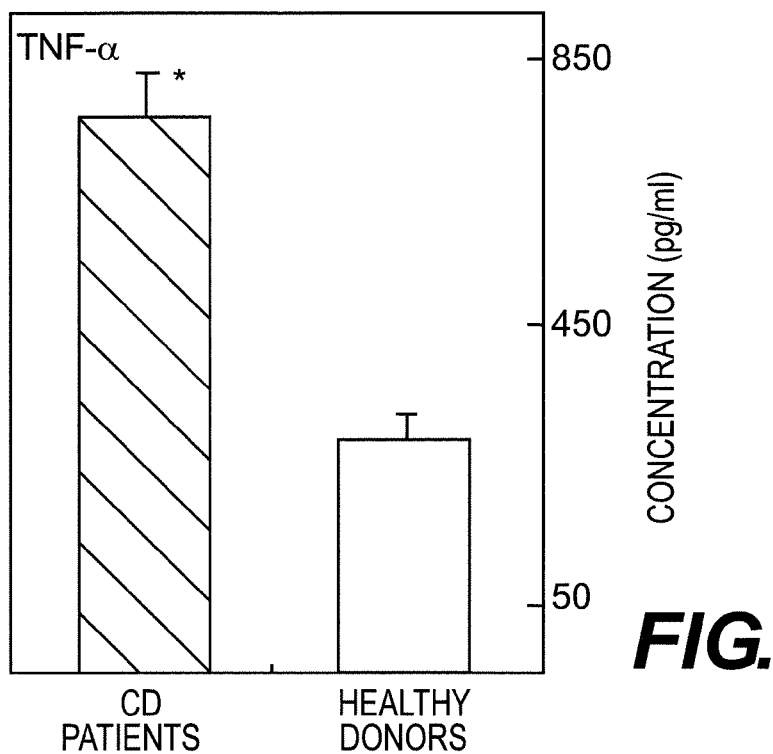
FIG. 29 shows inflammatory cytokine levels during active CD.
Figure 29B:
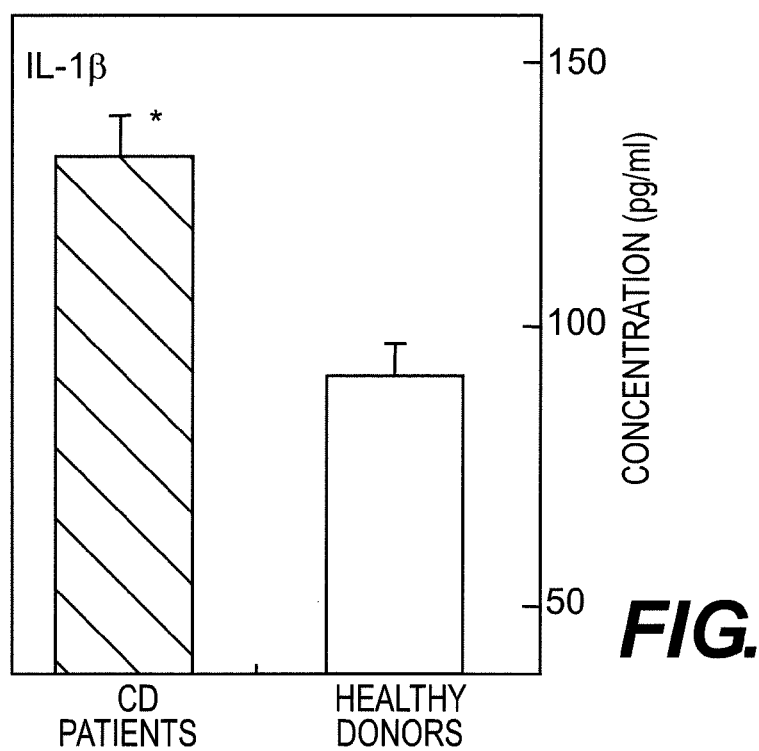

FIG. 29 shows inflammatory cytokine levels during active CD. Sera from CD patients (n=120) and normal healthy donors (n=30), not undergoing treatment were isolated and evaluated for the presence of TNF-α and IL-10. The levels of serum TNF-α and IL-1β were determined by ELISA that was capable of detecting >20 pg/ml of each cytokine. The data presented are the mean TNF-α (FIG. 29A) and IL-1β (FIG. 29B) concentrations±SEM from serum of CD patients and healthy donors. Asterisk(s) indicate statistically significant differences, i.e., $p<0.05$ (*), between the 2 groups.

The results in FIG. 29 show that CD patients exhibited significant increases in TNF-α and IL-1β compared to healthy donors.

Example 31

Histological Characteristics of Colitis by Normal and CD Patients

Figure 30:
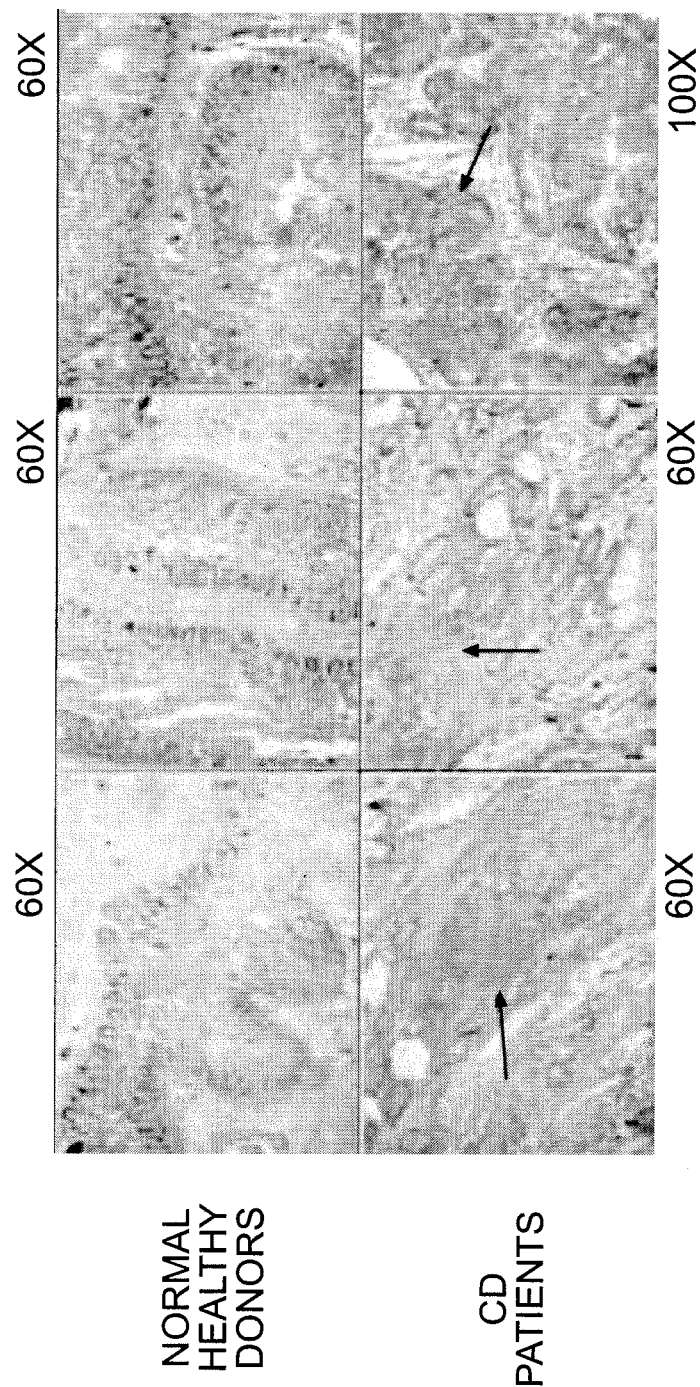
FIG. 30 shows histological characteristics of colitis in normal and CD patients with high serum CXCR3 ligand concentrations.

FIG. 30 shows histological characteristics of colitis in normal and CD patients with high serum CXCR3 ligand concentrations. Histopathology of colonic biopsy from normal healthy donors and CD patients were fixed, sectioned at 6 μm, and stained with hematoxylin and eosin. Sections were examined by microscopy.

FIG. 30 shows that the colon in CD patients demonstrates differences in crypt malformation, leukocyte infiltration, glandular elongation/hyperplasia, and edema between normal and CD patients.

Example 32

CXCL9, CXCL10, CXCL11 and TNFα Expression in Colons of CD Patients

Figure 31:
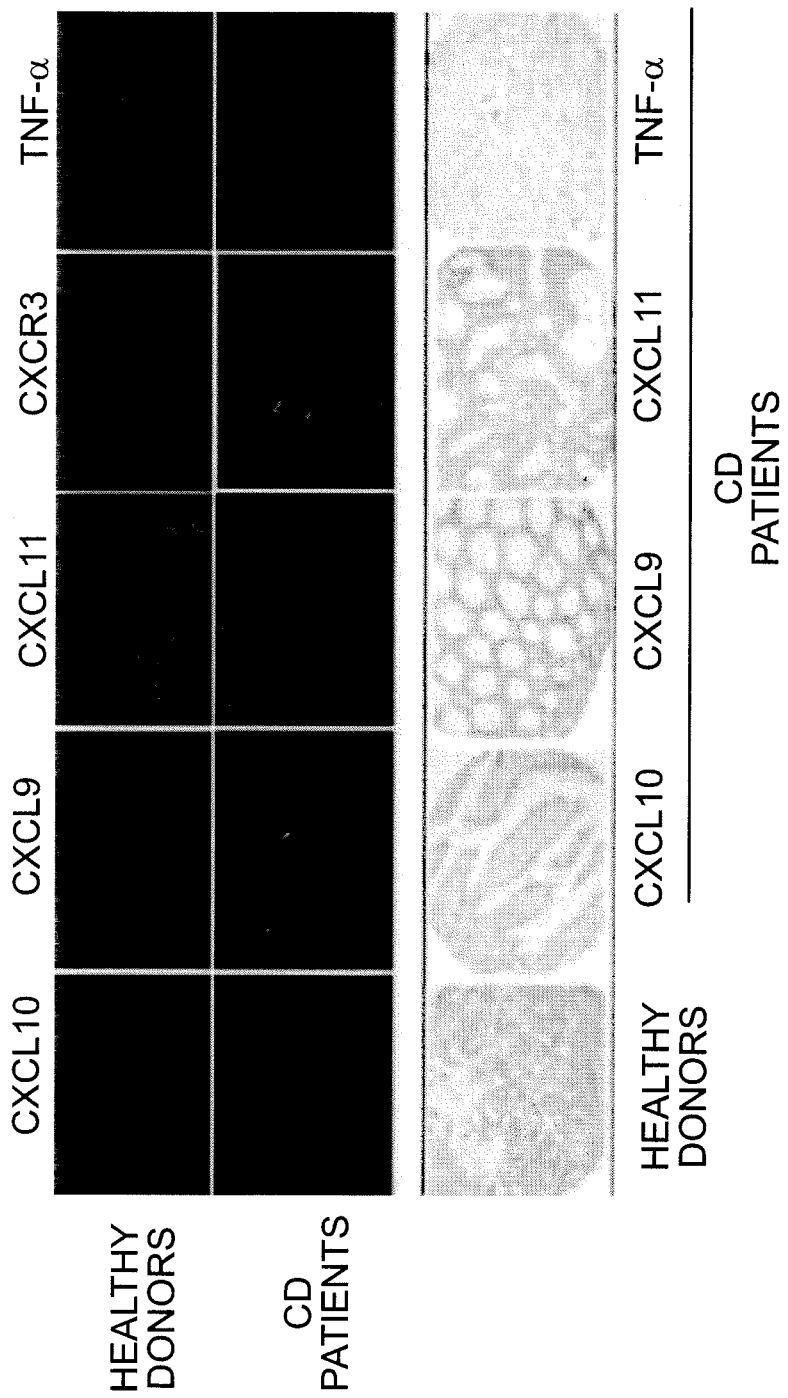
FIG. 31 shows CXCR3 ligands and TNFα expression in colons of normal and CD patients by histopathological examination.

FIG. 31 shows CXCR3 ligands and TNFα expression in colons of normal and CD patients by histopathological examination. The colons from normal and CD patients were frozen, fixed, sectioned at 6 μm, and stained fluorescently for CXCL9-, CXCL10-, CXCL11- and TNFα-positive cells. Sections were examined by fluorescent con-focal microscopy.

FIG. 31 shows that the colon from a CD patient shows increased leukocyte infiltration compared with a normal control patient. These micrographs further demonstrate reduced immunoreactive staining of CXCR3 ligands and TNFα expression in colon of normal control patients.

The above description is for the purpose of teaching the person of ordinary skill in the art how to practice the present application, and is not intended to detail all those obvious modifications and variations of it that will become apparent to the skilled worker upon reading the description. It is intended, however, that all such obvious modifications and variations be included within the scope of the present application, which is defined by the following claims. The claims are intended to cover the components and steps in any sequence that is effective to meet the objectives there intended, unless the context specifically indicates the contrary. All the references cited in the specification are herein incorporated by reference in their entirely.

What is claimed is:

1. A method for detecting an inflammatory disease in a subject, comprising:
   (a) detecting a level of expression of one or more inflammatory disease markers in a biological sample obtained from said subject; and
   (b) comparing the level of expression of said one or more inflammatory disease markers in said biological sample to a normal level of expression of said one or more inflammatory disease markers,
   wherein a higher than normal level of expression of one or more of said plurality of inflammatory disease markers in said biological sample is indicative of the presence of an inflammatory disease in said subject, wherein said normal levels of expression of said plurality of inflammatory disease markers is a predetermined value, and wherein said one or more inflammatory disease markers comprise one or more markers selected from the group consisting of CXCL9, CXCL10, CXCL11, CXCL13, CXCR3 and CXCR5 and
   wherein said one or more inflammatory disease markers further comprise one or more antibodies directed against, and/or one or more antigens derived from, inflammation-related microorganisms selected from the group consisting of *Mycobacterium, Bacteroides, Brucella, Campylobacter, Escherichia coli, Saccharomyces cerevisiae, Klebsiella, Yersinia pseudotuberculosis, Clostridium, Enterococcus, Eubacterium, Listeria monocytogenes, Peptostreptococcus, Helicobacter, Haemophilus influenzae, Pseudomanas fluorescens, Salmonella, Chlamydia,* human hepatitis virus and human rhinovirus.

2. The method of claim 1, wherein said one or more inflammatory disease markers further comprise one or more markers selected from the group consisting of: CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, XCL1, CX3CL1, CCR1, CCR2, CCR3, CCR4, CCR5, CCR6, CCR8, CCR9, CCR10, CXCR1, CXCR2, CXCR4, XCR1.

3. The method of claim 1, wherein said one or more inflammatory disease markers further comprise one or more markers selected from the group consisting of: leptin, tumor necrosis factor α (TNFα), interferon-γ (IF-γ), interleukin-1α (IL-1α), IL-1β, IL-6, IL-12, IL-17, and IL-23.

4. The method of claim 1, wherein said inflammatory disease is selected from the group consisting of anaphylaxis, septic shock, septic arthritis, rheumatoid arthritis, psoriatic arthritis, asthma, delayed type hypersensitivity, dermatitis, diabetes mellitus, juvenile onset diabetes, graft rejection, inflammatory bowel diseases, Crohn's disease, ulcerative colitis, enteritis, interstitial cystitis, multiple sclerosis, myasthemia gravis, Grave's disease, Hashimoto's thyroiditis, pneumonitis, nephritis, pneumonitis, obstructive pulmonary disease, bronchitis, bronchitis rhinitis, spondyloarthropathies, scleroderma, systemic lupus erythematosus, and hepatitis.

5. The method of claim 1, wherein said biological sample is a plasma sample, a saliva sample, synovial fluid sample, a urine sample, or a fecal sample.

6. The method of claim 1, wherein said detecting step comprises contacting said biological sample with one or more binding agents that bind specifically to said one or more inflammatory disease markers.

7. The method of claim 6, wherein said one or more binding agents bind to said one or more inflammatory disease markers with kd value in the range of 0.01 pM to 1 μM.

8. The method of claim 6, wherein said binding agents comprise one or more peptides or polypeptides.

9. The method of claim 8, wherein the binding agents comprise one or more antibodies, peptide aptamers, and/or synbodies.

10. The method of claim 1, wherein said one or more inflammatory disease markers comprise:
   (1) at least one inflammatory disease marker selected from the group consisting of CXCL9, CXCL10, CXCL11, CXCL13, CXCR3 and CXCR5;
   (2) at least one inflammatory disease marker selected from the group consisting of CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, XCL1, CX3CL1, CCR1, CCR2, CCR3, CCR4, CCR5, CCR6, CCR8, CCR9, CCR10, CXCR1, CXCR2, CXCR4, XCR1; and (3) at least one inflammatory disease marker selected from the group consisting of leptin, tumor necrosis factor α (TNFα), interferon-γ (IF-γ), interleukin-1α (IL-1α), IL-1β, IL-6, IL-12, IL-17, and IL-23.

11. The method of claim 1, wherein said inflammatory disease is arthritis and wherein the one or more inflammatory disease markers further comprises one or more inflammatory disease markers selected from the group consisting of CXCL12, CCL20, XCL1, CX3CL1, CXCR4, CXCR5, CCR6, XCR1, CX3CR1.

12. The method of claim 1, wherein said inflammatory disease is asthma and wherein the one or more inflammatory disease markers further comprises one or more inflammatory disease markers selected from the group consisting of CCL3, CCL4, CCL5, CCL7, CCL8, CCR3, CCR4, CCR5, CCL11, CCL15, CCL17, CCL22, CCL24, and CCL26.

13. The method of claim 1, wherein said inflammatory disease is septic shock or anaphylaxis and wherein the one or more inflammatory disease markers further comprises one or more inflammatory disease markers selected from the group consisting of CXCL1, CXCL2, CXCL3, CXCL5, CXCL6, CXCL7, CXCL8, CCL5, CXCR1, and CXCR2.

14. The method of claim 1, wherein said inflammatory disease is diabetes and wherein the one or more inflammatory disease markers further comprises one or more inflammatory disease markers selected from the group consisting of CCL2, CCL9, CX3CL1, CCR2, CCR4, and CX3CR1.

15. The method of claim 1, wherein said inflammatory disease is dermatitis or delayed-type hypersensitivity and wherein the one or more inflammatory disease markers further comprises one or more inflammatory disease markers selected from the group consisting of CCL2, CCL3, CCL4, CCL5, CCL17, CCL29, CCL22, CCL27, CCR4, CCR5, CCR6, and CCR10.

16. The method of claim 1, wherein said inflammatory disease is graft rejection and wherein the one or more inflammatory disease markers further comprises one or more inflammatory disease markers selected from the group consisting of CCL3, CCL4, CCL5, XCL1, CCR5, and XCR1.

17. The method of claim 1, wherein said inflammatory disease is multiple sclerosis and wherein the one or more inflammatory disease markers further comprises one or more inflammatory disease markers selected from the group consisting of CCL3, CCL4, CCL5, CCL7, CCL14, CCL15, CCL23, CCR1, and CCR5.

18. The method of claim 1, wherein said inflammatory disease is mysasthemia gravis, Grave's disease or Hashimoto thyroiditis and wherein the one or more inflammatory disease markers further comprises one or more inflammatory disease markers selected from the group consisting of CCL3, CCL4, CCL5, XCL1, CCR5, and XCR1.

19. The method of claim 1, wherein said inflammatory disease is nephritis or systemic lupus ethematosus and wherein the one or more inflammatory disease markers further comprises one or more inflammatory disease markers selected from the group consisting of CCL2, CCL3, CCL4, CCL5, CCL8, CCL12, CCL13, CX3CL1, CCR2, CCR4, and CX3CR1.

20. The method of claim 1, wherein said inflammatory disease is pneumonitis, chronic obstructive pulmonary disease (COPD) or chronic bronchitis and wherein the one or more inflammatory disease markers further comprises one or more inflammatory disease markers selected from the group consisting of CXCL1, CXCL2, CXCL3, CXCL5, CXCL7, CXCL8, CCL3, CCL5, CCL7, CCL8, CCL11, CCL13, CCL24, CCL26, CXCR2, and CCR3.

21. A method for monitoring the course of treatment for an inflammatory disease in a subject, comprising:

determining the expression levels of one or more inflammatory disease markers in one or more biological samples obtained from said subject during or after said treatment; and comparing the level of expression of said one or more inflammatory disease markers in said one or more biological samples to a control level of expression of said one or more inflammatory disease markers, wherein said control level of said one or more inflammatory disease markers is a pre-treatment level of said one or more inflammatory disease markers in said subject or a predetermined reference level, wherein said treatment is deemed efficacious if the levels of expression of said one or more inflammatory disease markers in said one or more biological samples obtained from said subject during or after said treatment are similar to, or lower than, said control level, wherein said one or more inflammation markers comprise one or more inflammatory disease markers selected from the group consisting of CXCL9, CXCL10, CXCL11, CXCL13, CXCR3 and CXCR5.

22. A method for detecting an inflammatory disease in a subject, comprising:

(a) detecting a level of expression of one or more inflammatory disease markers in a biological sample obtained from said subject; and (b) comparing the level of expression of said one or more inflammatory disease markers in said biological sample to a normal level of expression of said one or more inflammatory disease markers, wherein a higher than normal level of expression of one or more of said plurality of inflammatory disease markers in said biological sample is indicative of the presence of an inflammatory disease in said subject, wherein said normal levels of expression of said plurality of inflammatory disease markers is a predetermined value, and wherein said one or more inflammatory disease markers comprise one or more markers selected from the group consisting of CXCL9, CXCL10, CXCL11, CXCL13, CXCR3 and CXCR5, and wherein said one or more inflammatory disease markers further comprise:

(1) at least one inflammatory disease marker selected from the group consisting of CCL1, CCL2, CCL3, CCL4, CCL5, CCL7, CCL8, CCL9, CCL11, CCL12, CCL13, CCL17, CCL20, CCL22, CCL23, CCL24, CCL25, CCL26, CCL27, CXCL1, CXCL2, CXCL3, CXCL5, CXCL6, CXCL7, CXCL8, CXCL12, XCL1, CX3CL1, CCR1, CCR2, CCR3, CCR4, CCR5, CCR6, CCR8, CCR9, CCR10, CXCR1, CXCR2, CXCR4, XCR1; leptin, tumor necrosis factor α (TNFα), interferon-γ (IF-γ), interleukin-1α (IL-1α), IL-1β, IL-6, IL-12, IL-17, and IL-23; and (2) at least one antibody directed against an inflammation-related microorganism selected from the group consisting of *Mycobacterium, Bacteroides, Brucella, Campylobacter, Escherichia coli, Saccharomyces cerevisiae, Klebsiella, Yersinia pseudotuberculosis, Clostridium, Enterococcus, Eubacterium, Listeria monocytogenes, Peptostreptococcus, Helicobacter, Haemophilus influenzae, Pseudomanas fluorescens, Salmonella, Chlamydia*, human hepatitis virus and human rhinovirus.

23. A method for detecting an inflammatory disease in a subject, comprising:
(a) detecting a level of expression of one or more inflammatory disease markers in a biological sample obtained from said subject; and
(b) comparing the level of expression of said one or more inflammatory disease markers in said biological sample to a normal level of expression of said one or more inflammatory disease markers,
wherein a higher than normal level of expression of one or more of said plurality of inflammatory disease markers in said biological sample is indicative of the presence of an inflammatory disease in said subject, wherein said normal levels of expression of said plurality of inflammatory disease markers is a predetermined value, and wherein said one or more inflammatory disease markers comprise one or more markers selected from the group consisting of CXCL9, CXCL10, CXCL11, CXCL13, CXCR3 and CXCR5, and
wherein said inflammatory disease is interstitial cystitis and wherein the one or more inflammatory disease markers further comprises one or more inflammatory disease markers selected from the group consisting of CCL3, CCL4, CCL5 and CCR5.

* * * * *